(12) United States Patent
Tamai

(10) Patent No.: US 12,226,409 B2
(45) Date of Patent: Feb. 18, 2025

(54) TREATMENT OF HEPATOCELLULAR CARCINOMA

(71) Applicant: Eisai R&D Management Co., Ltd., Tokyo (JP)

(72) Inventor: Toshiyuki Tamai, Tokyo (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 17/407,742

(22) Filed: Aug. 20, 2021

(65) Prior Publication Data

US 2022/0040168 A1 Feb. 10, 2022

Related U.S. Application Data

(63) Continuation of application No. 16/609,895, filed as application No. PCT/JP2018/018810 on May 15, 2018, now abandoned.

(60) Provisional application No. 62/506,900, filed on May 16, 2017.

(51) Int. Cl.
| A61K 31/47 | (2006.01) |
| A61K 9/48 | (2006.01) |
| A61P 35/00 | (2006.01) |

(52) U.S. Cl.
CPC .............. *A61K 31/47* (2013.01); *A61K 9/48* (2013.01); *A61P 35/00* (2018.01)

(58) Field of Classification Search
CPC ...................................................... A61K 31/47
USPC ........................................................ 514/312
See application file for complete search history.

(56) References Cited

U.S. PATENT DOCUMENTS

| 4,000,278 A | 12/1976 | Curran |
| 4,526,988 A | 7/1985 | Hertel |
| 4,563,417 A | 1/1986 | Albarella et al. |
| 4,582,789 A | 4/1986 | Sheldon, III et al. |
| 4,742,003 A | 5/1988 | Derynck et al. |
| 4,743,450 A | 5/1988 | Harris et al. |
| 4,764,454 A | 8/1988 | Ichijima et al. |
| 5,009,894 A | 4/1991 | Hsiao |
| 5,120,548 A | 6/1992 | McClelland et al. |
| 5,180,818 A | 1/1993 | Cech et al. |
| 5,211,951 A | 5/1993 | Sparer et al. |
| 5,445,934 A | 8/1995 | Fodor et al. |
| 5,464,826 A | 11/1995 | Grindey et al. |
| 5,487,889 A | 1/1996 | Eckert et al. |
| 5,553,037 A | 9/1996 | Tachibana |
| 5,624,937 A | 4/1997 | Reel et al. |
| 5,633,006 A | 5/1997 | Catania et al. |
| 5,650,376 A | 7/1997 | Badaye et al. |
| 5,656,454 A | 8/1997 | Lee et al. |
| 5,658,374 A | 8/1997 | Glover |
| 5,686,104 A | 11/1997 | Mills et al. |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,242,002 B1 | 6/2001 | Tritthart et al. |
| 6,261,776 B1 | 7/2001 | Pirrung et al. |
| 6,262,046 B1 | 7/2001 | Alker et al. |
| 6,346,398 B1 | 2/2002 | Pavco et al. |
| 6,351,255 B1 | 2/2002 | Ishizuka et al. |
| 6,475,525 B1 | 11/2002 | Komuro et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,544,552 B2 | 4/2003 | Sparks et al. |
| 6,576,424 B2 | 6/2003 | Fodor et al. |
| 6,596,311 B1 | 7/2003 | Dobetti et al. |
| 6,676,941 B2 | 1/2004 | Thorpe et al. |
| 6,762,180 B1 | 7/2004 | Roth et al. |
| 6,797,823 B1 | 9/2004 | Kubo et al. |

(Continued)

FOREIGN PATENT DOCUMENTS

| AU | 2012246490 | 8/2016 |
| CA | 2 361 057 | 7/2000 |

(Continued)

OTHER PUBLICATIONS

Eisai Inc. (2015) Lenvima, Prescribing Information, pp. 1-43. (Applicant's publication).*
ClinicalTrial.gov (NCT01761266) (2013) pp. 1-13. (Applicant's work).*
EU Clical Trial (2012-002992-33) (2013) pp. 1-18. (Applicant's work).*
"Carboxymethyl Cellulose Sodium." Chemical Land 21. Retrieved Apr. 24, 2012. <http://www.chemicalland21.comlindustrialchem/perfonnancepolymer/CARBOXYMETHYL%20CELLULOSE%20SODIUM%20SAL T.htm>.

(Continued)

*Primary Examiner* — Taofiq A Solola
(74) *Attorney, Agent, or Firm* — Fish & Richardson P.C.

(57) ABSTRACT

This disclosure provides methods for treating a hepatocellular carcinoma (e.g., unresectable HCC) with lenvatinib or a pharmaceutically acceptable salt thereof. Also encompassed by the disclosure are dosage regimens described herein of lenvatinib or a pharmaceutically acceptable salt thereof for use in treating hepatocellular carcinoma (e.g., unresectable hepatocellular carcinoma) according to any of the methods described herein. Particularly useful dosages and dose modifications upon the occurrence of an adverse event or events are also disclosed.

25 Claims, 15 Drawing Sheets

(56) References Cited

U.S. PATENT DOCUMENTS

| | | |
|---|---|---|
| 6,811,779 B2 | 11/2004 | Rockwell et al. |
| 6,812,341 B1 | 11/2004 | Conrad |
| 6,821,987 B2 | 11/2004 | Kubo et al. |
| 6,984,403 B2 | 1/2006 | Hagen et al. |
| 7,005,430 B2 | 2/2006 | Ueno et al. |
| 7,074,880 B2 | 7/2006 | Rhine et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,175,856 B2 | 2/2007 | Ullah et al. |
| 7,211,587 B2 | 5/2007 | Kubo et al. |
| 7,253,286 B2 | 8/2007 | Funahashi et al. |
| 7,312,243 B1 | 12/2007 | Pravda |
| 7,435,590 B2 | 10/2008 | Komurasaki |
| 7,485,658 B2 | 2/2009 | Bolger et al. |
| 7,495,104 B2 | 2/2009 | Miwa et al. |
| 7,547,703 B2 | 6/2009 | Roth et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,683,172 B2 | 3/2010 | Naito et al. |
| 7,725,303 B2 | 5/2010 | Tramontana |
| 7,759,518 B2 | 7/2010 | Maderna et al. |
| 7,790,885 B2 | 9/2010 | Nagai et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 7,994,159 B2 | 8/2011 | Yamamoto et al. |
| 7,998,948 B2 | 8/2011 | Obaishi et al. |
| 8,044,240 B2 | 10/2011 | Dimock |
| 8,063,049 B2 | 11/2011 | Koh et al. |
| 8,080,657 B2 | 12/2011 | Chung et al. |
| 8,101,799 B2 | 1/2012 | Maderna et al. |
| 8,143,271 B2 | 3/2012 | Ibrahim et al. |
| 8,252,842 B2 | 8/2012 | Dimock |
| 8,288,538 B2 | 10/2012 | Matsushima et al. |
| 8,309,126 B2 | 11/2012 | Holman et al. |
| 8,372,981 B2 | 2/2013 | Funahashi et al. |
| 8,377,938 B2 | 2/2013 | Matsushima et al. |
| 8,415,469 B2 | 4/2013 | Ibrahim et al. |
| 8,466,316 B2 | 6/2013 | Dimock |
| 8,470,818 B2 | 6/2013 | Ibrahim et al. |
| 8,492,560 B2 | 7/2013 | Stokes et al. |
| 8,580,254 B2 | 11/2013 | Adam et al. |
| 8,648,116 B2 | 2/2014 | Vernier et al. |
| 8,759,577 B2 | 6/2014 | Dimock |
| 8,808,742 B2 | 8/2014 | Quart et al. |
| 8,815,241 B2 | 8/2014 | Yamamoto |
| 8,871,450 B2 | 10/2014 | Hacker |
| 8,962,650 B2 | 2/2015 | Narita et al. |
| 8,969,379 B2 | 3/2015 | Furitsu et al. |
| 8,992,915 B2 | 3/2015 | Heider et al. |
| 9,174,998 B2 | 11/2015 | Inoue et al. |
| 9,945,862 B2 | 4/2018 | Funahashi et al. |
| 10,259,791 B2 | 4/2019 | Nakamura et al. |
| 10,259,817 B2 | 4/2019 | Kushida et al. |
| 10,407,393 B2 | 9/2019 | Nakamura et al. |
| 10,583,133 B2 | 3/2020 | Math et al. |
| 10,822,307 B2 | 11/2020 | Nakamura et al. |
| 2002/0010203 A1 | 1/2002 | Lipson et al. |
| 2002/0032217 A1 | 3/2002 | Fanara et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0124129 A1 | 7/2003 | Oliner |
| 2003/0187019 A1 | 10/2003 | Ullah et al. |
| 2003/0215523 A1 | 11/2003 | Ozawa et al. |
| 2004/0002505 A1 | 1/2004 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0132772 A1 | 7/2004 | Awad et al. |
| 2004/0152759 A1 | 8/2004 | Abrams et al. |
| 2004/0162333 A1 | 8/2004 | Mezaache et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0198806 A1 | 10/2004 | Littlefield et al. |
| 2004/0224972 A1 | 11/2004 | Ozawa et al. |
| 2004/0229876 A1 | 11/2004 | Kubo et al. |
| 2004/0242506 A1 | 12/2004 | Barges Causeret et al. |
| 2004/0243205 A1 | 12/2004 | Keravel et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0261337 A1 | 11/2005 | Wang et al. |
| 2005/0272688 A1 | 12/2005 | Higgins et al. |
| 2005/0277652 A1 | 12/2005 | Matsushima et al. |
| 2005/0288521 A1 | 12/2005 | Naidu et al. |
| 2006/0004017 A1 | 1/2006 | Stokes et al. |
| 2006/0004029 A1 | 1/2006 | Tsuruoka et al. |
| 2006/0018909 A1 | 1/2006 | Oliner et al. |
| 2006/0057159 A1 | 3/2006 | Huang et al. |
| 2006/0057195 A1 | 3/2006 | Nonomura et al. |
| 2006/0079494 A1 | 4/2006 | Santi et al. |
| 2006/0104984 A1 | 5/2006 | Littlefield et al. |
| 2006/0135486 A1 | 6/2006 | Owa et al. |
| 2006/0160832 A1 | 7/2006 | Funahashi et al. |
| 2006/0178399 A1 | 8/2006 | Nishizawa et al. |
| 2006/0189629 A1 | 8/2006 | Bolger et al. |
| 2006/0198885 A1 | 9/2006 | Dharmadhikari et al. |
| 2006/0246071 A1 | 11/2006 | Green et al. |
| 2006/0247259 A1 | 11/2006 | Funahashi et al. |
| 2006/0252777 A1 | 11/2006 | Kim et al. |
| 2006/0292192 A1 | 12/2006 | Hasenzahl et al. |
| 2007/0004773 A1 | 1/2007 | Sakaguchi et al. |
| 2007/0014856 A1 | 1/2007 | Takagi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2007/0254930 A1 | 11/2007 | Ryu et al. |
| 2007/0292515 A1 | 12/2007 | Schobel et al. |
| 2007/0298111 A1 | 12/2007 | Ueki |
| 2008/0114039 A1 | 5/2008 | Hirawat et al. |
| 2008/0207617 A1 | 8/2008 | Miwa et al. |
| 2008/0214557 A1 | 9/2008 | Ueki et al. |
| 2008/0214604 A1 | 9/2008 | Furitsu et al. |
| 2008/0214606 A1 | 9/2008 | Szakacs et al. |
| 2008/0241835 A1 | 10/2008 | Mehraban et al. |
| 2008/0246404 A1 | 10/2008 | Shelton et al. |
| 2008/0267971 A1 | 10/2008 | Green et al. |
| 2008/0286282 A1 | 11/2008 | Semba et al. |
| 2009/0028858 A1 | 1/2009 | Wang et al. |
| 2009/0042213 A1 | 2/2009 | Hoofnagle et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0104285 A1 | 4/2009 | Littlefield et al. |
| 2009/0171112 A1 | 7/2009 | Naito et al. |
| 2009/0191212 A1 | 7/2009 | Oliner et al. |
| 2009/0202541 A1 | 8/2009 | Bruns et al. |
| 2009/0209580 A1 | 8/2009 | Matsui |
| 2009/0217401 A1 | 8/2009 | Korman et al. |
| 2009/0247576 A1 | 10/2009 | Kamata |
| 2009/0264464 A1 | 10/2009 | Yamamoto et al. |
| 2009/0304694 A1 | 12/2009 | Oliner et al. |
| 2009/0311175 A1 | 12/2009 | Brose |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |

(56) References Cited

U.S. PATENT DOCUMENTS

| | | |
|---|---|---|
| 2010/0197911 A1 | 8/2010 | Funahashi et al. |
| 2010/0239688 A1 | 9/2010 | Yamamoto |
| 2010/0286094 A1 | 11/2010 | Chung et al. |
| 2010/0324087 A1 | 12/2010 | Yamamoto |
| 2011/0020410 A1 | 1/2011 | Nonomura et al. |
| 2011/0060049 A1 | 1/2011 | Vernier et al. |
| 2011/0028498 A1 | 2/2011 | Ryan et al. |
| 2011/0104161 A1 | 5/2011 | Burgess et al. |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0172446 A1 | 7/2011 | Littlefield et al. |
| 2011/0207756 A1 | 8/2011 | Matsui |
| 2011/0293615 A1 | 12/2011 | Yamamoto |
| 2011/0311546 A1 | 12/2011 | Oliner et al. |
| 2012/0022076 A1 | 1/2012 | Maderna et al. |
| 2012/0052073 A1 | 3/2012 | Green et al. |
| 2012/0053177 A1 | 3/2012 | Ibrahim et al. |
| 2012/0077837 A1 | 3/2012 | Okamoto et al. |
| 2012/0077842 A1 | 3/2012 | Bando |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0071403 A1 | 3/2013 | Rolland et al. |
| 2013/0085152 A1 | 4/2013 | Matsui et al. |
| 2013/0108626 A1 | 5/2013 | Delmar et al. |
| 2013/0121999 A1 | 5/2013 | De Haas et al. |
| 2013/0123274 A1 | 5/2013 | Nakagawa et al. |
| 2013/0133091 A1 | 5/2013 | Korman et al. |
| 2013/0142799 A1 | 6/2013 | Oliner et al. |
| 2013/0171135 A1 | 7/2013 | Andres et al. |
| 2013/0171160 A1 | 7/2013 | Green et al. |
| 2013/0183300 A1 | 7/2013 | Andres et al. |
| 2013/0183301 A1 | 7/2013 | Delmar et al. |
| 2013/0183302 A1 | 7/2013 | De Haas et al. |
| 2013/0183303 A1 | 7/2013 | De Haas et al. |
| 2013/0195857 A1 | 8/2013 | Delmar et al. |
| 2013/0196972 A1 | 8/2013 | Chung et al. |
| 2013/0225581 A1 | 8/2013 | Furuta et al. |
| 2013/0237565 A1 | 9/2013 | Furitsu et al. |
| 2013/0243758 A1 | 9/2013 | Andres et al. |
| 2013/0296365 A1 | 11/2013 | Bando |
| 2013/0309250 A1 | 11/2013 | Cogswell et al. |
| 2013/0336959 A1 | 12/2013 | Andres et al. |
| 2013/0336960 A1 | 12/2013 | Andres et al. |
| 2013/0344059 A1 | 12/2013 | Andres et al. |
| 2013/0344060 A1 | 12/2013 | Andres et al. |
| 2014/0017231 A1 | 1/2014 | Andres et al. |
| 2014/0017232 A1 | 1/2014 | Andres et al. |
| 2014/0023639 A1 | 1/2014 | Andres et al. |
| 2014/0023640 A1 | 1/2014 | Andres et al. |
| 2014/0031384 A1 | 1/2014 | Narita et al. |
| 2014/0056874 A1 | 2/2014 | Andres et al. |
| 2014/0056875 A1 | 2/2014 | Andres et al. |
| 2014/0056876 A1 | 2/2014 | Andres et al. |
| 2014/0148483 A1 | 5/2014 | Semba et al. |
| 2014/0193397 A1 | 7/2014 | Andres et al. |
| 2014/0212422 A1 | 7/2014 | Korman et al. |
| 2014/0234296 A1 | 8/2014 | Sharma et al. |
| 2014/0243316 A1 | 8/2014 | Takaishi et al. |
| 2014/0294852 A1 | 10/2014 | Korman et al. |
| 2014/0302019 A1 | 10/2014 | Delmar et al. |
| 2014/0328833 A1 | 11/2014 | Korman et al. |
| 2014/0348743 A1 | 11/2014 | Korman et al. |
| 2015/0005343 A1 | 1/2015 | Nomoto et al. |
| 2015/0125455 A1 | 5/2015 | Green et al. |
| 2015/0165025 A1 | 6/2015 | Korman et al. |
| 2015/0175615 A1 | 6/2015 | Inoue et al. |
| 2015/0210769 A1 | 7/2015 | Freeman et al. |
| 2015/0366866 A1 | 12/2015 | Ali et al. |
| 2016/0222118 A1 | 8/2016 | Chen et al. |
| 2017/0088615 A1 | 3/2017 | Korman et al. |
| 2017/0191137 A1 | 7/2017 | Semba et al. |
| 2017/0233344 A1 | 8/2017 | Nakamura et al. |
| 2018/0092901 A1 | 4/2018 | Denker et al. |
| 2018/0141950 A1 | 5/2018 | Kushida et al. |
| 2020/0375975 A1 | 12/2020 | Kremer et al. |
| 2022/0023285 A1 | 1/2022 | Denker et al. |

FOREIGN PATENT DOCUMENTS

| | | |
|---|---|---|
| CA | 2606719 | 12/2006 |
| CA | 3044658 | 8/2018 |
| CH | 656535 | 7/1986 |
| CL | 201102116 | 3/2009 |
| CL | 200003576 | 10/2009 |
| CL | 201402511 | 4/2012 |
| CL | 201502363 | 2/2013 |
| CL | 201601367 | 2/2013 |
| CN | 1083728 | 3/1994 |
| CN | 1293041 | 5/2001 |
| CN | 1473041 | 2/2004 |
| CN | 1478078 | 2/2004 |
| CN | 1585770 | 2/2005 |
| CN | 1634043 | 7/2005 |
| CN | 1642415 | 7/2005 |
| CN | 1744881 | 3/2006 |
| CN | 1772052 | 5/2006 |
| CN | 1878751 | 12/2006 |
| CN | 1890220 | 1/2007 |
| CN | 101001629 | 7/2007 |
| CN | 101029022 | 9/2007 |
| CN | 101198590 | 6/2008 |
| CN | 101316590 | 12/2008 |
| CN | 101337931 | 1/2009 |
| CN | 101443009 | 5/2009 |
| CN | 101454286 | 6/2009 |
| CN | 101454311 | 6/2009 |
| CN | 101616671 | 12/2009 |
| CN | 101827849 | 9/2010 |
| CN | 101848895 | 9/2010 |
| CN | 101896485 | 11/2010 |
| CN | 102036962 | 4/2011 |
| CN | 102046628 | 5/2011 |
| CN | 102470133 | 5/2012 |
| CN | 102958523 | 3/2013 |
| CN | 103003262 | 3/2013 |
| CN | 103209982 | 7/2013 |
| CN | 103402519 | 11/2013 |
| CN | 107305202 A | 10/2017 |
| CN | 107305202 B | 4/2020 |
| EP | 0 203 126 | 12/1986 |
| EP | 0 297 580 | 1/1989 |
| EP | 0 405 425 | 1/1991 |
| EP | 0 408 496 | 1/1991 |
| EP | 0 427 519 | 5/1991 |
| EP | 0 602 851 | 6/1994 |
| EP | 0 684 637 | 11/1995 |
| EP | 0 684 820 | 12/1995 |
| EP | 0 712 863 | 5/1996 |
| EP | 0 795 556 | 9/1997 |
| EP | 0 837 063 | 4/1998 |
| EP | 0 860 433 | 8/1998 |
| EP | 0 870 842 | 10/1998 |
| EP | 0 930 305 | 7/1999 |
| EP | 0 930 310 | 7/1999 |
| EP | 1 029 853 | 8/2000 |
| EP | 1 044 969 | 10/2000 |
| EP | 0 543 942 | 1/2001 |
| EP | 1 153 920 | 11/2001 |
| EP | 1 382 604 | 1/2004 |
| EP | 1 411 046 | 4/2004 |
| EP | 1 415 987 | 5/2004 |
| EP | 1 447 045 | 8/2004 |
| EP | 1 447 405 | 8/2004 |
| EP | 1 473 043 | 11/2004 |
| EP | 1 506 962 | 2/2005 |
| EP | 1 522 540 | 4/2005 |
| EP | 1 535 910 | 6/2005 |
| EP | 1 552 833 | 7/2005 |
| EP | 1 566 379 | 8/2005 |
| EP | 1 604 665 | 12/2005 |

(56) References Cited

FOREIGN PATENT DOCUMENTS

| | | |
|---|---|---|
| EP | 1 331 005 | 4/2006 |
| EP | 1 683 785 | 7/2006 |
| EP | 1 698 623 | 9/2006 |
| EP | 1 719 763 | 11/2006 |
| EP | 1 777 218 | 4/2007 |
| EP | 1 797 877 | 6/2007 |
| EP | 1 797 881 | 6/2007 |
| EP | 1 859 793 | 11/2007 |
| EP | 1 859 797 | 11/2007 |
| EP | 1 889 836 | 2/2008 |
| EP | 1 894 918 | 3/2008 |
| EP | 1 925 676 | 5/2008 |
| EP | 1 925 941 | 5/2008 |
| EP | 1 949 902 | 7/2008 |
| EP | 1 964 837 | 9/2008 |
| EP | 2 058 302 | 5/2009 |
| EP | 2 062 886 | 5/2009 |
| EP | 2 116 246 | 11/2009 |
| EP | 2 119 707 | 11/2009 |
| EP | 2 133 094 | 12/2009 |
| EP | 2 133 095 | 12/2009 |
| EP | 2 218 712 | 8/2010 |
| EP | 2 293 071 | 3/2011 |
| EP | 2 711 433 | 3/2014 |
| EP | 2821066 | 1/2015 |
| EP | 2 700 403 | 11/2015 |
| EP | 3 088 401 | 11/2016 |
| EP | 3384901 | 10/2018 |
| EP | 3 524 595 A1 | 8/2019 |
| EP | 3 524 595 B1 | 8/2022 |
| EP | 4147689 | 3/2023 |
| GB | 2253848 | 9/1992 |
| GB | 2456907 | 8/2009 |
| IL | 148756 | 10/2007 |
| IN | 236500 | 11/2009 |
| IN | 201747040368 | 11/2017 |
| JP | 61-148115 | 7/1986 |
| JP | 63-028427 | 6/1988 |
| JP | 1-022874 | 1/1989 |
| JP | 2-291295 | 12/1990 |
| JP | 4-341454 | 11/1992 |
| JP | H05194259 | 8/1993 |
| JP | 6-153952 | 6/1994 |
| JP | 6-287148 | 10/1994 |
| JP | 7-176103 | 7/1995 |
| JP | 8-045927 | 2/1996 |
| JP | 8-048078 | 2/1996 |
| JP | 9-023885 | 1/1997 |
| JP | 9-234074 | 9/1997 |
| JP | 10-114655 | 5/1998 |
| JP | 10-147524 | 6/1998 |
| JP | 3088018 | 6/1998 |
| JP | 10-316576 | 12/1998 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 5/2000 |
| JP | 3420549 | 10/2000 |
| JP | 2000-325080 | 11/2000 |
| JP | 2000-328080 | 11/2000 |
| JP | 2001-047890 | 2/2001 |
| JP | 2001-131071 | 5/2001 |
| JP | 2002-003365 | 1/2002 |
| JP | 2002-505269 | 2/2002 |
| JP | 2002-114710 | 4/2002 |
| JP | 2002-509872 | 4/2002 |
| JP | 2002-518384 | 6/2002 |
| JP | 2002-536056 | 10/2002 |
| JP | 2002-536414 | 10/2002 |
| JP | 2003-012668 | 1/2003 |
| JP | 2003-026576 | 1/2003 |
| JP | 2003-033472 | 2/2003 |
| JP | 2003-252737 | 9/2003 |
| JP | 2003-525595 | 9/2003 |
| JP | 2004-513964 | 5/2004 |
| JP | 2004-155773 | 6/2004 |
| JP | 2004-517859 | 6/2004 |
| JP | 2004-531549 | 10/2004 |
| JP | 2005-272474 | 10/2004 |
| JP | 2005-501074 | 1/2005 |
| JP | 2005-504111 | 2/2005 |
| JP | 2005-124034 | 5/2005 |
| JP | 2005-520834 | 7/2005 |
| JP | 3712393 | 11/2005 |
| JP | 2006-508981 | 3/2006 |
| JP | 2006-514968 | 5/2006 |
| JP | 2006-515884 | 6/2006 |
| JP | 2006-230816 | 9/2006 |
| JP | 2006-340714 | 12/2006 |
| JP | 2007-153894 | 6/2007 |
| JP | 2008-546797 | 12/2008 |
| JP | 2009-132660 | 6/2009 |
| JP | 2009-263298 | 11/2009 |
| JP | 2010-502209 | 1/2010 |
| JP | 2010-535233 | 11/2010 |
| JP | 2011-500666 | 1/2011 |
| JP | 2011-522037 | 7/2011 |
| JP | 2013-540774 | 11/2013 |
| JP | 2014-521308 | 8/2014 |
| JP | 2016-528162 | 9/2016 |
| JP | 6788600 | 11/2020 |
| KR | 10-2003-0040552 | 5/2003 |
| KR | 2003-40552 | 5/2003 |
| KR | 10-0589032 | 11/2005 |
| KR | 10-2006-0113759 | 11/2006 |
| KR | 10-2007-0053205 | 5/2007 |
| KR | 20070116217 | 12/2007 |
| KR | 10-2008-0008374 | 1/2008 |
| RU | 2192863 | 11/2002 |
| RU | 2264389 | 11/2005 |
| RU | 2328489 | 7/2008 |
| RU | 2404992 | 10/2008 |
| RU | 2362771 | 7/2009 |
| RU | 2385867 | 4/2010 |
| RU | 2448708 | 6/2010 |
| RU | 2457210 | 7/2012 |
| RU | 2470024 | 12/2012 |
| RU | 2582964 | 4/2016 |
| TW | I304061 | 12/2008 |
| WO | WO 1986/003222 | 6/1986 |
| WO | WO 1992/020642 | 11/1992 |
| WO | WO 1993/011748 | 6/1993 |
| WO | WO 1994/009010 | 4/1994 |
| WO | WO 1995/015758 | 6/1995 |
| WO | WO 1995/017181 | 6/1995 |
| WO | WO 1995/019774 | 7/1995 |
| WO | WO 1996/009294 | 3/1996 |
| WO | WO 1996/026997 | 9/1996 |
| WO | WO 1996/030347 | 10/1996 |
| WO | WO 1996/033980 | 10/1996 |
| WO | WO 1996/039145 | 12/1996 |
| WO | WO 1996/040080 | 12/1996 |
| WO | WO 1996/040142 | 12/1996 |
| WO | WO 1997/003069 | 1/1997 |
| WO | WO 1997/013760 | 4/1997 |
| WO | WO 1997/013771 | 4/1997 |
| WO | WO 1997/017329 | 5/1997 |
| WO | WO 1997/021437 | 6/1997 |
| WO | WO 1997/038984 | 10/1997 |
| WO | WO 1997/048693 | 12/1997 |
| WO | WO 1998/000134 | 1/1998 |
| WO | WO 1998/002434 | 1/1998 |
| WO | WO 1998/002437 | 1/1998 |
| WO | WO 1998/002438 | 1/1998 |
| WO | WO 1998/013350 | 4/1998 |
| WO | WO 1998/014437 | 4/1998 |
| WO | WO 1998/023613 | 6/1998 |
| WO | WO 1998/029137 | 7/1998 |
| WO | WO 1998/032436 | 7/1998 |
| WO | WO 1998/035958 | 8/1998 |
| WO | WO 1998/037079 | 8/1998 |
| WO | WO 1998/050346 | 11/1998 |
| WO | WO 1998/052558 | 11/1998 |

(56) References Cited

FOREIGN PATENT DOCUMENTS

| | | |
|---|---|---|
| WO | WO 1998/056787 | 12/1998 |
| WO | WO 1999/000357 | 1/1999 |
| WO | WO 1999/003854 | 1/1999 |
| WO | WO 1999/032106 | 7/1999 |
| WO | WO 1999/032110 | 7/1999 |
| WO | WO 1999/032111 | 7/1999 |
| WO | WO 1999/032436 | 7/1999 |
| WO | WO 1999/035132 | 7/1999 |
| WO | WO 1999/035146 | 7/1999 |
| WO | WO 1999/043654 | 9/1999 |
| WO | WO 1999/062890 | 12/1999 |
| WO | WO 2000/019985 | 4/2000 |
| WO | WO 2000/031048 | 6/2000 |
| WO | WO 2000/042012 | 7/2000 |
| WO | WO 2000/043366 | 7/2000 |
| WO | WO 2000/043384 | 7/2000 |
| WO | WO 2000/044728 | 8/2000 |
| WO | WO 2000/047212 | 8/2000 |
| WO | WO 2000/050405 | 8/2000 |
| WO | WO 2000/071097 | 11/2000 |
| WO | WO 2001/002369 | 1/2001 |
| WO | WO 2001/023375 | 4/2001 |
| WO | WO 2001/027081 | 4/2001 |
| WO | WO 2001/032926 | 5/2001 |
| WO | WO 2001/036403 | 5/2001 |
| WO | WO 2001/040217 | 6/2001 |
| WO | WO 2001/045689 | 6/2001 |
| WO | WO 2001/046196 | 6/2001 |
| WO | WO 2001/047890 | 7/2001 |
| WO | WO 2001/047931 | 7/2001 |
| WO | WO 2001/060814 | 8/2001 |
| WO | WO 2002/016348 | 2/2002 |
| WO | WO 2002/032872 | 4/2002 |
| WO | WO 2002/036117 | 5/2002 |
| WO | WO 2002/041882 | 5/2002 |
| WO | WO 2002/044156 | 6/2002 |
| WO | WO 2002/072578 | 9/2002 |
| WO | WO 2002/080975 | 10/2002 |
| WO | WO 2002/088110 | 11/2002 |
| WO | WO 2002/092091 | 11/2002 |
| WO | WO 2002/096361 | 12/2002 |
| WO | WO 2003/000660 | 1/2003 |
| WO | WO 2003/006462 | 1/2003 |
| WO | WO 2003/013529 | 2/2003 |
| WO | WO 2003/024386 | 3/2003 |
| WO | WO 2003/027102 | 3/2003 |
| WO | WO 2003/028711 | 4/2003 |
| WO | WO 2003/033472 | 4/2003 |
| WO | WO 2003/050090 | 6/2003 |
| WO | WO 2003/074045 | 9/2003 |
| WO | WO 2003/075840 | 9/2003 |
| WO | WO 2003/079020 | 9/2003 |
| WO | WO 2003/087026 | 10/2003 |
| WO | WO 2003/099771 | 12/2003 |
| WO | WO 2004/006862 | 1/2004 |
| WO | WO 2004/020434 | 3/2004 |
| WO | WO 2004/032872 | 4/2004 |
| WO | WO 2004/032937 | 4/2004 |
| WO | WO 2004/035052 | 4/2004 |
| WO | WO 2004/039782 | 5/2004 |
| WO | WO 2004/041308 | 5/2004 |
| WO | WO 2004/043472 | 5/2004 |
| WO | WO 2004/045523 | 6/2004 |
| WO | WO 2004/064730 | 8/2004 |
| WO | WO 2004/076412 | 9/2004 |
| WO | WO 2004/078144 | 9/2004 |
| WO | WO 2004/080462 | 9/2004 |
| WO | WO 2004/080966 | 9/2004 |
| WO | WO 2004/087096 | 10/2004 |
| WO | WO 2004/089286 | 10/2004 |
| WO | WO 2004/101526 | 11/2004 |
| WO | WO 2005/004870 | 1/2005 |
| WO | WO 2005/021537 | 3/2005 |
| WO | WO 2005/027972 | 3/2005 |
| WO | WO 2005/030140 | 4/2005 |
| WO | WO 2005/044788 | 5/2005 |
| WO | WO 2005/051366 | 6/2005 |
| WO | WO 2005/056764 | 6/2005 |
| WO | WO 2005/063713 | 7/2005 |
| WO | WO 2005/070891 | 8/2005 |
| WO | WO 2005/082854 | 9/2005 |
| WO | WO 2005/082855 | 9/2005 |
| WO | WO 2005/092896 | 10/2005 |
| WO | WO 2005/117867 | 12/2005 |
| WO | WO 2005/117887 | 12/2005 |
| WO | WO 2006/004636 | 1/2006 |
| WO | WO 2006/014325 | 2/2006 |
| WO | WO 2006/030826 | 3/2006 |
| WO | WO 2006/030941 | 3/2006 |
| WO | WO 2006/030947 | 3/2006 |
| WO | WO 2006/036941 | 4/2006 |
| WO | WO 2006/038552 | 4/2006 |
| WO | WO 2006/062984 | 6/2006 |
| WO | WO 2006/090930 | 8/2006 |
| WO | WO 2006/090931 | 8/2006 |
| WO | WO 2006/105798 | 10/2006 |
| WO | WO 2006/123517 | 11/2006 |
| WO | WO 2006/137474 | 12/2006 |
| WO | WO 2007/000347 | 1/2007 |
| WO | WO 2007/002325 | 1/2007 |
| WO | WO 2007/014335 | 2/2007 |
| WO | WO 2007/015569 | 2/2007 |
| WO | WO 2007/015578 | 2/2007 |
| WO | WO 2007/023768 | 3/2007 |
| WO | WO 2007/040565 | 4/2007 |
| WO | WO 2007/052849 | 5/2007 |
| WO | WO 2007/052850 | 5/2007 |
| WO | WO 2007/061127 | 5/2007 |
| WO | WO 2007/061130 | 5/2007 |
| WO | WO 2007/061874 | 5/2007 |
| WO | WO 2007/136103 | 11/2007 |
| WO | WO 2008/023698 | 2/2008 |
| WO | WO 2008/026577 | 3/2008 |
| WO | WO 2008/026748 | 3/2008 |
| WO | WO 2008/053602 | 5/2008 |
| WO | WO 2008/088088 | 7/2008 |
| WO | WO 2008/093855 | 8/2008 |
| WO | WO 2008/102870 | 8/2008 |
| WO | WO 2008/155387 | 12/2008 |
| WO | WO 2009/018238 | 2/2009 |
| WO | WO 2009/051397 | 4/2009 |
| WO | WO 2009/060945 | 5/2009 |
| WO | WO 2009/077874 | 6/2009 |
| WO | WO 2009/096377 | 8/2009 |
| WO | WO 2009/114335 | 9/2009 |
| WO | WO 2009/140549 | 11/2009 |
| WO | WO 2009/148192 | 12/2009 |
| WO | WO 2009/150256 | 12/2009 |
| WO | WO 2010/006225 | 1/2010 |
| WO | WO 2010/048304 | 4/2010 |
| WO | WO 2010/086964 | 8/2010 |
| WO | WO 2010/101849 | 9/2010 |
| WO | WO 2010/120112 | 10/2010 |
| WO | WO 2011/017583 | 2/2011 |
| WO | WO 2011/021597 | 2/2011 |
| WO | WO 2011/022335 | 2/2011 |
| WO | WO 2011/162343 | 12/2011 |
| WO | WO 2012/019300 | 2/2012 |
| WO | WO 2012/029913 | 3/2012 |
| WO | WO 2012/115286 | 8/2012 |
| WO | WO 2012/144463 | 10/2012 |
| WO | WO 2012/154935 | 11/2012 |
| WO | WO 2012/157672 | 11/2012 |
| WO | WO 2012/166899 | 12/2012 |
| WO | WO 2013/019906 | 2/2013 |
| WO | WO 2013/132044 | 9/2013 |
| WO | WO 2013/151708 | 10/2013 |
| WO | WO 2014/055648 | 4/2014 |
| WO | WO 2014/087230 | 6/2014 |
| WO | WO 2014/113729 | 7/2014 |
| WO | WO 2014/130869 | 8/2014 |
| WO | WO 2014/133022 | 9/2014 |
| WO | WO 2014/151006 | 9/2014 |
| WO | WO 2014/185540 | 11/2014 |

(56) References Cited

FOREIGN PATENT DOCUMENTS

| WO | WO 2014/208774 | 12/2014 |
|---|---|---|
| WO | WO 2015/098853 | 7/2015 |
| WO | WO 2015/119944 | 8/2015 |
| WO | WO 2016/141218 | 9/2016 |
| WO | WO 2016/196389 | 12/2016 |
| WO | WO 2016/204193 | 12/2016 |
| WO | WO 2016/208576 | 12/2016 |

OTHER PUBLICATIONS

"Carboxymethylcellulose Sodium." Merck Index: An Encyclopedia of Chemicals, Drugs, & Biologicals: 13th Ed. New Jersey: Merck & Co (2001), p. 308.
"Clinical Trial: AMG 706 20040273 Thyroid Cancer Study: Stage 4 Cancer Treatments, Chat w/a Cancer Info Expert About Stage 4 Cancer Treatment Options," accessed from www.CancerCenter.com, 4 pages (2005).
"Current Protocols in Molecular Biology", John Wiley & Sons Section 11.4-11.13 (1987), 62, pages.
"FDA-AACR Oncology Dose Finding Workshop—Session 3 Transcript [URL:https://www.aacr.org/AdvocacyPolicy/GovernmentAffairs/Documents/6.13.16%20FDA-AACR%20Oncology%20Dose%20Finding%20Workshop%20Session%203%20Transcript.pdf]", Jun. 13, 2016, 27 pages.
"FMC BioPolymer; http://www.fmcbiopolymer.com/portals/pharm/content/docs/fmc_alubra_brochurefinal.pdf," Mar. 16, 2015, 6 pages.
"Impurities in New Drug Substances Q3A (R2)", ICH Harmonized—Tripartite Guideline, Oct. 25, 2006.
"IN 1571/CHENP/2007", Aug. 31, 2007, 50 pages (English Translation).
"IN 2045/CHENP/2006", Jun. 1, 2007, 13 pages (English Translation).
"IN 2572/CHENP/2006", Jun. 8, 2007, 74 pages (English Translation).
"IN 383/CHENP/2008", Sep. 19, 2008, 26 pages (English Translation).
"Mix: Merriam-Webster Dictionary (Year: 2018)," 2018.
"Molecular Targets and Cancer Therapeutics," Poster Session A, A92, Nov. 6, 2015, p64.
"Patent Term Extension document filed before the USPTO in respect of the U.S. Pat. No. 7,253,286," Apr. 8, 2015, 89 pages.
"Pharmacokinetics (PK) and tolerability of GW786034, a VEGFR tyrosine kinase inhibitor, after daily oral administration to patients with solid tumors.", Proc. Am. Soc. Clin. Oncology, (Abstract 3054), 2004.
"Prescribing Information of Afinitor (everolimus) tables for oral administration, Afinitor Disperz (everolimus tables for oral suspension) [Retrieved on Jun. 12, 2017 URL:https://www.accessdata.fda.gov/drugsatfda_docs/label/2016/022334s036Ib1.pdf,2.2,]", Novartis Pharmaceuticals Corporation, Feb. 2016, 42 pages.
"Prescribing Information of Lenvima (lenvatinib) capsules, for oral use, Eisai Inc. [URL:https://www.accessdata.fda.gov/drugsatfda_docs/label/2015/206947s000lb1.pdf,2.1,2.2,8.6,8.7,Tablesl-3]", Feb. 2015, 25 pages.
"Recent Results and Ongoing Trials with Panitumumab (ABX-EGF), a Fully Human Anti-Epidermal Growth Factor Receptor Antibody, in Metastatic Colorectal Cancer", Clinical Colorectal Cancer. 2005; 5(1):21-3.
"Specification: Test Procedures and Acceptance Criteria for New Drug Substances and New Drug Products: Chemical Substances," Q6A, ICH Harmonized—Tripartite Guideline, Oct. 6, 1999, 35 pages.
[No Author], "Study of Pembrolizumab (MK-3475) in Participants With Advanced Solid Tumors (MK-3475-012/KEYNOTE-012)," Apr. 2014, [Retrieved on Feb. 25, 2020], retrieved from, URL<https://clinicaltrials.gov/ct2/show/study/NCT01848834?term=01848834&draw=1&rank=1>, 38 pages.
[No Author], "Unique Protocol ID: E7080-G000-207; Phase 1/2 Study of Lenvatinib in Children and Adolescents with Refractory or Relapsed Solid Malignancies and Young Adults with Osteosarcoma,"
ClinicalTrials.gov PRS, results summary NIH resolution Review 1, Last Update: Aug. 10, 2020, 117 pages.
[No Author], "Crossover Study to Evaluate the Relative Bioavailability and Palatability of a Lenvatinib Suspension Compared to the Capsule Formulation in Adult Healthy Volunteers," ClinicalTrials.gov, Jun. 8, 2016, 11 pages, retrieved from: URL<https://clinicaltrials.gov/ct2/show/NCT02792829?term=NCT02792829&rank=1>.
[No Author], "Highlights of Prescribing Information: Lenvima," U.S. Food and Drug Administration, revised Feb. 2017, 34 pages.
[No Author], "Pharmaceuticals Interview Form: Lenvima" Pharmaceuticals and Medical Devices Agency, Version No. 1, 2015, 165 pages (with English Translation).
[No Author], "Pharmaceuticals Interview Form: Lenvima" Pharmaceuticals and Medical Devices Agency, Version No. 5, 2018, 248 pages (with English Translation).
"Arzneimittelwirkungen Lehrbuch der Pharmakologie und Toxikologie," Ernst Mutschler Ed Mutschler E et al., Arzneimittelwirkungen Lehrbuch der Pharmakologie und Toxikologie, Wissenschaftliche Verlagsgesellschaft, Stuttgart, Jan. 1, 1999, p. 1-p. 5, XP007919509 (English translation).
"Chapter 2.2 Loslichkeit, Losungsgeschwindigkeit, Loslichkeitsverbesserung," Rudolf Voigt Ed—Voigt R et al., Pharmazeutische Technologie fuer Studium und Beruf, DT. Apotheker-Verl, Stuttgart; DE, Jan. 1, 2000, p. 40-p. 52, XP008143620 (English translation).
AACR American Association Cancer Research, 92nd Annual Meeting, 42:583, Mar. 24-28, 2001, New Orleans, LA, USA, 3126.
Abrams et al., SU11248 Inhibits KIT and Platelet-derived Growth Factor Receptor Beta in Preclinical Models of Human Small Cell Lung Cancer*Molecular Cancer Therapeutics.*, 2: 471-478, 2003.
Abuzar et al., "Synthesis of some new 7-chloro-4-substituted quinolines as potential antiparasitic agents," Eur. J. Med. Chem., 21(1):5-8 (1986).
Additional Response in IL Application No. 188670, dated Oct. 25, 2011, 4 pages (with English translation).
Advisory Action for U.S. Appl. No. 12/092,539 issued on Jun. 28, 2011.
Advisory Action in U.S. Appl. No. 12/315,291, dated Mar. 24, 2011, 10 pages.
Agarwal et al., "Binding of discoidin domain receptor 2 to collagen I: an atomic force microscopy investigation," Biochemistry, 41(37):11091-11098 (2002).
Agnieszka et al., "Emergence of potential biomarkers of response to anti-angiogenic anti-tumor agents," Int J Cancer, Sep. 2010, 127(6):1251-1258.
Almarsson et al., "High-Throughput Surveys of Crystal Form Diversity of Highly Polymorphic Pharmaceutical Compounds," Crystal Growth & Design, Sep. 10, 2003, 3(6):927-933.
Altschul et al., "Basic Local Alignment Search Tool", J. Mol. Biol. 215:403-410 (1990).
Amended Claims filed in European Application No. 11798224.9, filed Aug. 2, 2013, 35 pages.
Amended Claims filed in Korean Application No. 10-2010-7011023, filed Jul. 17, 2013, 15 pages, with English translation.
Amended Claims filed in Russian Application No. 2013140169, dated Aug. 29, 2013, 17 pages, with English translation.
Amended Claims in Brazilian Application No. BR112012003592-4, dated Oct. 23, 2014, 12 pages, with English translation.
Amended claims in European Application No. 04807580.8, dated Jun. 16, 2014, 7 pages.
Amended Claims in Malaysian Application No. PI2011700172, dated in Jul. 3, 2014, 15 pages.
Amended description filed after receipt of search report in European Patent App. No. 10809938.3, filed Dec. 8, 2011.
Amended description filed after receipt of search report in European Patent App. No. 10809938.3, filed Sep. 14, 2010.
Amended Drawing in Filipino Application No. 1-2011-502441, dated Oct. 17, 2014, 2 pages.
Amended Drawing in Israeli Application No. 217197, dated Oct. 22, 2014, 4 pages, with English translation.
Amended Drawings in European Application No. 10809938.3, dated Nov. 11, 2014, 14 pages.

(56) References Cited

OTHER PUBLICATIONS

Amended set of Claims in European Application No. 11798224.9, dated Sep. 19, 2014, 53 pages.
Amended Specification filed in Australian Application No. 2012246490, filed Aug. 2, 2013, 15 pages.
Amendment after Allowance dated Jan. 4, 2011 in CA Application No. 2426461.
Amendment and Argument dated Apr. 27, 2012 in response to the Japanese Office Action in JP2007-542863, 13 pages and English translation.
Amendment and RCE submission documents filed in U.S. Appl. No. 12/039,381, dated Oct. 23, 2013, 13 pages.
Amendment and Request in Continued Examiner in U.S. Appl. No. 13/083,338, dated Oct. 10, 2014, 5 pages.
Amendment and Response filed in U.S. Appl. No. 11/997,543, dated Dec. 19, 2013, 38 pages.
Amendment and Response to Final Office Action in U.S. Appl. No. 12/092,539, dated Jun. 15, 2011.
Amendment and Response to Final Office Action in U.S. Appl. No. 12/864,817, dated Dec. 5, 2011.
Amendment and Response to Non-Final Office Action in U.S. Appl. No. 11/997,543, dated Aug. 19, 2011.
Amendment and Response to Office Action dated Apr. 2, 2013 in U.S. Appl. No. 13/083,338, 9 pages.
Amendment and Response to Office Action in U.S. Appl. No. 11/997,543, dated Jan. 9, 2012.
Amendment and Response to Office Action in U.S. Appl. No. 11/997,719, dated Dec. 23, 2010.
Amendment and Response to Office Action in U.S. Appl. No. 12/092,539, dated Mar. 11, 2011.
Amendment and Response to Office Action in U.S. Appl. No. 12/439,339, dated Aug. 22, 2013, 14 pages.
Amendment and Response to Office Action in U.S. Appl. No. 12/439,339, dated Feb. 7, 2012.
Amendment and Response to Office Action in U.S. Appl. No. 12/439,339, dated Jul. 30, 2012.
Amendment and Response to Office Action in U.S. Appl. No. 12/524,754, dated Feb. 17, 2012.
Amendment and Response to Office Action in U.S. Appl. No. 12/741,682, dated Jul. 30, 2012.
Amendment and Response to Office Action in U.S. Appl. No. 12/864,817, dated Aug. 9, 2011.
Amendment and Response to Office Action in U.S. Appl. No. 13/205,328, dated Apr. 11, 2012.
Amendment dated Apr. 11, 2006 in Chinese Application No. 01819710.8, with English translation.
Amendment dated Apr. 17, 2002 in Taiwanese U.S. Appl. No. 90/125,928, with English translation.
Amendment dated Apr. 19, 2005 in Japanese Application No. 2002-536056, with English translation.
Amendment dated Aug. 13, 2013 in Japanese Application No. P2009-540099, 8 pages, with English translation.
Amendment dated Aug. 17, 2004 in South African Application No. 2003/3567.
Amendment dated Aug. 29, 2013 in Chinese Application No. 201280010898.X, 24 pages, with English translation.
Amendment dated Aug. 4, 2004 in South African Application No. 2003/3567.
Amendment dated Aug. 6, 2013, in Japanese Application No. 2009-551518, 6 pages, with English translation.
Amendment dated Dec. 12, 2011 in JO Patent App. No. 55/2011, with English translation.
Amendment dated Dec. 15, 2011 in VN Application No. 1-2011-03484, with English translation.
Amendment dated Dec. 22, 2011 in South African Application No. 2011/08697.
Amendment dated Feb. 9, 2011 in Taiwanese Application No. 100104281.
Amendment dated Jan. 11, 2010 in Chinese Application No. 200580026468.7, with English translation.
Amendment dated Jan. 26, 2010 in Chinese Application No. 200710007097.9, with English translation.
Amendment dated Jul. 2, 2009 in Chinese Application No. 200710007097.9, with English translation.
Amendment dated Jun. 22, 2010 in Chinese Application No. 200710007097.9, with English translation.
Amendment dated Mar. 20, 2012 in Korean Patent App. No. 10-2012-7003846.
Amendment dated Mar. 23, 2009 in Japanese Application No. 2005-124034, with English translation.
Amendment dated Mar. 6, 2006 in Korean Application No. 10-2003-7005506, with English translation.
Amendment dated Mar. 7, 2005 in Japanese Application No. 2002-536056, with English translation.
Amendment dated Mar. 8, 2006 in Korean Application No. 10-2005-7020292, with English translation.
Amendment dated May 10, 2012 in Japanese Patent Application No. 2011-527665.
Amendment dated May 21, 2009 in Japanese Application No. 2005-124034, with English translation.
Amendment dated May 28, 2003 in Chinese Application No. 01819710.8, with English translation.
Amendment dated Nov. 19, 2009 in Chinese Application No. 200710007097.9, with English translation.
Amendment dated Nov. 24, 2011 in Korean Application No. 10-2007-7001347, with English translation.
Amendment dated Oct. 1, 2013 in Indian Application No. 10502/CHENP/2012, 10 pages.
Amendment dated Oct. 25, 2005 in Korean Application No. 10-2003-7005506, with English translation.
Amendment dated Oct. 28, 2011 in LB Patent App. No. 9292.
Amendment dated Oct. 9, 2006 in Chinese Application No. 01819710.8, with English translation.
Amendment dated Sep. 13, 2005 in Chinese Application No. 01819710.8, with English translation.
Amendment dated Sep. 23, 2009 in Chinese Application No. 200580026468.7, with English translation.
Amendment dated Sep. 23, 2013 in Australian Application No. 2011270165, 35 pages.
Amendment filed in Brazilian Application No. BR112012032462-4, dated Nov. 4, 2013, 21 pages, with English translation.
Amendment filed in European Application No. 12774278.1, filed Aug. 13, 2013, 12 pages.
Amendment filed in European Application No. 12793322.4, dated Nov. 28, 2013, 6 pages.
Amendment filed in Japanese Application No. 2008-532141, filed Jul. 5, 2013, 2 pages, with English translation.
Amendment filed in Korean Application No. 10-2008-7027527, dated Jan. 27, 2014, 12 pages, with English translation.
Amendment filed in Korean Application No. 10-2008-7029472, dated May 1, 2014, 14 pages, with English translation.
Amendment filed in Korean Application No. 10-2008-7029472, dated Nov. 20, 2013, 81 pages, with English translation.
Amendment filed in Korean Application No. 10-2009-7005657, dated May 7, 2014, 15 pages, with English translation.
Amendment filed in Korean Application No. 10-2009-7017694, dated Feb. 28, 2014, 7 pages.
Amendment filed in Korean Application No. 10-2013-7020616, dated Nov. 22, 2013, 22 pages, with English translation.
Amendment filed in U.S. Appl. No. 13/805,826, dated Sep. 9, 2013, 14 pages.
Amendment in Australian Application No. 2005217325, dated Aug. 9, 2006, 11 pages.
Amendment in Australian Application No. 2005217328, dated Aug. 9, 2006, 10 pages.
Amendment in Australian Application No. 2006282456, dated Apr. 26, 2012, 6 pages.
Amendment in Australian Application No. 2006282456, dated Jan. 25, 2008, 26 pages.
Amendment in Australian Application No. 2007289787, dated Apr. 7, 2009, 16 pages.
Amendment in Bangladesh Application No. 184/2006, dated May 6, 2008, 3 pages.

(56) References Cited

OTHER PUBLICATIONS

Amendment in Bangladesh Application No. 184/2006, dated Sep. 26, 2007, 4 pages.
Amendment in Brazilian Application No. PI0616799/3, dated May 29, 2012, 6 pages.
Amendment in Canadian Application No. 2828946, dated Aug. 30, 2013, 14 pages.
Amendment in Chinese Application No. 200580001760.3, dated May 15, 2007, 31 pages, with English translation.
Amendment in Chinese Application No. 200680021939.X, dated Dec. 18, 2007, 23 pages, with English translation.
Amendment in Chinese Application No. 200780019520.5, dated Nov. 27, 2008, 10 pages, with English translation.
Amendment in Chinese Application No. 2008800045113, dated Aug. 7, 2009, 36 pages, with English translation.
Amendment in Chinese Patent Application No. 201080030508.6 dated Feb. 7, 2013, 17 pages, with English translation.
Amendment in European Application No. 05719973.9, dated Oct. 30, 2006, 2 pages.
Amendment in European Application No. 06796594.7, dated Apr. 19, 2012, 3 pages.
Amendment in European Application No. 06796594.7, dated Jan. 11, 2008, 3 pages.
Amendment in European Application No. 06796594.7, dated Nov. 16, 2007, 3 pages.
Amendment in European Application No. 07793075.8, dated Jan. 26, 2011, 12 pages.
Amendment in European Application No. 07793075.8, dated Mar. 3, 2009, 5 pages.
Amendment in European Application No. 08711837.8, dated Sep. 8, 2009, 23 pages.
Amendment in European Application No. 09713617.0, dated Sep. 1, 2010, 3 pages.
Amendment in European Patent Application No. 12793322.4, dated Sep. 15, 2017, 20 pages.
Amendment in Filipino Application No. 1-2007-502319, dated May 14, 2012, 3 pages.
Amendment in Indian Application No. 1424/CHENP/2008, dated Apr. 27, 2012, 4 pages.
Amendment in Indian Application No. 2371/CHENP/2012, dated Oct. 30, 2014, 2 pages.
Amendment in Indian Application No. 7026/CHENP/2013, dated Sep. 5, 2013, 8 pages.
Amendment in Israeli Application No. 188670, dated May 2, 2012, 7 pages, with English translation.
Amendment in Israeli Application No. 197002, dated Feb. 11, 2009, 4 pages.
Amendment in Israeli Application No. 200090, dated Oct. 2, 2013, 10 pages, with English translation.
Amendment in Israeli Application No. 200466, dated Aug. 18, 2009, 28 pages.
Amendment in Israeli Application No. 217197, dated Dec. 24, 2015, 5 pages, with English translation.
Amendment in Japanese Application No. 2007-532099, dated Dec. 25, 2007, 6 pages, with English translation.
Amendment in Japanese Application No. 2007-532099, dated Sep. 25, 2007, 28 pages, with English translation.
Amendment in Japanese Application No. 2008-530917, dated Dec. 13, 2012, 6 pages, with English translation.
Amendment in Japanese Application No. 2009-554285, dated Aug. 19, 2010, 7 pages, with English translation.
Amendment in Japanese Application No. P2009-510543, dated Nov. 9, 2009, 25 pages, with English translation.
Amendment in JO Application No. 280/2006, dated Oct. 19, 2007, 3 pages, with English translation.
Amendment in Korean Application No. 10-2006-7013907, dated Sep. 28, 2007, 10 pages, with English translation.
Amendment in Korean Application No. 10-2006-7013940, dated Oct. 1, 2007, 43 pages, with English translation.
Amendment in Korean Application No. 10-2007-7026886, dated Dec. 27, 2007, 4 pages, with English translation.
Amendment in Korean Application No. 10-2007-7026886, dated Nov. 21, 2007, 9 pages, with English translation.
Amendment in Korean Application No. 10-2007-7026886, dated Oct. 27, 2009, 4 pages, with English translation.
Amendment in Korean Application No. 10-2008-7029577, dated Apr. 1, 2009, 6 pages, with English translation.
Amendment in Korean Application No. 10-2009-7013723, dated Aug. 10, 2009, 17 pages, with English translation.
Amendment in Korean Application No. 10-2010-7011023, dated Oct. 21, 2014, 31 pages.
Amendment in Korean Application No. 10-2010-7018835, dated Dec. 1, 2014, 18 pages, with English translation.
Amendment in Korean Application No. 10-2012-7003846, dated Nov. 26, 2014, 20 pages, with English translation.
Amendment in Korean Application No. 10-2012-7033886, dated Sep. 27, 2013, 34 pages, with English translation.
Amendment in Malaysian Application No. PI20071922, dated Jul. 17, 2008, 243 pages.
Amendment in Mexican Application No. MX/a/2012/014776, dated Oct. 21, 2013, 5 pages.
Amendment in Norwegian Application No. 20080460, dated May 14, 2012, 4 pages, with English translation.
Amendment in Russian Application No. 2012158142, dated Oct. 17, 2013, 48 pages, with English translation.
Amendment in Saudi Arabian Application No. 06270287, dated Oct. 22, 2007, 12 pages.
Amendment in Singapore Application No. 200718614/1, dated Aug. 24, 2010, 13 pages.
Amendment in Taiwanese Application No. 100104281, dated Oct. 22, 2014, 8 pages.
Amendment in TH Application No. 0601004017, dated Sep. 25, 2007, 6 pages, with English translation.
Amendment in U.S. Appl. No. 11/065,631, dated May 28, 2008, 16 pages.
Amendment in U.S. Appl. No. 11/662,425, dated Sep. 2, 2014, 6 pages.
Amendment in U.S. Appl. No. 11/892,785, dated Dec. 17, 2008, 17 pages.
Amendment, Response to Office Action under 37 C.F.R. § 1.111 and Information Disclosure Statement for U.S. Appl. No. 13/624,278, filed Jun. 28, 2013, 23 pages.
Amendments received before examination for EP Application No. 01976786.2, dated Sep. 10, 2004.
Amendments to the specification filed on Mar. 26, 2012 for AU Patent Appl. No. 2010285740.
American Association for Cancer Research, "Redefining the Frontiers of Science," 94th Annual Meeting, vol. 44, 2nd Edition, Washington Convention Center, Washington, DC (Jul. 11-14, 2003).
Amin et al., "Nivolumab (ANTI-PD-1; BMS-936558, ONO-4538) in Combination With Sunit Inib or Pazopanib in Patients (PTS) With Metastatic Renal Cell Carcinoma (MRCC), " Abstract, Journal of Clinical Oncology, 2014, 32(15_suppl):5010, 2 pages.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 200.
Anderson and Flora, "Preparation of Water-Soluble Compounds Through Salt Formation," Practice of Medicinal Chem., 1996, pp. 739-754.
Anderson et al., "Clinical, Safety, and Economic Evidence in Radioactive Iodine-Refractory Differentiated Thyroid Cancer: A Systematic Literature Review", Thyroid, 23(4):392-407, 2013.
Anderson et al., "Preparation of Water -soluble Compounds through Salt Formation. The Practice of Medicinal Chemistry," Technomics, 347-349 and 355-356 (Sep. 25, 1999).
Ang, "Role of the fibroblast growth factor receptor axis in cholangiocarcinoma", Journal of Gastroenterology and Hepatology, 2015 vol.30, p. 1116-p. 1122.

(56) References Cited

OTHER PUBLICATIONS

Anonymous, "Scientific Discussion," EMEA, URL: http://www.ema.europa.eu/docs/en_GB/document_library/EPARScientific_Discussion/human/000406/WC500022203.pdf, 1-61 (2004) (XP007918143).
Antibodies: A Laboratory Manual, E. Harlow and D. Lane, ed. Cold Spring Harbor Laboratory (Cold Spring Harbour, NY, 1988), 190 pages.
Anzeninfo.mhlw.go.jp [online]. "Report No. 166; Strong Mutagenic Chemical Substance," Ministry of Health, Labor and Welfare of Japan, Dec. 11, 2012, retrieved from: URL<https://anzeninfo.mhlw.go.jp/user/anzen/kag/20121211_heni.html>, 46 pages (with Partial Translation).
Appeal for Reversal in CO Application No. 12-022608, dated Jan. 28, 2014, 17 pages (with English translation).
Appeal in SA Application No. 06270287, dated Jun. 23, 2010, 4 pages (with English translation).
Applicant Interview Summary Under 37 C.F.R. § 1.133(b) for U.S. Appl. No. 12/439,339, dated May 31, 2013, 7 pages.
Applicant Observation for CN Application No. 200780017371.9, filed May 29, 2013, 6 pages (with English translation).
Application for Patent Term Adjustment in U.S. Appl. No. 12/439,339, dated Dec. 18, 2014, 8 pages.
Approval of request for amendments for EP Application No. 04025700.8, dated Mar. 13, 2008.
Argument and Amendment for JP Application No. 2008-556208, filed Mar. 21, 2013, 15 pages (with English translation).
Argument and Amendment for CN 200880002425.9 filed on Jul. 18, 2011, 8 pages with English translation.
Argument and Amendment for JP Application No. 2008-532141, filed Nov. 29, 2012, 12 pages (with English translation).
Argument and Amendment for JP. Application No. 2008-516724, filed Nov. 28, 2012, 22 pages (with English translation).
Argument and Amendment for JP. Application No. 2009-123432, dated Jun. 12, 2012, 12 pages (with English translation).
Argument and Amendment for JP. Application No. 2009-529019, dated Jul. 3, 2012, 14 pages (with English translation).
Argument Brief filed in KR Application No. 10-2008-7029577, dated Feb. 27, 2014, 30 pages (with English translation).
Argument Brief filed on Mar. 6, 2006 for KR Application No. 10-2003-7005506 (with English translation).
Argument Brief filed on Mar. 8, 2006 for KR Application No. 10-2005-7020292 (with English translation).
Argument Brief filed on Nov. 24, 2011 for KR Application No. 10-2007-7001347 (with English translation).
Argument Brief filed on Oct. 25, 2005 for KR Application No. 10-2003-7005506 (with English translation).
Argument Brief in KR Application No. 10-2007-7026886, dated Oct. 27, 2009, 7 pages (with English translation).
Argument filed in KR Application No. 10-2009-7017694, dated Feb. 28, 2014, 48 pages.
Argument filed on Apr. 19, 2005 for JP Application No. 2002-536056 (with English translation).
Argument filed on Aug. 13, 2013 in JP Application No. 2009-540099, 10 pages (with English translation).
Argument filed on Aug. 6, 2013 for JP Patent Application No. 2009-551518, 18 pages (with English translation).
Argument filed on Mar. 23, 2009 for JP Application No. 2005-124034 (with English translation).
Argument filed on May 21, 2009 for JP Application No. 2005-124034 (with English translation).
Asai et al., "Mechanism of Ret Activation by a Mutation of Aspartic Acid 631 Identified in Sporadic Pheochromocytoma", Biochemical and Biophysical Research Communications, 255, 587-590 (1999).
Asano et al., "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
Asano et al., "Broad-spectrum preclinical combination activity of eribulin combined with various anticancer agents in human breast cancer, lung cancer, ovarian cancer, and melanoma xenograft models," European J Cancer, 50(Suppl 6):20, Nov. 19, 2014.
Asu no Shinyaku ("The New Drugs of Tomorrow"), editing/printing by Technomics, Inc., 81-83 (Dec. 2006) (English translation), 14 pages.
Auburn University, "Thyroid Cancer," (as of Feb. 25, 2006, using Wayback machine), Feb. 25, 2006, 8 pages.
Australian ("AU") Notice of Allowance dated Nov. 22, 2010 for corresponding AU Application No. 2006285673.
Australian ("AU") Office Action issued on May 19, 2010 for corresponding AU Application No. 2006285673.
Australian ("AU") Office Action issued on May 7, 2009 for corresponding AU Application No. 2006285673.
Australian ("AU") Office Action issued on Oct. 29, 2009 for corresponding AU Application No. 2006285673.
Australian Notice of Allowance in Application No. 2011270165, dated Dec. 14, 2015, 3 pages.
Australian Office Action directed at Appl. No. 2007252506 issued on Jan. 13, 2012, 2 pages.
Australian Office Action directed at Appl. No. 2007252506 issued on Nov. 7, 2011, 5 pages.
Australian Office Action for Application No. 2008205847, issued on Apr. 11, 2012.
Australian Office Action for Application No. 2008211952, issued on Apr. 3, 2012.
Australian Office Action for Application No. AU2006309551 issued on Apr. 28, 2011.
Australian Office Action in Application No. 2011271065, dated Nov. 6, 2015, 3 pages.
Australian Response to Office Action directed at Appl. No. 2007252506 filed on Jan. 4, 2012, 74 pages.
Australian Response to Office Action directed at Appl. No. 2007252506 filed on Mar. 2, 2012, 4 pages.
Australian Response to Office Action for Application No. 2006309551 filed on Jan. 27, 2012.
Australian Second Statement of Proposed Amendments in Application No. 2011270165, dated Dec. 4, 2015, 5 pages.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Baj-Krzyworzeka et al., "Elevated level of some chemokines in plasma of gastric cancer patients," Central European Journal of Immunology, 2016, 41(4):358-362, XP002793963.
Bajwa et al., "Antimalarials. 1. Heterocyclic Analogs of N-Substituted Naphthalenebisoxazines," J Med Chem., 16(2):134-138, Aug. 9, 1972.
Baker et al., "Blockade of vascular endothelial growth factor receptor and epidermal growth factor receptor signaling for therapy of metastatic human pancreatic cancer," Cancer Res., 62:1996-2003 (2002).
Banker et al., "Modern Pharmaceutics," 4th Edition, Marcel Dekker Inc., 2002, p. 172-174.
Barker and Clevers, "Mining the Wnt pathway for cancer therapeutics," Reviews Drug Discovery, Dec. 2006, 5:997-1014.
Bartsch et al., "A RET double mutation in the germline of a kindred with FMTC", Exp. Clin Endocrinol Diabetes, 108, 128-132, 2000.
Bastin et al., "Salt Selection and Optimisation Procedures for Pharmaceutical New Chemical Entities," Organic Process Research & Development, 4(5):427-435 (2000) (XP002228592).
Bavin, "Polymorphism in process development," Chemistry & Industry, 1989, 21:527-529.
Beebe et al., "Pharmacological Characterization of CP-547,632, a Novel Vascular Endothelial Growth Factor Receptor-2 Tyrosine Kinase Inhibitor for Cancer Therapy 1", Cancer Research. 63:7301-9, 2003.
Behr et al., Improved Treatment of Medullary Thyroid Cancer in a Nude Mouse Model by Combined Radioimmunochemotherapy: Doxorubicin Potentiates the Therapeutic Efficacy of Radiolabeled Antibodies in a Radioresistant Tumor Type, 57 Cancer Res. 5309-5319 (Dec. 1, 1997).

(56) References Cited

OTHER PUBLICATIONS

Bellone et al., "Growth Stimulation of Colorectal Carcinoma Cells via the c-kit Receptor is Inhibited by TGF-β-1," Journal of Cellular Physiology, 172:1-11 (1997).
Benjamin et al., "Selective ablation of immature blood vessels in established human tumors follows vascular endothelial growth factor withdrawal," J. Clin. Invest., 103(2):159-165 (1999).
Bennett et al., "Cecil Textbook of Medicine," W.B. Saunders Company, 20th Edition vol. 1, 1996, p. 1004-p. 1010.
Berdel et al., "Recombinant Human Stem Cell Factor Stimulates Growth of a Human Glioblastoma Cell Line Expressing c-kit Protooncogene," Cancer Res., 52:3498-3502 (1992).
Berge et al., "Pharmaceutical Salts," Journal of Pharmaceutical Sciences, 66(1):1-19 (Jan. 1977) (XP002550655).
Bergers et al., "Benefits of targeting both pericytes and endothelial cells in the tumor vasculature with kinase inhibitors," J. Clin. Invest., 111(9):1287-1295 (2003).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Bernex et al., "Spatial and temporal patterns of c-kit-expressing cells in WlacZ/+ and WlacZ/WlacZ mouse embryos", Development 122:3023-3033 (1996).
Besson et al., "PTEN/MMACI/TEP1 in signal transduction and tumorigenesis," EP J Biochem., 1999, 263:605-611.
Blume-Jensen et al., "Activation of the Human c-kit Product by Ligand-Induced Dimerization Mediates Circular Actin Reorganization and Chemotaxis," The EMBO Journal, 10(13):4121-4128 (1991).
Board of Appeal of the European Patent Office, "Decision—T1212/01 3.3.2," dated Feb. 3, 2015, 55 pages.
Boissan et al., "c-Kit and c-kit mutations in mastocytosis and other hematological diseases," J. Leukocyte Biol., 67:135-148 (2000).
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Bonferoni et al, "Influence of medium on dissolution-erosion behavior of Na carboxymethylcellulose and on viscoelastic properties of gels," International journal of pharmaceutics, 1995, vol. 117, No. 1, pp. 41-48.
Boss et al., "A Phase I study of E7080, a multitargeted tyrosine kinase inhibitor, in patients with advanced solid tumours," British Journal of Cancer, 106:1598-1604 (2012).
Bramhall, S., "The Matrix Metalloproteinases and Their Inhibitors in Pancreatic Cancer", International J. Pancreatol., 21, 1-12, 1997.
Brazilian Office Action in Application No. PI0418200-6, dated Jun. 16, 2015, 1 page.
Brief communication to applicant for EP Application No. 01976786.2, dated Sep. 9, 2005.
Brose et al, "Sorafenib in radioactive iodine-refractory, locally advanced or metastatic differentiated thyroid cancer: a randomised, double-blind, phase 3 trial", The Lancet, 384:319-328, Jul. 26, 2014.
Brueggen et al., "Preclinical profile of ABP309, a potent $2^{nd}$ generation VEGF receptor tyrosine kinase inhibitor belonging to the class of aminonicotinamides," EORTC-NCI-AACR Symp Mol Targets Cancer Ther., 2, (Abstract 172), 2004, 2 pages.
Bruheim et al., "Antitumour activity of oral E7080, a novel inhibitor of multiple tyrosine kinases, in human sarcoma xenografts," XP002789540, International Journal of Cancer, 2011, 129(3):742-750.
Bruns et al., "Effect of the vascular endothelial growth factor receptor-2 antibody DC101 plus gemcitabine on growth, metastasis and angiogenesis of human pancreatic cancer growing orthotopically in nude mice," J. Cancer, 102:101-108 (2002).
Burwell, Jr, "The Cleavage of Ethers," Chem Rev., 54(4):615-685, Feb. 26, 1954.
Bussolino et al., "Role of Soluble Mediators in Angiogenesis," Eur. J. Cancer, 32A(14):2401-2412 (1996).
Byrn et al., "Pharmaceutical Solids: A Strategic Approach to Regulatory Considerations," Pharmaceutical Research, 1995, 12(7):945-954.
Cainap et al., "Linifanib Versus Sorafenib in Patients With Advanced Hepatocellular Carcinoma: Results of a Randomized Phase III Trial," Journal of Clinical Oncology, 2015, 33(2):172-179.
Cairns et al., "New antiallergic pyrano[3,2g]quinoline-2,8-dicarboxylic acids with potential for the topical treatment of asthma," J. Med. Chem., 28(12):1832-1842 (1985).
Canadian ("CA") Office Action issued on Jan. 14, 2010 for corresponding CA Application No. 2,620,594.
Canadian ("CA") Office Action issued on Jan. 6, 2011 for corresponding CA Application No. 2,620,594.
Canadian Notice of Allowance in Application No. 2676796, dated Oct. 8, 2015, 1 page.
Canadian Office Action for Application No. 2426461, dated Dec. 6, 2007.
Canadian Office Action for Application No. 2426461, dated Feb. 10, 2010.
Canadian Office Action for Application No. 2426461, dated May 8, 2009.
Canadian Office Action for Application No. 2426461, dated Nov. 20, 2008.
Canadian Office Action in Application No. 2828946, dated Nov. 30, 2015, 4 pages.
Canadian Office Action in Application No. 2704000, dated Jan. 14, 2016, 3 pages.
Canadian Office Action in Application No. 2704000, dated Jul. 14, 2015, 3 pages.
Canadian Response to Office Action in Application No. 2802644, dated Apr. 18, 2016, 9 pages.
Canadian Submission Documents in Application No. 2713930, dated Jun. 22, 2015, 8 pages.
CanCercare, "Types of Lung Cancer," Cancer Care, Inc. [online] [retrieved on Nov. 12, 2009]. Retrieved from the Internet: www.lungcancer.org/reading/types.php?printable=true (2009).
Cappellen et al., "Frequent activating mutations of FGFR3 in human bladder and cervix carcinomas," Nat. Genet., 23:18-20 (1999).
Carey, "Organic Chemistry 4e: Chapter 24: Phenols," McGraw Hill, http://www.mhhe.com/physsci/chemistry/carey/student/olc/ch24reactionsarylethers.html. Accessed Oct. 3, 2014, 2000, 4 pages.
Carlomagno et al., "Point Mutation of the RET Proto-Oncogene in the TT Human Medullary Thyroid Carcinoma cell Line", Biochemical and Biophysical Research Communications, 207,1022-1028 (1995).
Carlomagno et al., "BAY 43-9006 inhibition of oncogenic RET mutants," J. Natl. Cancer Inst., 98(5):326-34 (2006).
Carlomagno et al., "ZD6474, an orally available inhibitor of KDR tyrosine kinase activity, efficiently blocks oncogenic RET kinases," Cancer Res., 62:7284-7290 (2002).
Carniti et al., "The RetC620R Mutation Affects Renal and Enteric Development in a mouse Model of Hirschprung's Disease", American Journal of Pathology, 168, 1262-1275, (2006).
Carr et al., "Phase II Study of Daily Sunitinib in FDG-PET-Positive, Iodine-Refractory Differentiated Thyroid Cancer and Metastatic Medullary Carcinoma of the Thyroid with Functional Imaging Correlation," XP055539627, Clinical Cancer Research, 2010, 16(21):5260-5268.
Carter et al., "Inhibition of drug-resistant mutants of ABL, KIT and EGF receptor kinases", Proceedings of the National Academy of Sciences of the United States of America., 102, 11011-11016, 2005.
Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Chaki et al., "mGlu2/3 and mGlu5 receptors: Potential targets for novel antidepressants," Neuropharmacology, 2013, 66:40-52.
Chemical & Engineering News, "The Top Pharmaceuticals That Changed the World," 83, [cited: Mar. 29, 2016], Jun. 20, 2005, 3 pages.

(56) References Cited

OTHER PUBLICATIONS

Chen et al., "Solid-state nuclear magnetic resonance and its application in research of drug polymorphs," Chinese Journal of New Drugs, 2013, 22(16):1921-1924, 1955 (with English Translation).
Chen et al., "FGFR3 as a therapeutic target of the small molecule inhibitor PKC412 in hematopoietic malignancies," Oncogene, 24:8259-8267 (2005).
Chen et al., "Small molecule-mediated disruption of Wnt-dependent signaling in tissue regeneration and cancer," Nat Chem Biol., Feb. 2009, 5(2):100-107.
Cheng et al., "Sunitinib Versus Sorafenib in Advanced Hepatocellular Cancer: Results of a Randomized Phase III Trial," Journal of Clinical Oncology, 2013, 31(32):4067-4075.
Chesi et al., "Activated fibroblast growth factor receptor 3 is an oncogene that contributes to tumor progression in multiple myeloma," Blood, 97:729-736 (2001).
Chesi et al., "Frequent translocation t(4;14)(p16.3;q32.3) in multiple myeloma is associated with increased expression and activating mutations of fibroblast growth factor receptor 3," Nat. Genet., 16:260-264 (1997).
Cheung et al., "Discovery of indazolylpyrimidines as potent inhibitors of VEGFR2 tyrosine kinase," Proceedings of the American Association for Cancer Research, 44, 9, (Abstract 40), 2003, 2 pages.
Chikahisa et al., "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Chilean Response to Examiner's Report in Application No. 2012-00412, dated Mar. 30, 2015, 16 pages, with English translation.
Chinese ("CN") Office Action issued on Dec. 4, 2009 for corresponding CN Application No. 200680036592.6, with English translation.
Chinese Notice of Allowance in Application No. 201280010898.X, dated Sep. 2, 2015, 4 pages.
Chinese Office Action directed at Appl. No. 200780017371.9 mailed on Oct. 20, 2010, 13 pages with English translation.
Chinese Office Action for Application No. 200580026468.7, issued on Jun. 26, 2009.
Chinese Office Action for Application No. 200710007097.9, issued on Mar. 6, 2009.
Chinese Office Action for Application No. 200780017371.9, issued on Mar. 7, 2012, with English translation.
Chinese Office Action for Application No. 200880002425.9, issued on Mar. 7, 2012, with English translation.
Chinese Office Action for Application No. 200880003336.6, issued on May 24, 2011, with English translation.
Chinese Office Action for Application No. 200880115011.7, issued on Feb. 20, 2012, with English translation.
Chinese Office Action for Application No. 201080030508.6, issued on Nov. 30, 2012.
Chinese Office Action for Application No. 200680041355.9 issued on Aug. 24, 2010 with English translation.
Chinese Office Action for Application No. 200680041355.9 issued on Mar. 5, 2010 with English translation.
Chinese Office Action in Application No. 201280010898.X, dated Mar. 30, 2015, 13 pages, with English translation.
Chinese Office Action with the English translation dated, Feb. 29, 2012, for Application No., 200680036592.6.
Chinese Response in Reexamination and Invalidation Procedure in Application No. 200780017371.9, dated Jan. 19, 2015, 8 pages, with English translation.
Chinese Response to Office Action directed at Appl. No. 200780017371.9 filed on Feb. 24, 2011, 10 pages with English translation.
Chinese Response to Office Action for Application No. 200680041355.9 filed on Jul. 19, 2010 with English translation.
Chinese Response to Office Action for Application No. 200680041355.9 filed on Nov. 8, 2010 with English translation.
Chinese Response to the Chinese Decision of Rejection, filed on Feb. 7, 2013, for corresponding Chinese Application No. 200680036592.6.
Chinese Submission Documents in Application No. 201280010898.X, dated Jun. 15, 2015, 12 pages.
Chinese Voluntary Amendment in Application No. 201510031628.2, dated Oct. 10, 2015, 5 pages, with English translation.
Ciardiello et al., "ZD1839 (IRESSA), an EGFR-selective tyrosine kinase inhibitor, enhances taxane activity in bcl-2 overexpressing, multidrug-resistant MCF-7 Adr human breast cancer cells," Int. J. Cancer, 98:463-469 (2002).
CIPO Notice of Allowance for Appl. No. 2,620,594 dated May 3, 2012.
Clark et al., "Safety and Pharmacokinetics of the Dual Action Raf Kinase and Vascular Endothelial Growth Factor Receptor Inhibitor, BAY43-9006, in Patients with Advanced Refractory Solid Tumors," Clin. Cancer Res., 11:5472-5480 (2005).
ClinicalTrials.gov [online], "A Phase 1 Study of BMS-936558 Plus Sunitinib or Pazopanib in Subjects With Metastatic Renal Cell Carcinoma," Nov. 2011, retrieved from: URL<https://clinicaltrials.gov/archive/NCT01472081/2011_11_15>, 4 pages.
ClinicalTrials.gov [online], "A Phase I/II Study to Assess the Safety and Efficacy of Pazopanib and MK 3475 In Subjects With Advanced Renal Cell Carcinoma," Dec. 2013, retrieved from: URL<https://clinicaltrials.gov/archive/NCT02014636/2013_12_17>, 8 pages.
ClinicalTrials.gov, "A Study of E7080 Alone, and in Combination With Everolimus in Subjects With Unresectable Advanced or Metastatic Renal Cell Carcinoma Following One Prior Vascular Endothelial Growth Factor (VEGF)-Targeted Treatment," National Institutes of Health, Food and Drug Administration, National Library of Medicine, [online] [retrieved on Sep. 27, 2010]. Retrieved from the Internet: http://clinicaltrials.gov/ct2/show/NCT01136733, (May 26, 2010).
CN200780032071.8 Office Action issued on Oct. 13, 2010 with English translation.
CN200780032071.8 Response to Office Action filed on Feb. 16, 2011 with English translation.
CN200880003336.6 Response to Office Action filed on Oct. 8, 2011, 10 pages.
Cohen et al., "Expression of Stem Cell Factor and c-kit in Human Neuroblastoma," Blood, 84(10):3465-3472 (1994).
Colombian Office Action for Application No. 12-022608, dated Oct. 7, 2013, 10 pages (with English translation).
Colombian Official Notification in Application No. 12-022608, dated Jan. 6, 2015, 8 pages, with English translation.
Comments re Board of Appeal in EP Application No. 04807580.8, dated Jul. 7, 2014, 3 pages.
Communication about intention to grant a European patent for EP Application No. 01976786.2, dated Sep. 4, 2006.
Communication about intention to grant a European patent for EP Application No. 04025700.8, dated Oct. 15, 2007.
Communication about intention to grant a European patent for EP Application No. 05783232.1, dated Nov. 20, 2008.
Communication about intention to grant a European patent for EP Application No. 06023078.6, dated Jul. 18, 2008.
Communication from the Examining Division for EP Application No. 01976786.2, dated Aug. 17, 2005.
Communication from the Examining Division for EP Application No. 01976786.2, dated Mar. 21, 2006.
Communication from the Examining Division for EP Application No. 01976786.2, dated Sep. 19, 2005.
Communication from the Examining Division for EP Application No. 04025700.8, dated Apr. 10, 2006.
Communication from the Examining Division for EP Application No. 04025700.8, dated Oct. 23, 2006.
Communication from the Examining Division for EP Application No. 05783232.1, dated Feb. 7, 2008.
Communication from the Examining Division for EP Application No. 06023078.6, dated Aug. 2, 2007.
Communication from the Examining Division for EP Application No. 06023078.6, dated Sep. 26, 2007.
Communication re Intention to Grant Patent in EP Application No. 07793075.8, dated Nov. 9, 2012, 97 pages.

(56) References Cited

OTHER PUBLICATIONS

Communication re Intention to Grant Patent in EP Application No. 07805959.9, dated Jun. 21, 2011, 70 pages.
Communication regarding the expiry of opposition period for EP Application No. 01976786.2, dated Jan. 4, 2008.
Communication regarding the expiry of opposition period for Ep Application No. 04025700.8, dated May 7, 2009.
Communication regarding the expiry of opposition period for EP Application No. 05783232.1, dated Feb. 19, 2010.
Communication regarding the expiry of opposition period for EP Application No. 06023078.6, dated Nov. 4, 2009.
Complete Specification in Indian Patent Application No. 2371/CHENP/2012, dated May 17, 2013, 15 pages.
Complete Specification in Indian Patent Application No. 6415/CHENP/2008, "Antitumor Agent for Thyroid Cancer," dated Nov. 24, 2008, 53 pages.
Continuation Patent Application, Preliminary Amendment and Information Disclosure Statement for U.S. Appl. No. 13/923,858, filed Jun. 21, 2013, 97 pages.
Cooper et al., "Revised American Thyroid Association Management Guidelines for Patients with Thyroid Nodules and Differentiated Thyroid Cancer The American Thyroid Association (ATA) Guidelines Taskforce on Thyroid Nodules and Differentiated Thyroid Cancer Background," XP055539610, Thyroid, 2009, 19(11):1167-1214.
Corbin et al., "Sensitivity of oncogenic KIT mutants to the kinase inhibitors MLN518 and PD180970", Blood., 104, 3754-3757, 2004.
Correction Request in CO Application No. 12-022608, dated Dec. 24, 2014, 3 pages (with English translation).
Corvi et al., "RET IPCM-1: a novel fusion gene in papillary thyroid carcinoma", Oncogene, 19:4236- 4242 (2000).
Coupling Reagents, "Advanced Automated Peptide Protein Technologies," Published Aug. 3, 2007, 4 pages.
Croom et al., "Imatinib mesylate," Drugs, 63(5):513-522 (2003).
Da Silva et al., "A novel germ-line point mutation in RET exon 8 (Gly(533)Cys) in a large kindred with familial medullary thyroid carcinoma," J. Clin. Endocrinol. Metab., 88:5438-5443 (2003).
Dankort et al., "Braf V660E cooperates with Pten loss to induce metastic melanoma," Nature Genetics, 2009, 41(5):544-552.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
Davies et al., "Mutations of the BRAF gene in human cancer," Nature, Jun. 27, 2002, 417:949-954.
De Araujo et al., "Polymorphism in drug production," Journal of Basic and Applied Pharmaceutical Sciences—Revista de Ciências Farmacêuticas Básica e Aplicada, Dec. 6, 2019, p. 27-p. 36 (with English Translation).
De Lange et al., "Phase II trial of cisplatin and gemcitabine in patients with advanced gastric cancer," Annals of Oncology, 15:484-488 (2004).
De Robertis et al., "Identification and characterization of a small-molecule inhibitor of Wnt signaling in glioblastoma cells," Mol Cancer Ther, 2013, 12:1180-1189.
Decision of Final Rejection issued in CN Application No. 200780017371.9, dated Jul. 3, 2013, 16 pages (with English translation).
Decision of Grant in RU Application No. 2008110932, dated Feb. 6, 2009, 29 pages (with English translation).
Decision of Rejection mailed on Oct. 30, 2012 issued for corresponding Chinese Application No. 200680036592.6 with full English language translation.
Decision to grant a European patent for EP Application No. 01976786.2, dated Feb. 1, 2007.
Decision to grant a European patent for EP Application No. 04025700.8, dated Jun. 5, 2008.
Decision to grant a European patent for EP Application No. 05783232.1, dated Mar. 19, 2009.
Decision to grant a European patent for EP Application No. 06023078.6, dated Dec. 4, 2008.
Decision to Grant Patent in EP Application No. 05719973.9, dated Jun. 1, 2012, 1 page.
Decision to Grant Patent in EP Application No. 07805959.9, dated Nov. 4, 2011, 2 pages.
Decision to Grant Patent in JP Application No. 2007-532099, dated Jan. 8, 2008, 5 pages (with English translation).
Decision to Grant Patent in JP Application No. 2008-530917, dated Jan. 15, 2013, 6 pages (with English translation).
Decision to Grant Patent in JP Application No. 2008-532065, dated Nov. 13, 2012, 6 pages (with English translation).
Decision to Grant Patent in JP Application No. P2009-510543, dated Feb. 2, 2010, 6 pages (with English translation).
Deficiencies in sequence listing for EP Application No. 06023078.6, dated Dec. 5, 2006.
Demand for Appeal Trial filed in JP Application No. 2008-532141, filed Jul. 5, 2013, 10 pages (with English translation).
Deplanque et al., "Anti-Angiogenic Agents: Clinical Trial Design and Therapies in Development," European Journal of Cancer, 36:1713-1724 (2000).
Dermer, "Another Anniversary for the War on Cancer," Bio/Technology, 12:320 (1994).
Dezso et al., Systems biology analysis to identify biomarkers for lenvatinib in the preclinical cancer cell line panels. Abstract of the presentation #6 (abstract 1371), AACR Annual Meeting, 2015, 2 pages.
Di Raimondo et al., "Antiogenic Factors in multiple myeloma: higher levels in bone than in peripheral blood," Haematologica, 85:800-805 (2000).
Dias et al., "IL-12 Regulates VEGF and MMPs in a Murine Breast Cancer Model", International J. Cancer., 78, 361-5, 1998.
Dietrich, "BRAF Inhibition in Refractory Hairy-Cell Leukemia," N Eng J Med, 366(21):2038-2040, May 24, 2012.
DiLorenzo et al., "Targeted Therapy in the Treatment of Metastatic Renal Cell Cancer," Oncology, 77(suppl 1):122-131 (2009).
Dourisboure et al., "Penetrance and Clinical Manifestations of Non-Hotspot Germ line RET Mutation, C630R, in a Family with Medullary Thyroid Carcinoma", Thyroid, 15, 668-671, 2005.
Dupont et al., "Phase 1 study of VEGF Trap in patients with solid tumors and lymphoma," Proc. Am. Soc. Clin. Oncology, (Abstract 776), 2003, 2 pages.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
Egyptian Submission Documents in Application No. PCT 283/2012, dated Jan. 18, 2015, 26 pages, with English translation.
Eisai Co., Ltd., "Phase II Study Results Showed Eisai's Lenvatinib (E7080) Demonstrated an Objective Response Rate of 59% in Advance Radioiodine-Refractory Differentiated Thyroid Cancer", News Release: 2011 PR Department, Eisai Co., Ltd.,No. 11-44, https://www.eisai.co.jp/news/news201144.html, Jun. 2, 2011, p. 11-p. 44.
El-Abseri et al., "Chemoprevention of UV Light-Induced Skin Tumorigenesis by Inhibition of the Epidermal Growth Factor Receptor", Cancer Research., 64, 3958-3965, 2004.
Elisei et al., "Identification of a novel point mutation in the RET gene (Ala883Thr), which is associated with medullary thyroid carcinoma phenotype only in homozygous condition," J. Clin. Endocrinol. Metab., 89:5823-5827 (2004).
Elisei et al., "Subgroup Analyses of a Phase 3 Multicenter, Double-Blind, Placebo-Controlled Trial of Lenvatinib (E7080) in Patients with 131I-Refractory Differentiated Thyroid Cancer," Poster, No. 1033P, presented at European Society for Medical Oncology 2014 Congress, Sep. 26-30, 2014, 1 page.
Emami et al., "A small molecule inhibitor of ß-catenin /CREB-binding protein transcription," PNAS, Aug. 24, 2004, 101(34):12682-12687.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.

(56) References Cited

OTHER PUBLICATIONS

Emoto et al., "Localization of the VEGF and angiopoietin genes in uterine carcinosarcome," Gynecologic Oncology, 95:474-482 (2004).
EP Communication under Rule 71(3) EPC for Application No. 06832529.9 issued on Nov. 25, 2011.
EP07806561.2 Office Action issued on Dec. 9, 2011.
EP07806561.2 Office Action issued on Feb. 7, 2011, 1 page.
EP07806561.2 Office Actions issued on Jan. 19.
EP07806561.2 Response to Office Action filed on Aug. 9, 2011.
Erber et al., "Combined inhibition of VEGF and PDGF signaling enforces tumor vessel regression by interfering with pericyte-mediated endothelial cell survival mechanisms," Faseb J., 18(2):338-340 (2004).
Erdem et al., "Correlation of E-cadherin, VEGF, COX-2 expression to prognostic parameters in papillary thyroid carcinoma", Experimental Mole Pathol., 90:312-317, Feb. 16, 2011.
European Notice of Allowance in Application No. 07743994.1, dated May 8, 2015, 51 pages.
European Notice of Allowance in Application No. 10809938.3, dated Jan. 8, 2016, 2 pages.
European Notice of Allowance in Application No. 10809938.3, dated Sep. 3, 2015, 30 pages.
European Notice of Allowance in Application No. 11798224.9, dated Sep. 29, 2015, 37 pages.
European Notice of Allowance in Application No. 12774278.1, dated Jun. 29, 2015, 34 pages.
European Office Action in Application No. 04719054.1, dated Oct. 30, 2009.
European Office Action in Application No. 04807580.8, dated Apr. 18, 2011.
European Office Action in Application No. 04807580.8, dated Dec. 3, 2010.
European Office Action in Application No. 04807580.8, dated Oct. 25, 2011.
European Office Action in Application No. 04818213.3, dated Feb. 2, 2012.
European Office Action in Application No. 06832529.9, dated Oct. 15, 2009.
European Office Action in Application No. 06832529.9, dated Sep. 12, 2011.
European Office Action in Application No. 07743994.1, dated Oct. 10, 2012.
European Office Action in Application No. 12786619.2, dated Dec. 8, 2015, 4 pages.
European Response to Communication Pursuant to Article 94(3) EPC in Application No. 10809938.3, dated Apr. 13, 2015, 12 pages.
European Response to EESR in Application No. 07743994.1-2123, dated Nov. 23, 2010, 22 pages.
European Response to Office Action in Application No. 06832529.9, dated Apr. 22, 2010.
European Response to Office Action in Application No. 06832529.9, dated Oct. 4, 2011.
European Response to Office Action in Application No. 12786619.2, dated May 12, 2015, 99 pages.
European Search Report in Application No. 03791389.4, dated Jul. 7, 2011.
European Search Report in Application No. 04025700.8, dated Jan. 13, 2005.
European Search Report in Application No. 04719054.1, dated Apr. 17, 2009.
European Search Report in Application No. 04818213.3, dated Jul. 30, 2007.
European Search Report in Application No. 05783232.1, dated Sep. 7, 2007.
European Search Report in Application No. 06023078.6, dated Mar. 16, 2007.
European Search Report in Application No. 06767145.3, dated May 23, 2011.
European Search Report in Application No. 06768437.3, dated Oct. 11, 2010.
European Search Report in Application No. 06782407.8, dated Jul. 23, 2010.
European Search Report in Application No. 06832529.9, dated Jul. 29, 2009.
European Search Report in Application No. 06833681.7, dated Nov. 24, 2010.
European Search Report in Application No. 07743994.1, dated May 4, 2010.
European Search Report in Application No. 07806561.2, dated Jan. 19, 2011.
European Search Report in Application No. 10015141.4, dated Sep. 9, 2011.
European Search Report in Application No. 10809938.3, dated Jan. 2, 2013.
European Search Report in Application No. 12793322.4, dated May 26, 2015, 9 pages.
European Search Report in Application No. 12793322.4, dated Sep. 10, 2015, 13 pages.
European Search Report in Application No. 13865671.5, dated May 23, 2016, 7 pages.
European Search Report in EP 08704376.6 dated Jun. 14, 2012, 12 pages.
European Submission Document in Application No. 09705712.9, dated Feb. 24, 2015, 196 pages.
Examination Decision and Determination in Chinese Patent Application No. 201380034056.2, dated Jun. 10, 2019, 18 pages (with English Translation).
Examination Report in Australian Application No. 2001295986, dated May 4, 2006.
Examination Report in Australian Application No. 2001295986, dated Sep. 20, 2005.
Examination Report in Australian Application No. 2005217325, dated Aug. 1, 2007, 2 pages.
Examination Report in Australian Application No. 2005217328, dated Aug. 1, 2007, 2 pages.
Examination Report in Australian Application No. 2006203099, dated Feb. 21, 2008.
Examination Report in Australian Application No. 2006236039, dated Mar. 26, 2008.
Examination Report in Australian Application No. 2007288793, dated Dec. 22, 2011, 2 pages.
Examination Report in Australian Application No. 2007289787, dated Nov. 25, 2011, 2 pages.
Examination Report in Australian Application No. 2008217931, dated Jun. 28, 2012, 3 pages.
Examination Report in Australian Application No. 2008325608, dated Nov. 24, 2012.
Examination Report in Australian Application No. 2009210098, dated Jan. 30, 2013 10 pages.
Examination Report in New Zealand Application No. 525324, dated Feb. 18, 2005.
Examination Report in New Zealand Application No. 525324, dated Oct. 13, 2003.
Examination Report in New Zealand Application No. 525324, dated Sep. 2, 2004.
Examination Report in Pakistan Application No. 155/2005, dated Mar. 11, 2009, 2 pages.
Experimental Medicine, Supplementary Volume, "A New Handbook of Genetic Engineering", Section 4, YODOSHA, 2003(Japanese).
Explanation of Circumstances Concerning Accelerated Examination filed May 10, 2012 for JP Patent Application No. 2011-527665, 21 pages (with English Translation).
Extended European Search Report in Application No. 06796594.7, dated Sep. 7, 2011, 5 pages.
Extended European Search Report in Application No. 06797249.7, dated Dec. 7, 2012,.
Extended European Search Report in Application No. 07793075.8, dated Sep. 8, 2010, 6 pages.
Extended European Search Report in Application No. 07805959.9, dated Nov. 16, 2010, 6 pages.
Extended European Search Report in Application No. 08711837.8, dated Mar. 28, 2011, 5 pages.

(56) References Cited

OTHER PUBLICATIONS

Extended European Search Report in Application No. 09713617.0, dated Apr. 28, 2011, 5 pages.
Extended European Search Report in Application No. 12195436.6, dated Feb. 21, 2013 8 pages.
Extended European Search Report in Application No. 12786619.2, dated Nov. 25, 2014, 6 pages.
Extended European Search Report in Application No. 16755489.8, dated Jul. 30, 2018, 8 pages.
Ezzat et al., "Dual Inhibition of RET and FGFR4 Retains Medullary Thyroid Cancer Cell Growth," Clinical Cancer Research, Feb. 2005, 11:1336-1341.
Fala et al., "Lenvima (Lenvatinib), a Multireceptor Tyrosine Kinase Inhibitor, Approved by the FDA for the Treatment of Patients with Differentiated Thyroid Cancer," XP002789351, American Health & Drug Benefits, 2015, 8(Special Feature):176-179.
Fargnoli et al., "Preclinical studies of BMS-582664, an alanine prodrug of BMS-540215, a potent, dual inhibitor of VEGFR-2 and FGFR-1 kinases," AACR American Association Cancer Research, 96th Annual Meeting, 46 (Abstract 3033), Anaheim, Orange County CA USA Apr. 16-20, 2005, 2 pages.
FDA.gov [online], "Prescribing Information of AFINITOR (everolimus) tablets for oral administration, Afinitor Disperz (Everolimus Tablets for Oral Suspension," Feb. 2016, [Retrieved on Jan. 27, 2020], retrieved from: URL<https://www.accessdata.fda.gov/drugsatfda_docs/label/2016/022334s036lbl.pdf>, 44 pages.
FDA.gov [online], "Prescribing Information of LENVIMA (lenvatinib) capsules, for oral use," Feb. 2015, [Retrieved on Jan. 27, 2020], retrieved from: URL<https://www.accessdata.fda.gov/drugsatfda_docs/label/2015/206947s000lbl.pdf>, 25 pages.
Ferrara, "Vascular Endothelial Growth Factor: Basic Science and Clinical Progress," Endocrine Reviews, 25(4):581-611, Aug. 2004.
FGBU [online], "Research Institute of Influenza of the Ministry of Health of the Russian Federation, Federal Center for Influenza and ARD, National Center for Influenza, WHO Guidelines for the Treatment and Prevention of Influenza in Adults," St. Petersburg, 2014, 42 pages, retrieved from: URL<http://gkb12.mznso.ru/media/cms_page_media/2149/rekomendaciipo-diagnostike-i-iecheniyu-grippa-u-vzroslyh 2.pdf,> (with English Translation).
Filipino Office Action in Application No. 1-2011-502441, dated May 8, 2015, 2 pages.
Filipino Submission Documents in Application No. 1-2011-502441, dated May 22, 2015, 25 pages.
Finn et al., "A multicenter, open-label, phase 3 trial to compare the efficacy and safety of lenvatinib (E7080) versus sorafenib in first-line treatment of subjects with unresectable hepatocellular carinoma," Am Soc Clin Oncol Annual Meeting Abstract, May 31, 2014, 5 pages.
First Office Action issued on Mar. 6, 2012 for the corresponding JP application, JP2007-542863, 17 pages and English translation.
Folkman et al., "Angiogenesis," The Journal of Biological Chemistry, 267(16):10931-10934 (1992).
Folkman et al., "Seminars in Medicine of the Beth Israel Hospital, Boston: Clinical Applications of Research on Angiogenesis," The New England Journal of Medicine, 333(26):1757-1763 (1995).
Folkman et al., "What is the Evidence That Tumors are Angiogenesis Dependent?," Journal of the National Cancer Institute, 82(1):4-6 (1990).
Folkman, "What is the evidence that tumors are angiogenesis dependent," J Nat Can Inst 82(1), 1990.
Folkman, "New Perspective in Clinical Oncology From Angiogenesis Research," J. Eur. J. Cancer, 32A(4):2534-2539 (1996).
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Forbes et al., "Dissolution kinetics and solubilities of p-aminosalicylic acid and its salts," International Journal of Pharmaceutics, 126:199-208 (1995).

Formality Requirement dated Jun. 18, 2003 for PH Application No. 1-2003-500266.
Freshney, "Culture of Animal Cells," A Manual of Basic Technique, Alan R. Liss, Inc., 1983, p4.
Freshney, R. Ian, "Culture of Animal Cells, A Manual of Basic Technique," Alan R. Liss, New York, 29-32 (1983).
Frings, "New Molecular Targeted Therapeutic Drugs Clinical Results of Bevacizumab in Non-Small Cell Lung Cancer (NSCLC)", Jap. J. Lung Cancer, Jun. 2006, 46(3):277-281 (with English Translation).
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Fujii et al., "Angiogenesis Inhibitor/Kekkan Shinsei Sogaiyaku," Clin Gastroenterol., May 25, 2004, 19:220-227.
Fujii et al., "MP-412, a dual EGFR/HER2 tyrosine kinase inhibitor: 2. In vivo antitumor effects," Am. Assoc. Cancer Research, A3394, 2005, 2 pages.
Funahashi et al., "ASCO Annual Meeting Abstracts," Jounral of Clinical Oncology, 1(29):8566, 2011.
Funahashi et al., "P-2123, Lenvatinib treatment of differentiated thyroid cancer (DTC): Analysis to identify biomarkers associated with response," The $71^{st}$ Annual Meeting of the Japanese Cancer Association, Sep. 19-21, 2012, p. 339.
Furitsu et al., "Identification of Mutations in the Coding Sequence of the Proto-Oncogene c-kit in a Human Mast Cell Leukemia Cell Line Causing Ligand-Independent Activation of c-kit Product," J. Clin. Invest., 92:1736-1744 (1993).
Furitsu et al., "Stable medicinal compositions of quinolinecarboxamide derivative," Database Caplus Chemical Abstracts Service, Columbus, OH, US (2006) (XP002520305).
Furuta et al., "Synthesis and Biological Evaluation of Selective Inhibitors of PDGF Receptor Auto Phosphorylation," #64, American Chemical Society, $226^{th}$ ACS National Meeting, New York, NY (Sep. 7-11, 2003).
Gall-Istok et al., "Notes on the Synthesis of 4-Amino-6,7-Di-Sec-Butoxyquinoline, -6,7-Methylene-Dioxyquinoline and its N-Alkylaminoacetyl Derivatives," Acta Chimica Hungarica, 112(2):241-247 (1983).
Gardner et al., "In Vitro Activity Sorghum-Selective Fluorophenyl Urea Herbicides," Pesticide Biochemistry and Physiology, 24(3):285-297 (1985).
Gaspar et al., "Single-agent Dose-finding Cohort of a Phase 1/2 Study of Lenvatinib in Children and Adolescents With Refractory or Relapsed Solid Tumors", ASCO 2017 Poater 301, ITCC-50 Study, Jun. 2-6, 2017.
Gaspar et al., Single-agent Expansion Cohort of Lenvatinib (LEN) and Combination Dose-finding Cohort of LEN + Etoposide (ETP) + Ifosfamide (IFM) in Patients (pts) Aged 2 to ≤ 25 Years With Relapsed/Refractory Osteosarcoma (OS), International Society for Paediatric Oncology, 2018, 1 page.
Gaspar et al., "Single-agent Expansion Cohort of Lenvatinib (LEN) and Combination Dose-finding Cohort of LEN + Etoposide (ETP) + Ifosfamide (IFM) in Patients (pts) Aged 2 to ≤ 25 Years With Relapsed/Refractory Osteosarcoma (OS)," Presentation at American Society of Clinical Oncology Annual Meeting, 2018, 1 page.
Gaspar et al., "Single-agent expansion cohort of lenvatinib (LEN) and combination dose-finding cohort of LEN + etoposide (ETP) + ifosfamide (IFM) in patients (pts) aged 2 to ≤25 years with relapsed/refractory osteosarcoma (OS), " Journal of Clinical Oncology, 2018, 36(15):11527.
Gatzemeier et al., "Phase III comparative study of high-dose cisplatin versus a combination of paclitaxel and cisplatin in patients with advanced non-small-cell lung cancer," J. Clin. Oncol., 18(19):3390-3399 (2000).
Gayed et al., "Prospective evaluation of plasma levels of ANGPT2, TuM2PK, and VEGF in patients with renal cell carcinoma", BMC Urology, Biomed Central, London, GB, vol. 15, No. 1, Apr. 3, 2015, p. 24, XP021217372.
Genitourinary Cancers, Prostate Cancer Genitourinary, http://www.merkmanuals.com/professional/print/sec17/ch241/ch241e.html Mar. 16, 2011.

(56) References Cited

OTHER PUBLICATIONS

Gentet et al., "Ifosfamide and etoposide in childhood osteosarcoma. A phase II study of the French Society of Paediatric Oncology", European Journal of Cancer, vol. 33, 1997, p. 232-p. 237.
Gild et al., "Multikinase inhibitors: a new option for the treatment of thyroid cancer", Nature Reviews Endocrinol., 7:617-624, Oct. 2011.
Giles, "The vascular endothelial growth factor (VEGF) signaling pathway: a therapeutic target in patients with hematologic malignancies," Oncologist, 6(suppl 5):32-39 (2001).
Gingrich et al., "A New Class of Potent Vascular Endothelial Growth Factor Receptor Tyrosine . . . Clinical Candidate CEP-7055", Journal of Medicinal Chemistry., 46: 5375-88, 2003.
Glen et al., "432 Correlative analyses of serum biomarkers and clinical outcomes in the phase 2 study of lenvatinib, everolimus, and the combination, in patients with metastatic renal cell carcinoma following 1 VEGF-targeted therapy", European Journal of Cancer, vol. 51, Sep. 1, 2015, p. S89, XP055510094.
Glen et al., "Correlative Analyses of Serum Biomarkers and Clinical Outcomes in the Phase 2 Study of Lenvatinib, Everolimus, and the Combination, in Patients With A Metastatic Renal Cell Carcinoma Following 1 VEGF-Targeted Therapy", Poster presentation at 18th ECCO—40th ESMO European Cancer Congress, Vienna, Sep. 25-29, 2015.
Glen, "Pre-clinical investigation and clinical development of E7080, a multi-targeted tyrosine kinase inhibitor: implications for melanoma," Ph.D. thesis submitted to the Faculty of Medicine, Division of Cancer Sciences and Molecular Pathology, University of Glasgow, Aug. 11, 2010, 2 pages.
Goede, "Identification of serum angiopoietin-2 as a biomarker -for clinical outcome of colorectal cancer patients treated with bevacizumab-containing therapy," Br J Cancer, 103(9):1407-1414, Oct. 2010.
Golkar et al., "Mastocytosis," Lancet, 349:1379-1385 (1997).
Gong et al., "Expression of CC Chemokine Receptor 4 In Human Follicular Thyroid Carcinoma," Academic Journal of Military Medical University, 28:701-703, 2007 English Translation.
Goorin et al., "Phase II/III trial of etoposide and high-dose ifosfamide in newly diagnosed metastatic osteosarcoma: a pediatric oncology group trial," XP009511743, Journal of Clinical Oncology: Official Journal of the American Society of Clinical Oncology, 2002, 20(2):426-433.
Gould, "Salt Selection for Basic Drugs," International Journal of Pharmaceutics, 33:201-217, (1986) (XP025813036).
Grieco et al., "PTC is a Novel Rearranged Form of the ret Proto—Oncogene and Is Frequentrly Detected in Vivo in Human Thyroid Papillary Carcinomas", Cell, 60: 557-563 (1990).
Grier et al., "Addition of Ifosfamide and Etoposide to Standard Chemotherapy for Ewing's Sarcoma and Primitive Neuroectodermal Tumor of Bone", The New England Journal of Medicine, vol. 348, 2003, p. 694-p. 701.
Guo et al., "Expression of gastric cancer-associated MG7 antigen in gastric cancer, precancerous lesions and H. pylori-associated gastric diseases", Word J. Gastroenterol, 8(6):1009-1013 (2002).
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Guo, "Dose Optimization Study: E7080-G000-218 [URL:https://www.aacr.org/AdvocacyPolicy/GovernmentAffairs/Documents/6.13.16%20FDA-AACR%20Dose%20Finding%20for%20Online.pdf]", Presentation slides at FDA-AACR: Oncology Dose-finding Workshop, Jun. 13, 2016, 25 pages.
Gura, "Cancer Models Systems for Identifying new drugs are often faulty," Science, 278:1041-1042 (1997).
Gurney et al., "Wnt pathway inhibition via the targeting of Frizzled receptors results in decreased growth and tumorigenicity of human tumors," PNAS, Jul. 17, 2012, 109(29):11717-11722.
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Haleblian,"Characterization of habits and crystalline modification of solids and their pharmaceutical applications," J. Pharm. Sci., 64(8):1269-1288 (1975).
Haller, "Chemotherapy for advanced pancreatic cancer," Int. J. Radiation Oncol. Biol. Phys., 56:16-23 (2003).
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Hamel et al., "The Road Less Travelled: c-kit and Stem Cell Factor," Journal of Neuro-Oncology, 35:327-333 (1997).
Hancock et al., "Molecular Mobility of Amorphous Pharmaceutical Solids Below Their Glass Transition Temperatures, " Pharmaceutical Research, 1995, 12(6):799-806.
Hao et al., "Targeted Inhibition of β-Catenin/CBP Signaling Ameliorates Renal Interstitial Fibrosis," J Am Soc Nephrol., 2011, 22:1642-1653.
Hara et al., "Amplification of c-myc, K-sam, and c-met in Gastric Cancers: Detection by Fluorescence In Situ Hybridization", Laboratory Investigation, 78, 1143-1153, 1998.
Hattori et al., "Immunohistochemical detection of K-sam protein in stomach cancer," Clin. Cancer Res., 2(8):1373-1381 (1996).
Havel et al., "E7080 (lenvatinib) in addition to best supportive care (BSC) versus (BSC) alone in third-line or greater nonsquamous, non-small cell lung cancer (NSCLC)," Am Soc Clin Oncol Annual Meeting Abstract, May 31, 2014, abstract 8043, 4 pages.
Hayamo et al., "Pericytes in experimental MDA-MB231 tumor angiogenesis," Histochemistry and Cell Biology, 117(6):527-534, Abstract (Jun. 2002).
Hayato, "In-silico trial to evaluate the utility of a postmarketing trial for dose optimization-Lenvatinib in Renal Cell Carcinoma—[URL:https://insp.memberclicks.net/mcdatafiles/receiptattach/insp/11395454/7966299/ACOP7_Sessio n4a_SeiichiHayato_19Oct2016.pptx]", Presentation slides at the Seventh American Conference on Pharmacometrics, Oct. 25, 2016, 17 pages.
Hayek et al., "An In Vivo Model for Study of the Angiogenic Effects of Basic Fibroblast Growth Factor," Biochemical and Biophysical Research Communications, 147(2):876-880 (1987).
Hearing Notice issued May 4, 2012, in India Patent Application No. 383/CHENP/2008.
Heinemann, V., et al., "Comparison of the Cellular Pharmacokinetics and Toxicity of . . . 1-beta-d-Arabinofuranosylcytosine", Cancer Research, 48, 4024-4031, 1988.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Heinrich et al., "Inhibition of c-kit receptor tyrosine kinase activity by STI 571, a selective tyrosine kinase inhibitor," Blood, 96(3):925-932 (2000) (XP001097629).
Heinrich et al., "Inhibition of KIT tyrosine kinase activity: a novel molecular approach to the treatment of KIT-positive malignancies," J. Clin. Oncol., 20(6):1692-1703 (2002).
Helfrich et al., "Angiopoietin-2 Levels Are Associated with Disease Progression in Metastatic Malignant Melanoma," Clin Cancer Res 15(4):1384-1392, Feb. 15, 2009.
Henderson, Jr. et al., "Inhibition of Wnt/β-catenin/CREB binding protein(CBP) signaling reverses pulmonary fibrosis," PNAS, Aug. 10, 2010, 107(32):14309-14314.
Hennequin et al., "Design and Structure-Activity Relationship of a New Class of Potent VEGF Receptor Tyrosine Kinase Inhibitors", Journal of Medicinal Chemistry., 42: 5369-5389, 1999Wedge.
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 45:1300-1312 (2002).
Herbst and Khuri et al., "Mode of action of docetaxel—a basis for combination with novel anticancer agents," Cancer Treat Rev, 29:407-415, 2003.
Herbst et al., "AMG 706 first in human, open-label, dose-finding study evaluating the safety and pharmacokinetics (PK) in subjects with advanced sold tumors," EORTC-NCI-AACR Symp Mol Targets Cancer Ther., 2, (Abstract 151), 2004, 1 page.

(56) References Cited

OTHER PUBLICATIONS

Hertel L.W., et al., "Evaluation of the Antitumor Activity of Gemcitabine (2',2' -Difluoro-2'-deoxycytidine)", Cancer Research, 50, 4417-4422, 1990.
Hibi et al., "Coexpression of the Stem Cell Factor and the c-kit Genes in Small-Cell Lung Cancer," Oncogene, 6:2291-2296 (1991).
Highlights of Prescribing Information: GLEEVEC® (imatinib mesylate) Tablets for Oral Use (Initial U.S. Approval 2001; Label Revised Jan. 2012).
Hines et al., "Coexpression of the c-kit and Stem Cell Factor Genes in Breast Carcinomas," Cell Growth & Differentiation, 6:769-779 (1995).
Hogaboam et al., "Novel Role of Transmembrane SCF for Mast Cell Activation and Eotaxin Production in Mast Cell-Fibroblast Interactions," J. Immunol., 160:6166-6171 (1998).
Hori et al., "Suppression of Solid Tumor Growth by Immunoneutralizing Monoclonal Antibody against Human Basic Fibroblast Growth Factor", Cancer Research., 51, 6180-4, 1991.
Huang et al., "Tankyrase inhibition stabilizes axin and antagonizes Wnt signaling," Nature, 2009, 461:614-620.
Hu-Lowe et al., "SU014813 is a novel multireceptor tyrosine kinase inhibitor with potent antiangiogenic and antitumor activity," AACR American Association Cancer Research., 96th Annual Meeting, 46, (Abstract 2031), Anaheim, Orange County, CA, USA Apr. 2005, 2 pages.
Hungarian Amendment to the Specification in Application No. P0302603, dated Jul. 7, 2015, 45 pages, with English translation.
Hungarian Notice of Allowance in Application No. P0302603, dated Aug. 19, 2015, 4 pages, with English translation.
Hungarian Office Action in Application No. P0302603, dated Apr. 7, 2015, 5 pages, with English translation.
Hungarian Office Action in Application No. P0302603, dated Nov. 26, 2015, 4 pages.
Hurwitz et al., "Bevacizumab plus irinotecan, fluorouracil, and leucovorin for metastatic colorectal cancer," N. Engl. J. Med., 350(23):2335-2342 (2004).
Huston et al., "Protein engineering of antibody binding sites: Recovery of specific activity in an anti-digoxin single-chain Fv analogue produced in *Escherichia coli*", Proc. Natl. Acad. Sci. USA 85: 5879-83, 1988.
Ikeda et al, "A Phase 2 Study of Lenvatinib Monotherapy as Second-line Treatment in Unresectable Biliary Tract Cancer: Primary Analysis Results", ESMO 2017 Congress, Sep. 8-12, 2017.
Ikeda et al., "Changes in Phenotype and Proliferative Potential of Human Acute Myeloblastic Leukemia Cells in Culture with Stem Cell Factor," Experimental Hematology, 21:1686-1694 (1993).
Ikeda et al., "Expression and Functional Role of the Proto-Oncogene c-kit in Acute Myeloblastic Leukemia Cells," Blood, 78(11):2962-2968 (1991).
Ikeda et al., "Phase 2 study of lenvatinib in patients with advanced hepatocellular carcinoma," J. Gastroenterol., 2016, 52:512-519.
Ikeda et al., "Safety and Pharmacokinetics of Lenvatinib in Patients with Advanced Hepatocellular Carcinoma," Clinical Cancer Research, 2015, 22:1385-1394.
Ikuta et al., "E7080, a Multi-Tyrosine Kinase Inhibitor, Suppresses the Progression of Malignant Pleural Mesothelioma with Different Proangiogenic Cytokine Production Profiles," Clin Cancer Res., Nov. 24, 2009, 15(23):7229-7237.
Inai et al., "Inhibition of vascular endothelial growth factor (VEGF) signaling in cancer causes loss of endothelial fenestrations, regression of tumor vessels, and appearance of basement membrane ghosts," American Journal of Pathology, 165:35-52 (2004).
Indian Office Action for Application No. 1571/CHENP/2007, issued on Oct. 30, 2012.
Indian Office Action in Application No. 2365/CHENP/2015, dated Sep. 6, 2018, 6 pages (with English Translation).
Indian Office Action in Application No. 6415/CHENP/2008, dated Oct. 3, 2013, 2 pages.
Indian Patent Application No. 2572/CHENP/2006 filed Jul. 13, 2006.
Information about decision on request for EP Application No. 06023078.6, dated Mar. 21, 2007.
Inoue et al., "Molecular Target Therapy Targeting Angiogenesis Pathways," The Nishinihon Journal of Urology, 66:425-432 (2004).
International Adjuvant Lung Cancer Trial Collaborative Group, "Cisplatin-Based Adjuvant Chemotherapy in Patients with Completely Resec," The New England Journal of Medicine, 350(4):351-360, Jan. 22, 2004.
International Preliminary Report in International Application No. PCT/IB2008/003880, dated Aug. 11, 2009, 4 pages.
International Preliminary Report in International Application No. PCT/JP2007/066185, dated Mar. 5, 2009, 6 pages.
International Preliminary Report in International Application No. PCT/JP2007/066635, dated Mar. 12, 2009, 9 page.
International Preliminary Report in International Application No. PCT/JP2008/053066, dated Sep. 11, 2009, 12 pages.
International Preliminary Report in International Application No. PCT/JP2008/071881, dated Jul. 14, 2011, 7 pages pages.
International Preliminary Report in International Application No. PCT/JP2009/0524001, dated Oct. 14, 2010, 5 pages.
International Preliminary Report in Patentability in International Application No. PCT/JP2006/316331, dated Feb. 26, 2008, 5 pages.
International Preliminary Report on Patentability and Written Opition of the International Searching Authroity for Application No. PCT/JP2006/312487, issued on Dec. 24, 2007.
International Preliminary Report on Patentability for Application No. PCT/JP01/09221, dated Jan. 8, 2003.
International Preliminary Report on Patentability for Application No. PCT/JP2004/003087, issued on Feb. 13, 2006.
International Preliminary Report on Patentability for Application No. PCT/JP2005/016941, dated on Mar. 20, 2007.
International Preliminary Report on Patentability for Application No. PCT/JP2010/063804, issued on Mar. 13, 2012.
International Preliminary Report on Patentability for Application No. PCT/JP2011/064430, dated Jan. 24, 2013, 6 pages.
International Preliminary Report on Patentability for Application No. PCT/JP2018/018810, dated Aug. 7, 2018, 10 pages.
International Preliminary Report on Patentability for International Application No. PCT/JP2003/010964 dated Aug. 10, 2004, 7 pages.
International Preliminary Report on Patentability for International Application No. PCT/JP2007/060560 on Nov. 18, 2008, 6 pages with English translation.
International Preliminary Report on Patentability for International Application No. PCT/JP2007/060560, dated Dec. 10, 2008, 7 pages.
International Preliminary Report on Patentability for International Application No. PCT/JP2007/067088 dated Mar. 3, 2009, 16 pages with English translation.
International Preliminary Report on Patentability for International Application No. PCT/JP2008/051024 dated Jul. 21, 2009, 15 pages with English translation.
International Preliminary Report on Patentability for International Application No. PCT/JP2008/051697, issued on Aug. 4, 2009, 18 pages.
International Preliminary Report on Patentability for International Application No. PCT/JP2008/070321, issued May 11, 2010, 15 pages with English translation.
International Preliminary Report on Patentability for International Application No. PCT/JP2009/051244 issued on Aug. 31, 2010, 12 pages (with English translation).
International Preliminary Report on Patentability in Application No. PCT/JP2013/084052, dated Jul. 2, 2015, 7 pages.
International Preliminary Report on Patentability in International Application No. PCT/JP2005/003701, dated Sep. 16, 2006, 7 pages.
International Preliminary Report on Patentability in International Application No. PCT/JP2005/003704, dated Sep. 19, 2006, 7 pages.
International Preliminary Report on Patentability in International Application No. PCT/JP2006/315563 dated Feb. 5, 2008, 10 pages with English translation.
International Preliminary Report on Patentability in International Application No. PCT/JP2006/315698 dated Feb. 5, 2008, 17 pages English translation.

(56) References Cited

OTHER PUBLICATIONS

International Preliminary Report on Patentability in International Application No. PCT/JP2006/322514 issued on May 7, 2008, 8 pages.
International Preliminary Report on Patentability in International Application No. PCT/JP2006/322516 issued on May 7, 2008, 8 pages.
International Preliminary Report on Patentability in International Application No. PCT/JP2012/060279, dated Oct. 23, 2013, 11 pages.
International Preliminary Report on Patentability in International Application No. PCT/JP2012/062509, dated Nov. 28, 2013, 11 pages.
International Preliminary Report on Patentability in International Application No. PCT/JP2016/055268, dated Sep. 8, 2017, 9 pages [English Translation].
International Preliminary Report on Patentability in International Application No. PCT/JP2018/004007, dated Aug. 22, 2019, 7 pages.
International Preliminary Report on Patentability in International Patent Application No. PCT/JP2014/083932, dated Jul. 7, 2016, 5 pages.
International Preliminary Report on Patentability in International Patent Application No. PCT/JP2015/073946, dated Mar. 9, 2017, 8 pages (English Translation).
International Preliminary Report on Patentability in International Patent Application No. PCT/JP2016/002562, dated Aug. 9, 2016, 4 pages (English Translation).
International Preliminary Report on Patentability in International Patent Application No. PCT/JP2016/068381, dated Jan. 4, 2018, 9 pages (English Translation).
International Preliminary Report on Patentability in International Patent Application No. PCT/JP2016/074090, dated Mar. 1, 2018, 6 pages (English Translation).
International Preliminary Report on Patentability in PCT Application No. PCT/US2012/040183, dated Apr. 3, 2014, 9 pages.
International Search Report and International Preliminary Report on Patentability for PCT Application No. PCT/JP2011/064430, Sep. 13, 2011, 8 pages.
International Search Report and Written Opinion in Application No. PCT/JP2014/063134, dated Sep. 9, 2014, 8 pages.
International Search Report and Written Opinion in International Application No. PCT/JP2008/071881, dated Jan. 27, 2009, 12 pages.
International Search Report and Written Opinion in International Application No. PCT/JP2009/0524001, dated Mar. 10, 2009, 9 pages.
International Search Report and Written Opinion in International Application No. PCT/JP2014/083932, dated Mar. 17, 2015, 9 pages.
International Search Report and Written Opinion in International Application No. PCT/JP2017/015461, dated Jun. 27, 2017, 8 pages.
International Search Report and Written Opinion in International Application No. PCT/JP2018/018810, dated Aug. 7, 2018, 7 pages.
International Search Report and Written Opinion in International Application No. PCT/US2019/031967, dated Sep. 17, 2019, 15 pages.
International Search Report and Written Opinion in International Application No. PCT/US2020/057650, dated Feb. 12, 2021, 16 pages.
International Search Report for Application No. PCT/JP01/09221, issued on Jan. 15, 2002.
International Search Report for Application No. PCT/JP2004/003087, issued on Jul. 13, 2004.
International Search Report for Application No. PCT/JP2005/016941, dated on Nov. 15, 2005.
International Search Report for Application No. PCT/JP2006/315563, issued on Sep. 5, 2006.
International Search Report for Application No. PCT/JP2006/315698, issued on Oct. 17, 2006.
International Search Report for Application No. PCT/JP2006/322514, issued on Jan. 23, 2007.
International Search Report for Application No. PCT/JP2006/323881, issued on Jan. 23, 2007.
International Search Report for Application No. PCT/JP2007/060560, issued on Sep. 11, 2007.
International Search Report for Application No. PCT/JP2007/063525, issued on Sep. 4, 2007.
International Search Report for Application No. PCT/JP2007/067088, issued on Nov. 20, 2007.
International Search Report for Application No. PCT/JP2008/051024, issued on Apr. 1, 2008.
International Search Report for Application No. PCT/JP2008/051697, issued on Mar. 4, 2008.
International Search Report for Application No. PCT/JP2008/070321, issued on Jun. 20, 2009.
International Search Report for Application No. PCT/JP2009/051244, issued on Mar. 24, 2009.
International Search Report for Application No. PCT/JP2010/063804, issued on Sep. 14, 2010.
International Search Report for International Application No. PCT/JP2006/317307, issued on Dec. 12, 2006, 3 pages.
International Search Report for PCT/JP2012/060279, May 29, 2012.
International Search Report in International Application No. PCT/IB2008/003880, dated Aug. 11, 2009, 7 pages.
International Search Report in International Application No. PCT/JP2005/003701, dated May 31, 2005, 6 pages (with English translation).
International Search Report in International Application No. PCT/JP2005/003704, dated May 31, 2005, 6 pages (with English translation).
International Search Report in International Application No. PCT/JP2006/316331, dated Oct. 17, 2006, 5 pages (with English translation).
International Search Report in International Application No. PCT/JP2006/322516 issued on Jan. 23, 2007, 5 pages.
International Search Report in International Application No. PCT/JP2007/066185, dated Sep. 25, 2007, 4 pages.
International Search Report in International Application No. PCT/JP2007/066635, dated Oct. 16, 2007, 5 pages.
International Search Report in International Application No. PCT/JP2008/053066, dated May 20, 2008, 8 pages.
International Search Report in International Application No. PCT/JP2013/084052, dated Mar. 4, 2014, 2 pages.
International Search Report in International Patent Application No. PCT/JP2015/073946, dated Dec. 1, 2015, 3 pages.
International Search Report in International Patent Application No. PCT/JP2016/002562, dated Aug. 9, 2016, 2 pages (English Translation).
International Search Report in International Patent Application No. PCT/JP2016/055268, dated May 17, 2016, 2 pages (English Translation).
International Search Report in International Patent Application No. PCT/JP2016/068381, mailed on Sep. 6, 2016, 2 pages (English Translation).
International Search Report in International Patent Application No. PCT/JP2018/004007, dated Apr. 3, 2018, 4 pages (English Translation).
Interview Summary in U.S. Appl. No. 12/558,982, dated Oct. 20, 2011, 3 pages.
Invitation to declare maintenance of the application for EP Application No. 01976786.2, dated Jul. 12, 2004.
Invitation to declare maintenance of the application for EP Application No. 05783232.1, dated Sep. 25, 2007.
Invitation to declare maintenance of the application for EP Application No. 06023078.6, dated May 2, 2007.
Israel 200090 Office Actions issued on Jun. 22, 2010, 3 pages (with English translation).
Israel 200090 Response to Office Action filed on Oct. 12, 2010, 3 pages.
Israel Appl. No. 195282 IDS List filed on Jul. 1, 2010, 3 pages.
Israel Office Action directed at Appl. No. 195282 issued on Jan. 26, 2010, 4 pages with English translation.
Israel Office Action directed at Appl. No. 205512 issued on Nov. 13, 2011, 4 pages with English translation.

(56) References Cited

OTHER PUBLICATIONS

Israel Response (IDS List) to Office Action directed at Appl. No. 195282 filed on May 3, 2010, 6 pages with English translation.
Israeli Notice of Allowance in Application No. 205512, dated Feb. 15, 2015, 5 pages, with English translation.
Israeli Office Action dated Mar. 27. 2012 for Israeli Application No. 189589 with English translation.
Israeli Office Action for Application No. 155447, issued on Oct. 16, 2007 (with English translation).
Israeli Office Action for Application No. 189677, issued on Feb. 18, 2009 (with English translation).
Israeli Office Action for Application No. 195282, issued on Feb. 5, 2012 (with English translation).
Israeli Office Action for Application No. 199907, issued on Apr. 22, 2012 (with English translation).
Israeli Office Action in Application No. 217197, dated Oct. 25, 2015, 4 pages.
Israeli Office Action in Application No. 223695, dated Aug. 25, 2015, 6 pages, with English translation.
Israeli Office Action in Application No. 223695, dated Feb. 16, 2015, 5 pages, with English translation.
Israeli Office Action in Application No. 227558, dated Aug. 2, 2015, 5 pages, with English translation.
Israeli Office Action in Application No. 238463, dated Oct. 28, 2015, 5 pages, with English translation.
Israeli Office Action issued on May 16, 2010 for corresponding Israeli Application No. 189589, with English translation.
Israeli Response to Office Action in Application No. 217197, dated Dec. 24, 2015, 6 pages.
Israeli Submission Documents in Application No. 223695, dated May 4, 2015, 4 pages, with English translation.
Issue Notification in U.S. Appl. No. 11/508,322, dated Dec. 1, 2010, 1 page.
Issue Notification in U.S. Appl. No. 12/031,568, dated Jan. 30, 2013, 4 pages (with English translation).
Issue Notification in U.S. Appl. No. 12/315,291, dated Jul. 27, 2011, 5 pages.
Issue Notification in U.S. Appl. No. 12/558,982, dated Sep. 26, 2012, 1 page.
Issued Notification in US App. U.S. Appl. No. 11/892,785, dated Aug. 18, 2010, 1 page.
Itoh et al., "Preferential alternative splicing in cancer generates a K-sam messenger RNA with higher transforming activity," Cancer Res., 54:3237-3241 (1994).
Jain, "Normalizing tumor vasculature with anti-angiogenic therapy: A new paradigm for combination therapy," Nature Medicine 7(9):987-989, Sep. 2001.
Jakeman et al., "Developmental Expression of Binding Sites and Messenger Ribonucleic Acid for Vascular Endothelial Growth Factor Suggests a Role for This Protein in Vasculogenesis and Angiogenesis," Endocrinology, 133(2):848-859 (1993).
Jang et al., "Mutations in Fibroblast Growth Factor Receptor 2 and Fibroblast Growth Factor Receptor 3 Genes Associated with Human Gastric and Colorectal Cancers", Cancer Research, 61:3541-3543 (2001).
Japanese Allowance for Application No. P2005-515330, issued on Apr. 21, 2009.
Japanese Allowance for Application No. P2005-516605, issued on Dec. 7, 2010.
Japanese Classification of Gastric Carcinoma "Igan-Toriatsukai Kiyaku" (Jun. 1999, 13th ed.) and an English translation, 10 pages.
Japanese Decision to Grant A Patent dated Jan. 30, 2013 for Japanese Application No. 2007-533350, with English translation.
Japanese Notice of Allowance in Application No. P2011-206481, dated Aug. 4, 2015, 7 pages, with English translation.
Japanese Notice of Reasons for Rejection dated May 15. 2012 for Japanese Application No. 2007- 533350 with English translation.
Japanese Office Action dated Apr. 11, 2005 for Application No. 2002-536056 (with English translation).
Japanese Office Action dated Jun. 19, 2018 for Application No. P2016-214593, 7 pages (with English translation).
Japanese Office Action for Application No. 2007-522356, issued on Feb. 8, 2011.
Japanese Office Action for Application No. P2005-516605, issued on Nov. 4, 2009.
Japanese Office Action for Application No. P2008-516724, issued on Oct. 9, 2012 (with English translation).
Japanese Office Action in Application No. P2011-206481, dated Jun. 2, 2015, 7 pages, with English translation.
Japanese Office Action in Application No. P2012-521531, dated Mar. 3, 2015, 6 pages, with English translation.
Japanese Office Action in Application No. P2012-521531, dated Sep. 29, 2015, 4 pages, with English translation.
Japanese Office Action in Application No. P2013-510994, dated Jul. 28, 2015, 5 pages, with English translation.
Japanese Office Action in Application No. P2013-510994, dated Jun. 9, 2015, 6 pages, with English translation.
Jhiang, "The RET proto-oncogene inn human cancers," Oncogene, 19:5590-5597 (2000).
Jiang et al., "Inactivating mutations of RNF43 confer Wnt dependency in pancreatic ductal adenocarcinoma," PNAS, Jul. 30, 2013, 110(31):12649-12654.
Jiang, "ZD6474: an Agent That Selectively Targets Both VEGFR Tyrosine Kinase and EGFR Tyrosine Kinase", Jap. J. Lung Cancer, Jun. 2006, 46(3):283-288 (with English translation).
Jimenez et al., "Pheochromocytoma and medullary thyroid carcinoma: a new genotype-phenotype correlation of the RET protooncogene 891 germline mutation," J. Clin. Endocrinol. Metab., 89:4142-4145 (2004).
Joao et al., "Somatic trinucleotide change encompassing codons 882 and 883 of the RET proto-oncogene in a patient with sporadic medullary thyroid carcinoma", European Journal of Endocrinology, 142,573-575, (2000).
Johnson et al., "Influence of ionic strength on matrix integrity and drug release from hydroxypropyl cellulose compacts," International journal of pharmaceutics, 1993, vol. 90, No. 2, pp. 151-159.
Johnson et al., "Randomized phase II trial comparing bevacizumab plus carboplatin and paclitaxel with carboplatin and paclitaxel alone in previously untreated locally advanced or metastatic non-small-cell lung cancer," J Clin Oncol 22(11):2184-2191, Jun. 1, 2004.
Johnson et al., "Brivanib Versus Sorafenib as First-Line Therapy in Patients With Unresectable, Advanced Hepatocellular Carcinoma: Results From the Randomized Phase III Brisk-Fl Study," Journal of Clinical Oncology, 2013, 31(28):3517-3524.
Johnson et al., "Paclitaxel plus carboplatin in advanced non-small-cell lung cancer: a phase II trial," J. Clin. Oncol., 14(7):2054-2060 (1996).
Joly et al., "In vitro and in vivo characterization of exel-7647, a novel spectrum selective receptor tyrosine kinase inhibitor that modulates angiogenesis and tumor cell proliferation," EORTC-NCI-AACR Symp Mol Targets Cancer Ther., (Abstract 134), 2004, 1 page.
Jung et al., "Effects of combination anti-vascular endothelial growth factor receptor and anti-epidermal growth factor receptor therapies on the growth of gastric cancer in a nude mouse model," Eur. J. Cancer, 38:1133-1140 (2002).
Juurikivi et al., "Inhibition of c-kit tyrosine kinase by imatinib mesylate induces apoptosis in mast cells in rheumatoid synovia: a potential approach to the treatment of arthritis," Ann Rheum. Dis., 64:1126-1131 (2005).
Kanai et al., "Development Status and Future Prospects of Novel Molecular Target Drugs for Hepatocellular Carcinoma", Journal of the Japanese Society of Gastroenterology, 106:1727-1735 (2009).
Kanai et al., "Current status and future perspective of molecular targeted therapy for hepatocellular carcinoma," Journal of the Japanese Society of Gastroenterology, 106:1727-1735 (2009) (English translation).
Kanakura et al., "Expression, Function and Activation of the Proto-Oncogene c-kit Product in Human Leukemia Cells," Leukemia and Lymphorma, 10:35-41 (1993).

(56) References Cited

OTHER PUBLICATIONS

Kashuk et al., "Phenotype-genotype correlation in Hirschsprung disease is illuminated by comparative analysis of the RET protein sequence," PNAS, 102(25):8949-8954 (2005).
Kato et al., "Effects of lenvatinib on tumor-associated macrophages enhance antitumor activity of PD-1 signal Inhibitors," Molecular Targets and Cancer Therapeutics, Abstract A92, Nov. 6, 2015, 1 page.
Kawano et al., "Presentation Abstract, Abstract No. 1619, Combination of VEGFR inhibitor lenvatinib (E7080) and Met/EphB4inhibitor golvatinib (E7050) overcomes VEGFR inhibitor—resistant tumor vascular", Annual Meeting 2013, Walter E. Washington Convention Center, Washington, D.C., Apr. 6-10, 2013, 1 page.
Kay et al., "Eosinophils and Eosinophil-Associated Cytokines in Allergic Inflammation," Int. Arch. Allergy Immunol., 113:196-199 (1997).
Kelly et al., "Randomized phase III trial of paclitaxel plus carboplatin versus vinorelbine plus cisplatin in the treatment of patients with advanced non—small-cell lung cancer: a Southwest Oncology Group trial," J. Clin. Oncol., 19(13):3210-3218 (2001).
Kharkyevitch, "Farmakologiya," Third addition, and revised supplemented, Moscow, "Meditsina," 1987, partial translation, 5 pages.
Kibbe, Handbook of Pharmaceutical Excipients. Third Edition, 2000, pp. 6-1 through 6-6.
Kim et al., "RET Oligonucleotide Microarray for the Detection of RET Mutations in Multiple Endocrine Neoplasia Type 2 Syndromes", Clinical Cancer Research, 8,457-463, (2002).
Kim et al., "A phase II study of irinotecan plus cisplatin for patients with advanced stage IIIB or IV NSCLC previously treated with nonplatinum-based chemotherapy," Cancer, 107(4):799-805 (2006).
Kim et al., "An orally administered multitarget tyrosine kinase inhibitor, SU11248, is a novel potent inhibitor of thyroid oncogenic RET/papillary thyroid cancer kinases," J. Clin. Endocrinol. Metlab., 91(10):4070-4076 (2006).
Kim, "Technology evaluation: Matuzumab, Merck KGaA", Curr Opin Mol Ther. 2004; 6(1):96-103.
Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.
Kitamura et al., "Regulation of Development, Survival and Neoplastic Growth of Mast Cells through the c-kit Receptor," Int. Arch Allergy Immunol., 107:54-56 (1995).
Kitteringham et al., "A Simple Method for the Synthesis of Unsymmetrical Ureas," Synthetic Communications, 30(11):1937-1943 (2000).
Kleespies et al., "Tyrosine kinase inhibitors and gemcitabine: New treatment options in pancreatic cancer,?" Drug Resistance Updates, 9:1-18 (2006).
Klein et al, "Vascular endothelial growth factor gene and protein: strong expression in thyroiditis and thyroid carcinoma", Journal of endocrinology, Nov. 30, 1999, 41-49.
Klugbauer and Rabes, "The transcription coactivator HT1 F1 and a related protein are fused to the RET receptor tyrosine kinase in childhood papillary thyroid carcinomas", Oncogene, 18: 4388-4393 (1999).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).
Klugbauer et al., "Detection of a Novel Type of RET Rearrangement (PTC5) in Thyroid Carcinomas after Chernobyl and Analysis of the Involved RET-fused Gene RFG5", Cancer Research, 58:198-203 (1998).
Ko, "Stomach Cancer," Cancer Supportive Care.com [published online Feb. 2003], [retrieved on Dec. 28, 2011]. Retrieved from the Internet: http://web.archive.org/web/20030224212825/http://www.cancersupportivecare.com/stomach.html.
Kolibaba et al., "Protein Tyrosine Kinases and Cancer," Biochimica et Biophysica Acta, 1333:F217-F248 (1997).
Kondo, "Molecular Target Drugs for Renal Cell Carcinoma—Angiogenesis Inhibitor; The role of VEGFR-TKI's in the treatment of renal cell carcinoma," The Japanese Journal of Nephrology, 2012, 54(5):574-580 (with English Translation).
Konno, "Physical and Chemical Changes of Medicinals in Mixtures with Adsorbents in the Solid State IV," Study on Reduced-Pressure Mixing for Practical Use of Amorphous Mixtures of Flufenamic Acid, Chem. Pharm Bull, 1990, p. 2003.
Korean ("KR") Notice of Allowance issued on Aug. 25, 2010 corresponding KR Application No. 10-2008-7005195, with English translation.
Korean ("KR") Office Action issued on Dec. 24, 2009 for corresponding KR Application No. 10-2008-7005195, with English translation.
Korean ("KR") Office Action issued on May 29, 2010 for corresponding KR Application No. 10-2008-7005195, with English translation.
Korean Notice of Allowance in Application No. 10-2010-7011023, dated Mar. 24, 2015, 3 pages, with English translation.
Korean Office Action for Application No. 10-2003-7005506, issued on Jan. 5, 2006 (with English translation).
Korean Office Action for Application No. 10-2005-7020292, issued on Dec. 8, 2005 (with English translation).
Korean Office Action for Application No. 10-2006-7013993, issued on Jul. 31, 2007 (with English translation).
Korean Office Action for Application No. 10-2007-7001347, issued on Apr. 27, 2012 (with English translation).
Korean Office Action for Application No. 10-2007-7001347, issued on Sep. 28, 2011 (with English translation).
Korean Office Action for Application No. 10-2009-7005657, issued on Sep. 30, 2013, 27 pages (with English translation).
Korean Office Action in KR Application No. 10-2008-7029472, dated Sep. 30, 2013, 27 pages (with English translation).
Korean Request for Examination in Application No. 10-2012-7033886, dated Aug. 26, 2015, 12 pages, with English translation.
Kotva et al., "Substances with Antineoplastic Activity, LIII. N-(δ-(4-Pyrrolo[2,3-d]Pyrimidinylthio) Valeryl]} Amino Acids and Analogous Derivatives of Di-and Triglycine," Collection Czechoslov. Chem. Commun., 38:1438-1444 (1973).
Koyama et al, "Anti-tumor effect of E7080, a novel angiogenesis inhibitor," *Folia Pharmacol. Japan.*, 2008, 132: 100-104 (with English translation).
Kremer, "Lenvatinib Advisory Board", The presentation document, American Society of Clinical Oncology, Annual meeting 2014, May 31, 2014, 138 pages.
Kruckeberg et al., "Pyrosequencing Technology as a Method for the Diagnosis of Multiple Endocrine Neoplasia Type 2", Clinical Chemistry, 50, 522-529, 2004.
Krystal et al., "Indolinone Tyrosine Kinase Inhibitors Block Kit Activation and Growth of Small Cell Lung Cancer Cells", Cancer Research., 61, 3660-3668, 2001.
Kubo et al., "a novel series of 4-phenoxyquinolines: potent and highly selective inhibitors of pdgf receptor autophosphorylation", Bioorganic and Medicinal Chemistry Letters., 7, 2935-2940, 1997.
Kubo et al., "Novel Potent Orally Active Selective VEGFR-2 Tyrosine Kinase Inhibitors: . . . ureas", Journal of Medicinal Chemistry., 48, 1359-1366, 2005.
Kudo et al., "Lenvatinib versus sorafenib in first-line treatment of patients with unresectable hepatocellular carcinoma: a randomised phase 3 non-inferiority trial," Lancet, 2018, 391:1163-1173.
Kumar et al., "Survival and failure outcomes in primary thyroid lymphomas: A single centre experience of combined modality approach," Journal of Thyroid Research, vol. 2013, Jun. 18, 2013, 6 pages.
Kumar et al., "Discovery and biological evaluation of GW654652: A pan inhibitor of VEGF receptors," Proceedings of the American Association for Cancer Research, 44, 9, (Abstract 39), 2003, 2 pages.
Laird et al., "SU6668 Is a Potent Antiangiogenic and Antitumor Agent That Induces Regression of Established Tumors1", Cancer Research., 60, 4152-4160, 2000.

(56) References Cited

OTHER PUBLICATIONS

Lam et al., "Extemporaneous Compounding of Oral Liquid Dosage Formulations and Alternative Drug Delivery Methods for Anticancer Drugs," Reviews of Therapeutics, Pharmacotherapy, 2011, 31(2):164-192.
Lam et al., "High prevalence of RET proto-oncogene activation (RET/PTe) in papillary thyroid carcinomas", Eur J Endocrinology, 147: 741-745 (2002).
Lam et al., "β-catenin signaling: a novel mediator of fibrosis and potential therapeutic target," Curr Opin Rheumatol., 2011, 23(6):562-567 (Author Manuscript).
Lasota et al., "Mutations in Exons 9 and 13 of KIT Gene Are Rare Events in Gastrointestinal Stromal Tumors," American Journal of Pathology, 157(4):1091-1095 (2000).
LeDoussal et al. "bispecific-antibody-mediated targeting of radiolabeled bivalent haptens: theoretical, experimental and clinical results", Int. J. Cancer Suppl. 7: 58-62, 1992.
Lee et al., "In vivo TargetModulation and Biological Activity of CHIR-258, aMultitargeted Growth Factor Receptor Kinase Inhibitor, in Colon CancerModels", Clinical Cancer Research., 11, 3633-3641, 2005.
Lehtio et al., "Tankyrases as drug targets," FEBS J., 2013, 280:3576-3593.
Lennartsson et al., The Stem Cell Factor Receptor/c-Kit as a Drug Target in Cancer, Current Cancer Drug Targets, 6:p. 65-75 (2006).
Lenvatinib in Wikipedia: The Free Encyclopedia, http://en/wikipeida/org/wiki/Lenvatinib (accessed Dec. 18, 2013), 2 pages.
Leonetti et al., "Clinical use of lenvatinib in combination with everolimus for the treatment of advanced renal cell carcinoma," Therapeutics and Clinical Risk Management, 2017, 13:799-806.
Leow et al. "MEDI3617, a human anti-angiopoietin 2 monoclonal antibody, inhibits angiogenesis and tumor growth in human tumor xenograft models", International Journal of Oncology, Demetrios A. Spandidos Ed. & Pub, GR, vol. 40, No. 5, May 1, 2012, p. 1321-p. 1330, XP002721374.
Lesueur et al., "Polymorphisms in RET and its coreceptors and ligands as genetic modifiers of multiple endocrine neoplasia type 2A," Cancer Res., 66:1177-1180 (2006).
Leukemias, Hematology, and Oncology, http://www.merkmanuals.com/professional/print/sec11/ch142a.html Mar. 16, 2011, 5 pages.
Lev et al., "A Specific Combination of Substrates is Involved in Signal Transduction by the Kit-Encoded Receptor," The EMBO Journal, 10(3):647-654 (1991).
Li et al., "Abrogation of c-kit/Steel factor-dependent tumorigenesis by kinase defective mutants of the c-kit receptor: c-kit kinase defective mutants as candidate tools for cancer gene therapy," Cancer Res., 56:4343-4346 (1996) (XP002522473).
Li et al., "ABT-869 a novel multi-targeted receptor tyrosine kinase inhibitor: characterization of FLT3 phosphorylation in a model of acute myelogenous leukemia," AACR American Association Cancer Research, 96th Annual Meeting, 46:1407, (Abstract 5981), Anaheim, Orange County CA USA Apr. 16-20, 2005, 2 pages.
Lin et al., "The vascular endothelial growth factor receptor tyrosine kinase inhibitor PTK787/ZK222584 inhibits growth and migration of multiple myeloma cells in the bone marrow microenvironment," Cancer Res., 62(17):5019-5026 (2002).
Liu et al., "Dose Adjustment Integrated Exposure Response Analysis (DAIER) for Dose Optimization Lenvatinib Renal Call Carcinoma [URL:https://www.aacr.org/AdvocacyPolicy/GovernmentAffairs/Documents/6.13.16%20FDA-AACR%20Dose%20Finding%20for%20Online.pdf]", Presentation slides at FDA-AACR: Oncology Dose—finding Workshop, Jun. 13, 2016, 19 pages.
Liu et al., "Structure of Human Methionine Aminopeptidase-2 Complexed with Fumagillin", Science., 282, 1324-1327, 1998.
Liu, "Water-Insoluble Drug Formation, " Interpharm Press, 2000, p. 525, 557-561.
Llovet et al., "Plasma biomarkers as predictors of outcome in patients with advanced hepatocellular carcinoma," Clinical Cancer Res, 2012, 18(8):2290-2300.

Llovet et al., "Sorafenib in advanced hepatocellular carcinoma," New England Journal of Medicine, 2008, 359(4):378-390.
Logie et al., "Activating mutations of the tyrosine kinase receptor FGFR3 are associated with benign skin tumors in mice and humans," Human Mol. Genet., 14:1153-1160 (2005).
Longley et al., "Altered Metabolism of Mast-Cell Growth Factor (c-kit Ligand) in Cutaneous Mastocytosis," The New England Journal of Medicine, 328(18):1302-1307 (1993).
Longley et al., "Classes of c-KIT activating mutations: proposed mechanisms of action and implications for disease classification and therapy," Leuk. Res., 25:571-576 (2001).
Longley et al., "Somatic c-KIT Activating Mutation in Urticaria Pigmentosa and Aggressive Mastocytosis: Establishment of Clonality in a Human Mast Cell Neoplasm," Nature Genetics, 12:312-314 (1996).
Lu et al., "Tailoring in Vitro Selection for a Picomolar Affinity Human Antibody Directed Against Vascular Endothelial Growth Factor Receptor 2 for Enhanced Neutralizing Activity," J Biol Chem., 2003, 278(44):43496-43507.
Lukacs et al., "Stem Cell Factor (c-kit Ligand) Influences Eosinophil Recruitment and Histamine Levels in Allergic Airway Inflammation," J. Immunol., 156:3945-3951 (1996).
Macedonian Notice of Allowance in Application No. P/2015/231, dated Oct. 13, 2015, 2 pages, with English translation.
Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).
Maintenance and Response to EP Search Report in EP Application No. 06796594.7, dated Dec. 21, 2011, 43 pages.
Maintenance of the application for EP Application No. 01976786.2, dated Sep. 6, 2004.
Maintenance of the application for EP Application No. 05783232.1, dated Nov. 9, 2007.
Maintenance of the application for EP Application No. 06023078.6, dated Jun. 19, 2007.
Marchetti et al., "Clinical Features and Outcome of Patients with Non-Small-Cell Lung Cancer Harboring BRAF Mutations," J Clin Oncol, 29(26):3574-3579, Aug. 8, 2011.
Marzioni et al., "Clinical Implications of novel aspects of biliary pathophysiology," XP026942498, 20th National Congress of Digestive Diseases/Digestive and Liver Disease, 2010, 42(4):238-244.
Masferrer et al., "COX-2 Inhibitors a New Class of Antiangiogenic Agents", Annals of N.Y. Acad. Science., 889:84-6, 1999.
Matsui et al, "a novel multi-targeted tyrosine kinase inhibitor, exhibits anti-angiogenic activity via inhibition of KIT signaling in a small cell lung cancer xenograft model", European Journal of Cancer, Sep. 29, 2004, p. 47.
Matsui et al., "Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase," Clin Cancer Res., 2008, 14:5459-5465.
Matsui et al., "E7080 (ER-203492-00), a Novel VEGF Receptor )Tyrosine Kinase Inhibitor-I. Characterization as an Angiogenesis Inhibitor," Abstract # 51, AACR, Washington, USA (Jul. 11-14, 2003).
Matsui et al., "E7080 (ER-203492-00), a Novel VEGF Receptor Tyrosine Kinase Inhibitor-I. Characterization as an Angiogenesis Inhibitor," Abstract # 51, AACR, Toronto, Canada (Apr. 5-9, 2003).
Matsui et al., "E7080, a novel inhibitor that targets multiple kinases, has potent antitumor activities against stem cell factor producing human small cell lung cancer H146, based on angionenesis inhibition," Int. J. Cancer, 122:664-671 (2008).
Matsui et al., "E7080, a novel multi-receptor Tyrosine Kinase Inhibitor, inhibited in vitro / in vivo VEGF- and SCF-driven angiogenesis SCLC cell line," Abstract #146, EORTC-NCI-AACR, Geneva, Switzerland (Sep. 28-Oct. 1, 2004).
Matsui et al., "Mechanism of antitumor activity of E7080, a selective VEGFR and FGFR tyrosine kinase inhibitor (TKI), in combination with selective mutant BRAF inhibition," J Clin Oncol., May 20, 2011, 29(15), Suppl., Asco Meeting Abstracts, Part 1, Abstract No. 8567, 2 pages.

(56) References Cited

OTHER PUBLICATIONS

Matsui et al., "Quantitative analysis of the profile of tumor vessels may be useful as predictive biomarkers for E7080," Abstract #4631, 98th AACR annual meeting, Los Angeles, CA, (Apr. 14-18, 2007).
Matsui et al., "VEGFRs inhibitor E7080 inhibits lymph node metastasis of human breast carcinoma, by preventing murine lymphatic endothelial cells from lymphangiogenesis," Abstract #PD12-8, 18$^{th}$ EORTC-NCI-AACR Symposium on "Molecular Targets and Cancer Therapeutics," Prague, Czech Republic (Nov. 7-10, 2006).
Matsui, "Extracellular matrix of linitis plastica as a possible new therapeutic target," Surgical Treatment, Sep. 2003, 89(3):301-306 (with English translation).
Matsuki et al., "Antitumor activity of a combination of lenvatinib mesilate, ifosfamide, and etoposide against human pediatric osteosarcoma cell lines," XP009511737, Cancer Research; 107$^{th}$ Annual Meeting of the American-Association-Of-Cancerresearch (AACR), American Association for Cancer Research, 2016, 76(Suppl. 14):3266.
Matsushima et al., "Preparation of pyridine and pyrimidine derivatives as inhibitors of hepatocyte growth factor receptor (HGFR)," Hcaplus, 2005, 977021.
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer," Mol. Cancer Ther., 3(9):1041-1048 (2004).
McCulloch et al., "Astragalus-based Chinese herbs and platinum-based chemotherapy for advanced non-small-cell lung cancer: meta-analysis of randomized trials," J. Clin. Oncol., 24(3):419-430 (2006).
Medicines.org.uk [online], "Lenvima 4 mg hard capsules," XP002789352, Electronic Medicines Compendium, Jun. 2015, [Retrieved on Jan. 3, 2019], retrieved from: URL<https://www.medicines.org.uk/emc/product/6840/smpc/print>, 23 pages.
Meltzer, "The Pharmacological Basis for the Treatment of Perennial Allergic Rhinitis and Non-Allergic Rhinitis with Topical Corticosteroids," Allergy, 52:33-40 (1997).
Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," Clin. Cancer Res., 9:327-337 (2003).
Metcalfe et al., "Lineage Commitment in the Progeny of Murine Hematopoietic Preprogenitor Cells: Influence of Thrombopoietin and Interleukin 5," Proc. Nat'l Acad. Sci. USA, 95:6408-6412 (1998).
Metcalfe et al., "Mast cells," Physiol. Rev., 77(4):1033-1079 (1997).
Metcalfe, "Classification and Diagnosis of Mastocytosis: Current Status," J. Invest. Dermatol., 96:2S-4S (1991).
Mexican Notice of Allowance in Application No. MX/a/2012/014776, dated Mar. 18, 2015, 3 pages, with English translation.
Mexican Notice of Allowance in Application No. MX/a/2013/009931, dated Jun. 29, 2015, 3 pages, with English translation.
Mexican Office Action in Application No. MX/a/2010/008187, dated Aug. 21, 2013, 6 pages (with English translation).
Mexican Office Action in Application No. MX/a/2013/009931, dated Apr. 9, 2015, 3 pages, with English translation.
Mexican Office Action in Application No. MX/a/2014/010594, dated Oct. 13, 2015, 8 pages, with English translation.
Mexican Submission Documents in Application No. MX/a/2014/010594, dated Oct. 8, 2015, 10 pages, with English translation.
Mexican Submission Documents in Application No. MX/a/2014/010594, dated Sep. 24, 2015, 2 pages, with English translation.
Micke et al., "Characterization of c-kit expression in small cell lung cancer: prognostic and therapeutic implications," Clin. Cancer Res., 9:188-194 (2003).
Miknis et al., "AARY-334543, A potent, orally active small molecule inhibitor of EGFR and ErbB-2," Am. Assoc. Cancer Res. Abstract 3399, 2005, 2 pages.
Miller et al., "Genomic amplification of MET with boundaries within fragile site FRA7G and upregulation of MET pathways in esophageal adenocarcinoma," Oncogene, 2005, 25(3):409-418.
Miller et al., "Paclitaxel plus bevacizumab versus paclitaxel alone for metastatic breast cancer," N. Engl. J. Med., 357(26):2666-2676 (2007).
Millstein and Cuello, "Hybrid hybridomas and their use in immunohistochemistry", Nature 305: 537-9, 1983.
Mitchell et al, "The influence of additives on the cloud point, disintegration and dissolution of hydroxypropylmethylcellulose gels and matrix tablets," International iournal of pharmaceutics, 1990, vol. 66, No. 1/3, pp. 233-242.
Miyauchi et al., "Two Germline Missense Mutations of Co dons 804 and 806 of the RET proto-oncogene in the Same 15 Allele in a Patient with Multiple Endocrine Neoplasia Type 2B without Codon 915 Mutation", Japanese Journal of D Cancer Research, 90, 1-5, (1999).
Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," AIMECS03, Kyoto, Japan (Oct. 14-17, 2003).
Mizushima, "Drug Repositioning," Bio Industry, 2014, 31(11):4-10 (with English Translation).
Mohammadi et al., "Crystal structure of an angiogenesis inhibitor bound to the FGF receptor tyrosine kinase domain", EMBO J., 17, 5896-5904, 1998.
Molina et al., "A phase 1b clinical trial of the multitargeted tyrosine kinase inhibitor lenvatinib (E7080) in combination with everolimus for treatment of metastatic renal cell carcinoma (RCC)", Cancer Chemotherapy and Pharmacology, 2014.01, vol. 73, No. 1, p. 181-p. 189.
Mologni et al., "Inhibition of RET tyrosine kinase by SU5416," J. Mol. Endocrinol., 37(2):199-212 (2006).
Montalbetti and Falque, "Tetrahedron report No. 740: Amide bond formation and peptide coupling," Tetrahedron, 2005, 61:10827-10852.
Morgan et al., "Dynamic contrast-enhanced magnetic resonance imaging as a biomarker for the pharmacological response of PTK787/ZK 222584, an inhibitor of the vascular endothelial growth factor receptor tyrosine kinases, in patients with advanced colorectal cancer and liver metastases: results from two phase I studies," J. Clin. Oncol., 21(21):3955-3964 (2003).
Morikawa et al., "Angiogenesis and Pericytes," The Cell, 37(4):164-168 (2005) (English translation).
Morris et al., "An Integrated Approach to the Selection of optimal Salt Form for a New Drug Candidate," International Journal of Pharmaceutics, 105:209-217 (1994) (XP023724810).
Mototsugu, "mTOR inhibitors," Nippohn Rinsho, Jun. 2010, 68(6):1067-1072 (with English abstract).
Motzer et al., "Independent assessment of lenvatinib plus everolimus in patients with metastatic renal cell carcinoma," Lancet Oncol., 2016, 17(1), p. E4-p. E5.
Motzer et al., "Investigation of novel circulating proteins, germ line single nucleotide polymorphisms, and molecular tumor markers as potential efficacy biomarkers of first-line sunitinib therapy for advanceed renal cell carcinoma," Cancer Chemotherapy and Pharmacology, Aug. 7, 2014, vol. 74 No. 4, p. 739-p. 750.
Motzer et al., "Lenvatinib, everolimus, and the combination in patients with metastatic renal cell carcinoma: a randomised, phase 2, open-label, multicentre trial," Lancet Oncol, (2015), 11(16):1473-1482.
Motzer et al., "Lenvatinib, everolimus, and the combination in patients with metastatic renal cell carcinoma: a randomised, phase 2, open-label, multicentre trial," Lancet Oncol., 2015, 16(15):1473-1482.
Motzer et al., "Randomized phase 2 three-arm trial of lenvatinib (LEN), everolimus (EVE), and LEN+EVE in patients (pts) with metastatic renal cell carcinoma (mRCC)," Oral presentation at ASCO Annual Meetingm, Chicago, May 29-Jun. 2, 2015.
Motzer et al., "Randomized phase II, three-arm trial of lenvatinib (LEN), everolimus (EVE), and LEN+EVE in patients pts) with

(56) References Cited

OTHER PUBLICATIONS metastatic renal cell carcinoma (mRCC)," Journal of Clinical Oncology, May 20, 2015, vol. 33, Issue 15S, p. 248.
Myers et al., "The Preparation and SAR of 4-(Anilino), 4-(Phenoxy), and 4-(Thiophenoxy)-Quinazolines: Inhibitors of p56lck and EGF-R Tyrosine Kinase Activity," Bioorgan. & Med. Chem. Letters, 7:417-420 (1997).
Naclerio et al., "Rhinitis and Inhalant Allergens," JAMA, 278(22):1842-1848 (1997).
Nagata et al., "Elevated Expression of the Proto-Oncogene c-kit in Patients with Mastocytosis," Leukemia, 12:175-181 (1998).
Nakagawa et al., "E7050: A dual c-Met and VEGFR-2 tyrosine kinase inhibitor promotes tumor regression and prolongs survival in mouse xengraft models," Cancer Sci., Jan. 2010, 101(1):210-215.
Nakagawa, Takayuki et al., "Lenvatinib in combination with golvatinib overcomes hepatocyte growth factor pathway-induced resistance to vascular endothelial growth factor receptor inhibitor", Cancer Science, 2014.06, vol. 105, No. 6, p. 723-p. 730.
Nakamura et al., "In Vitro selectivity and potency of KRN951, a novel inhibitor of VEGF receptor tyrosine kinases", Cancer Research, cited Jul. 13, 2016, 2 pages.
Nakamura et al., "KRN633: A Selective inhibitor of vascular endothelial growth factor receptor-2 tyrosine kinase that suppresses tumor angiogenesis and growth", Molecular Cancer Therapeutics., 2004, 3:1639-49.
Nakamura et al., "E7080 (ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract #52, AACR, Toronto, Canada (Apr. 5-9, 2003).
Nakamura et al., "In vitro selectivity and potency of KRN951, a novel inhibitor of VEGF receptor tyrosine kinases," Proceedings of the American Association for Cancer Research, 45, 594, (Abstract 2571), 2004, 1 page.
Nakanishi, "Molecular diversity of glutamate receptors and implications for brain function," Science, 1992, pp. 597-603.
Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).
Nakazawa et al., "Multitargeting strategy using lenvatinib and golvatinib: Maximizing anti-angiogenesis activity in a preclinical cancer model", Cancer Science, Feb. 2015, vol. 106, No. 2, p. 201-p. 207.
Nakazawa et al., "Maximizing the efficacy of anti-angiogenesis cancer therapy: A multi-targeting strategy by tyrosine kinase inhibitors," AACR Annual Meeting 2014, Presentation Abstract and Poster, Apr. 5-9, 2014, 2 pages.
Nakazawa, "Combination strategy of lenvatinib: Maximizing its anti-angiogenesis efficacy," Tsukuba Res Laboratory, Eisai Co., Ltd., Ibaraki, Japan, Jun. 27, 2014, 10 pages.
Naran eta l., "Inhibition of HGF/MET as therapy for malignancy," Expert Opin. Ther. Targets, 2009, p. 569-581.
Naruse et al., "Antitumor activity of the selective epidermal growth factor receptor-tyrosine kinase inhibitor (EGFR-TKI) Iressa (ZD1839) in an EGFR-expressing multidrug-resistant cell line in vitro and in vivo," Int. J. Cancer, 98:310-315 (2002).
Naski et al., "Graded activation of fibroblast growth factor receptor 3 by mutations causing achondroplasia and thanatophoric dysplasia," Nat. Genet., 13:233-237 (1996).
Natali et al., "Breast Cancer is Associated with Loss of the c-kit Oncogene Product," Int. J. Cancer, 52:713-717 (1992).
NCBI GenBank Accession No. NM_000222, Coffey et al. (Feb. 11, 2008).
Neidle, "Cancer Drug Design and Discovery" Elsevier/Academic Press, 2008, pp. 427-431.
Nicolaus, "Symbiotic Approach to Drug Design," Decision Making Drug Res., Jan. 1983, 173-186.
Nishikawa et al., "Cys611Ser mutation in RET proto-oncogene in a kindred with medullary thryroid carcinoma and Hirschsprung's disease", European Journal of Human Genetics, 11,364-368 (2003).
Nishio et al, "Phase 1 study of lenvatinib combined with carboplatin and paclitaxel in patients with non-small-cell lung cancer", British Journal of Cancer, 2013, 109:538-544.
Nocka et al., "Expression of c-kit gene products in known cellular targets of W mutations in normal and W mutant mice—evidence for an impaired c-kit kinase in mutant mice," Cold Spring Harbor Laboratory Press, 3:816-826 (1989) (XP002522472).
Noriyuki et al., "Anti-tumor effect of E7080, a novel angiogenesis inhibitor," Database BIOSIS [Online] Biosciences Information Service, Philadelphia, PA, US: Database accession No. PREV200800475929, Aug. 2008, XP002677323.
Norwegian Office Action in Application No. 20063383, dated Apr. 15, 2015, 2 pages, with English translation.
Notice of Acceptance dated Aug. 10, 2004 for ZA Patent App. No. 2003/3567.
Notice of Acceptance dated Aug. 3, 2006 for AU Application No. 2001295986.
Notice of Acceptance dated May 13, 2008 for AU Application No. 2006236039.
Notice of Acceptance for AU Application No. 2009210098, dated Jun. 4, 2013, 3 pages.
Notice of Acceptance in AU Application No. 2005217325, dated Nov. 20, 2007, 3 pages.
Notice of Acceptance in AU Application No. 2005217328, dated Sep. 24, 2007, 3 pages.
Notice of Acceptance in AU Application No. 2006282456, dated Aug. 17, 2009, 1 page.
Notice of Acceptance in AU Application No. 2007288793, dated Apr. 10, 2012, 3 pages.
Notice of Acceptance in AU Application No. 2007289787, dated Mar. 16, 2012, 3 pages.
Notice of Acceptance in DB Application No. 60/2005, dated Nov. 16, 2006, 1 page.
Notice of Acceptance in NZ Application No. 547517, dated Mar. 6, 2009, 1 page.
Notice of Acceptance in NZ Application No. 566793, dated Feb. 12, 2010, 2 pages.
Notice of Acceptance of Complete Specification dated Mar. 4, 2005 for NZ Application No. 525324.
Notice of Allowability dated Nov. 28, 2007 for PH Application No. 1-2003-500266.
Notice of Allowability in PH Application No. 1-2007-502319, dated Feb. 29, 2012, 1 page.
Notice of Allowance dated Apr. 19, 2005 for RU Application No. 2003114740 (with English translation).
Notice of Allowance dated Apr. 19, 2011 for JP Application No. 2007-522356.
Notice of Allowance dated Apr. 24, 2012 for U.S. Appl. No. 12/524,754.
Notice of Allowance dated Apr. 29, 2010 for AU Application No. 2005283422.
Notice of Allowance dated Aug. 2, 2005 for JP Application No. 2002-536056 (with English translation).
Notice of Allowance dated Aug. 7, 2012 for Japanese Application No. P2007-529565 (with English translation).
Notice of Allowance dated Dec. 15, 2006 for CN Application No. 01819710.8.
Notice of Allowance dated Dec. 26, 2007 for IL Application No. 155447 (with English translation).
Notice of Allowance dated Feb. 15, 2013 for NZ Application No. 598291, 1 page.
Notice of Allowance dated Feb. 27, 2009 for U.S. Appl. No. 11/293,785.
Notice of Allowance dated Feb. 5, 2010 for CN Application No. 200580026468.7 (with English translation).
Notice of Allowance dated Jul. 17, 2012 for JP Application No. P2011-527665 (with English translation).
Notice of Allowance dated Jul. 21, 2009 for JP Application No. 2005-124034 (with English translation).
Notice of Allowance dated Jun. 13, 2006 for U.S. Appl. No. 10/420,466.
Notice of Allowance dated Jun. 20, 2012 for EP Application No. 06782407.8.

(56) References Cited

OTHER PUBLICATIONS

Notice of Allowance dated Jun. 25, 2012 for EP Application No. 07806561.2.
Notice of Allowance dated Jun. 3, 2008 for U.S. Appl. No. 11/293,785.
Notice of Allowance dated Mar. 14, 2010 for IL Application No. 189677 (with English translation).
Notice of Allowance dated Mar. 16, 2007 for U.S. Appl. No. 10/420,466.
Notice of Allowance dated Mar. 21, 2013 for EP Application No. 07793075.8, 2 pages.
Notice of Allowance dated Mar. 22, 2012 for U.S. Appl. No. 12/986,638.
Notice of Allowance dated Mar. 8, 2013 for CA Application No. 2627598, 1 page.
Notice of Allowance dated May 16, 2013 for EP Application No. 06796594.7, 2 pages.
Notice of Allowance dated May 18, 2009 for U.S. Appl. No. 11/293,785.
Notice of Allowance dated May 6, 2013 for EP Application No. 04818213.3, 22 pages.
Notice of Allowance dated Nov. 14, 2011 for IL Application No. 181697 (with English translation).
Notice of Allowance dated Nov. 19, 2008 for U.S. Appl. No. 11/293,785.
Notice of Allowance dated Nov. 2, 2012 for EP Application No. 06782407.8.
Notice of Allowance dated Nov. 2, 2012 for EP Application No. 07806561.2.
Notice of Allowance dated Oct. 14, 2010 for CA Application No. 2426461.
Notice of Allowance dated Oct. 17, 2011 for CA Application No. 2579810.
Notice of Allowance dated Oct. 18, 2006 for MX Application No. PA/a/2003/003362 (with English translation).
Notice of Allowance dated Oct. 20, 2008 for TW Application No. 90125928 (with English translation).
Notice of Allowance dated Oct. 31, 2008 for NO Application No. 20031731 (with English translation).
Notice of Allowance dated Oct. 9, 2010 for CN Application No. 200710007097.9 (with English translation).
Notice of Allowance dated Sep. 12, 2005 for U.S. Appl. No. 10/420,466.
Notice of Allowance dated Sep. 20, 2011 for JP Application No. 2006-535174.
Notice of Allowance dated Sep. 25, 2012 for U.S. Appl. No. 12/986,638.
Notice of Allowance dated Sep. 4, 2012 in JP Application No. P2009-123432 (with English translation).
Notice of Allowance for CN Application No. 200980103218.7, dated May 27, 2013, 4 pages (with English translation).
Notice of Allowance for JP Application No. 2008-516724, dated Jan. 22, 2013, 4 pages, with English translation.
Notice of Allowance for JP Application No. P2008-532141, dated Sep. 10, 2013, 5 pages (with English translation).
Notice of Allowance for U.S. Appl. No. 12/524,754, dated Jan. 18, 2013, 9 pages.
Notice of Allowance for U.S. Appl. No. 12/741,682, dated Feb. 19, 2013, 65 pages.
Notice of Allowance for U.S. Appl. No. 12/741,682, dated Jun. 19, 2013, 10 pages.
Notice of Allowance for U.S. Appl. No. 12/524,754 dated Oct. 9, 2012.
Notice of Allowance for U.S. Appl. No. 11/997,719, dated Sep. 13, 2013, 20 pages.
Notice of Allowance for U.S. Appl. No. 13/083,338, dated Jun. 4, 2013, 57 pages.
Notice of Allowance for U.S. Appl. No. 13/083,338, dated Sep. 26, 2013, 28 pages.
Notice of Allowance for U.S. Appl. No. 13/205,328, dated Jun. 10, 2013, 58 pages.
Notice of Allowance for U.S. Appl. No. 13/205,328, dated Oct. 3, 2013, 11 pages.
Notice of Allowance in AU Application No. 2010285740, dated Nov. 19, 2014, 1 page.
Notice of Allowance in Australian Patent Application No. 2012246490, dated Jul. 25, 2016, 4 pages.
Notice of Allowance in Australian Patent Application No. 2014266223, dated Jun. 10, 2020, 3 pages.
Notice of Allowance in Australian Patent Application No. 2014371148, dated Jul. 26, 2018, 4 pages (English Translation).
Notice of Allowance in Australian Patent Application No. 2015309862, dated Mar. 31, 2020, 3 pages.
Notice of Allowance in Australian Patent Application No. 2016224583, dated May 20, 2021, 3 pages.
Notice of Allowance in Australian Patent Application No. 2016309356, dated Jun. 10, 2021, 4 pages.
Notice of Allowance in Brazilian Patent Application No. BR112012003592-4, dated Jun. 9, 2020, 2 pages (with English Translation).
Notice of Allowance in CA Application No. 2605854, dated Apr. 7, 2010, 1 page.
Notice of Allowance in CA Application No. 2652442, dated Apr. 16, 2014, 1 page.
Notice of Allowance in CA Application No. 2661333, dated Dec. 19, 2013, 1 page.
Notice of Allowance in CA Application No. 2661702, dated Sep. 26, 2013, 1 page.
Notice of Allowance in CA Application No. 2771403, dated Oct. 22, 2014, 1 page.
Notice of Allowance in Canadian Patent Application No. 2704000, dated Jul. 7, 2016, 1 page.
Notice of Allowance in Canadian Patent Application No. 2802644, dated Aug. 5, 2016, 1 page.
Notice of Allowance in Canadian Patent Application No. 2828946, dated Feb. 22, 2016, 1 page.
Notice of Allowance in Canadian Patent Application No. 2912219, dated May 18, 2021, 1 page (with English Translation).
Notice of Allowance in Canadian Patent Application No. 2957005, dated Aug. 3, 2021, 1 page (with English Translation).
Notice of Allowance in Chilean Patent Application No. 2012-00412, dated Jan. 29, 2019, 21 pages (with English Translation).
Notice of Allowance in Chinese Patent Application No. 201480026871.9, dated Jun. 28, 2017, 8 pages (English Translation).
Notice of Allowance in Chinese Patent Application No. 201480067017.7, dated Sep. 13, 2018, 4 pages (English Translation).
Notice of Allowance in Chinese Patent Application No. 201580042365.3, dated Jun. 2, 2021, 4 pages (with English Translation).
Notice of Allowance in Chinese Patent Application No. 201680027234.2, dated Jan. 28, 2021, 4 pages (with English Translation).
Notice of Allowance in Chinese Patent Application No. 201680046598.5, dated Dec. 31, 2020, 4 pages (with English Translation).
Notice of Allowance in CN Application No. 200680021939.X, dated Jan. 11, 2012, 4 pages (with English translation).
Notice of Allowance in CN Application No. 200780019200.X, dated Jan. 15, 2013, 4 pages (with English translation).
Notice of Allowance in CN Application No. 200780019520.5, dated Apr. 27, 2011, 4 pages (with English translation).
Notice of Allowance in CN Application No. 201180030568.2, dated Sep. 9, 2014, 4 pages (with English translation).
Notice of Allowance in EP Application No. 04807580.8, dated Dec. 15, 2014, 103 pages.
Notice of Allowance in EP Application No. 04818213.3, dated Sep. 19, 2013, 2 pages.
Notice of Allowance in EP Application No. 07743994.1, dated May 8, 2015, 51 pages.
Notice of Allowance in EP Application No. 08704376.6, dated Aug. 19, 2014, 62 pages.
Notice of Allowance in EP Application No. 08846814.5, dated Jan. 8, 2015, 36 pages.
Notice of Allowance in European Patent Application No. 12786619.2, dated Sep. 30, 2016, 155 pages.
Notice of Allowance in European Patent Application No. 12793322.4, dated Feb. 14, 2018, 82 pages.

(56) References Cited

OTHER PUBLICATIONS

Notice of Allowance in European Patent Application No. 12793322.4, dated Jun. 4, 2018, 7 pages.
Notice of Allowance in European Patent Application No. 14727633.1, dated Feb. 9, 2018, 72 pages.
Notice of Allowance in European Patent Application No. 14873998.0, dated Oct. 17, 2018, 141 pages.
Notice of Allowance in European Patent Application No. 16802790.2, dated Aug. 14, 2020, 35 pages.
Notice of Allowance in European Patent Application No. 16837150.8, dated Feb. 11, 2021, 27 pages.
Notice of Allowance in European Patent Application No. 18197141.7, dated Jun. 25, 2020, 83 pages.
Notice of Allowance in Gulf Cooperation Council Patent Application No. GC2014-28624, dated May 9, 2018, 2 pages (English Translation).
Notice of Allowance in ID App. Ser No. W-00 2008 00601, dated Oct. 17, 2012, 12 pages (with English translation).
Notice of Allowance in IL Application No. 195282, dated Aug. 11, 2014, 5 pages (with English translation).
Notice of Allowance in IL Application No. 197141, dated Oct. 27, 2013, 2 pages (with English translation).
Notice of Allowance in IL Application No. 200090, dated Nov. 18, 2013, 5 pages (with English translation).
Notice of Allowance in IL Application No. 207089, dated Nov. 10, 2014, 5 pages (with English translation).
Notice of Allowance in Indonesian Patent Application No. W-00201201031, dated Dec. 28, 2016, 5 pages (English Translation).
Notice of Allowance in Israeli Patent Application No. 217197, dated Jun. 26, 2016, 3 pages, (English translation).
Notice of Allowance in Israeli Patent Application No. 223695, dated Apr. 4, 2017, 3 pages (English Translation).
Notice of Allowance in Israeli Patent Application No. 227558, dated May 8, 2017, 6 pages (English Translation).
Notice of Allowance in Israeli Patent Application No. 242519, dated Dec. 13, 2017, 6 pages (English Translation).
Notice of Allowance in Israeli Patent Application No. 245961, dated Jul. 26, 2018, 15 pages (English Translation).
Notice of Allowance in Israeli Patent Application No. 255564, dated Dec. 1, 2020, 8 pages (with English Translation).
Notice of Allowance in Israeli Patent Application No. 257433, dated Jul. 21, 2020, 8 pages (with English Translation).
Notice of Allowance in Japanese Patent Application No. P2012-521531, dated Mar. 1, 2016, 6 pages (English Translation).
Notice of Allowance in Japanese Patent Application No. P2013-515178, dated May 17, 2016, 6 pages (English Translation).
Notice of Allowance in Japanese Patent Application No. P2014-513691, dated Oct. 4, 2016, 6 pages (English Translation).
Notice of Allowance in Japanese Patent Application No. P2015-554886, dated Jan. 24, 2017, 6 pages, (English Translation).
Notice of Allowance in Japanese Patent Application No. P2015-555882, dated Sep. 4, 2018, 6 pages (English Translation).
Notice of Allowance in Japanese Patent Application No. P2016-214593, dated Sep. 4, 2018, 6 pages (English Translation).
Notice of Allowance in Japanese Patent Application No. P2016-545564, dated Feb. 4, 2020, 5 pages (with English Translation).
Notice of Allowance in Japanese Patent Application No. P2016-572771, dated Apr. 4, 2017, 6 pages (English Translation).
Notice of Allowance in Japanese Patent Application No. P2017-502388, dated Nov. 4, 2020, 5 pages (with English Translation).
Notice of Allowance in Japanese Patent Application No. P2017-535558, dated Jul. 2, 2019, 6 pages (with English Translation).
Notice of Allowance in Japanese Patent Application No. P2017-546133, dated Oct. 6, 2020, 8 pages (with English Translation).
Notice of Allowance in Japanese Patent Application No. P2017-560343, dated Aug. 4, 2020, 5 pages (with English Translation).
Notice of Allowance in Japanese Patent Application No. P2018-567437, dated Aug. 27, 2019, 5 pages (with English Translation).
Notice of Allowance in Jordan Patent Application No. 55/2011, dated Apr. 16, 2017, 2 pages (English Translation).
Notice of Allowance in JP Application No. P2009-540099, dated Oct. 21, 2014, 6 pages (with English translation).
Notice of Allowance in JP Application No. P2009-551518, dated Oct. 22, 2013, 5 pages (with English translation).
Notice of Allowance in Korean Patent Application No. 10-2012-7033886, dated Oct. 18, 2016, 3 pages (English Translation).
Notice of Allowance in Korean Patent Application No. 10-2013-7020616, dated Jun. 29, 2017, 3 pages (English Translation).
Notice of Allowance in Korean Patent Application No. 10-2015-7032202, dated Oct. 21, 2020, 3 pages (with English Translation).
Notice of Allowance in KR Application No. 10-2006-7013907, dated Jan. 14, 2008, 3 pages (with English translation).
Notice of Allowance in KR Application No. 10-2006-7013940, dated Jan. 14, 2008, 3 pages (with English translation).
Notice of Allowance in KR Application No. 10-2008-7013685, dated Nov. 29, 2013, 3 pages (with English translation).
Notice of Allowance in KR Application No. 10-2008-7027527, dated Mar. 3, 2014, 4 pages (with English translation).
Notice of Allowance in KR Application No. 10-2008-7029472, dated Sep. 16, 2014, 3 pages (with English translation).
Notice of Allowance in KR Application No. 10-2009-7005657, dated Sep. 19, 2014, 3 pages (with English translation).
Notice of Allowance in KR Application No. 10-2009-7017694, dated Jul. 28, 2014, 3 pages (with English translation).
Notice of Allowance in KR Application No. 10-2010-7018835, dated Jan. 20, 2015, 3 pages (with English translation).
Notice of Allowance in KR Application No. 10-2012-7003846, dated Feb. 3, 2015, 3 pages.
Notice of Allowance in Mexican Patent Application No. MX/a/2014/010594, dated Nov. 17, 2016, 3 pages (English Translation).
Notice of Allowance in Mexican Patent Application No. MX/a/2015/015605, dated Jul. 24, 2019, 4 pages (with English Translation).
Notice of Allowance in Mexican Patent Application No. MX/a/2017/010474, dated Jun. 14, 2021, 5 pages (with English Translation).
Notice of Allowance in Mexican Patent Application No. MX/a/2017/014540, dated Apr. 28, 2021, 4 pages (with English Translation).
Notice of Allowance in Mexican Patent Application No. MX/a/2018/001439, dated Nov. 13, 2020, 6 pages.
Notice of Allowance in Mexican Patent Application No. MX/a/2018/001658, dated Mar. 2, 2021, 5 pages (with English Translation).
Notice of Allowance in Mexican Patent Application No. MX/a/2019/006504, dated Jan. 13, 2021, 6 pages (with English Translation).
Notice of Allowance in MX Application No. MX/a/2008/002156, dated Oct. 15, 2010, 3 pages (with English translation).
Notice of Allowance in MX Application No. MX/a/2010/008187, dated Jul. 17, 2014, 3 pages (with English translation).
Notice of Allowance in MY Application No. PI20071922, dated Jan. 15, 2010, 3 pages.
Notice of Allowance in New Zealand Patent Application No. 714049, dated May 21, 2020, 1 page.
Notice of Allowance in Pakistani Patent Application No. 907/2014, dated May 2, 2018, 1 page (English Translation).
Notice of Allowance in Pakistani Patent Application No. 94/2011, dated Oct. 21, 2019, 2 pages.
Notice of Allowance in PK Application No. 1024/2006, dated Nov. 2, 2010, 1 page.
Notice of Allowance in PK Application No. 375/2008, dated Nov. 2, 2010, 1 page.
Notice of Allowance in RU Application No. 2006134254, dated Jan. 14, 2008, 30 pages (with English translation).
Notice of Allowance in RU Application No. 2012103471, dated Dec. 19, 2014, 12 pages (with English translation).
Notice of Allowance in RU Application No. 2012158142, dated May 5, 2015, 15 pages (with English translation).
Notice of Allowance in Russian Patent Application No. 2015148193, dated Apr. 23, 2018, 15 pages (English Translation).

(56) References Cited

OTHER PUBLICATIONS

Notice of Allowance in Russian Patent Application No. 2016122867, dated Aug. 31, 2018, 30 pages (English Translation).
Notice of Allowance in Russian Patent Application No. 2017139090, dated Jan. 25, 2021, 8 pages.
Notice of Allowance in Russian Patent Application No. 2018103737, dated May 22, 2020, 12 pages (with English Translation).
Notice of Allowance in Russian Patent Application No. 2018104697, dated Feb. 3, 2020, 13 pages (with English Translation).
Notice of Allowance in Singapore Patent Application No. 11201509278X, dated Nov. 22, 2017, 5 pages (English Translation).
Notice of Allowance in Singaporean Patent Application No. 11201604496Y, dated Nov. 23, 2016, 5 pages.
Notice of Allowance in Singaporean Patent Application No. 11201700855X, dated Nov. 26, 2020, 4 pages.
Notice of Allowance in South African Patent Application No. 2016/03956, dated Nov. 2, 2017, 2 pages.
Notice of Allowance in Taiwanese Patent Application No. 104127982, dated Jan. 26, 2021, 5 pages (with English Translation).
Notice of Allowance in TW Application No. 095130665, dated Sep. 7, 2012, 4 pages (with English translation).
Notice of Allowance in U.S. Appl. No. 10/797,903, dated Mar. 10, 2011, 22 pages.
Notice of Allowance in U.S. Appl. No. 13/870,507, dated Jul. 26, 2016, 13 pages.
Notice of Allowance in U.S. Appl. No. 14/577,660, dated Jul. 9, 2015, 10 pages.
Notice of Allowance in U.S. Appl. No. 15/554,577, dated Jun. 8, 2021, 32 pages.
Notice of Allowance in U.S. Appl. No. 15/750,712, dated Apr. 1, 2019, 125 pages.
Notice of Allowance in U.S. Appl. No. 15/750,712, dated Apr. 30, 2021, 14 pages.
Notice of Allowance in U.S. Appl. No. 15/750,712, dated Jan. 13, 2021, 19 pages.
Notice of Allowance in U.S. Appl. No. 15/750,712, dated Jul. 22, 2020, 12 pages.
Notice of Allowance in U.S. Appl. No. 16/038,710, dated Jan. 6, 2021, 16 pages.
Notice of Allowance in U.S. Appl. No. 16/038,710, dated Jul. 1, 2021, 19 pages.
Notice of Allowance in U.S. Appl. No. 16/038,710, dated Jun. 30, 2020, 32 pages.
Notice of Allowance in U.S. Appl. No. 16/465,277, dated Apr. 26, 2021, 12 pages.
Notice of Allowance in U.S. Appl. No. 16/465,277, dated Jun. 25, 2020, 16 pages.
Notice of Allowance in U.S. Appl. No. 16/465,277, dated Oct. 21, 2020, 11 pages.
Notice of Allowance in U.S. Appl. No. 16/559,293, dated Jun. 16, 2020, 5 pages.
Notice of Allowance in UA Application No. a201203132, dated Mar. 21, 2014, 6 pages.
Notice of Allowance in Ukraine Patent Application No. a201606261, dated Feb. 22, 2018, 18 pages (English Translation).
Notice of Allowance in U.S. Appl. No. 11/892,785, dated Apr. 5, 2010, 23 pages.
Notice of Allowance in U.S. Appl. No. 11/065,631, dated Jan. 2, 2009, 6 pages.
Notice of Allowance in U.S. Appl. No. 11/065,631, dated Sep. 9, 2008, 10 pages.
Notice of Allowance in U.S. Appl. No. 11/508,322, dated Sep. 15, 2009, 6 pages.
Notice of Allowance in U.S. Appl. No. 11/662,425, dated Oct. 21, 2014, 49 pages.
Notice of Allowance in U.S. Appl. No. 11/997,719, dated Dec. 2, 2014, 21 pages.
Notice of Allowance in U.S. Appl. No. 11/997,719, dated Jun. 5, 2014, 14 pages.
Notice of Allowance in U.S. Appl. No. 12/031,568, dated Jun. 1, 2012, 23 pages.
Notice of Allowance in U.S. Appl. No. 12/031,568, dated Oct. 19, 2011, 11 pages.
Notice of Allowance in U.S. Appl. No. 12/031,568, dated Sep. 18, 2012, 6 pages.
Notice of Allowance in U.S. Appl. No. 12/315,291, dated Apr. 26, 2011, 6 pages.
Notice of Allowance in U.S. Appl. No. 12/439,339, dated Apr. 1, 2014, 17 pages.
Notice of Allowance in U.S. Appl. No. 12/439,339, dated Nov. 7, 2013, 64 pages.
Notice of Allowance in U.S. Appl. No. 12/524,754, dated Feb. 13, 2014, 18 pages.
Notice of Allowance in U.S. Appl. No. 12/524,754, dated Nov. 22, 2013, 12 pages.
Notice of Allowance in U.S. Appl. No. 12/524,754, dated Sep. 18, 2014, 35 pages.
Notice of Allowance in U.S. Appl. No. 12/558,982, dated Apr. 3, 2012, 11 pages.
Notice of Allowance in U.S. Appl. No. 12/558,982, dated May 25, 2012, 20 pages.
Notice of Allowance in U.S. Appl. No. 12/741,682, dated Feb. 7, 2014, 11 pages.
Notice of Allowance in U.S. Appl. No. 12/741,682, dated May 15, 2014, 13 pages.
Notice of Allowance in U.S. Appl. No. 12/741,682, dated Oct. 21, 2013, 12 pages.
Notice of Allowance in U.S. Appl. No. 12/741,682, dated Oct. 6, 2014, 11 pages.
Notice of Allowance in U.S. Appl. No. 13/083,338, dated Dec. 5, 2014, 19 pages.
Notice of Allowance in U.S. Appl. No. 13/083,338, dated Feb. 6, 2014, 15 pages.
Notice of Allowance in U.S. Appl. No. 13/083,338, dated Jul. 10, 2014, 22 pages.
Notice of Allowance in U.S. Appl. No. 13/205,328, dated Jan. 30, 2014, 11 pages.
Notice of Allowance in U.S. Appl. No. 13/205,328, dated May 8, 2014, 10 pages.
Notice of Allowance in U.S. Appl. No. 13/624,278, dated Jun. 25, 2014, 57 pages.
Notice of Allowance in U.S. Appl. No. 13/624,278, dated Oct. 31, 2014, 14 pages.
Notice of Allowance in U.S. Appl. No. 13/624,278, dated Sep. 16, 2013, 20 pages.
Notice of Allowance in U.S. Appl. No. 13/805,826, dated Dec. 17, 2014, 15 pages.
Notice of Allowance in U.S. Appl. No. 13/983,891, dated Mar. 20, 2014, 9 pages.
Notice of Allowance in U.S. Appl. No. 14/002,018, dated Oct. 24, 2014, 70 pages.
Notice of Allowance in U.S. Appl. No. 14/122,339, dated Dec. 21, 2017, 8 pages.
Notice of Allowance in U.S. Appl. No. 14/890,207, dated Aug. 28, 2019, 9 pages.
Notice of Allowance in U.S. Appl. No. 14/890,207, dated Nov. 21, 2018, 12 pages.
Notice of Allowance in U.S. Appl. No. 15/503,108, dated Apr. 11, 2018, 7 pages.
Notice of Allowance in U.S. Appl. No. 15/503,108, dated Dec. 12, 2018, 8 pages.
Notice of Allowance in U.S. Appl. No. 15/503,108, dated Feb. 7, 2019, 4 pages.
Notice of Allowance in U.S. Appl. No. 15/503,108, dated Jan. 4, 2019, 6 pages.
Notice of Allowance in U.S. Appl. No. 15/750,712, dated Jul. 8, 2019, 11 pages.
Notice of Allowance in U.S. Appl. No. 15/750,712, dated Oct. 22, 2019, 10 pages.
Notice of Allowance in U.S. Appl. No. 16/229,805, dated Jun. 24, 2019, 10 pages.

(56) References Cited

OTHER PUBLICATIONS

Notice of Allowance in Vietnamese Patent Application No. 1-2016-02104, dated Aug. 27, 2018, 2 pages (English Translation).
Notice of Allowance in VN Application No. 1-2008-00723, dated Aug. 19, 2010, 2 pages (with English translation).
Notice of Allowance in VN Application No. 1-2011-03484, dated Apr. 28, 2014, 2 pages.
Notice of Allowance in ZA Application No. 2007/09572, dated Mar. 12, 2009, 1 pages.
Notice of Allowance issued in CN Application No. 200880115011.7, dated Aug. 5, 2013, 4 pages (with English translation).
Notice of Allowance issued in CN Application No. 201080030508.6, dated Jul. 4, 2013, 4 pages (with English translation).
Notice of Allowance issued in EP Application No. 10015141.4, dated Jul. 1, 2013, 41 pages.
Notice of Allowance issued in IL Application No. 175363, dated Aug. 13, 2013, 2 pages (with English translation).
Notice of Allowance issued in JP Application No. P2008-556208, dated Jul. 9, 2013, 4 pages (with English translation).
Notice of Allowance issued in U.S. Appl. No. 12/524,754, dated Jul. 19, 2013, 11 pages.
Notice of Appeal in European Patent Application No. 08846814.5, dated Jul. 5, 2017, 3 pages.
Notice of Appeal in U.S. Appl. No. 11/662,425, dated Sep. 5, 2014, 11 pages.
Notice of Appeal in U.S. Appl. No. 12/039,381, dated Aug. 29, 2014, 9 pages.
Notice of decision for patent dated Apr. 17, 2006 for KR Application No. 10-2005-7020292, (with English translation).
Notice of decision for patent dated Jun. 12, 2006 for KR Application No. 10-2003-7005506 (with English translation).
Notice of Final Rejection in KR Application No. 10-2009-7013723, dated Jul. 29, 2011, 4 pages (with English translation).
Notice of Grant in KR Application No. 10-2007-7026886, dated Dec. 31, 2009, 5 pages (with English translation).
Notice of Non-Substantive Deficiencies Prior to Allowance in IL Application No. 197141, dated Feb. 3, 2013, 16 pages (with English translation).
Notice of Opposition in Indian Patent Application No. 201747040368, dated Dec. 31, 2020, 1 page.
Notice of Reasons for Rejection issued in JP Application No. P2009-540099, dated Jul. 2, 2013, 7 pages (with English translation).
Notice of Reasons for Rejection mailed on Nov. 13, 2012 issued for corresponding Japanese Application No. 2007-533350 with full English language translation.
Notice Prior to Allowance in IL Application No. 188670, dated Sep. 12, 2011, 2 pages (with English translation).
Notice Prior to Allowance in IL Application No. 197002, dated Oct. 28, 2012, 2 pages (with English translation).
Notice Prior to Examination dated Jun. 29, 2008 for IL Application No. 189677 (with English translation).
Notice Prior to Examination dated Mar. 9, 2009 for IL Application No. 181697 (with English translation).
Notice Prior to Examination in IL Application No. 188670, dated Aug. 13, 2009, 3 pages (with English translation).
Notice Prior to Examination in IL Application No. 197002, dated Mar. 23, 2010, 3 pages (with English translation).
Notice Prior to Examination in IL Application No. 197141, dated Mar. 23, 2010, 3 pages (with English translation).
Notice Prior to Examination in IL Application No. 200466, dated Jun. 22, 2010, 3 pages (with English translation).
Notification dated Apr. 25, 2008 for PH Application No. 1-2003-500266.
Notification of Defects for IL Application No. 195282, dated Apr. 10, 2013, 4 pages (with English Translation).
Notification of Non-Compliant Amendment filed on Jan. 13, 2005 for U.S. Appl. No. 10/420,466.
Noy et al., "Tumor-Associated Macrophages: From Mechanisms to Therapy," Immunity 41:49-61, Jul. 17, 2014.
Nugiel et al., "Synthesis and evaluation of indenopyrazoles as cyclin-dependent kinase inhibitors. 2. Probing the indeno ring substituent pattern," J. Med. Chem., 45(24):5224-5232 (2002).
Nyati et al., "Radiosensitization by Pan ErbB Inhibitor CI-1033 in Vitro and in Vivo", Clinical Cancer Research., 10:691-700, 2004.
Observation for CN Application No. 200880115011.7, dated Apr. 11, 2013, 10 pages (with English translation).
Observations for CN Application No. 201080030508.6, dated May 27, 2013, 7 pages (with English translation).
Ocqueteau et al., Expression of the CD117 antigen (C-Kit) on normal and myelomatous plasma cells, Br. J. Haematol., 95:489-493 (1996).
Office Action dated May 13, 2005 for Chinese Application No. 01819710.8 (with English translation).
Office Action dated May 16, 2008 for Norwegian Application No. 20031731 (with English translation).
Office Action dated May 3, 2013 for Canadian Application No. 2661702, 2 pages.
Office Action dated Nov. 13, 2012 for Japanese Application No. P2008-532141 (with English translation).
Office Action dated Nov. 20, 2009 for Chinese Application No. 200580026468.7 (with English translation).
Office Action dated Nov. 26, 2007 for Mexican Application No. PA/a/2005/013764 (with English translation).
Office Action dated Oct. 11, 2007 for Taiwanese Application No. 90125928 (with English translation).
Office Action dated Oct. 15, 2012 for Israeli Application No. 200090 (with English translation).
Office Action dated Oct. 15, 2012 for New Zealand Application No. 598291.
Office Action dated Oct. 4, 2005 for Mexican Application No. PA/a/2003/003362 (with English translation).
Office Action dated Oct. 4, 2007 for Norwegian Application No. 20031731 (with English translation).
Office Action dated Sep. 11, 2009 for Chinese Application No. 200710007097.9 (with English translation).
Office Action dated Sep. 19, 2012 for Canadian Application No. 2627598.
Office Action dated Sep. 28, 2011 for Korean Application No. 10-2007-7001347 (with English translation).
Office Action dated Sep. 28, 2012 for Chinese Application No. 200780017371.9 (with English translation).
Office Action dated Sep. 29, 2012 for Chinese Application No. 200980103218.7 (with English translation).
Office Action dated Sep. 5, 2008 for Norwegian Application No. 20031731 (with English translation).
Office Action dated Sep. 5, 2012 for Chinese Application No. 200880003336.6 (with English translation).
Office Action dated Sep. 5, 2012 for Chinese Application No. 200880115011.7 (with English translation).
Office Action dated Sep. 7, 2007 for Filipino Application No. 1-2003-500266.
Office Action for Canadian Application No. 2,620,594, dated Aug. 15, 2011.
Office Action for Canadian Application No. 2579810 dated Jul. 15, 2011.
Office Action for Canadian Application No. 2652442, dated Apr. 16, 2013 2 pages.
Office Action for Chinese Application No. 01819710.8 dated Feb. 10, 2006 (with English translation).
Office Action for Chinese Application No. 01819710.8, dated Aug. 11, 2006 (with English translation).
Office Action for Chinese Application No. 200580026468.7 dated Jun. 26, 2009 (with English translation).
Office Action for Chinese Application No. 200680020317.5, dated Aug. 3, 2012 (with English translation).
Office Action for Chinese Application No. 200710007096.4 dated Jul. 24, 2009 (with English translation).
Office Action for Chinese Application No. 200710007097.9 dated Apr. 27, 2010 (with English translation).
Office Action for Chinese Application No. 200710007097.9 dated Dec. 25, 2009 (with English translation).

(56) References Cited

OTHER PUBLICATIONS

Office Action for Chinese Application No. 200710007097.9 dated Mar. 6, 2009 (with English translation).
Office Action for Chinese Application No. 200780017371.9, dated Mar. 14, 2013 9 pages (with English translation).
Office Action for Chinese Application No. 201080030508.6, dated Apr. 9, 2013, 6 pages (with English translation).
Office Action for EP Application No. 08846814.5, dated Apr. 16, 2013, 5 pages.
Office Action for Filipino Application No. 1-2003-500266 dated Aug. 8, 2003.
Office Action for Filipino Application No. 1-2003-500266 dated Jul. 21, 2006.
Office Action for Filipino Application No. 1-2003-500266 dated Jun. 27, 2007.
Office Action for Filipino Application No. 1-2003-500266 dated Mar. 21, 2007.
Office Action for IL 199907 issued on Jun. 17, 2010, 3 pages with English translation.
Office Action for Israeli Application No. 181697 dated Dec. 20, 2010 (with English translation).
Office Action for Israeli Application No. 217197, dated Apr. 11, 2013 4 pages (with English translation).
Office Action for Japanese Application No. 2005-124034 dated Apr. 28, 2009 (with English translation).
Office Action for Japanese Application No. 2005-124034 dated Jan. 27, 2009 (with English translation).
Office Action for Japanese Application No. 2009-123432 dated Jun. 5, 2012 (with English translation).
Office Action for Korean Application No. 10-2003-7005506 dated Jul. 27, 2005 (with English translation).
Office Action for Mexican Application No. PA/a/2003/003362 dated Jun. 7, 2006 (with English translation).
Office Action for Norwegian Application No. 20031731 dated Mar. 7, 2007 (with English translation).
Office Action for U.S. Appl. No. 11/997,719, dated Apr. 8, 2013 55 pages.
Office Action for U.S. Appl. No. 13/624,278, dated Mar. 29, 2013 73 pages.
Office Action in Algerian Patent Application No. 120036, dated Dec. 31, 2017, 2 pages (English Translation).
Office Action in Argentine Patent Application No. P110100513, dated Jul. 23, 2020, 6 pages (with English Translation).
Office Action in Argentine Patent Application No. P110100513, dated Mar. 11, 2019, 10 pages (with English Translation).
Office Action in Argentine Patent Application No. P110100513, dated Nov. 11, 2019, 12 pages (with English Translation).
Office Action in Argentine Patent Application No. P20150102731, dated Jun. 10, 2020, 6 pages (with English Translation).
Office Action in AU Application No. 2006282456, dated Jun. 12, 2009, 1 pages.
Office Action in AU Application No. 2010285740, dated Aug. 22, 2014, 3 pages.
Office Action in Australian Patent Application No. 2012246490, dated Apr. 20, 2016, 3 pages.
Office Action in Australian Patent Application No. 2012246490, dated Feb. 5, 2016, 3 pages.
Office Action in Australian Patent Application No. 2013364953, dated Apr. 19, 2017, 3 pages.
Office Action in Australian Patent Application No. 2013364953, dated Feb. 16, 2017, 3 pages.
Office Action in Australian Patent Application No. 2014266223, dated Jun. 14, 2019, 4 pages.
Office Action in Australian Patent Application No. 2014371148, dated Mar. 28, 2018, 2 pages.
Office Action in Australian Patent Application No. 2015309862, dated Apr. 2, 2019, 3 pages.
Office Action in Australian Patent Application No. 2016224583, dated Jun. 30, 2020, 4 pages.
Office Action in Australian Patent Application No. 2016224583, dated Mar. 30, 2021, 4 pages.
Office Action in Australian Patent Application No. 2016273230, dated Jun. 21, 2021, 4 pages.
Office Action in Australian Patent Application No. 2016273230, dated Mar. 3, 2020, 1 page.
Office Action in Australian Patent Application No. 2016308390, dated Feb. 2, 2021, 5 pages.
Office Action in Australian Patent Application No. 2016308390, dated Jun. 2, 2021, 3 pages.
Office Action in Australian Patent Application No. 2016309356, dated Feb. 3, 2021, 4 pages.
Office Action in BD Application No. 184/2006, dated May 11, 2007, 2 pages.
Office Action in Brazilian Patent Application No. BR112012003592-4, dated Jan. 28, 2020, 11 pages (with English Translation).
Office Action in Brazilian Patent Application No. BR112012032462-4, dated Jan. 19, 2021, 3 pages (with English Translation).
Office Action in Brazilian Patent Application No. BR112012032462-4, dated Jan. 26, 2021, 8 pages (with English Translation).
Office Action in Brazilian Patent Application No. BR112012032462-4, dated May 18, 2021, 11 pages (with English Translation).
Office Action in Brazilian Patent Application No. BR112013021941-6, dated May 26, 2020, 4 pages (with English Translation).
Office Action in Brazilian Patent Application No. PI0418200-6, dated Apr. 24, 2019, 31 pages (with English Translation).
Office Action in Brazilian Patent Application No. PI0418200-6, dated Apr. 27, 2021, 29 pages (with English Translation).
Office Action in Brazilian Patent Application No. PI0418200-6, dated Jul. 28, 2020, 60 pages (with English Translation).
Office Action in Brazilian Patent Application No. PI0906576-08, dated Mar. 17, 2020, 7 pages (with English Translation).
Office Action in Brazilian Patent Application No. PI0906576-08, dated Oct. 27, 2020, 6 pages (with English Translation).
Office Action in Brazilian Patent Application No. PI0906576-08, dated Oct. 28, 2020, 6 page (with English Translation).
Office Action in Brazilian Patent Application No. PI0906576-08, dated Sep. 10, 2019, 8 pages (with English Translation).
Office Action in Canadian Application No. 2543859, dated Aug. 19, 2008, 5 pages.
Office Action in Canadian Application No. 2543861, dated Aug. 19, 2008, 4 pages.
Office Action in Canadian Application No. 2605854, dated Jul. 29, 2009, 2 pages.
Office Action in Canadian Application No. 2652442, dated Oct. 4, 2013, 2 pages.
Office Action in Canadian Application No. 2676796, dated Dec. 30, 2013, 5 pages.
Office Action in Canadian Application No. 2676796, dated Jan. 29, 2015, 5 pages.
Office Action in Canadian Application No. 2704000, dated Nov. 4, 2014, 3 pages.
Office Action in Canadian Application No. 2713930, dated Jan. 30, 2015, 5 pages.
Office Action in Canadian Application No. 2771403, dated Jul. 16, 2014, 3 pages.
Office Action in Canadian Patent Application No. 2704000, dated Mar. 27, 2015, 3 pages.
Office Action in Canadian Patent Application No. 2713930, dated Mar. 7, 2016, 5 pages.
Office Action in Canadian Patent Application No. 2889866, dated Sep. 25, 2019, 5 pages.
Office Action in Canadian Patent Application No. 2912219, dated Aug. 31, 2020, 4 pages.
Office Action in Canadian Patent Application No. 2957005, dated Apr. 9, 2021, 4 pages.
Office Action in Canadian Patent Application No. 2957005, dated Oct. 15, 2020, 4 pages.
Office Action in Chilean Patent Applciation No. 2012-00412, dated Jan. 23, 2017, 4 pages (English Translation).
Office Action in Chilean Patent Application No. 2012-00412, dated Jan. 28, 2015, 17 pages, with English translation.

(56) References Cited

OTHER PUBLICATIONS

Office Action in Chilean Patent Application No. 201601419, dated Feb. 13, 2018, 18 pages (English Translation).
Office Action in Chinese Application No. 200680020317.5, dated Mar. 4, 2014, 13 pages.
Office Action in Chinese Application No. 200680020317.5, dated Nov. 28, 2013, 8 pages (with English translation).
Office Action in Chinese Application No. 200680021939.X, dated Mar. 30, 2011, 7 pages (with English translation).
Office Action in Chinese Application No. 200680021939.X, dated May 27, 2010, 9 pages (with English translation).
Office Action in Chinese Application No. 200680021939.X, dated Sep. 2, 2010, 10 pages (with English translation).
Office Action in Chinese Application No. 200780017371.9, dated Dec. 11, 2014, 9 pages (with English translation).
Office Action in Chinese Application No. 200780017371.9, dated May 15, 2015, 17 pages (with English translation).
Office Action in Chinese Application No. 200780019200.X, dated Apr. 6, 2012, 9 pages (with English translation).
Office Action in Chinese Application No. 200780019520.5, dated Dec. 21, 2010, 7 pages (with English translation).
Office Action in Chinese Application No. 200780019520.5, dated Sep. 27, 2010, 8 pages (with English translation).
Office Action in Chinese Application No. 2008800045113, dated Jul. 5, 2011, 10 pages (with English translation).
Office Action in Chinese Application No. 201180030568.2, dated Mar. 24, 2014, 8 pages (with English translation).
Office Action in Chinese Application No. 201180030568.2, dated Oct. 12, 2013, 11 pages (with English translation.
Office Action in Chinese Application No. 201280010898.X, dated Aug. 11, 2014, 14 pages (with English translation).
Office Action in Chinese Patent Application No. 201380054667.3 dated Aug. 9, 2017, 11 pages (English Translation).
Office Action in Chinese Patent Application No. 201380054667.3, dated Feb. 14, 2017, 9 pages (English Translation.
Office Action in Chinese Patent Application No. 201380054667.3, dated Jul. 18, 2016, 18 pages (English Translation).
Office Action in Chinese Patent Application No. 201480026871.9, dated Feb. 21, 2017, 10 pages (English Translation).
Office Action in Chinese Patent Application No. 201480067017.7, dated Mar. 1, 2017, 11 pages (English Translation).
Office Action in Chinese Patent Application No. 201510031628.2, dated Apr. 5, 2017, 8 pages (English Translation).
Office Action in Chinese Patent Application No. 201510031628.2, dated Dec. 12, 2017, 11 pages (English Translation).
Office Action in Chinese Patent Application No. 201510031628.2, dated Jul. 19, 2018, 11 pages (English Translation).
Office Action in Chinese Patent Application No. 201510031628.2, dated Jun. 2, 2016, 11 pages (English Translation).
Office Action in Chinese Patent Application No. 201510031628.2, dated May 27, 2019, 16 pages (with English Translation).
Office Action in Chinese Patent Application No. 201580042365.3, dated Feb. 21, 2020, 17 pages (with English Translation).
Office Action in Chinese Patent Application No. 201580042365.3, dated Mar. 12, 2021, 67 pages (with English Translation).
Office Action in Chinese Patent Application No. 201580042365.3, dated Mar. 5, 2019, 21 pages (with English Translation).
Office Action in Chinese Patent Application No. 201580042365.3, dated Oct. 30, 2020, 13 pages (with English Translation).
Office Action in Chinese Patent Application No. 201680009824.2, dated Dec. 18, 2019, 31 pages (with English Translation).
Office Action in Chinese Patent Application No. 201680009824.2, dated Jan. 12, 2021, 15 pages (with English Translation).
Office Action in Chinese Patent Application No. 201680009824.2, dated Jun. 3, 2020, 26 pages (with English Translation).
Office Action in Chinese Patent Application No. 201680009824.2, dated Sep. 27, 2020, 14 pages (with English Translation).
Office Action in Chinese Patent Application No. 201680022734.2, dated Oct. 22, 2018, 12 pages (English Translation).
Office Action in Chinese Patent Application No. 201680027234.2, dated Feb. 19, 2020, 7 pages (with English Translation).
Office Action in Chinese Patent Application No. 201680027234.2, dated Jun. 19, 2019, 9 pages (with English Translation).
Office Action in Chinese Patent Application No. 201680027234.2, dated Sep. 27, 2020, 12 pages (with English Translation).
Office Action in Chinese Patent Application No. 201680030060.5, dated Jan. 30, 2019, 15 pages (with English Translation).
Office Action in Chinese Patent Application No. 201680044979.X, dated Mar. 12, 2020, 13 pages (with English Translation).
Office Action in Chinese Patent Application No. 201680044979.X, dated Mar. 25, 2021, 8 pages (with English Translation).
Office Action in Chinese Patent Application No. 201680044979.X, dated Oct. 13, 2020, 9 pages (with English Translation).
Office Action in Chinese Patent Application No. 201680046598.5, dated Aug. 14, 2020, 8 pages (with English Translation).
Office Action in Chinese Patent Application No. 201680046598.5, dated Mar. 23, 2020, 17 pages (with English Translation).
Office Action in Chinese Patent Application No. 201780020786.5, dated Apr. 17, 2020, 19 pages (with English Translation).
Office Action in CL Application No. 2012-00412, dated Sep. 3, 2014, 22 pages (with English translation).
Office Action in CO Application No. 12-022608, dated Dec. 17, 2013, 12 pages (with English translation).
Office Action in Colombian Patent Application No. 16147681, dated Jun. 27, 2018, 16 pages (English Translation).
Office Action in DB Application No. 60/2005, dated Jul. 25, 2006, 2 pages.
Office Action in Egyptian Patent Application No. D1 PCT 283/2012, dated Apr. 29, 2020, 6 pages (with English Translation).
Office Action in Egyptian Patent Application No. PCT 283/2012, dated Apr. 13, 2021, 10 pages (with English Translation).
Office Action in Egyptian Patent Application No. PCT 283/2012, dated Apr. 28, 2019, 9 pages (with English Translation).
Office Action in Egyptian Patent Application No. PCT 283/2012, dated Feb. 19, 2018, 10 pages (English Translation).
Office Action in Egyptian Patent Application No. PCT 283/2012, dated May 4, 2020, 10 pages (with English Translation).
Office Action in Egyptian Patent Application No. PCT 283/2012, dated Oct. 23, 2019, 10 pages (with English Translation).
Office Action in European Application No. 03791389.4, dated Dec. 2, 2014, 5 pages.
Office Action in European Application No. 03791389.4, dated Jun. 10, 2014, 4 pages.
Office Action in European Application No. 04807580.8, dated Mar. 18, 2014, 12 pages.
Office Action in European Application No. 05719973.9, dated Feb. 11, 2011, 7 pages.
Office Action in European Application No. 05719973.9, dated Nov. 2, 2011, 4 pages.
Office Action in European Application No. 07743994.1, dated Sep. 9, 2014, 8 pages.
Office Action in European Application No. 07793075.8, dated Mar. 1, 2011, 3 pages.
Office Action in European Application No. 08704376.6, dated Feb. 24, 2014, 4 pages.
Office Action in European Application No. 08846814.5, dated Jun. 4, 2014, 4 pages.
Office Action in European Application No. 10809938.3, dated Feb. 10, 2015, 4 pages.
Office Action in European Application No. 10809938.3, dated Oct. 16, 2014, 5 pages.
Office Action in European Patent Application No. 07743994.1, dated Apr. 18, 2017, 5 pages.
Office Action in European Patent Application No. 07743994.1, dated Mar. 8, 2017, 5 pages.
Office Action in European Patent Application No. 08846814.5, dated Apr. 29, 2016, 28 pages.
Office Action in European Patent Application No. 08846814.5, dated Sep. 13, 2017, 19 pages.
Office Action in European Patent Application No. 08846814.5, dated Sep. 28, 2016, 14 pages.

(56) References Cited

OTHER PUBLICATIONS

Office Action in European Patent Application No. 09705712.9, dated Apr. 11, 2018, 5 pages.
Office Action in European Patent Application No. 12774278.1, dated Mar. 9, 2015, 6 pages.
Office Action in European Patent Application No. 12793322.4, dated May 19, 2017, 4 pages.
Office Action in European Patent Application No. 13865671.5, dated Mar. 7, 2017, 4 pages.
Office Action in European Patent Application No. 14727633.1, dated Oct. 13, 2016, 4 pages.
Office Action in European Patent Application No. 15836577.5, dated Mar. 23, 2018, 9 pages.
Office Action in European Patent Application No. 16755489.8, dated Mar. 19, 2020, 8 pages.
Office Action in European Patent Application No. 16755489.8, dated May 14, 2021, 9 pages.
Office Action in European Patent Application No. 16802790.2, dated Apr. 1, 2020, 6 pages.
Office Action in European Patent Application No. 16802790.2, dated Sep. 19, 2019, 6 pages.
Office Action in European Patent Application No. 16837135.9, dated May 10, 2021, 4 pages.
Office Action in European Patent Application No. 16837135.9, dated Sep. 28, 2020, 4 pages.
Office Action in European Patent Application No. 16837150.8, dated Apr. 8, 2020, 3 pages.
Office Action in European Patent Application No. 17782552.8, dated Mar. 16, 2021, 4 pages.
Office Action in European Patent Application No. 19151846.3, dated Aug. 6, 2021, 7 pages.
Office Action in European Patent Application No. 19151846.3, dated Jul. 22, 2020, 5 pages.
Office Action in Gulf Cooperation Council Patent Application No. GC2011-17812, dated Aug. 2, 2018, 8 pages (English Translation).
Office Action in Gulf Cooperation Council Patent Application No. GC2011-17812, dated Oct. 16, 2019, 9 pages (with English Translation).
Office Action in Gulf Cooperation Council Patent Application No. GC2014-28624, dated Jan. 7, 2018, 7 pages (English Translation).
Office Action in Gulf Cooperation Council Patent Application No. GC2015-29939, dated Apr. 8, 2020, 9 pages (with English Translation).
Office Action in Gulf Cooperation Council Patent Application No. GC2015-29939, dated Feb. 22, 2018, 16 pages (English Translation).
Office Action in Gulf Cooperation Council Patent Application No. GC2015-29939, dated Jul. 4, 2019, 9 pages (English Translation).
Office Action in Gulf Cooperation Council Patent Application No. GC2015-40053, dated Jan. 26, 2021, 9 pages (with English Translation).
Office Action in Gulf Cooperation Council Patent Application No. GC2015-40053, dated Jun. 20, 2021, 6 pages (with English Translation).
Office Action in ID App. Ser No. W-00 2008 00601, dated Jan. 13, 2012, 4 pages (with English translation).
Office Action in Indian Application No. 1424/CHENP/2008, dated Sep. 19, 2011, 18 pages.
Office Action in Indian Application No. 1571/CHENP/2007, dated Oct. 23, 2013, 2 pages.
Office Action in Indian Application No. 1571/CHENP/2007, Dec. 9, 2013, 2 pages.
Office Action in Indian Application No. 1908/DELNP/2008, dated Feb. 2, 2012.
Office Action in Indian Patent Application No. 10502/CHENP/2012, dated Apr. 16, 2019, 2 pages (with English Translation).
Office Action in Indian Patent Application No. 10502/CHENP/2012, dated Dec. 29, 2017, 5 pages (English Translation).
Office Action in Indian Patent Application No. 1511/CHENP/2009, dated Aug. 11, 2020, 3 pages (with English Translation).
Office Action in Indian Patent Application No. 1511/CHENP/2009, dated Feb. 27, 2017, 7 pages (English Translation).
Office Action in Indian Patent Application No. 1511/CHENP/2009, dated Jul. 31, 2019, 2 pages.
Office Action in Indian Patent Application No. 1511/CHENP/2009, dated Nov. 21, 2019, 23 pages.
Office Action in Indian Patent Application No. 201747004829, dated Nov. 6, 2019, 1 page.
Office Action in Indian Patent Application No. 201747028834, dated Feb. 20, 2020, 276 pages.
Office Action in Indian Patent Application No. 201747028834, dated Feb. 20, 2020, 6 pages (with English Translation).
Office Action in Indian Patent Application No. 201747040368, dated Dec. 31, 2020, 8 pages (with English Translation).
Office Action in Indian Patent Application No. 201747040368, dated Jan. 3, 2020, 19 pages.
Office Action in Indian Patent Application No. 201847003846, dated Mar. 2, 2020, 27 pages.
Office Action in Indian Patent Application No. 201847003846, dated Mar. 3, 2020, 6 pages (with English Translation).
Office Action in Indian Patent Application No. 201847004787, dated Jan. 30, 2020, 5 pages (with English Translation).
Office Action in Indian Patent Application No. 201847004787, dated Jul. 10, 2020, 2 pages (with English Translation).
Office Action in Indian Patent Application No. 201847037747, dated Dec. 3, 2019, 25 pages.
Office Action in Indian Patent Application No. 201847037747, dated Sep. 9, 2020, 5 pages (with English Translation).
Office Action in Indian Patent Application No. 201947022655, dated Jan. 19, 2021, 5 pages (with English Translation).
Office Action in Indian Patent Application No. 201947044328, dated Jun. 8, 2021, 7 pages (with English Translation).
Office Action in Indian Patent Application No. 2371/CHENP/2012, dated Apr. 18, 2020, 190 pages.
Office Action in Indian Patent Application No. 2371/CHENP/2012, dated Jan. 10, 2020, 1 page.
Office Action in Indian Patent Application No. 2371/CHENP/2012, dated Jan. 4, 2021, 1 page.
Office Action in Indian Patent Application No. 2371/CHENP/2012, dated Jul. 27, 2017, 5 pages (English Translation).
Office Action in Indian Patent Application No. 2371/CHENP/2012, dated Jun. 18, 2018, 3 pages (English Translation).
Office Action in Indian Patent Application No. 2371/CHENP/2012, dated May 21, 2020, 191 pages.
Office Action in Indian Patent Application No. 2371/CHENP/2012, dated Oct. 29, 2018, 1 page (English Translation).
Office Action in Indian Patent Application No. 2371/CHENP/2012, dated Sep. 17, 2018, 3 pages (English Translation).
Office Action in Indian Patent Application No. 2793/CHENP/2013, dated Feb. 28, 2018, 2 pages (English Translation).
Office Action in Indian Patent Application No. 2793/CHENP/2013, dated Sep. 13, 2017, 12 pages (English Translation).
Office Action in Indian Patent Application No. 3334/CHENP/2010, dated Feb. 6, 2017, 13 pages (English Translation).
Office Action in Indian Patent Application No. 5022/CHENP/2009, dated Jun. 28, 2016, 7 pages.
Office Action in Indian Patent Application No. 5022/CHENP/2009, dated Jun. 29, 2017, 3 pages (English Translation).
Office Action in Indian Patent Application No. 5287/CHENP/2010, dated Mar. 15, 2017, 8 pages (English Translation).
Office Action in Indian Patent Application No. 5287/CHENP/2010, Dated Mar. 22, 2018, 2 pages (English Translation).
Office Action in Indian Patent Application No. 6415/CHENP/2008, dated Jan. 19, 2017, 5 pages (English Translation).
Office Action in Indian Patent Application No. 6971/CHENP/2015, dated Sep. 13, 2019, 6 pages (with English Translation).
Office Action in Indian Patent Application No. 7026/CHENP/2013, dated Feb. 5, 2019, 4 pages (English Translation).
Office Action in Indian Patent Application No. 7026/CHENP/2013, dated Mar. 8, 2018, 7 pages (English Translation).
Office Action in Indian Patent Application No. 7026/CHENP/2013, dated Sep. 18, 2020, 16 pages.

(56) References Cited

OTHER PUBLICATIONS

Office Action in Indonesian Patent Application No. W-00201201031, dated Mar. 14, 2016, 4 pages (English translation).
Office Action in Israeli Application No. 175363, dated Jan. 2, 2013, 2 pages, with English translation.
Office Action in Israeli Application No. 188670, dated Jul. 3, 2011, 2 pages (with English translation).
Office Action in Israeli Application No. 197002, dated Feb. 8, 2012, 2 pages (with English translation).
Office Action in Israeli Application No. 197141, dated Feb. 22, 2012, 18 pages (with English translation).
Office Action in Israeli Application No. 200090, dated Jul. 24, 2013, 5 pages (with English translation).
Office Action in Israeli Application No. 205512, dated Dec. 20, 2012, 8 pages, with English translation.
Office Action in Israeli Application No. 205512, dated Oct. 28, 2013, 5 pages (with English translation).
Office Action in Israeli Application No. 205512, dated Sep. 22, 2014, 5 pages (with English translation).
Office Action in Israeli Application No. 207089, dated Jan. 6, 2013, 5 pages (with English translation).
Office Action in Israeli Application No. 207089, dated Nov. 25, 2013, 6 pages (with English translation).
Office Action in Israeli Application No. 217197, dated Oct. 22, 2014, 4 pages (with English translation).
Office Action in Israeli Application No. 255564, dated Aug. 15, 2018, 5 pages (English Translation).
Office Action in Israeli Patent Application No. 227558, dated Mar. 13, 2016, 5 pages (English Translation).
Office Action in Israeli Patent Application No. 238463, dated Feb. 1, 2018, 6 pages (English Translation).
Office Action in Israeli Patent Application No. 242519, dated Aug. 9, 2017, 7 pages (English Translation).
Office Action in Israeli Patent Application No. 245961, dated Jul. 20, 2016, 5 pages (English Translation).
Office Action in Israeli Patent Application No. 250454, dated Feb. 11, 2018, 4 pages (English Translation).
Office Action in Israeli Patent Application No. 253946, dated Oct. 17, 2018, 5 pages (with English Translation).
Office Action in Israeli Patent Application No. 255564, dated Apr. 11, 2019, 7 pages (with English Translation).
Office Action in Israeli Patent Application No. 257292, dated Jan. 27, 2021, 8 pages (with English Translation).
Office Action in Israeli Patent Application No. 257292, dated Jan. 8, 2019, 5 pages (with English Translation).
Office Action in Israeli Patent Application No. 257292, dated May 14, 2020, 7 pages (with English Translation).
Office Action in Israeli Patent Application No. 257433, dated Apr. 1, 2020, 5 pages (with English Translation).
Office Action in Israeli Patent Application No. 257433, dated Jan. 8, 2019, 5 pages (with English Translation).
Office Action in Israeli Patent Application No. 262076, dated Nov. 24, 2019, 5 pages (with English Translation).
Office Action in Israeli Patent Application No. 267159, dated Feb. 5, 2020, 5 pages (with English Translation).
Office Action in Israeli Patent Application No. 270317, dated Aug. 23, 2020, 5 pages (with English Translation).
Office Action in Japanese Application No. 2008-530917, dated Oct. 23, 2012, 4 pages (with English translation).
Office Action in Japanese Application No. 2008-556208, dated Jan. 22, 2013, 8 pages, with English translation.
Office Action in Japanese Application No. P2005-516605 mailed Jun. 1, 2010, 3 pages.
Office Action in Japanese Application No. P2008-532141, dated May 21, 2013, 4 pages (with English translation).
Office Action in Japanese Application No. P2009-510543, dated Sep. 29, 2009, 7 pages (with English translation).
Office Action in Japanese Application No. P2009-540099, dated Mar. 25, 2014, 6 pages (with English translation).
Office Action in Japanese Application No. P2009-551518, dated Jun. 18, 2013, 5 pages (with English translation).
Office Action in Japanese Application No. P2014-553200, dated Jun. 6, 2017, 6 pages (with English tranlsation).
Office Action in Japanese Patent Application No. P2014-513691, dated Jun. 21, 2016, 4 pages, (English Translation).
Office Action in Japanese Patent Application No. P2014-513691, dated Mar. 8, 2016, 6 pages (English Translation).
Office Action in Japanese Patent Application No. P2015-555882, dated Mar. 27, 2018, 4 pages (English Translation).
Office Action in Japanese Patent Application No. P2016-214593, dated Oct. 17, 2017, 9 pages (English Translation).
Office Action in Japanese Patent Application No. P2016-545564, dated Aug. 20, 2019, 7 pages (with English Translation).
Office Action in Japanese Patent Application No. P2016-572771, dated Feb. 7, 2017, 6 pages (English Translation).
Office Action in Japanese Patent Application No. P2017-502388, dated Dec. 17, 2019, 9 pages (with English Translation).
Office Action in Japanese Patent Application No. P2017-502388, dated Jun. 2, 2020, 6 pages (with English Translation).
Office Action in Japanese Patent Application No. P2017-535551, dated Aug. 3, 2021, 2 pages (with English Translation).
Office Action in Japanese Patent Application No. P2017-535551, dated Dec. 15, 2020, 6 pages (with English Translation).
Office Action in Japanese Patent Application No. P2017-535551, dated Jun. 16, 2020, 8 pages (with English Translation).
Office Action in Japanese Patent Application No. P2017-546075, dated Jan. 7, 2020, 6 pages (with English Translation).
Office Action in Japanese Patent Application No. P2017-546075, dated Jul. 21, 2020, 5 pages (with English Translation).
Office Action in Japanese Patent Application No. P2017-546075, dated Mar. 23, 2021, 8 pages (with English Translation).
Office Action in Japanese Patent Application No. P2017-546133, dated Mar. 10, 2020, 10 pages (with English Translation).
Office Action in Japanese Patent Application No. P2017-560343, dated Mar. 10, 2020, 5 pages (with English Translation).
Office Action in Japanese Patent Application No. P2018-552092, dated Feb. 2, 2021, 10 pages (with English Translation).
Office Action in Japanese Patent Application No. P2018-552092, dated May 11, 2021, 10 pages (with English Translation).
Office Action in Jordan Patent Application No. 203/2015, dated Dec. 28, 2020, 2 pages (with English Translation).
Office Action in Jordan Patent Application No. 203/2015, dated Jul. 26, 2020, 2 pages (with English Translation).
Office Action in Jordan Patent Application No. 203/2015, dated Mar. 8, 2020, 2 pages (with English Translation).
Office Action in Jordan Patent Application No. 225/2020, dated Jan. 5, 2021, 2 pages (with English Translation).
Office Action in Jordan Patent Application No. 55/2011, dated Feb. 16, 2017, 2 pages (English Translation).
Office Action in JP2007-542863 dated May 29, 2012, 8 pages with English translation.
Office Action in Korean Application No. 10-2006-7013907, dated Jul. 28, 2007, 7 pages (with English translation).
Office Action in Korean Application No. 10-2006-7013940, dated Jul. 31, 2007, 19 pages (with English translation).
Office Action in Korean Application No. 10-2007-7026886, dated Aug. 27, 2009, 5 pages (with English translation).
Office Action in Korean Application No. 10-2008-7013685, dated May 20, 2013, 10 pages (with English translation).
Office Action in Korean Application No. 10-2008-7027527, dated Dec. 9, 2013, 6 pages (with English translation).
Office Action in Korean Application No. 10-2008-7029472, dated Mar. 28, 2014, 6 pages (with English translation).
Office Action in Korean Application No. 10-2008-7029577, dated Dec. 30, 2013, 7 pages (with English translation).
Office Action in Korean Application No. 10-2009-7005657, dated Mar. 28, 2014, 6 pages (with English translation).
Office Action in Korean Application No. 10-2009-7013723, dated May 19, 2011, 10 pages (with English translation).
Office Action in Korean Application No. 10-2009-7017694, dated Jan. 29, 2014, 26 pages (with English translation).

(56) References Cited

OTHER PUBLICATIONS

Office Action in Korean Application No. 10-2010-7011023, dated Sep. 3, 2014, 14 pages (with English translation).
Office Action in Korean Application No. 10-2010-7018835, dated Sep. 30, 2014, 6 pages (with English translation).
Office Action in Korean Application No. 10-2012-7003846, dated Oct. 7, 2014, 7 pages.
Office Action in Korean Patent Application No. 10-2013-7020616, dated Dec. 19, 2016, 12 pages (English Translation).
Office Action in Korean Patent Application No. 10-2015-7009430, dated Dec. 26, 2019, 3 pages (with English Translation).
Office Action in Korean Patent Application No. 10-2015-7032202, dated Mar. 10, 2020, 11 pages (with English Translation).
Office Action in Korean Patent Application No. 10-2017-7003226, dated Dec. 9, 2020, 15 pages (with English Translation).
Office Action in Korean Patent Application No. 10-2017-7003226, dated Jun. 24, 2021, 12 pages (with English Translation).
Office Action in Mexican Application No. MX/a/2010/008187, dated Apr. 28, 2014, 4 pages (with English translation).
Office Action in Mexican Application No. MX/a/2010/008187, dated Dec. 5, 2013, 8 pages (with English translation).
Office Action in Mexican Application No. MX/a/2012/002011, dated Apr. 28, 2014, 10 pages (with English translation).
Office Action in Mexican Application No. MX/a/2012/002011, dated Nov. 21, 2013, 8 pages (with English translation).
Office Action in Mexican Application No. MX/a/2012/014776, dated Apr. 4, 2014, 22 pages (with English Translation).
Office Action in Mexican Application No. MX/a/2012/014776, dated Oct. 15, 2014, 15 pages (with English translation).
Office Action in Mexican Application No. MX/a/2013/009931, dated Sep. 5, 2014, 15 pages (with English translation).
Office Action in Mexican Patent Application No. MX/a/2014/010594, dated Aug. 17, 2016, 10 pages (English Translation).
Office Action in Mexican Patent Application No. MX/a/2015/015605, dated Apr. 15, 2019, 8 pages (with English Translation).
Office Action in Mexican Patent Application No. MX/a/2017/001980, dated May 27, 2021, 7 pages (with English Translation).
Office Action in Mexican Patent Application No. MX/a/2017/010474, dated Apr. 16, 2021, 10 pages (with English Translation).
Office Action in Mexican Patent Application No. MX/a/2017/010474, dated Aug. 11, 2020, 8 pages (with English Translation).
Office Action in Mexican Patent Application No. MX/a/2017/010474, dated Nov. 27, 2020, 8 pages (with English Translation).
Office Action in Mexican Patent Application No. MX/a/2017/014540, dated Feb. 8, 2021, 15 pages (with English Translation).
Office Action in Mexican Patent Application No. MX/a/2018/001439, dated Dec. 3, 2019, 11 pages (with English Translation).
Office Action in Mexican Patent Application No. MX/a/2018/001439, dated Jul. 23, 2020, 8 pages (with English Translation).
Office Action in Mexican Patent Application No. MX/a/2018/001658, dated Dec. 6, 2019, 7 pages (with English Translation).
Office Action in Mexican Patent Application No. MX/a/2018/001658, dated Jul. 13, 2020, 6 pages (with English Translation).
Office Action in Mexican Patent Application No. MX/a/2018/012193, dated Feb. 23, 2021, 10 pages (with English Translation).
Office Action in Mexican Patent Application No. MX/a/2018/012193, dated Jul. 15, 2020, 8 pages (with English Translation).
Office Action in Mexican Patent Application No. MX/a/2019/006504, dated Sep. 3, 2020, 10 pages (with English Translation).
Office Action in Mexican Patent Application No. MX/a/2019/013014, dated Jul. 6, 2021, 16 pages (with English Translation).
Office Action in New Zealand Patent Application No. 714049, dated Apr. 23, 2020, 1 page.
Office Action in New Zealand Patent Application No. 714049, dated Dec. 23, 2019, 2 pages.
Office Action in New Zealand Patent Application No. 714049, dated May 21, 2019, 3 pages.
Office Action in Norwegian Patent Office Application No. 20063383, dated Mar. 15, 2016, 6 pages (English Translation) [citation change Dec. 1, 2017].
Office Action in NZ Application No. 566793, dated Dec. 4, 2009, 1 page.
Office Action in Pakistan Patent Application No. 548/2015, dated Oct. 18, 2017, 2 pages (English Abstract).
Office Action in Pakistani Patent Application No. 907/2014, dated Aug. 11, 2016, 2 pages.
Office Action in Peruvian Patent Application No. 2081-2011, dated Jul. 15, 2016, 12 pages (English Translation).
Office Action in PH Application No. 1-2007-502319, dated Dec. 16, 2011, 1 page.
Office Action in PH Application No. 1-2011-502441 on Oct. 1, 2013, 1 page.
Office Action in PH Application No. 1-2011-502441, dated Feb. 19, 2014, 2 pages.
Office Action in PK Application No. 1024/2006, dated Dec. 12, 2007, 3 pages.
Office Action in PK Application No. 1024/2006, dated Feb. 24, 2009, 2 pages.
Office Action in PK Application No. 1024/2006, dated Oct. 21, 2008, 2 pages.
Office Action in PK Application No. 155/2005, dated Nov. 17, 2007, 2 pages.
Office Action in PK Application No. 375/2008, dated Feb. 24, 2009, 1 page.
Office Action in PK Application No. 375/2008, dated Jul. 20, 2009, 2 pages.
Office Action in PK Application No. 375/2008, dated Oct. 21, 2008, 3 pages.
Office Action in Russian Application No. 2006134254, dated Oct. 13, 2006, 4 pages (with English translation).
Office Action in Russian Application No. 2006134254, dated Sep. 18, 2007, 9 pages (with English translation).
Office Action in Russian Application No. 2008110932, dated Dec. 3, 2008, 6 pages (with English translation).
Office Action in Russian Application No. 2012103471, dated May 20, 2014, 5 pages (with English translation).
Office Action in Russian Application No. 2012103471, dated Sep. 16, 2014, 5 pages (with English translation).
Office Action in Russian Application No. 2013139556, dated Dec. 2, 2013, 6 pages (with English translation).
Office Action in Russian Patent Application No. 2015115397, dated Oct. 26, 2017, 16 pages (English Translation).
Office Action in Russian Patent Application No. 2015148193, dated Dec. 25, 2017, 13 pages (English Translation).
Office Action in Russian Patent Application No. 2015148193, dated Jan. 27, 2016, 4 pages, (English Translation).
Office Action in Russian Patent Application No. 2015148193, dated May 10, 2016, 3 pages (English Translation).
Office Action in Russian Patent Application No. 2016122867, dated Jun. 18, 2018, 13 pages (English Translation).
Office Action in Russian Patent Application No. 2017104496, dated Jun. 23, 2020, 9 pages (with English Translation).
Office Action in Russian Patent Application No. 2017104496, dated Mar. 26, 2019, 15 pages (with English Translation).
Office Action in Russian Patent Application No. 2017128583, dated Apr. 30, 2020, 19 pages (with English Translation).
Office Action in Russian Patent Application No. 2017128583, dated Feb. 28, 2019, 30 pages (with English Translation).
Office Action in Russian Patent Application No. 2017139090, dated Apr. 2, 2020, 10 pages (with English Translation).
Office Action in Russian Patent Application No. 2017139090, dated Nov. 12, 2019, 16 pages (with English Translation).
Office Action in Russian Patent Application No. 2017139090, dated Sep. 1, 2020, 9 pages (with English Translation).
Office Action in Russian Patent Application No. 2018103737, dated Jan. 28, 2020, 16 pages (with English Translation).
Office Action in Russian Patent Application No. 2018103737, dated Oct. 11, 2019, 20 pages (with English Translation).
Office Action in Russian Patent Application No. 2018104697, dated Oct. 24, 2019, 12 pages (with English Translation).
Office Action in Russian Patent Application No. 2018134943, dated May 26, 2020, 16 pages (with English Translation).

(56) References Cited

OTHER PUBLICATIONS

Office Action in Russian Patent Application No. 2018134943, dated Nov. 23, 2020, 13 pages (with English Translation).
Office Action in Russian Patent Application No. 2019120680, dated Dec. 28, 2020, 18 pages (with English Translation).
Office Action in Russian Patent Application No. 2019120680, dated May 12, 2021, 13 pages (with English Translation).
Office Action in Singaporean Patent Application No. 11201706630U, dated Apr. 30, 2018, 8 pages (English Translation).
Office Action in Singaporean Patent Application No. 11201706630U, dated Feb. 8, 2021, 7 pages.
Office Action in Singaporean Patent Application No. 11201706630U, dated Nov. 5, 2019, 7 pages.
Office Action in Singaporean Patent Application No. 11201709335X, dated Jun. 28, 2021, 7 pages.
Office Action in Singaporean Patent Application No. 11201801083U, dated Jun. 16, 2021, 6 pages.
Office Action in Singaporean Patent Application No. 11201904020S, dated May 19, 2021, 5 pages.
Office Action in Taiwanese Application No. 095130665, dated Mar. 2, 2012, 8 pages (with English translation).
Office Action in Taiwanese Application No. 100104281, dated Dec. 9, 2014, 13 pages (with English translation).
Office Action in Taiwanese Patent Application No. 103144928, dated Jun. 7, 2018, 7 pages (English Translation).
Office Action in Taiwanese Patent Application No. 103144928, dated Nov. 13, 2018, 6 pages (English Translation).
Office Action in Taiwanese Patent Application No. 104127982, dated Apr. 30, 2019, 12 pages (with English Translation).
Office Action in Taiwanese Patent Application No. 104127982, dated Dec. 18, 2019, 10 pages (with English Translation).
Office Action in Thai Patent Application No. 0401005163, dated Dec. 15, 2020, 14 pages (with English Translation).
Office Action in U.S. Appl. No. 11/065,631, dated Feb. 28, 2008, 12 pages.
Office Action in U.S. Appl. No. 11/508,322, dated Dec. 18, 2008, 19 pages.
Office Action in U.S. Appl. No. 11/508,322, dated May 29, 2009, 8 pages.
Office Action in U.S. Appl. No. 11/662,425, dated Feb. 27, 2014, 152 pages.
Office Action in U.S. Appl. No. 11/662,425, dated Jun. 5, 2014, 30 pages.
Office Action in U.S. Appl. No. 11/662,425, dated Sep. 17, 2014, 3 pages.
Office Action in U.S. Appl. No. 11/997,543, dated Mar. 11, 2014, 20 pages.
Office Action in U.S. Appl. No. 12/031,568, dated Aug. 13, 2010, 15 pages.
Office Action in U.S. Appl. No. 12/031,568, dated Feb. 5, 2010, 16 pages.
Office Action in U.S. Appl. No. 12/031,568, dated May 12, 2011, 26 pages.
Office Action in U.S. Appl. No. 12/039,381, dated Jan. 9, 2014, 16 pages.
Office Action in U.S. Appl. No. 12/039,381, dated May 29, 2014, 78 pages.
Office Action in U.S. Appl. No. 12/039,381, dated Sep. 12, 2013, 15 pages.
Office Action in U.S. Appl. No. 12/315,291, dated Jan. 12, 2011, 9 pages.
Office Action in U.S. Appl. No. 12/315,291, dated Jun. 7, 2010, 20 pages.
Office Action in U.S. Appl. No. 12/439,339, dated May 23, 2013, 15 pages.
Office Action in U.S. Appl. No. 12/558,982, dated Apr. 5, 2011, 31 pages.
Office Action in U.S. Appl. No. 12/558,982, dated Aug. 29, 2011, 13 pages.
Office Action in U.S. Appl. No. 12/864,817, dated Aug. 15, 2014, 79 pages.
Office Action in U.S. Appl. No. 12/867,646, dated Oct. 26, 2011, 37 pages.
Office Action in U.S. Appl. No. 13/083,338, dated Jan. 3, 2013, 9 pages.
Office Action in U.S. Appl. No. 13/238,085, dated Nov. 12, 2013, 74 pages.
Office Action in U.S. Appl. No. 13/238,085, dated Sep. 6, 2013, 10 pages.
Office Action in U.S. Appl. No. 13/805,826, dated Apr. 2, 2014, 8 pages.
Office Action in U.S. Appl. No. 13/805,826, dated Jul. 1, 2014, 88 pages.
Office Action in U.S. Appl. No. 13/805,826, dated Sep. 23, 2014, 25 pages.
Office Action in U.S. Appl. No. 13/870,507, dated Dec. 12, 2014, 10 pages.
Office Action in U.S. Appl. No. 13/923,858, dated Apr. 18, 2014, 64 pages.
Office Action in U.S. Appl. No. 13/923,858, dated Dec. 5, 2014, 67 pages.
Office Action in U.S. Appl. No. 13/983,891, dated Jan. 22, 2014, 11 pages.
Office Action in U.S. Appl. No. 14/002,018, dated Apr. 14, 2014, 28 pages.
Office Action in U.S. Appl. No. 14/002,018, dated Jul. 25, 2014, 14 pages.
Office Action in U.S. Appl. No. 14/002,018, dated Jun. 9, 2014, 19 pages.
Office Action in U.S. Appl. No. 14/862,349, dated Mar. 10, 2016, 11 pages.
Office Action in U.S. Appl. No. 15/573,197, dated Feb. 14, 2020, 21 pages.
Office Action in U.S. Appl. No. 13/870,507, dated Feb. 17, 2016, 28 pages.
Office Action in U.S. Appl. No. 13/923,858, dated Aug. 27, 2020, 25 pages.
Office Action in U.S. Appl. No. 13/923,858, dated Dec. 14, 2020, 9 pages.
Office Action in U.S. Appl. No. 13/923,858, dated Feb. 21, 2020, 9 pages.
Office Action in U.S. Appl. No. 13/923,858, dated Feb. 22, 2018, 16 pages.
Office Action in U.S. Appl. No. 13/923,858, dated May 4, 2017, 31 pages.
Office Action in U.S. Appl. No. 13/923,858, dated May 16, 2019, 13 pages.
Office Action in U.S. Appl. No. 13/923,858, dated Oct. 4, 2018, 16 pages.
Office Action in U.S. Appl. No. 14/117,276, dated May 20, 2016, 11 pages.
Office Action in U.S. Appl. No. 14/122,339, dated Aug. 10, 2017, 10 pages.
Office Action in U.S. Appl. No. 14/122,339, dated Jan. 2, 2018, 3 pages.
Office Action in U.S. Appl. No. 14/122,339, dated Jul. 8, 2016, 12 pages.
Office Action in U.S. Appl. No. 15/460,629, dated Feb. 6, 2019, 27 pages.
Office Action in U.S. Appl. No. 15/460,629, dated Sep. 28, 2018, 10 pages.
Office Action in U.S. Appl. No. 15/503,108, dated Nov. 14, 2017, 12 pages.
Office Action in U.S. Appl. No. 15/550,124, dated May 3, 2018, 124 pages.
Office Action in U.S. Appl. No. 15/554,577, dated Jan. 3, 2019, 26 pages.
Office Action in U.S. Appl. No. 15/554,577, dated Jul. 17, 2019, 321 pages.
Office Action in U.S. Appl. No. 15/554,577, dated May 1, 2020, 38 pages.

(56) References Cited

OTHER PUBLICATIONS

Office Action in U.S. Appl. No. 15/554,577, dated Nov. 23, 2020, 51 pages.
Office Action in U.S. Appl. No. 15/573,197, dated Apr. 8, 2019, 133 pages.
Office Action in U.S. Appl. No. 15/573,197, dated May 13, 2021, 30 pages.
Office Action in U.S. Appl. No. 15/748,980, dated Apr. 2, 2021, 25 pages.
Office Action in U.S. Appl. No. 15/748,980, dated Aug. 6, 2020, 150 pages.
Office Action in U.S. Appl. No. 15/748,980, dated Jan. 2, 2019, 9 pages.
Office Action in U.S. Appl. No. 15/748,980, dated Jun. 3, 2019, 25 pages.
Office Action in U.S. Appl. No. 15/748,980, dated Nov. 29, 2019, 15 pages.
Office Action in U.S. Appl. No. 15/750,712, dated Jan. 11, 2019, 7 pages.
Office Action in U.S. Appl. No. 15/934,242, dated Jan. 26, 2021, 18 pages.
Office Action in U.S. Appl. No. 15/934,242, dated Jan. 3, 2020, 7 pages.
Office Action in U.S. Appl. No. 15/934,242, dated Jun. 15, 2020, 6 pages.
Office Action in U.S. Appl. No. 16/038,710, dated May 2, 2019, 21 pages.
Office Action in U.S. Appl. No. 16/038,710, dated Nov. 20, 2018, 124 pages.
Office Action in U.S. Appl. No. 16/092,245, dated Apr. 30, 2020, 7 pages.
Office Action in U.S. Appl. No. 16/092,245, dated Aug. 22, 2019, 6 pages.
Office Action in U.S. Appl. No. 16/092,245, dated Jun. 25, 2021, 30 pages.
Office Action in U.S. Appl. No. 16/092,245, dated Oct. 7, 2020, 6 pages.
Office Action in U.S. Appl. No. 16/229,805, dated Mar. 29, 2019, 120 pages.
Office Action in U.S. Appl. No. 16/465,277, dated Mar. 20, 2020, 150 pages.
Office Action in U.S. Appl. No. 16/559,293, dated Dec. 12, 2019, 129 pages.
Office Action in U.S. Appl. No. 16/809,301. dated Mar. 22, 2021, 10 pages.
Office Action in U.S. Appl. No. 17/228,025, dated Jun. 4, 2021, 3 pages.
Office Action in Vietnamese Patent Application No. 1-2016-02104, dated Apr. 26, 2018, 4 pages (English Translation).
Office Action in VN Application No. 1-2011-03484, dated Dec. 31, 2013, 2 pages (with English translation).
Office Action in Yemen Patent Application No. 592/2011, dated Jan. 16, 2017, 2 pages (English Translation).
Office Action Israel Application No. 207089 issued on Nov. 13, 2011, 4 pages (with English translation).
Office Action issued for CN 200880002425.9 on Mar. 2, 2011, 10 pages with English translation.
Office Action issued for EP 06768437.3 (EPO Form1224) issued on Oct. 28, 2010, 47 pages.
Office Action issued for European Search Report for European Application No. 06782407 on Sep. 29, 2011, 6 pages.
Office Action issued for Japanese Application No. 2007-529565 issued on Dec. 13, 2011, 7 pages with English full translation.
Office Action issued for JP Appl. No. 2007-529565 issued on May 8, 2012, 6 pages with English translation.
Office Action issued in MX Application No. MX/a/2012/002011, dated Jul. 17, 2013, 6 pages (with English translation).
Office Action issued Jan. 7, 2011, in U.S. Appl. No. 12/092,539.
Office Communication dated Sep. 13, 2004 for U.S. Appl. No. 10/420,466.
Office Letter Confirmation of Amendment After Allowance dated Jan. 11, 2011 for CA Application No. 2426461.
Office Letter re Notice of Allowance dated May 25, 2012 for ZA Application No. 201108697.
Official Letter and Notice of Allowance for AU Application No. 2008211952, dated Jul. 10, 2012.
Official Letter and Notice of Allowance for AU Application No. 2008325608, dated Feb. 27, 2013, 7 pages.
Official Letter in AU Application No. 2006282456, dated May 15, 2012, 1 page.
Official Letter in AU Application No. 2006282456, dated Sep. 24, 2012, 259 pages.
Official Letter in BD Application No. 184/2006, dated Feb. 2, 2012, 1 page.
Official Letter re Deficiencies in sequence listing in EP Application No. 06796594.7, dated Mar. 10, 2008, 3 pages.
Official Letter re Grant of Request for Correction of Specification for SG Application No. 201108602- 2, dated Aug. 8, 2012.
Official Letter re Granting Patent in EP Application No. 06796594.7, dated Sep. 25, 2012, 270 pages.
Official Letter re Intention to Grant Patent in EP Application No. 05719973.9, dated Feb. 6, 2012, 553 pages.
Official Letter re invitation to declare maintenance in EP Application No. 06796594.7, dated Sep. 26, 2011, 1 page.
Official Letter re invitation to declare maintenance in EP Application No. 07793075.8, dated Sep. 27, 2010, 1 page.
Official Letter re invitation to declare maintenance in EP Application No. 07805959.9, dated Dec. 3, 2010, 1 page.
Official Notification in Australian Patent Application No. 2005283422, dated Jul. 14, 2016, 8 pages.
Official Notification in Australian Patent Application No. 2005283422, dated Oct. 20, 2016, 1 pages.
Official Notification in Brazilian Patent Application No. BR112012003592-4, dated Apr. 15, 2019, 6 pages (with English Translation).
Official Notification in Brazilian Patent Application No. PI0418200-6, dated Jan. 26, 2021, 28 pages (with English Translation).
Official Notification in CA Application No. 2771403, dated Dec. 16, 2014, 1 page.
Official Notification in Chilean Patent Application No. 201601419, dated Sep. 21, 2018, 17 pages (English Translation).
Official Notification in EP Application No. 04807580.8, dated Jun. 16, 2014, 1 pages.
Official Notification in EP Application No. 04807580.8, dated Jun. 27, 2014, 17 pages.
Official Notification in European Patent Application No. 07743994.1, dated Jul. 22, 2016, 18 pages.
Official Notification in European Patent Application No. 14727633.1, dated Jun. 21, 2018, 2 pages.
Official Notification in European Patent Application No. 16755489.8, dated Oct. 30, 2019, 9 pages.
Official Notification in Gulf Cooperation Council Patent Application No. GC2014-28624, dated Apr. 5, 2018, 298 pages (English Translation).
Official Notification in Indian Patent Application No. 10502/CHENP/2012, dated Apr. 26, 2019, 2 pages (with English Translation).
Official Notification in Indian Patent Application No. 1511/CHENP/2009, dated Feb. 1, 2021, 6 pages.
Official Notification in Indian Patent Application No. 1511/CHENP/2009, dated Nov. 26, 2018, 173 pages.
Official Notification in Indian Patent Application No. 1511/CHENP/2009, dated Oct. 13, 2017, 105 pages.
Official Notification in Indian Patent Application No. 201747004829, dated Mar. 20, 2018, 87 pages (English Translation).
Official Notification in Indian Patent Application No. 201747028834, dated Jan. 9, 2018, 63 pages.
Official Notification in Indian Patent Application No. 201847037747, dated Sep. 9, 2020, 28 pages.
Official Notification in Indian Patent Application No. 2371/CHENP/2012, dated Jan. 25, 2018, 3 pages (English Translation).
Official Notification in Indian Patent Application No. 5287/CHENP/2010, dated Apr. 6, 2018, 2 pages (English Translation).

(56) References Cited

OTHER PUBLICATIONS

Official Notification in Indian Patent Application No. 6415/CHENP/2008, dated Apr. 28, 2017, 5 pages (English Translation).
Official Notification in Indian Patent Application No. 6415/CHENP/2008, dated Jul. 15, 2019, 2 pages.
Official Notification in Israeli Patent Application No. 223695, dated May 29, 2017, 1 page (English Translation).
Official Notification in Israeli Patent Application No. 253946, dated Feb. 10, 2019, 3 pages (with English Translation).
Official Notification in Jordan Patent Application No. 55/2011, dated Feb. 12, 2018, 2 pages (English Translation).
Official Notification in U.S. Appl. No. 13/923,858, dated Jul. 23, 2018, 15 pages.
Official Notification in U.S. Appl. No. 15/748,980, dated Jun. 23, 2020, 3 pages.
Official Notification in U.S. Appl. No. 16/038,710, dated Dec. 30, 2019, 3 pages.
Official Notification re Decision on Petition in U.S. Appl. No. 11/997,719, dated Sep. 23, 2014, 1 page.
Official Notification re Interview Summary in U.S. Appl. No. 14/002,018, dated Oct. 6, 2014, 2 pages.
Ohe et al, "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," Annals of Oncology 18(2):317-323, Nov. 1, 2006.
Oikonomopoulos et al., "Lenvatinib: a potential breakthrough in advanced hepatocellular carcinoma?," Future Oncology, 2016, 12(4):465-476.
Okayama et al., "Activation of Eosinophils with Cytokines Produced by Lung Mast Cells," Int Arch Allergy Immunol., 114(suppl 1):75-77 (1997).
Okayama et al., "Human Lung Mast Cells are Enriched in the Capacity to Produce Granulocyte-Macrophage Colony-Stimulating Factor in Response to IgE-Dependent Stimulation," Eur. J. Immunol., 28:708-715 (1998).
Okura et al., "Effects of monoclonal anti-c-kit antibody (ACK2) on melanocytes in newborn mice," J. Invest. Dermatol., 105(3):322-328 (1995).
Okusaka et al., "Chemotherapy for biliary tract cancer", biliary tract, 2013 vol. 27 No. 1, p. 124-p. 134 (Machine Translation).
Olaso et al., "DDR2 receptor promotes MMP-2-mediated proliferation and invasion by hepatic stellate cells," J. Clin. Invest., 108(9):1369-1378 (2001).
O'Reilly et al., "Hydrolysis of tert-Butyl Methyl Ether (MTBE) in Dilute Aqueous Acid," Environ. Sci. Technol., 2001, 35:3954-3961.
Ozawa et al., "E7386, an orally active CBP/beta-catenin modulator, effects tumor microenvironment, resulting to the enhancement of antitumor activity of lenvatinib," Eisai, 2017, 1 page.
Ozols et al., "Phase III trial of carboplatin and paclitaxel compared with cisplatin and paclitaxel in patients with optimally resected stage III ovarian cancer: a Gynecologic Oncology Group study," J. Clin. Oncol., 21(17):3194-3200 (2003).
Pacini, "38th Annual Meeting of the European Thyroid Association", European Thyroid Association, Santiago de Compostela, Spain, Aug. 15, 2014, p. 73-p. 226.
Pakistani Office Action for Application No. 94/2011, issued on May 9, 2012.
Pal et al., "A Phase 2 Trial of Lenvatinib 18 mg vs 14 mg Once Daily (QD) in Combination With Everolimus (5 mg QD) in Renal Cell Carcinoma", A poster presentation at 16th International Kidney Cancer Symposium, Miami, FL, USA, Nov. 3-4, 2017, 1 page.
Pandey et al., "Identification of Orally Active, Potent, and Selective 4-Piperazinylquinazolines as Antagonists of the Platelet-Derived Growth Factor Receptor Tyrosine Kinase Family", *Journal of Medicinal Chemistry.*, 45, 3772-3793, 2002.
Papai et al., "The efficacy of a combination of etoposide, ifosfamide, and cisplatin in the treatment of patients with soft tissue sarcoma", Cancer, 2000.07, vol. 89, No. 1, p. 177-p. 180.
Park et al., "Serum Angiopoietin-2 as a Clinical Marker for Lung Cancer," Chest 132(1):200-206, Jul. 2007.
Partial European Search Report for Application No. 01976786.2, dated Apr. 6, 2004.
Patel et al., "The effect of excipients on the stability of levothyroxine sodium pentahydrate tablets," Int'l J Pharm., 2003, 264:35-43.
Paterson et al., "Preclinical studies of fibroblast growth factor receptor 3 as a therapeutic target in multiple myeloma," British Journal of Haematology, 124:595-603 (2004).
Paulus, "Preparation and Biomedical Applications of Bispecific Antibodies", Behring Inst. Mitt. 78: 118-132 (1985).
Payment of Final Fee and Amendment after Allowance in CA Application No. 2771403, dated Nov. 24, 2014, 3 pages.
Paz et al., "Development of angiogenesis inhibitors to vascular endothelial growth factor receptor 2. Current status and future perspective," Frontiers in Bioscience, 10:1415-1439 (May 1, 2005).
Pearson, "Rapid and Sensitive Sequence Comparison with FASTP and FASTA", Methods in Enzymology 183 :63-98 (1990).
Peruvian Office Action in Application No. 2081-2011, dated Mar. 23, 2016, 12 pages, with English translation.
Petition in JP Application No. 2007-532099, dated Dec. 25, 2007, 3 pages (with English translation).
Petition in JP Application No. 2007-532099, dated Sep. 25, 2007, 3 pages (with English translation).
Petition in JP Application No. 2009-554285, dated Aug. 19, 2010, 3 pages (with English translation).
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Pilaniya et al., "Recent trends in the impurity profile of pharmaceuticals", J Adv Pharm Technol Res.; 1(3): 302-310, Jul.-Sep. 2010.
Pisters et al, "Induction chemotherapy before surgery for early-stage lung cancer: A novel approach," J Thoracic Cardiovasc Surg 119(3):429-439, Mar. 2000.
Plowright et al., "Ectopic expression of fibroblast growth factor receptor 3 promotes myeloma cell proliferation and prevents apoptosis," Blood, 95:992-998 (2000).
Podar et al., "GW654652, the pan-inhibitor of VEGF receptors, blocks the growth and migration of multiple myeloma cells in the bone marrow microenvironment", Blood., 103, 3474-3479, 2004.
Polverino et al, "AMG 706, an Oral, Multikinase Inhibitor that Selectively Targets Vascular Endothelial Growth Factor, Platelet—Derived Growth Factor, and Kit Receptors, Potently inhibits Angiogenesis and Induces Regression in Tumor Xenografts," Cancer Research, 66(17):8715-8721 (2006).
Preliminary Amendment and Response to Restriction Requirement in U.S. Appl. No. 12/439,339, filed Aug. 10, 2011.
Preliminary Amendment and Response to Restriction Requirement in U.S. Appl. No. 13/083,338, filed Apr. 30, 2012.
Preliminary Amendment dated Apr. 26, 2013 for U.S. Appl. No. 13/870,507, 10 pages.
Preliminary Amendment filed in EP Application No. 12786619.2, dated Nov. 13, 2013, 7 pages.
Preliminary Amendment filed in U.S. Appl. No. 14/117,276, dated Nov. 12, 2013, 11 pages.
Preliminary Amendment filed in U.S. Appl. No. 14/122,339, dated Nov. 26, 2013, 10 pages.
Preliminary Amendment filed on Apr. 18, 2003 for U.S. Appl. No. 10/420,466.
Preliminary Amendment filed on Dec. 2, 2005 for U.S. Appl. No. 10/420,466.
Preliminary Amendment filed on Feb. 3, 2006 for U.S. Appl. No. 11/293,785.
Preliminary Amendment filed on May 23, 2003 for KR Application No. 10-2003-7005506 (with English translation).
Preliminary Amendment filed on Oct. 27, 2003 for U.S. Appl. No. 10/420,517.
Preliminary Amendment for U.S. Appl. No. 13/624,278, filed Sep. 21, 2012, 7 pages.
Preliminary Amendment in U.S. Appl. No. 10/577,043, dated Apr. 24, 2006, 12 pages.

(56) References Cited

OTHER PUBLICATIONS

Preliminary Amendment in U.S. Appl. No. 10/577,065, dated Apr. 24, 2006, 11 pages.
Preliminary Amendment in U.S. Appl. No. 11/508,322, dated May 15, 2007, 4 pages.
Preliminary Amendment in U.S. Appl. No. 11/508,322, dated May 19, 2008, 15 pages.
Preliminary Amendment in U.S. Appl. No. 11/508,322, dated Nov. 5, 2007, 28 pages.
Preliminary Amendment in U.S. Appl. No. 11/892,785, dated Apr. 7, 2008, 16 pages.
Preliminary Amendment in U.S. Appl. No. 12/031,568, dated Jun. 6, 2008, 7 pages.
Preliminary Amendment in U.S. Appl. No. 12/315,291, dated Mar. 19, 2009, 17 pages.
Preliminary Amendment in U.S. Appl. No. 12/527,633, dated Apr. 14, 2010, 58 pages.
Preliminary Amendment in U.S. Appl. No. 12/527,633, dated Aug. 18, 2009, 62 page.
Preliminary Amendment in U.S. Appl. No. 12/867,646, dated Aug. 13, 2010, 5 pages.
Pritzker, "Cancer Biomarkers: Easier Said Than Done," Clinical Chemistry, 48(8):1147-1150 (2002).
Ramsden, "Angiogenesis in the thyroid gland," Journal of endocrinology, Apr. 11, 2000, 475-480.
Reasons for Reexamination dated Sep. 11, 2012 for CN Application No. 200680020317.5 (with English translation).
Reexamination filed on May 25, 2004 for TW Application No. 90125928 (with English translation).
Reexamination filed on Nov. 25, 2004 for TW Application No. 90125928 (with English translation).
Registered dated Feb. 24, 2009 for PH Application No. 1-2003-500266.
Registry's Letter in MT Application No. 3723, dated Sep. 29, 2007, 1 page.
Rejection dated Apr. 26, 2004 for TW Application No. 90125928 (with English translation).
Remington, "The Science and Practice of Pharmacy," Remington, 20th Edition, 2000, pp. 1123-1124.
Ren "Advances in Medical Therapy of Melanoma," J of Practical Oncology, 25(2):137-140, Dec. 31, 2010.
Reply to communication from the Examining Division for EP App. Ser. 06023078.6, dated Feb. 4, 2008.
Reply to communication from the Examining Division for EP App. Ser. 06023078.6, dated Sep. 11, 2007.
Reply to communication from the Examining Division for EP Application No. 01976786.2, dated Jan. 25, 2006.
Reply to communication from the Examining Division for EP Application No. 01976786.2, dated Jul. 19, 2006.
Reply to communication from the Examining Division for EP Application No. 04025700.8, dated Feb. 15, 2007.
Reply to communication from the Examining Division for EP Application No. 04025700.8, dated Jan. 26, 2007.
Reply to communication from the Examining Division for EP Application No. 04025700.8, dated Sep. 12, 2006.
Reply to Examination Report dated Feb. 8, 2013 for EP Application No. 07743994.1, 4 pages.
Reply to final office action in U.S. Appl. No. 13/805,826, dated Nov. 26, 2014, 7 pages.
Reply to Final Office Action in U.S. Appl. No. 14/002,018, dated Oct. 1, 2014, 6 pages.
Reply to Notice of Allowance in U.S. Appl. No. 11/662,425, dated Jan. 20, 2015, 5 pages.
Reply to Notice of Non-Compliant Amendment in U.S. Appl. No. 12/315,291, dated Nov. 12, 2010, 3 pages.
Reply to official communication for EP Application No. 05783232.1, dated Apr. 30, 2008.
Reply to the invitation to remedy deficiencies for EP Application No. 06023078.6, dated Jan. 11, 2007.
Request for accelerated examination in KR Application No. 10-2012-7003846, dated Jun. 18, 2014, 29 pages (with English translation).
Request for amendment of the text intended for grant and translation of claims for EP Application No. 04025700.8, dated Feb. 1, 2008.
Request for amendment of the text intended for grant and translation of claims for EP Application No. 06023078.6, dated Nov. 5, 2008.
Request for Continued Examination (RCE) in U.S. Appl. No. 13/624,278, dated Sep. 24, 2014, 1 page.
Request for Continued Examination (RCE) in U.S. Appl. No. 11/997,719, dated Aug. 29, 2014, 1 page.
Request for Continued Examination (RCE) transmittal for U.S. Appl. No. 12/864,817, filed Dec. 22, 2011.
Request for correction of errors in filed documents for EP Application No. 06023078.6, dated Feb. 13, 2007.
Request for Examination in CA Application No. 2713930, dated Oct. 21, 2013, 8 pages.
Request for Re-Examination in CN ApplicationA1452:A1470780017371.9, dated Oct. 11, 2013, 9 pages (with English translation).
Request for Substantive Examination for ID Application No. W-00201201031, filed Jun. 3, 2013, 6 pages (with English translation).
Request for Substantive Examination for UA Application No. a201203132, filed Apr. 15, 2013, 14 pages (with English translation).
Request for Voluntary Amendments filed May Oct. 2012, in Ukraine Patent Application No. a 2012 03132, with English Abstract.
Request to Amend Complete Specification dated Feb. 15, 2013 for AU Application No. 2008325608, 23 pages.
Request to Amend Complete Specification dated May 9, 2013 for AU Application No. 2009210098, 22 pages.
Response and Amended Claims filed in EP Application No. 08846814.5, filed Aug. 1, 2013, 14 pages.
Response and Amended Claims filed in EP Application No. 10809938.3, filed Jul. 19, 2013, 7 pages.
Response and Amendment for CA Application No. 2652442, dated Sep. 5, 2013, 17 pages.
Response filed in CA Application No. 2652442, dated Jan. 8, 2014, 5 pages.
Response filed in CO Application No. 12-022608, dated Nov. 13, 2013, 13 pages (with English translation).
Response filed in IL Application No. 195282, filed Jul. 11, 2013, 13 pages (with English translation).
Response filed in IN Application No. 1571/CHENP/2007, dated Oct. 30, 2013, 9 pages.
Response filed in KR Application No. 10-2009-7005657, dated Nov. 21, 2013, 46 pages (with English translation).
Response filed in MX Application No. MX/a/2010/008187, dated Nov. 4, 2013, 21 pages (with English translation).
Response filed in PH Application No. 1-2011-502441, dated Feb. 28, 2014, 4 pages.
Response filed in PH Application No. 1-2011-502441, dated Nov. 4, 2013, 28 pages.
Response filed in U.S. Appl. No. 10/797,903, dated Dec. 29, 2010, 13 pages.
Response filed in VN Application No. 1-2011-03484, dated Feb. 28, 2014, 40 pages (with English translation).
Response filed on Apr. 11, 2006 for CN Application No. 01819710.8 (with English translation).
Response filed on Apr. 17, 2007 for PH Application No. 1-2003-500266.
Response filed on Apr. 27, 2006 for AU Application No. 2001295986.
Response filed on Apr. 30, 2008 for PH Application No. 1-2003-500266.
Response filed on Aug. 13, 2009 for CA Application No. 2426461.
Response filed on Aug. 14, 2006 for PH Application No. 1-2003-500266.
Response filed on Aug. 18, 2008 for NO Application No. 20031731 (with English translation).
Response filed on Aug. 21, 2006 for MX Application No. PA/a/2003/003362 (with English translation).
Response filed on Aug. 26, 2004 for NZ Application No. 525324.

(56) References Cited

OTHER PUBLICATIONS

Response filed on Aug. 5, 2003 for PH Application No. 1-2003-500266.
Response filed on Dec. 11, 2007 for TW Application No. 90125928 (with English translation).
Response filed on Dec. 15, 2005 for MX Application No. PA/a/2003/003362 (with English translation).
Response filed on Dec. 4, 2007 for IL Application No. 155447 (with English translation).
Response filed on Feb. 23, 2009 for CA Application No. 2426461.
Response filed on Feb. 26, 2008 for U.S. Appl. No. 11/293,785.
Response filed on Jan. 11, 2010 for CN Application No. 200580026468.7 (with English translation).
Response filed on Jan. 21, 2005 for NZ Application No. 525324.
Response filed on Jan. 26, 2010 for CN Application No. 200710007097.9 (with English translation).
Response filed on Jan. 26, 2011 for IL Application No. 181697 (with English translation).
Response filed on Jul. 1, 2005 for U.S. Appl. No. 10/420,466.
Response filed on Jul. 2, 2009 for CN Application No. 200710007097.9 (with English translation).
Response filed on Jul. 26, 2006 for AU Application No. 2001295986.
Response filed on Jul. 31, 2007 for PH Application No. 1-2003-500266.
Response filed on Jun. 22, 2010 for CN Application No. 200710007097.9 (with English translation).
Response filed on Mar. 17, 2005 for RU Application No. 2003114740 (with English translation).
Response filed on May 13, 2009 for IL Application No. 189677 (with English translation).
Response filed on May 16, 2008 for CA Application No. 2426461.
Response filed on May 20, 2010 for CA Application No. 2426461.
Response filed on May 7, 2008 for NO Application No. 20031731 (with English translation).
Response filed on May 8, 2008 for AU Application No. 2006236039.
Response filed on Nov. 19, 2009 for CN Application No. 200710007097.9 (with English translation).
Response filed on Nov. 30, 2004 for RU Application No. 2003114740 (with English translation).
Response filed on Oct. 13, 2008 for NO Application No. 20031731 (with English translation).
Response filed on Oct. 15, 2007 for PH Application No. 1-2003-500266.
Response filed on Oct. 8, 2004 for U.S. Appl. No. 10/420,466.
Response filed on Oct. 9, 2006 for CN Application No. 01819710.8 (with English translation).
Response filed on Sep. 10, 2007 for NO Application No. 20031731 (with English translation).
Response filed on Sep. 13, 2005 for CN Application No. 01819710.8 (with English translation).
Response filed on Sep. 15, 2003 for PH Application No. 1-2003-500266.
Response filed on Sep. 21, 2011 for CA Application No. 2579810.
Response filed on Sep. 23, 2009 for CN Application No. 200580026468.7 (with English translation).
Response filed on Sep. 8, 2003 for PH Application No. 1-2003-500266.
Response in Chinese Patent Application No. 201510031628.2, dated Aug. 11, 2017, 8 pages (English Translation).
Response in EP Application No. 06796594.7, dated Mar. 31, 2008, 3 pages.
Response in EP Application No. 12774278.1, dated Oct. 13, 2014, 4 pages.
Response in Indian Patent Applciation No. 5287/CHENP/2010, dated Sep. 12, 2017, 6 pages (English Translation).
Response in U.S. Appl. No. 13/923,858 dated Oct. 3, 2017, 29 pages.
Response to Advisory Action in U.S. Appl. No. 12/315,291, dated Mar. 31, 2011, 6 pages.
Response to AU OA for AU 2008211952 filed on Jun. 28, 2012, 36 pages.
Response to Australian Office Action filed on Apr. 29, 2010 for corresponding AU Application No. 2006285673.
Response to Australian Office Action filed on Jul. 28, 2010 for corresponding AU Application No. 2006285673.
Response to Australian Office Action filed on Oct. 16, 2009 for corresponding AU Application No. 2006285673.
Response to Canadian Office Action filed Feb. 13, 2012, in Canadian Application No. 2,620,594.
Response to Canadian Office Action filed on Jun. 21, 2010 for corresponding CA Application No. 2,620,594.
Response to Chinese Office Action filed on Mar. 5, 2010 for corresponding CN Application No. 200680036592.6, with English translation.
Response to Chinese Office Action for CN 200680020317.5 dated Sep. 11, 2012, 7 pages with English translation.
Response to Chinese Office Action, filed Jul. 11, 2012 for Chinese Patent Application No. 200680036592.6, with English translation.
Response to CN OA for CN200880003336.6 filed on May 3, 2012, 15 pages.
Response to Communication in EP App. Ser. 07743994.1, dated Dec. 22, 2014, 62 pages.
Response to EESR in EP Application No. 09713617.0, dated Sep. 2, 2011, 12 pages.
Response to EP OA for EP 07806561.2 filed on Apr. 18, 2012, 8 pages.
Response to Examination Report in AU Application No. 2005217325, dated Oct. 26, 2007, 33 pages.
Response to Examination Report in AU Application No. 2005217328, dated Sep. 20, 2007, 6 pages.
Response to Examination Report in AU Application No. 2007288793, dated Mar. 30, 2012, 5 pages.
Response to Examination Report in Australian Patent Application No. 2012246490, dated Jul. 15, 2016, 30 pages.
Response to Examiner's Substantive Report in CL Application No. 2012-00412, dated Nov. 28, 2014, 39 pages (with English translation).
Response to Extended European Search Report in EP Application No. 07793075.8, dated Nov. 8, 2010, 11 pages.
Response to Extended European Search Report in EP Application No. 07805959.9, dated Mar. 29, 2011, 2 pages.
Response to Hearing Notice in IN Application No. 1424/CHENP/2008, dated Sep. 11, 2012, 14 pages.
Response to IL OA for IL 195282 filed on May 28, 2012, 5 pages.
Response to Indian Office Action issued Feb. 2, 2012, dated Jun. 22, 2012, for Application No. 1908/DELNP/2008.
Response to Israeli Office Action filed on Sep. 7, 2010 for the corresponding Israeli Application No. 189589.
Response to Israeli Office Action, filed Jul. 24, 2012 for corresponding Israeli Patent Application No. 189589.
Response to Japanese Office Action dated Jul. 17, 2012 for Japanese Application No. 2007-533350 with English translation.
Response to Japanese Office Action filed on Jan. 9, 2013 for corresponding Japanese Application JP-2007-533350.
Response to Korean Office Action filed on Feb. 24, 2010 for corresponding KR Application No. 10-2008-7005195, with English translation.
Response to Korean Office Action filed on Jul. 29, 2010 for corresponding KR Application No. 10-2008-7005195, with English translation.
Response to Notice of Allowability filed on Dec. 13, 2007 for PH Application No. 1-2003-500266.
Response to Notice of Allowance in U.S. Appl. No. 13/205,328, dated Jul. 8, 2014, 7 pages.
Response to Notice of Incomplete Reply in U.S. Appl. No. 11/892,785, dated Apr. 17, 2008, 7 pages.
Response to Notice of Missing Parts and Preliminary Amendment in U.S. Appl. No. 11/892,785, dated Mar. 17, 2008, 4 pages.
Response to Notice Prior to Examination filed in IL Application No. 217197, filed Jul. 31, 2013, 9 pages (with English translation).
Response to Notice Prior to Examination filed on Apr. 22, 2009 for IL Application No. 181697 (with English translation).

(56) References Cited

OTHER PUBLICATIONS

Response to Notice Prior to Examination filed on Jan. 11, 2009 for IL Application No. 189677 (with English translation).
Response to Notice Prior to Examination in IL Application No. 188670, dated Nov. 22, 2009, 29 pages (with English translation).
Response to Notice Prior to Examination in IL Application No. 197002, dated Oct. 13, 2010, 18 pages (with English translation).
Response to Notice Prior to Examination in IL Application No. 197141, dated Jun. 1, 2010, 22 pages (with English translation).
Response to OA for EP 10015141 filed on Mar. 5, 2012, 47 pages.
Response to Office Action dated Feb. 7, 2013 for CN Application No. 201080030508.6, 17 pages (with English translation).
Response to Office Action dated Jul. 5, 2012 for CN Application No. 200880115011.7 (with English translation).
Response to Office Action dated Nov. 30, 2012 for CN Application No. 200780017371.9, 4 pages (with English translation).
Response to Office Action filed in EP Application No. 04807580.8, dated May 16, 2014, 13 pages.
Response to Office Action filed on Jan. 25, 2013 for CA Application No. 2627598, 9 pages.
Response to Office Action filed on Jul. 11, 2012 for CN Application No. 200880003336.6 (with English translation).
Response to Office Action filed on May 29, 2012 for RU Application No. 2012103471 (with English translation).
Response to Office Action for Australian Application No. 2006309551, filed on Mar. 28, 2012.
Response to Office Action for CA Application No. 2661702, filed Jul. 16, 2013, 13 pages.
Response to Office Action for EP Applciation No. 0870437.6, dated Jan. 2, 2013, 22 pages.
Response to Office Action for IL 199907 filed on Oct. 11, 2010, 4 pages with English translation.
Response to Office Action for Israeli Application No. 205512, filed on Mar. 11, 2012 (with English translation).
Response to Office Action for Israeli Application No. 207089, filed on Mar. 11, 2012, with English translation.
Response to Office Action for MX Application No. MX/a/2012/002011, dated Aug. 29, 2013, 12 pages (with English translation).
Response to Office Action for U.S. Appl. No. 13/322,961, dated Jan. 25, 2013, 22 pages.
Response to Office Action for U.S. Appl. No. 10/420,466 dated Jun. 29, 2005.
Response to Office Action in AU Application No. 2006282456, dated Jul. 16, 2009, 2 pages.
Response to office action in AU Application No. 2007289787, dated Feb. 16, 2012, 27 pages.
Response to office action in AU Application No. 2010285740, dated Oct. 28, 2014, 14 pages.
Response to Office Action in BD Application No. 184/2006, dated Dec. 13, 2007, 2 pages.
Response to Office Action in CA Application No. 2605854, dated Oct. 8, 2009, 18 pages.
Response to Office Action in CA Application No. 2661333, dated Nov. 12, 2013, 18 pages.
Response to Office Action in CA Application No. 2676796, dated Jun. 27, 2014, 18 pages.
Response to Office Action in CA Application No. 2704000, dated Dec. 19, 2014, 13 pages.
Response to Office Action in CA Application No. 2704000, dated Dec. 24, 2015, 11 pages.
Response to Office Action in CA Application No. 2771403, dated Sep. 10, 2014, 11 pages.
Response to Office Action in Canadian Patent Application No. 2704000, dated May 19, 2016, 11 pages.
Response to Office Action in CN Application No. 200680020317.5 filed on Jan. 9, 2014, 7 pages (with English translation).
Response to Office Action in CN Application No. 200680021939.X, dated Jul. 27, 2010, 44 pages (with English translation).
Response to Office Action in CN Application No. 200680021939.X, dated May 20, 2011, 39 pages (with English translation).
Response to Office Action in CN Application No. 200680021939.X, dated Oct. 28, 2010, 40 pages (with English translation).
Response to office action in CN Application No. 200780019200.X, dated Jul. 24, 2012, 49 pages (with English translation).
Response to office action in CN Application No. 200780019520.5, dated Dec. 3, 2010, 28 pages (with English translation).
Response to office action in CN Application No. 200780019520.5, dated Feb. 21, 2011, 7 pages (with English translation).
Response to Office Action in CN Application No. 201180030568.2 filed on Jan. 13, 2014, 46 pages (with English translation).
Response to Office Action in CN Application No. 201180030568.2 filed on May 14, 2014, 10 pages (with English translation).
Response to Office Action in CN Application No. 201280010427.9, dated Jun. 12, 2014, 13 pages (with English translation).
Response to office action in CN Application No. 201280010898.X, dated Nov. 25, 2014, 7 pages (with English translation).
Response to Office Action in EP Application No. 03791389.4, dated Jul. 25, 2014, 75 pages.
Response to office action in EP Application No. 05719973.9, dated Dec. 21, 2011, 150 pages.
Response to office action in EP Application No. 05719973.9, dated May 24, 2011, 26 pages.
Response to office action in EP Application No. 07793075.8, dated May 27, 2011, 17 pages.
Response to Office Action in EP Application No. 08704376.6, dated Apr. 30, 2014, 73 pages.
Response to Office Action in EP Application No. 08846814.5, dated Jul. 24, 2014, 71 pages.
Response to Office Action in European Patent Application No. 12786619.2, dated Apr. 15, 2016, 41 pages.
Response to Office Action in European Patent Application No. 12793322.4, dated Apr. 8, 2016, 10 pages.
Response to office action in ID App. Ser No. W-00 2008 00601, dated Jun. 18, 2012, 3 pages (with English translation).
Response to office action in IL Application No. 188670, dated Aug. 15, 2011, 43 pages (with English translation).
Response to office action in IL Application No. 197002, dated Feb. 29, 2012, 7 pages (with English translation).
Response to office action in IL Application No. 197141, dated Jun. 6, 2012, 10 pages (with English translation).
Response to office action in IL Application No. 217197, dated Nov. 26, 2014, 7 pages (with English translation).
Response to office action in JP Application No. 2008-530917, dated Dec. 13, 2012, 9 pages (with English translation).
Response to office action in JP Application No. P2009-510543, dated Nov. 9, 2009, 12 pages (with English translation).
Response to Office Action in JP Application No. P2009-540099, dated Apr. 28, 2014, 9 pages (with English Translation).
Response to office action in KR Application No. 10-2006-7013907, dated Sep. 28, 2007, 10 pages (with English translation).
Response to office action in KR Application No. 10-2006-7013940, dated Oct. 1, 2007, 20 pages (with English translation).
Response to Office Action in MX Application No. MX/a/2010/008187, dated Feb. 17, 2014, 7 pages (with English translation).
Response to Office Action in MX Application No. MX/a/2010/008187, dated Jun. 25, 2014, 5 pages (with English translation).
Response to Office Action in MX Application No. MX/a/2012/002011 filed on Jan. 16, 2014, 20 pages (with English translation).
Response to Office Action in MX Application No. MX/a/2012/014776, dated Jan. 7, 2015, 20 pages (with English translation).
Response to Office Action in MX Application No. MX/a/2012/014776, dated Jun. 20, 2014, 16 pages (with English translation).
Response to Office Action in MX Application No. MX/a/2013/009931, dated Dec. 9, 2014, 24 pages (with English translation).
Response to office action in NZ Application No. 566793, dated Jan. 17, 2010, 17 pages.
Response to office action in PH Application No. 1-2007-502319, dated Feb. 6, 2012, 19 pages.
Response to office action in PK Application No. 1024/2006, dated Apr. 20, 2009, 14 pages.
Response to office action in PK Application No. 1024/2006, dated Apr. 7, 2008, 17 pages.

(56) References Cited

OTHER PUBLICATIONS

Response to office action in PK Application No. 1024/2006, dated Jan. 29, 2009, 6 pages.
Response to office action in PK Application No. 155/2005, dated Jan. 4, 2008, 34 pages.
Response to office action in PK Application No. 375/2008, dated Apr. 8, 2009, 19 pages.
Response to office action in PK Application No. 375/2008, dated Dec. 20, 2008, 1 page.
Response to office action in PK Application No. 375/2008, dated Sep. 1, 2009, 20 pages.
Response to office action in RU Application No. 2006134254, dated Dec. 15, 2006, 23 pages (with English translation).
Response to office action in RU Application No. 2006134254, dated Nov. 20, 2007, 32 pages (with English translation).
Response to office action in RU Application No. 2008110932, dated Jan. 26, 2009, 29 pages (with English translation).
Response to Office Action in RU Application No. 2012103471, dated Jul. 21, 2014, 7 pages (with English translation).
Response to office action in RU Application No. 2012103471, dated Nov. 18, 2014, 17 pages (with English translation).
Response to Office Action in RU Application No. 2013139556, dated Dec. 25, 2013, 10 pages (with English translation).
Response to Office Action in SG Application No. 201108602-2, dated May 22, 2014, 37 pages.
Response to office action in TW Application No. 095130665, dated May 28, 2012, 379 pages (with English translation).
Response to Office Action in U.S. Appl. No. 13/870,507, dated May 17, 2016, 12 pages.
Response to office action in U.S. Appl. No. 11/508,322, dated Aug. 31, 2009, 11 pages.
Response to office action in U.S. Appl. No. 11/508,322, dated Mar. 18, 2009, 20 pages.
Response to Office Action in U.S. Appl. No. 11/662,425, filed May 20, 2014, 8 pages.
Response to office action in U.S. Appl. No. 12/031,568, dated Aug. 12, 2011, 12 pages.
Response to office action in U.S. Appl. No. 12/031,568, dated Jun. 2, 2010, 13 pages.
Response to Office Action in U.S. Appl. No. 12/039,381, dated Apr. 3, 2014, 7 pages.
Response to office action in U.S. Appl. No. 12/315,291, dated Aug. 18, 2010, 8 pages.
Response to office action in U.S. Appl. No. 12/315,291, dated Feb. 28, 2011, 8 pages.
Response to office action in U.S. Appl. No. 12/558,982, dated Jul. 5, 2011, 21 pages.
Response to Office Action in U.S. Appl. No. 13/805,826, dated Aug. 8, 2014, 9 pages.
Response to Office Action in U.S. Appl. No. 13/923,858, dated Aug. 8, 2014, 24 pages.
Response to Office Action in U.S. Appl. No. 13/983,891, dated Feb. 27, 2014, 6 pages.
Response to Office Action in U.S. Appl. No. 14/002,018, dated Jul. 18, 2014, 8 pages.
Response to Office Action in U.S. Appl. No. 14/002,018, filed May 28, 2014, 7 pages.
Response to office action in VN Application No. 1-2008-00723, dated May 10, 2010, 7 pages (with English translation).
Response to Office Action under 37 C.F.R. §1.111 for U.S. Appl. No. 12/523,495, filed Dec. 7, 2011.
Response to Office Action under 37 C.F.R. §1.111 for U.S. Appl. No. 13/083,338, filed Apr. 8, 2011, 6 pages.
Response to Office Action under 37 C.F.R. §1.111 for U.S. Appl. No. 13/083,338, filed Sep. 6, 2012.
Response to Office Action under 37 C.F.R.S 1.111 and Information Disclosure Statement for U.S. Appl. No. 11/997,719, filed Jul. 3, 2013, 26 pages.
Response to Restriction Requirement for U.S. Appl. No. 11/997,543, filed Mar. 22, 2011.
Response to Restriction Requirement for U.S. Appl. No. 12/301,353, filed Nov. 23, 2010.
Response to Restriction Requirement for U.S. Appl. No. 12/524,754, filed Dec. 1, 2011.
Response to Restriction Requirement in U.S. Appl. No. 11/065,631, dated Nov. 26, 2007, 16 pages.
Response to Restriction Requirement in U.S. Appl. No. 11/892,785, dated Oct. 30, 2009, 16 pages.
Response to Restriction Requirement in U.S. Appl. No. 13/238,085, dated Oct. 4, 2013, 3 pages.
Response to Restriction Response in U.S. Appl. No. 13/805,826, dated Jun. 2, 2014, 2 pages.
Response to the European Search Report for European Application No. 06782407, filed Nov. 8, 2010.
Response to the Office Action for European Application No. 06782407, filed Jan. 23, 2012, 17 pages.
Response to the Office Action issued for IN Application No. 6415/CHENP/2008 filed on Jan. 17, 2014, 16 pages.
Response to the Office Action issued for Japanese Application No. 2007-529565 filed on Feb. 3, 2012, 44 pages with English full translation.
Restriction Requirement for U.S. Appl. No. 11/997,543, dated Feb. 23, 2011.
Restriction Requirement for U.S. Appl. No. 12/092,539, dated Oct. 29, 2010.
Restriction Requirement for U.S. Appl. No. 12/301,353, dated Oct. 29, 2010.
Restriction Requirement for U.S. Appl. No. 12/439,339, dated Jul. 29, 2011.
Restriction Requirement for U.S. Appl. No. 12/524,754, dated Nov. 3, 2011.
Restriction Requirement in U.S. Appl. No. 11/065,631, dated Oct. 25, 2007, 8 pages.
Restriction Requirement in U.S. Appl. No. 11/892,785, dated Oct. 7, 2009, 5 pages.
Restriction Requirement in U.S. Appl. No. 12/359,475, dated Mar. 7, 2011, 5 pages.
Restriction Requirement in U.S. Appl. No. 12/527,633, dated Aug. 13, 2012, 10 pages.
Ribas et al., "Oncolytic Virotherapy Promotes Intratumoral T Cell Infiltration and Improves Anti-PD-1 Immunotherapy," Cell Elsevier, 2017, 170(6):1109-1119, XP085189788.
Roberts et al., "Antiangiogenic and Antitumor Activity of a Selective PDGFR Tyrosine Kinase Inhibitor, CP-673,451", Cancer Research., 65, 957-966, 2005.
Robinson et al, "Characterization of Tumor Size Changes Over Time From the Phase 3 Study of (E7080) Lenvatinib in Differentiated Cancer of the Thyroid (Select)", The Poster, No. 1031P, presented at European Society for Medical Oncology 2014 Congress, Sep. 26-30, 2014, 1 page.
Rosen and Goldberg, "Scatter Factor and Angiogenesis," *Advances in Cancer Research*, 1995, 67:257- 279.
Rowe, R.C. et al. (ed.), Handbook of Pharmaceutical Excipients, 5th ed. Pharmaceutical Press, London, 2006, pp. 336-343.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models1", Cancer Research., 63, 5978-5991, 2003.
Ruggeri et al., "CEP-7055: An orally-active VEGF-R kinase inhibitor with potent anti-angiogenic activity and anti-tumor efficacy against human tumor xenograft growth," AACR American Association Cancer Research., 93rd Annual Meeting, 43:1080, Apr. 6-10, 2002, San Francisco, CA, USA, abstract 5347, 2 pages.
Ruiz-Garcia et al., "Gene expression profiling identifies Fibronectin 1 and CXCL9 as candidate biomarkers for breast cancer screening," British Journal of Cancer, 2010, 102(3):462-468, XP055403533.
Russian Decision of Grant directed at Appl. No. 2008149948115(065561) 16 pages with English translation.
Russian Notice of Allowance in Application No. 2012158142, dated May 5, 2015, 14 pages, with English translation.
Russian Office Action dated Apr. 11, 2012 for Application No. 2012103471, (with English translation).

(56) References Cited

OTHER PUBLICATIONS

Russian Office Action dated Jan. 19, 2005 for Application No. 2003114740 (with English translation).
Russian Office Action dated Jun. 29, 2004 for Application No. 2003114740 (with English translation).
Russian Office Action in Application No. 2012158142, dated Feb. 12, 2015, 21 pages, with English translation.
Russian Response to Office Action in Application No. 2012158142, dated Apr. 13, 2015, with English translation.
Russian Submission Documents in Application No. 2015148193, dated Apr. 27, 2016, 10 pages, with English translation.
Sacher et al., "Biomarkers for the Clinical Use of PD-1/PD-L1 Inhibitors in Non-Small-Cell Lung Cancer: A Review," JAMA Oncology, 2016, 2(9):1217-1222, XP055617261.
Saeki et al., "Concurrent overexpression of Ets-1 and c-Met correlates with a phenotype of high cellular motility in human esophageal cancer," International J Cancer, 2002, 98(1):8-13.
Saito et al., "Angiogenic factors in normal endometrium and endometrial adenocarcinoma," Pathology International, 57: 140-147, 2007.
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Salmon et al., "Anti-angiogenic treatment of gastrointestinal malignancies," Cancer Invest., 23(8):712-726 (2005).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Sandler et al, "Paclitaxel-carboplatin alone or with bevacizumab for non-small-cell lung cancer," N Engl J Med, 355(24):2542-2550, Dec. 14, 2006.
Sandler et al., "Phase III trial of gemcitabine plus cisplatin versus cisplatin alone in patients with locally advanced or metastatic non-small-cell lung cancer," J. Clin. Oncol., 18(1):122-130 (2000).
Sanger et al., "DNA sequencing with chain-terminating inhibitors", Proc. Natl. Acad. Sci. USA 74:5463 (1977).
Santoro et al., "Drug insight: Small-molecule inhibitors of protein kinases in the treatment of thyroid cancer," Nat. Clin. Pract. Endocrinol. Metab., 2(1):42-52 (2006).
Santoro et al., "Minireview: RET: normal and abnormal functions," Endocrinology, 145:5448-5451 (2004).
Santoro et al., "Molecular Mechanisms of RET Activation in Human Cancer," Ann. N.Y. Academy of Sciences, 963:116-121 (2002).
Sattler et al., "Targeting c-Kit mutations: basic science to novel therapies," Leukemia Research, 2004, 28S1:S11-S20.
Scheijen et al., "Tryosine Kinase Oncogenes in Normal Hematopoiesis and Hematological Disease," Oncogene, 21:3314-3333 (2002).
Schlumberger et al, "Lenvatinib versus Placebo in Radioiodine-Refractoly Thyroid Cancer (with supplementary material)", The New England Journal of Medicine 2015; 372, Feb. 12, 2015, p. 621-p. 630.
Schlumberger et al., "A phase 3, multicenter, double-blind, placebo-controlled trial of lenvatinib (E7080) in patients with [131]-refractory differentiated thyroid cancer (SELECT)," Am Soc Clin Oncol., Annual Meeting Abstract LBA6008, 2012, 4 pages.
Schlumberger et al., "A Phase 2 Trial of the Multi-Targeted Kinase Inhibitor Lenvatinib (E7080) in Advanced Medullary Thyroid Cancer (MTC)," 2012 ASCO Annual Meeting, Poster Presentation, Jun. 1-5, 2012.
Schoepp and Conn, "Metabotropic glutamate receptors in brain function and pathology," Trends in Pharmacological Sciences, 1993, pp. 13-20.
Search Report in EP Application No. 09705712.9, dated Aug. 7, 2014, 6 pages.
Search Report in EP Application No. 11798224.9, dated Mar. 21, 2014, 1 page.

Search Report in EP Application No. 11798224.9, dated Mar. 4, 2014, 6 pages.
Search Report in EP Application No. 12774278.1, dated Aug. 14, 2014, 8 pages.
Search Report in EP Application No. 12786619.2, dated Dec. 15, 2014, 6 pages.
Search Report in EP Application No. 16802790.2, dated Oct. 9, 2018, 10 pages.
Search Report in European Patent Application No. 14873998.0, dated May 29, 2017, 6 pages.
Search Report in European Patent Application No. 15836577.5, dated Jun. 28, 2018, 9 pages.
Search Report in European Patent Application No. 16814346.9, dated Nov. 15, 2018, 8 pages.
Search Report in European Patent Application No. 16837135.9, dated Mar. 18, 2019, 10 pages.
Search Report in European Patent Application No. 16837150.8, dated Mar. 22, 2019, 7 pages.
Search Report in European Patent Application No. 17782552.8 dated Nov. 12, 2019, 4 pages.
Search Report in European Patent Application No. 18197141.7, dated Jan. 21, 2019, 6 pages.
Search Report in European Patent Application No. 18751614.1, dated Nov. 5, 2020, 8 pages.
Search Report in European Patent Application No. 18801285.0, dated Jan. 20, 2021, 6 pages.
Search Report in European Patent Application No. 19151846.3, dated Jun. 3, 2019, 13 pages.
Search Report in European Patent Application No. 20207489.4, dated Mar. 10, 2021, 7 pages.
Second Preliminary Amendment and Response to Restriction Requirement for U.S. Appl. No. 12/092,539, filed Nov. 22, 2010.
Sekido et al., "Preferential Expression of c-kit Protooncogene Transcripts in Small Cell Lung Cancer," Cancer Res., 51:2416-2418 (1991).
Sennino and McDonald, "Controlling escape from angiogenesis inhibitors", Nature Rev Cancer, 12:699-709, Oct. 2012.
Sharma et al., "Thyroid Cancer," Feb. 18, 2015, pp. 1-16.
Sherman et al., "A phase II trial of the multitargeted kinase inhibitor E7080 in advanced radioiodine (RAI)-refractory differentiated thyroid cancer (DTC)," Journal of Clinical Oncology, 29(15):5503A, May 2011.
Shiang et al., "Mutations in the transmembrane domain of FGFR3 cause the most common genetic form of dwarfism, achondroplasia," Cell., 78:335-342 (1994).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Shimizu et al., "Orally active anti-proliferation agents: novel diphenylamine derivatives as FGF-R2 autophosphorylation inhibitors," Bioorganic and Medicinal Chemistry Letters, 14(4):875-879 (2004).
Shirai, Y., et al., "Role of low-substituted hydroxypropylcellulose in dissociation and bioavalability of novel fine granule system for masking bitter taste," Biol. Pharm. Bull, 17(3): 427-431 (1994).
Shitashige et al., "Traf2- and Nck-Interacting Kinase Is Essential for Wnt Signaling and Colorectal Cancer Growth," Cancer Res., 2010, 70:5024-5033.
Shumaker et al., "Effect of lenvatinib (E7080) on the QTc interval: results from a thorough QT study in healthy volunteers," Cancer Chemother Pharmacol., published online Mar. 23, 2014, 9 pages (with English abstract).
Siegel et al., "Sorafenib: Where Do We Go from Here?," Hepatology, 52:360-369 (2010).
Siemeister et al., "ZK304709, the oral Multitarget Tumor Growth Inhibitor™, acts via inihibition of cell cycle progression and tumor-induced angiogenesis," Proceedings of the American Association for Cancer Research, 46, (Abstract 5842), 2005, 3 pages.
Sihto et al., "KIT and platelet-derived growth factor receptor alpha tyrosine kinase gene mutations and KIT amplifications in human solid tumors," Journal of Clinical Oncology, 23(1):49-57 (2005).

(56) References Cited

OTHER PUBLICATIONS

Singaporean Submission Documents in Application No. 11201706630U, dated Aug. 21, 2018, 9 pages.
Soh et al, "Neutralizing vascular endothelial growth factor activity inhibits thyroid cancer growth in vivo", Surgery, 2000:1059-1066.
Sondergaard et al., Differential sensitivity of melanoma cell lines with $BRAF^{V600E}$ mutation to the specific Raf inhibitor PLX4032, J Translational Med., 2010, 8:39, 11 pages.
Spacey et al., "Indolocarbazoles, Potent and Selective Inhibitors of Platelet-Derived Growth Factor Receptor Autophosphorylation," Biochemical Pharmacology, 55:261-271 (1998).
St. Bernard et al., "Fibroblast Growth Factor Receptors as Molecular Targets in Thyroid Carcinoma," Endocrinology, Mar. 2005, 146(3):1145-1153.
Stahl and Wermuth, "Handbook of Pharmaceutical Salts: Properties, selection, and use," 2002, pp. 117-122.
Stahl et al., "Handbook of Pharmaceutical Salts, Properties, Selection and Use," Publisher—Wiley-VCH-2002, Chapters 5, 6, 7 and 8, 2002, 110 pages.
Stahl et al., "Handbook of Pharmaceutical Salts, Properties, Selection and Use," Publisher—Wiley-VCH-2002, Cover Pages 2002, 6 pages.
Stahl, "Preparation of water-soluble compounds through salt formation," edited by Camille G. Wermuth, The Practice of Medicinal Chemistry Second Edition, 2003, 601-615.
Stinchcombe "Targeted therapy of advanced non-small cell lung cancer: the role of bevacizumab," Biologics: Targets & Therapy 1(3):185-194, 2007.
Stinchcombe and Scoinski, "Bevacizumab in the treatment of non-small-cell lung cancer," Oncogene 26:3691-3698, May 28, 2007.
Stjepanovic and Capdevila, "Multikinase inhibitors in the treatment of thyroid cancer: specific role of lenvatinib," Biologics: Targets and Therapy, 8:129-139, Aug. 2014.
Strohmeyer et al., "Expression of the hst-1 and c-kit Protoonocogenes in Human Testicular Germ Cell Tumors," Cancer Res., 51:1811-1816 (1991).
Submission Document(s) Before the Patent Office for IL Application No. 200090, dated Dec. 23, 2012, 16 pages, with English translation.
Submission Document Before the Patent Office dated Apr. 22, 2013 for IL Application No. 207089, 7 pages (with English translation).
Submission Document Before the Patent Office dated Mar. 14, 2013 for IL Application No. 205512, 12 pages (with English translation).
Submission Document Before the Patent Office for CL Application No. 2012-00412, dated Aug. 31, 2012, 6 pages (with English translation).
Submission Document Before the Patent Office for EP Application No. 03791389.4, dated Dec. 20, 2012, 4 pages.
Submission Document Before the Patent Office for EP Application No. 08846814.5, dated Jan. 3, 2013, 102 pages.
Submission Document Before the Patent Office for EP Application No. 8704376.6, dated Jan. 2, 2013, 22 pages.
Submission Document Before the Patent Office re Observation dated Feb. 16, 2013 for CN Application No. 200980103218.7, 8 pages (with English translation).
Submission Document Before the Patent Office re RCE in U.S. Appl. No. 13/205,328, dated Sep. 10, 2013, 12 pages.
Submission Document in Algerian Patent Application No. 120036, dated Feb. 22, 2018, 16 pages (English Translation).
Submission Document in Argentine Patent Application No. P110100513, dated Apr. 6, 2020, 21 pages (with English Translation).
Submission Document in Argentine Patent Application No. P110100513, dated Aug. 2, 2019, 52 pages (with English Translation).
Submission Document in Argentine Patent Application No. P20150102731, dated Oct. 7, 2020, 67 pages (with English Translation).
Submission Document in Australian Patent Application No. 2013364953, dated Apr. 13, 2017, 15 pages.
Submission Document in Australian Patent Application No. 2014266223, dated May 22, 2020, 14 pages.
Submission Document in Australian Patent Application No. 2014371148, date Jul. 10, 2018, 8 pages.
Submission Document in Australian Patent Application No. 2015309862, dated Jul. 3, 2020, 30 pages.
Submission Document in Australian Patent Application No. 2015309862, dated Mar. 20, 2020, 28 pages.
Submission Document in Australian Patent Application No. 2016224583, dated Mar. 2, 2021, 53 pages.
Submission Document in Australian Patent Application No. 2016224583, dated May 11, 2021, 7 pages.
Submission Document in Australian Patent Application No. 2016308390, dated May 11, 2021, 9 pages.
Submission Document in Australian Patent Application No. 2016309356, dated Apr. 27, 2021, 7 pages.
Submission Document in Australian Patent Application No. 2017249459, dated Mar. 17, 2021, 36 pages.
Submission Document in Brazilian Patent Application No. BR112012003592-4, dated Apr. 13, 2020, 13 pages (with English Translation).
Submission Document in Brazilian Patent Application No. BR112012032462-4, dated Apr. 16, 2021, 29 pages (with English Translation).
Submission Document in Brazilian Patent Application No. BR1120190141278, dated Dec. 16, 2020, 16 pages (with English Translation).
Submission Document in Brazilian Patent Application No. BR1120190230645, dated Apr. 28, 2021. 148 pages (with English Translation).
Submission Document in Brazilian Patent Application No. PI0418200-6, dated Jul. 10, 2019, 16 pages (with English Translation).
Submission Document in Brazilian Patent Application No. PI0418200-6, dated Jun. 14, 2021, 10 pages (with English Translation).
Submission Document in Brazilian Patent Application No. PI0418200-6, dated Oct. 20, 2020, 112 pages (with English Translation).
Submission Document in Brazilian Patent Application No. PI0906576-08, dated Dec. 4, 2019, 124 pages (with English Translation).
Submission Document in Brazilian Patent Application No. PI0906576-08, dated May 28, 2020, 61 pages (with English Translation).
Submission Document in Canadian Patent Application No. 201380054667.3, dated Apr. 12, 2017, 9 pages.
Submission Document in Canadian Patent Application No. 2957005, dated Feb. 8, 2021, 19 pages.
Submission Document in Canadian Patent Application No. 2957005, dated May 12, 2021, 16 pages.
Submission Document in Canadian Patent Application No. 2978226, dated Sep. 21, 2020, 12 pages.
Submission Document in Chilean Patent Application No. 2012-00412, dated Mar. 6, 2017, 9 pages (English Translation).
Submission Document in Chilean Patent Application No. 2012-00412, dated Mar. 21, 2019, 24 pages.
Submission Document in Chilean Patent Application No. 201601419, dated Jul. 13, 2018, 30 pages (English Translation).
Submission Document in Chinese Patent Application No. 201480026871.9, dated May 8, 2017, 10 pages (English Translation).
Submission Document in Chinese Patent Application No. 201480067017.7, dated June, 5, 2017, 7 pages, (English Translation).
Submission Document in Chinese Patent Application No. 201510031628.2, dated Apr. 30, 2019, 7 pages (with English Translation).
Submission Document in Chinese Patent Application No. 201510031628.2, dated Oct. 10, 2018, 8 pages (English Translation).
Submission Document in Chinese Patent Application No. 201580042365.3, dated Apr. 27, 2021, 22 pages (with English Translation).
Submission Document in Chinese Patent Application No. 201580042365.3, dated Jul. 6, 2020, 170 pages (with English Translation).

(56) References Cited

OTHER PUBLICATIONS

Submission Document in Chinese Patent Application No. 201580042365.3, dated Sep. 18, 2019, 26 pages (with English Translation).
Submission Document in Chinese Patent Application No. 201680009824.2, dated Apr. 7, 2020, 28 pages (with English Translation).
Submission Document in Chinese Patent Application No. 201680009824.2, dated Nov. 20, 2020, 49 pages (with English Translation).
Submission Document in Chinese Patent Application No. 201680027234.2, dated Apr. 29, 2020, 16 pages (with English Translation).
Submission Document in Chinese Patent Application No. 201680027234.2, dated Dec. 25, 2020, 12 pages (with English Translation).
Submission Document in Chinese Patent Application No. 201680027234.2, dated Dec. 7, 2020, 39 pages (with English Translation).
Submission Document in Chinese Patent Application No. 201680027234.2, dated Mar. 6, 2019, 16 pages (with English Translation).
Submission Document in Chinese Patent Application No. 201680027234.2, dated Oct. 21, 2019, 19 pages (with English Translation).
Submission Document in Chinese Patent Application No. 201680044979.X, dated Dec. 7, 2020, 10 pages (with English Translation).
Submission Document in Chinese Patent Application No. 201680044979.X, dated Jul. 3, 2020, 14 pages (with English Translation).
Submission Document in Chinese Patent Application No. 201680046598.5, dated Oct. 13, 2020, 9 pages (with English Translation).
Submission Document in Chinese Patent Application No. 201780020786.5, dated Mar. 18, 2019, 35 pages (with English Translation).
Submission Document in Chinese Patent Application No. 201880028701.2, dated Jun. 4, 2020, 110 pages (with English Translation).
Submission Document in CL Application No. 2012-00412, dated Aug. 12, 2014, 2 pages (with English translation).
Submission Document in Colombian Patent Application No. 16147681, date Oct. 30, 2017, 39 pages (English Translation).
Submission Document in Egyptian Patent Application No. D1 PCT 283/2012, dated Jul. 20, 2020, 17 pages (with English Translation).
Submission Document in Egyptian Patent Application No. PCT 283/2012, dated Jan. 21, 2020, 11 pages (with English Translation).
Submission Document in Egyptian Patent Application No. PCT 283/2012, dated Jul. 17, 2019, 14 pages (English Translation).
Submission Document in Egyptian Patent Application No. PCT 283/2012, dated Jun. 28, 2021, 3 pages (with English Translation).
Submission Document in Egyptian Patent Application No. PCT 283/2012, dated May 9, 2018, 13 pages (English Translation).
Submission Document in European Patent Application No. 08846814.5, dated Mar. 31, 2017, 45 pages.
Submission Document in European Patent Application No. 12793322.4, dated Apr. 19, 2018, 8 pages.
Submission Document in European Patent Application No. 14873998.0, dated Dec. 13, 2017, 11 pages.
Submission Document in European Patent Application No. 16755489.8, dated Feb. 7, 2019, 10 pages.
Submission Document in European Patent Application No. 16755489.8, dated Jul. 16, 2020, 5 pages.
Submission Document in European Patent Application No. 16802790.2, Jan. 28, 2020, 12 pages.
Submission Document in European Patent Application No. 16814346.9, dated Feb. 22, 2019, 9 pages.
Submission Document in European Patent Application No. 16837135.9, dated Aug. 27, 2019, 21 pages.
Submission Document in European Patent Application No. 16837135.9, dated Jan. 20, 2021, 6 pages.
Submission Document in European Patent Application No. 16837135.9, dated Sep. 18, 2018, 2 pages.
Submission Document in European Patent Application No. 16837150.8, dated Aug. 28, 2019, 13 pages.
Submission Document in European Patent Application No. 16837150.8, dated Aug. 7, 2020, 6 pages.
Submission Document in European Patent Application No. 16837150.8, dated Sep. 19, 2018, 2 pages.
Submission Document in European Patent Application No. 17782552.8, dated Jun. 5, 2020, 4 pages.
Submission Document in European Patent Application No. 18197141.7, Aug. 13, 2019, 41 pages.
Submission Document in European Patent Application No. 18751614.1, dated Dec. 18, 2020, 6 pages.
Submission Document in European Patent Application No. 19151846.3, dated Feb. 10, 2020, 27 pages.
Submission Document in European Patent Application No. 19151846.3, dated Nov. 17, 2020, 9 pages.
Submission Document in Gulf Cooperation Council Patent Application No. GC2011-17812, dated Oct. 28, 2019, 3 pages (with English Translation).
Submission Document in Gulf Cooperation Council Patent Application No. GC2015-29939, dated May 21, 2018, 6 pages (English Translation).
Submission Document in Gulf Cooperation Council Patent Application No. GC2015-29939, dated Sep. 26, 2019, 17 pages (with English Translation).
Submission Document in Gulf Cooperation Council Patent Application No. GC2015-40053, dated Apr. 22, 2021, 10 pages (with English Translation).
Submission Document in Indian Patent Application No. 10502/CHENP/2012, dated Apr. 26, 2019, 1 page.
Submission Document in Indian Patent Application No. 10502/CHENP/2012, dated Jul. 17, 2019, 13 pages.
Submission Document in Indian Patent Application No. 10502/CHENP/2012, dated May 3, 2018, 10 pages (English Translation).
Submission Document in Indian Patent Application No. 1511/CHENP/2009, dated Feb. 20, 2020, 49 pages.
Submission Document in Indian Patent Application No. 1511/CHENP/2009, dated Jan. 27, 2021, 72 pages.
Submission Document in Indian Patent Application No. 1511/CHENP/2009, dated Mar. 18, 2021, 79 pages.
Submission Document in Indian Patent Application No. 1511/CHENP/2009, dated Oct. 29, 2019, 83 pages.
Submission Document in Indian Patent Application No. 201747004829, dated Apr. 16, 2020, 29 pages.
Submission Document in Indian Patent Application No. 201747004829, dated Feb. 4, 2020, 24 pages.
Submission Document in Indian Patent Application No. 201747028834, dated May 13, 2020, 21 pages.
Submission Document in Indian Patent Application No. 201747040368, dated Apr. 1, 2021, 38 pages.
Submission Document in Indian Patent Application No. 201847003846, dated May 29, 2020, 39 pages.
Submission Document in Indian Patent Application No. 201847004787, dated Aug. 21, 2020, 6 pages.
Submission Document in Indian Patent Application No. 201947022655, dated Apr. 16, 2021, 9 pages.
Submission Document in Indian Patent Application No. 201947044328, dated May 10, 2021, 95 pages.
Submission Document in Indian Patent Application No. 2371/CHENP/2012, dated Apr. 19, 2018, 21 pages (English Translation).
Submission Document in Indian Patent Application No. 2371/CHENP/2012, dated Aug. 19, 2020, 39 pages.
Submission Document in Indian Patent Application No. 2371/CHENP/2012, dated Aug. 21, 2018, 1 page (English Translation).
Submission Document in Indian Patent Application No. 2371/CHENP/2012, dated Aug. 21, 2019, 9 pages.
Submission Document in Indian Patent Application No. 2371/CHENP/2012, dated Jan. 8, 2018, 10 pages (English Translation).

(56) References Cited

OTHER PUBLICATIONS

Submission Document in Indian Patent Application No. 2371/CHENP/2012, dated Jan. 11, 2019, 31 pages.
Submission Document in Indian Patent Application No. 2371/CHENP/2012, dated Jan. 28, 2021, 74 pages.
Submission Document in Indian Patent Application No. 2371/CHENP/2012, dated Jun. 15, 2018, 14 pages (English Translation).
Submission Document in Indian Patent Application No. 2371/CHENP/2012, dated Jun. 5, 2019, 15 pages.
Submission Document in Indian Patent Application No. 2371/CHENP/2012, dated Mar. 24, 2020, 121 pages.
Submission Document in Indian Patent Application No. 2371/CHENP/2012, dated Oct. 22, 2018, 276 pages (English Translation).
Submission Document in Indian Patent Application No. 2371/CHENP/2012, dated Sep. 12, 2018, 18 pages (English Translation).
Submission Document in Indian Patent Application No. 2793/CHENP/2013, dated Apr. 20, 2018, 4 pages (English Translation).
Submission Document in Indian Patent Application No. 2793/CHENP/2013, dated Dec. 13, 2017, 10 pages (English Translation).
Submission Document in Indian Patent Application No. 3334/CHENP/2010, dated Jul. 26, 2017, 59 pages (English Translation).
Submission Document in Indian Patent Application No. 6415/CHENP/2008, dated Apr. 18, 2017, 317 pages (English Translation).
Submission Document in Indian Patent Application No. 6971/CHENP/2015, dated Mar. 4, 2020, 10 pages.
Submission Document in Indian Patent Application No. 7026/CHENP/2013, dated Dec. 16, 2020, 682 pages.
Submission Document in Indian Patent Application No. 7026/CHENP/2013, dated Jul. 9, 2018, 15 pages.
Submission Document in International Patent Application No. PCT/US2019/031967, dated Jul. 8, 2019, 5 pages.
Submission Document in Israeli Patent Application No. 242519, dated Nov. 29, 2017, 13 pages (English Translation).
Submission Document in Israeli Patent Application No. 250454, dated Dec. 2, 2018, 5 pages (with English Translation).
Submission Document in Israeli Patent Application No. 253946, dated Dec. 10, 2020, 5 pages (with English Translation).
Submission Document in Israeli Patent Application No. 253946, dated Feb. 5, 2019, 6 pages.
Submission Document in Israeli Patent Application No. 255564, dated Dec. 10, 2018, 4 pages.
Submission Document in Israeli Patent Application No. 255564, dated Dec. 9, 2019, 16 pages (with English Translation).
Submission Document in Israeli Patent Application No. 257292, dated Apr. 16, 2019, 6 pages (with English Translation).
Submission Document in Israeli Patent Application No. 257292, dated Apr. 29, 2021, 6 pages (with English Translation).
Submission Document in Israeli Patent Application No. 257433, dated Apr. 16, 2019, 6 pages (with English Translation).
Submission Document in Israeli Patent Application No. 262076, Request for Delayed Examination, dated Sep. 22, 2020, 3 pages (with English Translation).
Submission Document in Israeli Patent Application No. 262076, Section 18 Requirements, dated Sep. 22, 2020, 4 pages (with English Translation).
Submission Document in Israeli Patent Application No. 267159, dated May 28, 2020, 4 pages (with English Translation).
Submission Document in Israeli Patent Application No. 270317, dated Dec. 16, 2020, 14 pages (with English Translation).
Submission Document in Japanese Patent Application No. P2016-545564, dated Dec. 19, 2019, 23 pages (with English Translation).
Submission Document in Japanese Patent Application No. P2017-502388, dated Apr. 3, 2020, 13 pages (with English Translation).
Submission Document in Japanese Patent Application No. P2017-502388, dated Jul. 17, 2020, 9 pages (with English Translation).
Submission Document in Japanese Patent Application No. P2017-535551, dated Aug. 12, 2020, 8 pages (with English Translation).
Submission Document in Japanese Patent Application No. P2017-546133, dated Apr. 2, 2019, 7 pages (with English Translation).
Submission Document in Japanese Patent Application No. P2018-567437, dated Jul. 30, 2019, 15 pages (with English Translation).
Submission Document in Jordan Patent Application No. 225/2020, dated Jan. 10, 2021, 106 pages (with English Translation).
Submission Document in Jordan Patent Application No. 55/2011, dated Apr. 9, 2017, 7 pages (English Translation).
Submission Document in Jordan Patent Application No. 55/2011, dated Mar. 29, 2017, 5 pages (English Translation).
Submission Document in Korean Patent Application 10-2017-7032771, dated Jan. 8, 2018, 11 pages (English Translation).
Submission Document in Korean Patent Application No. 10-2015-7032202, dated May 19, 2020, 23 pages (with English Translation).
Submission Document in Korean Patent Application No. 10-2017-7003226, dated Jul. 26, 2021, 17 pages (with English Translation).
Submission Document in Korean Patent Application No. 10-2017-7027616, dated Oct. 20, 2020, 18 pages (with English Translation).
Submission Document in Korean Patent Application No. 10-2019-7032983, dated May 6, 2021, 41 pages (with English Translation).
Submission Document in Malaysian Patent Application No. PI2016702025, dated Oct. 4, 2018, 2 pages.
Submission Document in Mexican Patent Application No. MX/a/2015/015605, dated Jun. 25, 2019, 11 pages (with English Translation).
Submission Document in Mexican Patent Application No. MX/a/2017/010474, dated Jan. 25, 2021, 5 pages (with English Translation).
Submission Document in Mexican Patent Application No. MX/a/2017/010474, dated Jun. 11, 2021, 25 pages (with English Translation).
Submission Document in Mexican Patent Application No. MX/a/2017/010474, dated Oct. 8, 2020, 21 pages (with English Translation).
Submission Document in Mexican Patent Application No. MX/a/2017/014540, dated Apr. 15, 2021, 16 pages (with English Translation).
Submission Document in Mexican Patent Application No. MX/a/2018/001439, dated Feb. 4, 2020, 10 pages (with English Translation).
Submission Document in Mexican Patent Application No. MX/a/2018/001439, dated Sep. 24, 2020, 10 pages (with English Translation).
Submission Document in Mexican Patent Application No. MX/a/2018/001658, dated Jan. 8, 2020, 5 pages (with English Translation).
Submission Document in Mexican Patent Application No. MX/a/2018/012193, dated Dec. 3, 2020, 48 pages (with English Translation).
Submission Document in Mexican Patent Application No. MX/a/2018/012193, dated Jul. 1, 2021, 48 pages (with English Translation).
Submission Document in Mexican Patent Application No. MX/a/2019/006504, dated Oct. 23, 2020, 14 pages (with English Translation).
Submission Document in MX Application No. MX/a/2014/010594, dated Sep. 4, 2014, 70 pages (with English translation).
Submission Document in MY Application No. PI2011700172, dated Nov. 4, 2014, 3 pages.
Submission Document in New Zealand Patent Application No. 714049, dated Dec. 16, 2019, 13 pages.
Submission Document in New Zealand Patent Application No. 714049, dated Mar. 13, 2019, 7 pages.
Submission Document in New Zealand Patent Application No. 714049, dated Mar. 18, 2020, 1 page.
Submission Document in Pakistani Patent Application No. 907/2014, dated Nov. 23, 2016, 6 pages (English Translation).
Submission Document in PH App Ser. No. 1-2011-502441, dated May 22, 2015, 25 pages.
Submission Document in Russian Patent Application No. 2015148193, dated Mar. 23, 2018, 17 pages (English Translation).
Submission Document in Russian Patent Application No. 2016122867, dated Aug. 31, 2018, 8 pages.

(56) References Cited

OTHER PUBLICATIONS

Submission Document in Russian Patent Application No. 2017104496, dated Apr. 24, 2020, 42 pages (with English Translation).
Submission Document in Russian Patent Application No. 2017128583, dated Mar. 13, 2020, 18 pages (with English Translation).
Submission Document in Russian Patent Application No. 2017139090, dated Dec. 25, 2020, 16 pages (with English Translation).
Submission Document in Russian Patent Application No. 2017139090, dated Feb. 6, 2020, 13 pages (with English Translation).
Submission Document in Russian Patent Application No. 2017139090, dated Jul. 2, 2020, 14 pages (with English Translation).
Submission Document in Russian Patent Application No. 2018103737, dated Apr. 3, 2020, 9 pages (with English Translation).
Submission Document in Russian Patent Application No. 2018103737, dated Dec. 26, 2019, 10 pages (with English Translation).
Submission Document in Russian Patent Application No. 2018104697, dated Jan. 20, 2020, 8 pages (with English Translation).
Submission Document in Russian Patent Application No. 2018134943, dated Sep. 24, 2020, 46 pages (with English Translation).
Submission Document in Russian Patent Application No. 2019120680, dated Mar. 17, 2021, 10 pages (with English Translation).
Submission Document in Singaporean Patent Application No. 10202100272R, dated Jan. 11, 2021, 43 pages.
Submission Document in Singaporean Patent Application No. 11201700855X, dated Jun. 11, 2019, 33 pages.
Submission Document in Singaporean Patent Application No. 11201706630U, dated Feb. 17, 2020, 12 pages.
Submission Document in Singaporean Patent Application No. 11201709335X, dated Sep. 19, 2019, 5 pages.
Submission Document in Singaporean Patent Application No. 11201801083U, dated Aug. 3, 2021, 9 pages.
Submission Document in Singaporean Patent Application No. 11201801083U, dated Jan. 6, 2020, 10 pages.
Submission Document in Singaporean Patent Application No. 11201904020S, dated Jan. 31, 2020, 14 pages.
Submission Document in Singaporean Patent Application No. 11201904020S, dated Jul. 1, 2021, 13 pages.
Submission Document in Sri Lankan Patent Application No. 16523, dated Oct. 10, 2019, 3 pages.
Submission Document in Taiwanese Patent Application No. 103144928, dated Sep. 5, 2018, 32 pages (English Translation).
Submission Document in Taiwanese Patent Application No. 104127982, dated Feb. 10, 2020, 6 pages (with English Translation).
Submission Document in Taiwanese Patent Application No. 104127982, dated Oct. 30, 2019, 26 pages (with English Translation).
Submission Document in Thailand Patent Application No. 1201000221, dated Mar. 12, 2018, 3 pages (English Translation).
Submission Document in U.S. Appl. No. 13/870,507, dated Apr. 11, 2017, 4 pages.
Submission Document in U.S. Appl. No. 13/923,858, dated Jan. 2, 2019, 11 pages.
Submission Document in U.S. Appl. No. 13/923,858, dated Jun. 14, 2021, 7 pages.
Submission Document in U.S. Appl. No. 13/923,858, dated May 13, 2020, 8 pages.
Submission Document in U.S. Appl. No. 13/923,858, dated Nov. 4, 2020, 6 pages.
Submission Document in U.S. Appl. No. 13/923,858, dated Oct. 28, 2019, 2 pages.
Submission Document in U.S. Appl. No. 13/923,858, dated Sep. 5, 2019, 11 pages.
Submission Document in U.S. Appl. No. 14/122,339, date Jun. 12, 2017, 5 pages.
Submission Document in U.S. Appl. No. 14/122,339, dated Mar. 1, 2018, 15 pages.
Submission Document in U.S. Appl. No. 14/122,339, dated Mar. 27, 2017, 14 pages.
Submission Document in U.S. Appl. No. 14/890,207, dated Feb. 14, 2019, 1 page.
Submission Document in U.S. Appl. No. 14/890,207, dated Sep. 21, 2018, 40 pages.
Submission Document in U.S. Appl. No. 15/460,629, dated Aug. 5, 2019, 2 pages.
Submission Document in U.S. Appl. No. 15/460,629, dated Nov. 28, 2018, 2 pages.
Submission Document in U.S. Appl. No. 15/503,108, dated Apr. 17, 2018, 5 pages.
Submission Document in U.S. Appl. No. 15/503,108, dated Aug. 9, 2018, 15 pages.
Submission Document in U.S. Appl. No. 15/503,108, dated May 28, 2019, 4 pages.
Submission Document in U.S. Appl. No. 15/503,108, dated Nov. 28, 2018, 11 pages.
Submission Document in U.S. Appl. No. 15/550,124, dated Mar. 14, 2018, 3 pages.
Submission Document in U.S. Appl. No. 15/554,577, dated Aug. 31, 2020, 21 pages.
Submission Document in U.S. Appl. No. 15/554,577, dated Jul. 3, 2019, 35 pages.
Submission Document in U.S. Appl. No. 15/554,577, dated May 24, 2021, 15 pages.
Submission Document in U.S. Appl. No. 15/573,197, dated Jun. 15, 2020, 21 pages.
Submission Document in U.S. Appl. No. 15/748,980, dated Aug. 23, 2019, 10 pages.
Submission Document in U.S. Appl. No. 15/748,980, dated Feb. 15, 2019, 3 pages.
Submission Document in U.S. Appl. No. 15/748,980, dated Oct. 28, 2020, 8 pages.
Submission Document in U.S. Appl. No. 15/750,712, dated Apr. 9, 2021, 5 pages.
Submission Document in U.S. Appl. No. 15/750,712, dated Feb. 25, 2019, 1 page.
Submission Document in U.S. Appl. No. 15/750,712, dated Jan. 17, 2020, 18 pages.
Submission Document in U.S. Appl. No. 15/750,712, dated Jun. 27, 2019, 26 pages.
Submission Document in U.S. Appl. No. 15/750,712, dated Oct. 20, 2020, 53 pages.
Submission Document in U.S. Appl. No. 15/750,712, dated Oct. 7, 2019, 15 pages.
Submission Document in U.S. Appl. No. 15/934,242, dated Apr. 22, 2020, 6 pages.
Submission Document in U.S. Appl. No. 15/934,242, dated Dec. 9, 2020, 13 pages.
Submission Document in U.S. Appl. No. 15/934,242, dated Jul. 20, 2021, 7 pages.
Submission Document in U.S. Appl. No. 15/934,242, dated Mar. 23, 2018, 10 pages.
Submission Document in U.S. Appl. No. 16/038,710, dated Apr. 1, 2021, 5 pages.
Submission Document in U.S. Appl. No. 16/038,710, dated Feb. 8, 2019, 5 pages.
Submission Document in U.S. Appl. No. 16/038,710, dated Jan. 30, 2020, 3 pages.
Submission Document in U.S. Appl. No. 16/038,710, dated Jul. 9, 2021, 7 pages.
Submission Document in U.S. Appl. No. 16/038,710, dated Oct. 22, 2019, 46 pages.
Submission Document in U.S. Appl. No. 16/038,710, dated Sep. 29, 2020, 5 pages.
Submission Document in U.S. Appl. No. 16/092,245, dated Jan. 22, 2020, 17 pages.
Submission Document in U.S. Appl. No. 16/092,245, dated Mar. 31, 2021, 4 pages.
Submission Document in U.S. Appl. No. 16/229,805, dated May 30, 2019, 11 pages.
Submission Document in U.S. Appl. No. 16/465,277, dated Jun. 11, 2020, 16 pages.
Submission Document in U.S. Appl. No. 16/559,293, dated Jun. 2, 2020, 9 pages.

(56) References Cited

OTHER PUBLICATIONS

Submission Document in U.S. Appl. No. 16/809,301, dated Jun. 22, 2021, 6 pages.
Submission Document in U.S. Appl. No. 17/022,675, dated Oct. 20, 2020, 10 pages.
Submission Document in U.S. Appl. No. 17/022,675, dated Sep. 16, 2020, 85 pages.
Submission Document in U.S. Appl. No. 17/228,025, dated Jun. 15, 2021, 10 pages.
Submission Document in U.S. Appl. No. 17/228,025, dated Jun. 24, 2021, 3 pages.
Submission Document in Vietnamese Patent Application No. 1-2016-02104, dated Jun. 5, 2018, 18 pages (English Translation).
Submission Document re figures in AR Application No. P110100513, dated Oct. 22, 2014, 3 pages.
Submission Document re Petition on Oct. 2, 2013 in CL Application No. 2012-00412, 22 pages (with English translation).
Submission Document re RCE and Amendment in U.S. Appl. No. 12/031,568, dated Oct. 26, 2010, 23 pages.
Submission Document re RCE and Information Disclosure Statement in U.S. Appl. No. 11/065,631, dated Oct. 8, 2008, 7 pages.
Submission Document re RCE and Information Disclosure Statement in U.S. Appl. No. 12/558,982, dated May 9, 2012, 36 pages.
Submission Document re RCE and Information Disclosure Statement on Oct. 18, 2013, in U.S. Appl. No. 12/524,754, 17 pages.
Submission Document re RCE and Information Disclosure Statement on Sep. 19, 2013 in U.S. Appl. No. 12/741,682, 19 pages.
Submission Document re RCE in U.S. Appl. No. 12/031,568, dated Aug. 30, 2012, 12 pages.
Submission Document re RCE in U.S. Appl. No. 12/031,568, dated Jan. 18, 2012, 11 pages.
Submission Document re RCE in U.S. Appl. No. 12/558,982, dated Nov. 29, 2011, 13 pages.
Submission Document re RCE in U.S. Appl. No. 12/741,682, dated Aug. 14, 2014, 1 page.
Submission Documents Before the Patent Office for CN Application No. 201080030508.6, dated May 27, 2013, 7 pages (with English translation).
Submission Documents Before the Patent Office for GC Patent Application No. GC2011-17812, dated Oct. 24, 2018, 13 pages.
Submission Documents Before the Patent Office for KR Application No. 10-2009-7017694, dated Jan. 18, 2013, 22 pages, with English translation.
Submission Documents Before the Patent Office for U.S. Appl. No. 12/741,682, dated May 17, 2013, 16 pages.
Submission Documents in Canadian Patent Application No. 2828946, dated Feb. 5, 2016, 6 pages.
Submission Documents in Chinese Patent Application No. 201380054667.3, dated Nov. 17, 2016, 8 pages (English Translation).
Submission Documents in Chinese Patent Application No. 201480026871.9, dated Nov. 14, 2016, 11 pages (English Translation).
Submission Documents in Chinese Patent Application No. 201510031628.2, dated Nov. 29, 2016, 8 pages (English Translation).
Submission Documents in European Patent Applciaiton No. 08846814.5, dated Mar. 2, 2017, 18 pages.
Submission Documents in European Patent Application No. 13865671.5, dated Jul. 7, 2016, 3 pages.
Submission Documents in European Patent Application No. 14727633.1, dated Feb. 2, 2017, 12 pages.
Submission Documents in European Patent Application No. 14727633.1, dated Jul. 18, 2016, 8 pages.
Submission Documents in Indian Patent Application No. 1511/CHENP/2009, dated Aug. 18, 2017, 55 pages (English Translation.
Submission Documents in Indian Patent Application No. 5022/CHENP/2009, dated Sep. 23, 2016, 9 pages (English Translation).
Submission Documents in Indonesia Patent Application No. W-00201201031, dated Aug. 11, 2016, 13 pages (English Translation).
Submission Documents in Indonesia Patent Application No. W-00201201031, dated Dec. 9, 2016, 4 pages (English Translation).
Submission Documents in Israel Patent Application No. 223695, dated Dec. 22, 2016, 5 pages (English Translation).
Submission Documents in Israel Patent Application No. 227558, dated Jul. 12, 2016, 6 pages (English Translation).
Submission Documents in Israeli Patent Application No. 227558, dated Nov. 30, 2015, 3 pages.
Submission Documents in Israeli Patent Application No. 242519, dated Apr. 13, 2016, 4 pages (English Translation).
Submission Documents in Korean Patent Application No. 10-2013-7020616, dated Feb. 13, 2017, 47 pages (English Translation).
Submission Documents in Mexican Patent Application No. MX/a/2014/010594, dated Oct. 20, 2016, 15 pages (English Translation).
Submission Documents in Norwegian Patent Application No. 20063383, dated Jun. 15, 2016, 181 pages.
Submission Documents in Russian Patent Application No. 2015148193, dated Aug. 5, 2016, 16 pages (English Translation).
Submission Documents in U.S. Appl. No. 14/117,276, dated Jul. 18, 2016, 3 pages.
Submission Documents in U.S. Appl. No. 14/890,207, dated Nov. 30, 2017, 15 pages.
Submission Documents re New Claim Set Before the Patent Office for AR Application No. P110100513, dated Aug. 27, 2013, 8 pages (with English translation).
Submission Documents re Preliminary Amendment Before the Patent Office U.S. Appl. No. 14/002,018, dated Aug. 28, 2013, 9 pages.
Submission Documents re RCE Before the Patent Office for U.S. Appl. No. 13/083,338, dated Aug. 28, 2013, 20 pages.
Submission Documents re RCE Before the Patent Office for U.S. Appl. No. 12/524,754, dated Apr. 15, 2013, 17 pages.
Submission documents re RCE filed in U.S. Appl. No. 11/997,719, dated Dec. 11, 2013, 10 pages.
Submission Documents re RCE filed in U.S. Appl. No. 12/524,754, dated May 13, 2014, 1 page.
Submission documents re RCE filed in U.S. Appl. No. 12/741,682, dated Jan. 17, 2014, 1 page.
Submission documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 10 pages.
Submission documents re RCE in U.S. Appl. No. 12/439,339, dated Jan. 27, 2014, 1 page.
Submission documents re RCE in U.S. Appl. No. 12/524,754, filed Feb. 3, 2014, 1 page.
Submission Documents re Request for Continued Examination filed in U.S. Appl. No. 12/741,682, dated May 6, 2014, 1 page.
Submission Documents re Request for Continued Examination filed in U.S. Appl. No. 13/083,338, dated May 6, 2014, 1 page.
Submission documents re Request for Continued Examination in U.S. Appl. No. 13/205,328, dated Apr. 28, 2014, 1 page.
Submission in EP Application No. 04807580.8, dated Jun. 13, 2014, 18 pages.
Submission of Amendments and Complete Specification dated Apr. 10, 2013 for IN Application No. 1571/CHENP/2007, 15 pages.
Submission of Claims in IL Application No. 223695, dated Jan. 17, 2015, 16 pages.
Submission of Document Before the Patent Office re Request for Voluntary Amendments dated Jan. 30, 2013 for NZ Application No. 598291, 8 pages.
Submission of Document re Claims filed in Response to Second Office Action for CN Application No. 200880115011.7, filed on Nov. 20, 2012.
Submission of Document re Request for Examination in CO Application No. 12-022608, submitted on Jun. 12, 2012.

(56) References Cited

OTHER PUBLICATIONS

Submission of Documents before the Patent Office for CN Application No. 200880115011.7, dated Apr. 11, 2013, 10 pages (with English translation).
Submission of Documents before the Patent Office for CN Application No. 200980103218.7, dated Mar. 13, 2013, 6 pages (with English translation).
Submission of Documents Before the Patent Office for IL Application No. 175363, dated Feb. 27, 2013, 23 pages.
Submission of Documents re Amendment in UA Application No. a2012 03132, submitted on May 22, 2012.
Submission of Documents re Claim 3 and Figure 3 for KR Application No. 10-2009-7005657, filed on Jul. 13, 2012.
Submission of Reference Materials in KR Application No. 10-2008-7013685, filed Jul. 5, 2013, 43 pages, (with English translation).
Sugiyama et al., "Potent in vitro and in vivo antitumor activity of sorafenib against human intrahepatic cholangiocarcinoma cells," Journal of Gastroenterology, 2011, 46:779-789.
Sun et al., "Design, synthesis, and evaluations of substituted 3-[(3- or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5-[5-Fluoro-2-oxo-1,2-dihydroindol-(3Z)-ylidenemethyl]-2,4-dimethyl-1H-pyrrole-3carboxylic acid . . . Tyrosine Kinase", Journal of Medicinal Chemistry., 46:1116-1119 (2003).
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Supplemental Notice of Allowance in U.S. Appl. No. 12/315,291, dated Jul. 21, 2011, 4 pages.
Supplemental Search Report in EP Application No. 05719973.9, dated Dec. 6, 2007, 3 pages.
Supplemental Search Report in EP Application No. 05719976.2, dated Dec. 6, 2007, 3 pages.
Supplementary European Search Report for Application No. 01976786.2, dated Jul. 6, 2004.
Supplementary European Search Report for Application No. 08 70 4376, dated Jun. 14, 2012.
Supplementary European Search Report for Application No. 08846814.5, issued on Jun. 18, 2012.
Supplementary European Search Report issued Jul. 5, 2012, in European Patent Application No. 08846814.5.
Suzuki et al., "MP-412, a dual EGFR/HER2 tyrosine kinase inhibitor: 1. In vivo kinase inhibition profiled," Am. Assoc. Cancer Research, A3405, 2005, 2 pages.
Taguchi et al., "A novel orally active inhibitor of VEGF receptor tyrosine kinases KRN951: Anti-angiogenic and anti-tumor activity against human solid tumors," Proceedings of the AACR Annual Meeting, 45:595 (Mar. 2004) ( XP002536608).
Tahara et al, "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT)", The presentation document, presented at European Society for Medical Oncology 2014 Congress, Sep. 26-30, 2014, 24 pages.
Tahara et al., "Exploratory analysis of biomarkers associated with clinical outcomes from the study of lenvatinib in differentiated cancer of the thyroid," European Journal of Cancer, 2017, 75:213-221, XP029959213.
Taiwanese Notice of Allowance in Application No. 100104281, dated Jun. 9, 2015, 4 pages, with English translation.
Taiwanese Submission Documents in Application No. 100104281, dated Mar. 9, 2015, 12 pages, with English translation.
Takahashi et al, "Phase II Study of Lenvatinib, A Multitargeted Tyrosine Kinase Inhibitor, In Patients With All Histologic Subtypes of Advanced Thyroid Cancer (Differentiated, Medullary, And Anaplastic)", The Poster, presented at the European Society for Medical Oncology 2014 Congress, Sep. 26-30, 2014, 1 page.

Takahashi et al., "Axitinib (AG-013736), an oral specific VEGFR TKI, shows potential therapeutic utility against cholangiocarcinoma," Japanese Journal of Clinical Oncology, 2014, 44(6):570-578.
Takahashi et al., "Preclinical Study of VEGFR and EGFR Inhibitor—Are They Potential Therapeutic Targets in Biliary Tract Carcinoma?", The Biliary Tract & Pancreas, Feb. 2015 vol. 36 No. 2, p. 153-p. 160 (Machine Translation).
Takahashi et al., "A case of inoperable scirrhous gastric cancer that responded remarkably to a combination of TS-1+paclitaxel and showed complete loss of ascites," Japanese Journal of Cancer and Chemotherapy, 31(7): 1093-1095 (2004).
Takeda et al., "AZD2171 shows potent anti-tumor activity against gastric cancer expressing variant K-SAM/FGFR2," Abstract #3785, Proceeding of the American Association for Cancer Research, 47:890 (2006).
Tamai et al., "Developmental strategy of Lenvatinib and developmental status in gastrointestinal cancer", BIO Clinica, 2014 vol. 29 No. 2, p. 61-p. 65 (Machine Translation).
Tamura et al., "Molecular Characterization of Undifferentiated-Type Gastric Carcinoma," Laboratory Investigation, 81(4):593-598, Apr. 2001.
Tan et al., "Randomized study of vinorelbine—gemcitabine versus vinorelbine—carboplatin in patients with advanced non-small cell lung cancer," Lung Cancer, 49(2):233-240 (2005).
Tanaka et al., "Biological Equivalence Test on Tandospirone Citrate 10 mg Tablet "AMEL"," Journal of New Remedies & Clinics, 57(6):936-951 (Jun. 2008) (Partial English Translation).
Taniguchi et al., "Effect of c-kit Mutation on Prognosis of Gastrointestinal Stromal Tumors," Cancer Res., 59:4297-4300 (1999).
Tass.ru [online], "Combination of lenvatinib with everolimus increases progression-free survival in subjects with renal cell carcinoma," Jun. 2015, [Retrieved on Oct. 17, 2019], retrieved from: URL<https://tass.ru/press-relizy/2010118>, 20 pages (with English Translation).
Taylor et al., "A phase 1 trial of lenvatinib plus pembrolizumab in patients with selected solid tumors," Annals of Oncology, 2006, 27:XP002793962, 1 page.
Thailand Request for Examination in Application No. 0401005163, dated Aug. 21, 2015, 29 pages, with English translation.
The ESMO/European Sarcoma Network Working Group, "Bone sarcomas: ESMO Clinical Practice Guideline for diagnosis, treatment and follow-up", Annals of Oncology, vol. 23, supplement 7, 2012, p. vii100-p. vii109.
The Pharmacology of Monoclonal Antibody, vol. 113, Chapter 11, Rosenburg and Moore ed., Springer Verlag (1994) pp. 269-315.
Third Office Action dated Feb. 25, 2013 for CN Application No. 200880115011.7, 6 pages (with English translation).
Thomas et al., "The Eosinophil and its Role in Asthma," Gen. Pharmac., 27(4)593-597 (1996).
Thyroid Cancers, Endocrine and Metabolic Disorders, http://www.merkmanuals.com/professional/print/sec12/ch152/ch152j.html Mar. 16, 2011.
Tian et al., "Activating c-kit Gene Mutations in Human Germ Cell Tumors," American Journal of Pathology, 154(6):1643-1647 (1999).
To and Tsao, "The roles of hepatocyte growth factor/scatter factor and Met receptor in human cancers (Review)," *Oncology Reports*, 1998, 5:1013-1024.
Tohyama et al., "Antitumor Activity of Lenvatinib (E7080): An Angiogenesis Inhibitor That Targets Multiple Receptor Tyrosine Kinases in Preclinical Human Thyroid Cancer Models," J Thyroid Res, 2014:1-13, Sep. 10, 2014.
Tohyama et al., "P-3111, Preclinical effect of lenvatinib on human thyroid cancer targeting angiogenesis and receptor tyrosine kinase signaling," The 71$^{st}$ Annual Meeting of the Japanese Cancer Association, Sep. 19-21, 2012, p. 502.
Tonary et al., "Lack of expression of c-KIT in ovarian cancers is associated with poor prognosis," Int. J. Cancer, 89:242-250 (2000).
Tong et al., "Vascular normalization by vascular endothelial growth factor receptor 2 blockade induces a pressure gradient across the vasculature and improves drug penetration in tumors," Cancer Res., 64:3731-3736 (2004).
Toshiyuki et al., "Thermal recording materials with improved background stability," Database CA (Online) Chemical Abstracts Service, Columbus, OH, US (Feb. 20, 1996) (XP002443195).

(56) References Cited

OTHER PUBLICATIONS

Transmittal of Information Disclosure Statement, Terminal Disclaimer, Request for Continued Examination, and Response to Office Action under 37 C.F.R. §1.116 for U.S. Appl. No. 11/997,719, filed Jul. 6, 2011.
Traxler et al., "AEE788; A dual family epidermal growth factor receptor/ErbB2 and vascular endothelial growth factor receptor tyrosine kinase inhibitor with antitumor and antiangiogenic activity," Cancer Res., 64:4931-4941 (2004).
Trudel et al., "CHIR-258, a novel, multitargeted tyrosine kinase inhibitor for the potential treatment of t(4; 14) multiple myeloma," Blood, 105:2941-2948 (2005).
Trudel et al., "Inhibition of fibroblast growth factor receptor 3 induces differentiation and apoptosis in t(4; 14) myeloma," Blood, 103:3521-3528 (2004).
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Turner et al., "Fibroblast growth factor signalling: from development to cancer," Nature Reviews, Cancer, 10:116-129 (2010).
U.S. Certificate of Correction in U.S. Appl. No. 12/524,754, dated Aug. 11, 2015, 1 page.
U.S. Certificate of Correction in U.S. Appl. No. 12/741,682, dated Aug. 4, 2015, 2 pages.
U.S. Certificate of Correction in U.S. Appl. No. 13/624,278, dated Aug. 18, 2015, 1 page.
U.S. Notice of Allowance for U.S. Appl. No. 12/244,227, dated Oct. 22, 2010.
U.S. Notice of Allowance in U.S. Appl. No. 14/438,366, dated Feb. 12, 2016, 7 pages.
U.S. Notice of Panel Decision from Pre-Appeal Brief Review in U.S. Appl. No. 12/039,381, dated Mar. 4, 2016, 2 pages.
U.S. Office Action for U.S. Appl. No. 10/420,466, issued on Apr. 13, 2005.
U.S. Office Action for U.S. Appl. No. 10/577,531, issued on Sep. 23, 2008.
U.S. Office Action for U.S. Appl. No. 10/797,903, dated Jul. 23, 2008, 11 pages.
U.S. Office Action for U.S. Appl. No. 10/797,903, issued on Apr. 1, 2010.
U.S. Office Action for U.S. Appl. No. 10/797,903, issued on Aug. 20, 2009.
U.S. Office Action for U.S. Appl. No. 10/797,903, issued on Dec. 11, 2007.
U.S. Office Action for U.S. Appl. No. 10/797,903, issued on Sep. 1, 2010.
U.S. Office Action for U.S. Appl. No. 11/293,785, issued on Sep. 4, 2007.
U.S. Office Action for U.S. Appl. No. 11/347,749, issued on Feb. 9, 2009.
U.S. Office Action for U.S. Appl. No. 11/662,425, issued on May 3, 2010.
U.S. Office Action for U.S. Appl. No. 11/662,425, issued on Sep. 28, 2010.
U.S. Office Action for U.S. Appl. No. 11/997,543, issued on Feb. 23, 2011.
U.S. Office Action for U.S. Appl. No. 11/997,543, issued on May 19, 2011.
U.S. Office Action for U.S. Appl. No. 11/997,543, issued on Nov. 9, 2011.
U.S. Office Action for U.S. Appl. No. 11/997,719, issued on Apr. 6, 2011.
U.S. Office Action for U.S. Appl. No. 11/997,719, issued on Sep. 3, 2010.
U.S. Office Action for U.S. Appl. No. 12/092,539, issued on Jan. 7, 2011.
U.S. Office Action for U.S. Appl. No. 12/092,539, issued on Jun. 28, 2011.
U.S. Office Action for U.S. Appl. No. 12/092,539, issued on May 9, 2011.
U.S. Office Action for U.S. Appl. No. 12/094,492, issued on Mar. 24, 2011.
U.S. Office Action for U.S. Appl. No. 12/301,353, issued on Jan. 24, 2011.
U.S. Office Action for U.S. Appl. No. 12/400,562, issued on Mar. 31, 2010.
U.S. Office Action for U.S. Appl. No. 12/439,339, issued on Mar. 30, 2012.
U.S. Office Action for U.S. Appl. No. 12/439,339, issued on Nov. 14, 2011.
U.S. Office Action for U.S. Appl. No. 12/523,495, issued on Dec. 27, 2011.
U.S. Office Action for U.S. Appl. No. 12/523,495, issued on Sep. 27, 2011.
U.S. Office Action for U.S. Appl. No. 12/524,754, issued on Dec. 19, 2011.
U.S. Office Action for U.S. Appl. No. 12/741,682, issued on Apr. 30, 2012.
U.S. Office Action for U.S. Appl. No. 12/864,817, issued on Dec. 16, 2011.
U.S. Office Action for U.S. Appl. No. 12/864,817, issued on May 19, 2011.
U.S. Office Action for U.S. Appl. No. 12/864,817, issued on Nov. 3, 2011.
U.S. Office Action for U.S. Appl. No. 13/083,338, issued on Apr. 12, 2012.
U.S. Office Action for U.S. Appl. No. 13/083,338, issued on Jun. 8, 2012.
U.S. Office Action for U.S. Appl. No. 13/083,338, issued on Nov. 23, 2012.
U.S. Office Action for U.S. Appl. No. 13/205,328, issued on Jan. 12, 2012.
U.S. Office Action for U.S. Appl. No. 13/205,328, issued on May 1, 2012.
U.S. Office Action for U.S. Appl. No. 13/322,961, issued on Sep. 25, 2012.
U.S. Office Action in U.S. Appl. No. 12/039,381, dated Feb. 26, 2015, 13 pages.
U.S. Office Action in U.S. Appl. No. 12/092,539, dated May 9, 2011.
U.S. Office Action in U.S. Appl. No. 13/870,507, dated Apr. 1, 2015, 82 pages.
U.S. Office Action in U.S. Appl. No. 14/862,349, dated Mar. 10, 2016, 11 pages.
U.S. Response to Office Action in U.S. Appl. No. 12/039,381, dated Dec. 22, 2015, 10 pages.
U.S. Response to Office Action in U.S. Appl. No. 13/923,858, filed Apr. 1, 2015, 12 pages.
U.S. Response to Restriction Requirement in U.S. Appl. No. 13/870,507, dated Jan. 27, 2015, 3 pages.
U.S. Submission Documents in U.S. Appl. No. 13/870,507, dated Jun. 18, 2015, 13 pages.
Ueda et al., "VGA1155, a Novel Binding Antagonist of VEGF, Inhibits Angiogenesis In Vitro and In Vivo", Anticancer Research., 24, 3009-3017, 2004.
Ueda et al., "Deletion of the carboxyl-terminal exons of K-sam/FGFR2 by short homology-mediated recombination, generating preferential expression of specific messenger RNAs," Cancer Res., 59(24):6080-6086 (1999).
Ueno et al., "Phase 2 study of lenvatinib monotherapy as second-line treatment in unresectable biliary tract cancer: primary analysis results," BMC Cancer, 2020, 20:1105.
US Office Action for U.S. Appl. No. 11/997,543, dated Sep. 30, 2013, 88 pages.
US Response to Notice of Non-Compliant Amendment dated Jan. 18, 2005 for U.S. Appl. No. 10/420,466.
Valle et al., Cisplatin plus Gemcitabine versus Gemcitabine for Biliary Tract Cancer, The New England Journal of Medicine, Apr. 8, 2010 vol. 362, p. 1273-p. 1281.

(56) References Cited

OTHER PUBLICATIONS

Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
Van Oers et al., "A simple and fast method for the simultaneous detection of nine fibroblast growth factor receptor 3 mutations in bladder cancer and voided urine," Clin. Cancer Res., 11:7743-7748 (2005).
Varvoglis et al., "Chemical Transformations Induced by Hypervalent Iodine Reagents," Tetrahedron, 1997, 53(4):1179-1255.
Vergote et al., "A phase II trial of lenvatinib in patients with advanced or recurrent endometrial cancer: Angiopoietin-2 as a predictive marker for clinical outcomes.", J. Clin. Oncol, vol. 31, No. 15 supplement, 5520, May 20, 2013, XP002728918.
Vergote et al., "Prognostic and prediction role of circulating angiopoietin-2 in multiple solid tumors: An analysis of approximately 500 patients treated with lenvatinib across tumor types," Am Soc Clin Oncol Annual Meeting Abstract, May 31, 2014, abstract 11061, 3 pages.
Vianna et al, "The histological rarity of thyroid cancer," Braz J Otorhinolaryngol 78(4):48-51, Jul.-Aug. 2012.
Vieira et al, "Expression of vascular endothelial growth factor (VEGF) and its receptors in thyroid carcinomas of follicular origin: a potential autocrine loop", European Journal of Endocrinology, 2005;153:701-709.
Vippagunta et al., "Crystalline solids," Advanced Drug Delivery Reviews, 48:3-26 (2001).
Vogel et al., "Sensing extracellular matrix: an update on discoidin domain receptor function," Cell Signaling, 18:1108-1116 (2006).
Voluntary Amendment filed in CA Application No. 2704000, filed Aug. 6, 2013, 6 pages.
Voluntary Amendment filed in CA Application No. 2802644, dated Nov. 22, 2013, 25 pages.
Voluntary Amendment filed on Aug. 11, 2010 for CN Application No. 200710007097.9 (with English translation).
Voluntary Amendment filed on Aug. 19, 2010 for CA Application No. 2426461.
Voluntary Amendment filed on Aug. 30, 2006 for AU Application No. 2006203099.
Voluntary Amendment filed on Feb. 16, 2012 for BR Patent App. No. BR112012003592-4 (with partial English translation).
Voluntary Amendment filed on Feb. 21, 2007 for AU Application No. 2006203099.
Voluntary Amendment filed on Feb. 27, 2007 for AU Application No. 2006236039.
Voluntary Amendment filed on Feb. 9, 2010 for AU Application No. 2005283422.
Voluntary Amendment filed on Jul. 6, 2010 for AU Application No. 2005283422.
Voluntary Amendment filed on Sep. 10, 2010 for HU Application No. P0302603 (with English translation).
Voluntary Amendment for Australian Application No. 2010285740, filed on Nov. 21, 2011.
Voluntary Amendment for Chinese counterpart of App. No. PCT/JP2010/063804, filed on Jan. 5, 2012 (with English translation).
Voluntary Amendment for counterpart Canadian patent application, filed on Feb. 16, 2012.
Voluntary Amendment for Russian Application No. 2012103471, filed on Feb. 1, 2012 (with English translation).
Voluntary Amendment for Thailand Application No. 1201000221, filed on Feb. 17, 2012.
Voluntary Amendment in ID Application No. W-00201201031, dated Nov. 5, 2014, 2 pages (with English translation).
Voluntary Amendment in MX Application No. MX/a/2014/010594, dated Oct. 23, 2014, 4 pages (with English translation).
Waaler et al., "Novel Synthetic Antagonists of Canonical Wnt Signaling Inhibit Colorectal Cancer Cell Growth," Cancer Res., 2011, 71:197-205.

Wakeling et al., "ZD1839 (Iressa): an orally active inhibitor of epidermal growth factor signaling with potential for cancer therapy," Cancer Res., 62(20)5749-5754 (2002).
Wakui, "Chemotherapy of scirrhous gastric cancer," Japanese Journal of Cancer and Chemotherapy, 21(14):2398-2406 (1994) (English abstract).
Wang et al., "KRAS, BRAF, PIK3CA mutations and Pten Expression in Human Colorectal Cancer-Relationship with Metastatic Colorectal Cancer," Ann Oncol., 2010, 21(Supp 6):V164.
Wang et al., "Renal cell carcinoma: diffusion-weighted MR imaging for subtype differentiation at 3.0 T," Radiology, 2010, 257(1):135-143.
Wang et al., "The Role of Angiopoietins as Potential Therapeutic Targets in Renal Cell Carcinoma", Translational Oncology, vol. 7, No. 2, Apr. 1, 2014, p. 188-p. 195, XP055218621.
Wang et al., "A Convenient Set of Bidentate Pyridine Ligands for Combinatorial Synthesis," Tetrahedron Lett., 40:4779-1478 (1999).
Wang et al., "Phase II study of gemcitabine and carboplatin in patients with advanced non-small-cell lung cancer," Cancer Chemother Pharmacol., 60(4):601-607 (2007).
Wang et al., "The Expression of the Proto-Oncogene C-Kit in the Blast Cells of Acute Myeloblastic Leukemia," Leukemia, 3(10):699-702 (1989).
Wang, "Drugs of Today, Everolimus in renal cell carcinoma," Journals on the Web, Aug. 2010, vol. 46, issue 8, 1 page (abstract only).
Waterman, M., "Computer Analysis of Nucleic Acid Sequences", Methods in Enzymology, 164:765-793 (1988).
Watson et al., "Inhibition of c-Met as a therapeutic strategy for esophageal adenocarcinoma," Neoplasia, 2006, 8(11):949-955.
Wedge et al., "ZD4190: An Orally Active Inhibitor of Vascular Endothelial Growth Factor Signaling with Broad-Spectrum Antitumor Efficacy", Cancer Research., 60, 970-975, 2000.
Wedge et al., "AZD2171: a highly potent, orally bioavailable, vascular endothelial growth factor receptor-2 tyrosine kinase inhibitor for the treatment of cancer," Cancer Res., 65(10):4389-4400 (2005).
Wedge et al., "Pharmacological Efficacy of ZD6474, a VEGF Receptor Tyrosine Kinase Inhibitor, in Rat," AACR American Association Cancer Research, 92nd Annual Meeting, 42:583, Mar. 24-28, 2001, New Orleans, LA, USA, abstract 3126, 2 pages.
Wells et al., "Targeting the RET Pathway in Thyroid Cancer," Clin. Cancer Res., 15:7119-7123 (2009).
Wells Jr et al, "Vandetanib in Patients With Locally Advanced or Metastatic Medullary Thyroid Cancer: A Randomized, Double-Blind Phase III Trial", J Clinical Oncol., 30(2):134-141, Jan. 10, 2012, corrections published Aug. 20, 2013, p. 3049.
Went et al, "Prevalence of KIT Expression in Hnman Tumor", Journal of Clinical Oncology, Nov. 15, 2004, 4514-4522.
Werner et al., "Gastric adenocarcinoma: pathomorphology and molecular pathology," J. Cancer Res. Clin. Oncology, 127:207-216 (2001) (English abstract).
Wickman et al., "Further characterization of the potent VEGF/PDGF receptor tyrosine kinase inhibitor AG-013736 in preclinical tumor models for its antiangiogenesis and antitumor activity," Proceedings of the American Association for Cancer Research, 44, 865, (Abstract 3780), 2003, 1 page.
Wilbur, W.J. and Lipman, DJ., "Rapid similarity searches of nucleic acid and protein data banks", Natl. Acad. Sci, U.S.A. 80:726-730 (1983).
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Willett et al., "Direct evidence that the VEGF-specific antibody bevacizumab has antivascular effects in human rectal cancer," Nat. Med., 10(2):145-1147 (2004).
Winkler et al., "Kinetics of vascular normalization by VEGFR2 blockade governs brain tumor response to radiation: Role of oxygenation, angiopoietin-1, and matrix metalloproteinases," Cancer Cell, Dec. 2004, 6:553-563.
Wirth et al, "Treatment-Emergent Hypertension and Efficacy in the Phase 3 Study of (E7080) Lenvatinib in Differentiated Cancer of the

(56) References Cited

OTHER PUBLICATIONS

Thyroid (Select)", The Poster, No. 1030P, presented at the European Society for Medical Oncology 2014 Congress, Sep. 26-30, 2014, 1 page.
Wisniewski et al., "Characterization of Potent Inhibitors of the Bcr-Abl and the c-Kit Receptor Tyrosine Kinases", Cancer Research., 62, 4244-4255, 2002.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research., 64, 6652-6659. 2004.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Woyach et al., "New therapeutic advances in the management of progressive thyroid cancer," XP055539661, Endocrine-related cancer, 2009, 16(3):715-731.
Wozniak et al., "Randomized trial comparing cisplatin with cisplatin plus vinorelbine in the treatment of advanced non-small-cell lung cancer: a Southwest Oncology Group study," J. Clin. Oncol., 16(7):2459-2465 (1998).
Written Amendment filed on Jun. 16, 2009 for JP Application No. 2009-123432 (with English translation).
Written Amendment filed on Sep. 21, 2011 for JP Application No. 2011-527665 (with English translation).
Written Submission in Indian Patent Application No. 5022/CHENP/2009, dated Aug. 8, 2017, 16 pages (English Translation).
Written Submission regarding hearing in IN Application No. 1571/CHENP/2007 filed on Jan. 23, 2014, 8 pages.
Wu et al., "A fully human monoclonal antibody against VEGFR-1 inhibits growth of human breast cancers," Proceedings of the American Association for Cancer Research, 45, 694, (Abstract 3005), 2004, 3 pages.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Xu et al., "Research on novelty issue of method claims including use feature," Paper of IP Forum of 5th Annual Conference of ACPAA, Part III, Apr. 1, 2014, p. 1-p. 5 (with Full English Translation).
Yamada et al, "Phase I Dose-Escalation Study and Biomarker Analysis of E7080 in Patients with Advanced Solid Tumors," Clin Cancer Res 17(8):2528-2537, Mar. 3, 2011.
Yamada et al., "Antitumor and antiangiogenesis activities of E7386, an orally active CBP/β-catenin modulator, as a single agent and in combination with lenvatinib in human HCC xenograft models," Eisai, 2018, 1 page.
Yamada et al., "New technique for staining," Monthly Medical Technology Supplementary Volume (Apr. 1999) (with English translation).
Yamamoto et al., "Plasma biomarkers predictive for disease control duration in the phase I study of E7080, a multitarget kinase inhibitor," ASCO Annual Meeting Proceedings(Post Meeting Edition), Jonrnal of Clinical Oncology, 27:15S, 2009, 1 page.
Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract #50, AACR, Toronto, Canada (Apr. 5-9, 2003).
Yamamoto et al., "E7080 a novel multitargeted tyrosine kinase inhibitor, has direct anti-tumor activity via inhibition of KIT signaling in small cell lung cancer," Abstract #4636, AACR, Orlando, FL, (Mar. 27-31, 2004).
Yamamoto et al., "E7080, an oral multi-targeted tyrosine kinase inhibitor, has direct anti-tumor efficacy via inhibition of KIT signaling in gastrointestinal stromal tumor (GIST)," Abstract #4038, 97th Annual Meeting AACR, Washington, DC. (Apr. 1-5, 2006).
Yamamoto et al., "E7080, an oral multi-targeted tyrosine kinase inhibitor, has direct anti-tumor efficacy via inhibition of KIT signaling in small cell lung cancer," Proceedings of the American Association for Cancer Research, 45:1070-1071 (Mar. 2004).
Yamamoto et al., "Lenvatinib, an angiogenesis inhibitor targeting VEGFR/FGFR, shows broad antitumor activity in human tumor xenograft models associated with microvessel density and pericyte coverage," Vascular Cell, 6(18):1-13, 2014.
Yamamoto et al., "Lenvatinib, an angiogenesis inhibitor targeting VEGFR/FGFR, shows broad antitumor activity in human tumor xenograft models associated with microvessel density and pericyte coverage," Vascular Cell, Sep. 2014, 6(1), 19 pages.
Yamori et al., "Current Treatment of Solid Tumors New Approaches of Treatment, Drug Treatment, Kinase Inhibitors/Kokeigan no Saishin Chiryo Chiryo no Aratana Torikumi Yakubutsu Ryoho Kinase Inhibitors," Jp J Clin Med., Jun. 1, 2010, 68(6):1059-1066 (was listed as vol. 38).
Yanagihara et al., "Development and biological analysis of peritoneal metastasis mouse models for human scirrhous stomach cancer," Cancer Sci., 96(6):323-332 (2005).
Yang et al., "Improvement of Sirolimus Oral Dosing Method," Journal of Nursing Science (Surgery Edition), 2009, 24(18), 2 pages (with Partial Translation).
Yang et al., "RG7204 (PLX4032), a Selective BRAF V600E Inhibitor, Displays Potent Antitumor Activity in Preclinical Melanoma Models," Cancer Res., 2010, 70(13):5518-5527.
Yao et al., "AV-65, a novel Wnt/B-catenin signal inhibitor, successfully suppresses progression of multiple myeloma in a mouse model," Blood Cancer J, 2011, 1:e43, 9 pages.
Yigitbasi et al., "Tumor Cell and Endothelial Cell Therapy of Oral Cancer by Dual Tyrosine Kinase Receptor Blockade", Cancer Research, 64, 7977-7984, 2004.
Yokota, "ASCO report: Gastrointestinal Cancer field/ASCO Hokoku Shokakigan Ryoiki," Gan Bunshi Hyoteki Chiryo, 2010, 8(4):271-283.
Yoshikawa et al., "Clinicopathological and prognostic significance of EGFR, VEGF, and HER2 expression in cholangiocarcinoma," XP002789353, British Journal of Cancer, 2008, 98(2):418-425.
Yu, "Amorphous Pharmaceutical Solids:Preparation Characterization and Stabilization," Advanced Drug Delivery Reviews, 48:27-42 (2001) (XP009065056).
Zhang et al., "Stage 1 in vivo evaluation of multi-receptor tyrosine-kinase inhibitor lenvatinib in osteosarcoma patient derived mouse xenograft models", AACR 2017, Abstract 697, Jul. 2017.
Zhang et al., "Induction of apoptosis in EMT-6 breast cancer cell in line by a Sigma-2 selective ligand," Am. Assoc. Cancer Research, Abstract 5353, 2005, 2 pages.
Zhang et al., "Inhibition of both autocrine and paracrine growth and propagation of human myeloid leukemia with antibodies directed against VEGF receptor 2," Proceedings of the American Association for Cancer Research, 44, 1479, (Abstract 6454), 2003, 2 pages.
Zhang et al., "Overexpression of Platelet-Derived Growth Factor Receptor a in Endothelial Cells of Hepatocellular Carcinoma Associated with High Metastatic Potential," Clin. Cancer Res., 11(24):8557-8563 (2005).
Zhang et al., "Synergic antiproliferative effect of DNA methyltransferase inhibitor in combination with anticancer drugs in gastric carcinoma," Cancer Sci., Sep. 2006, 97(9):938-944.
Zhao et al., "Basics for the design and development of new drugs," Shandong University Press, 2015, p. 93-p. 94 (with English Translation).
Zhong et al., "Mechanisms underlying the synergistic effect of SU5416 and cisplatin on cytotoxicity in human ovarian tumor cells," Inter'l J Oncol., 25(2):445-451, 2001 2004.
Zhou et al., "Correlation Research on VEGF Testing in Primary Gastric Cancer and Clinical Pathology Factor," Journal of Practical Oncology, 20(2):103-105 (Apr. 25, 2006) with English translation.
Zhu et al., "Fibroblast growth factor receptor 3 inhibition by short hairpin RNAs leads to apoptosis in multiple myeloma," Mol. Cancer Ther., 4(5):787-798 (2005).
Zhu et al., "Inhibition of human leukemia in an animal model with human antibodies directed against vascular endothelial growth

(56) References Cited

OTHER PUBLICATIONS factor receptor 2. Correlation between antibody affinity and biological activity," Leukemia, 17:604-611 (2003).
Zhu et al., "Search: A Phase III, Randomized, Double-Blind, Placebo-Controlled Trial of Sorafenib Plus Erlotinib in Patients With Advanced Hepatocellular Carcinoma," Journal of Clinical Oncology, 2015, 33(6):559-566.
Zieger et al., "Role of activating fibroblast growth factor receptor 3 mutations in the development of bladder tumors," Clin. Cancer Res., 11:7709-7719 (2005).
Zimmermann et al., "Potent and Selective Inhibitors of the Abl-Kinase:Phenylamino-Pyrimidine (PAP) Derivatives", Bioorganic and Medicinal Chemistry Letters., 7(2):187-192, 1997.
Zimmermann, "Electrical Breakdown, Electropermeabilization and Electrofusion", Rev. Physiol. Biochem. Pharmacol. 105:176-260 (1986).
Zurita et al., "A cytokine and angiogenic factor (CAF) analysis in plasma for selection of sorafenib therapy in patients with metastatic renal cell carcinoma," Annals of Oncology, 23(1):46-52, Apr. 4, 2011.
Zurita et al., "Circulating biomarkers for vascular endothelial growth factor inhibitors in renal cell carcinoma," Cancer 115(S10):2346-2354, May 15, 2009.
Notice of Allowance in Brazilian Patent Application No. BR112013021941-6, dated Oct. 11, 2022, 2 pages (with English Translation).
Notice of Allowance in European Patent Application No. 16755489.8, dated Apr. 12, 2022, 49 pages.
Notice of Allowance in European Patent Application No. 16755489.8, dated Oct. 10, 2022, 49 pages.
Notice of Allowance in Mexican Patent Application No. MX/a/2017/001980, dated May 30, 2022, 4 pages (with English Translation).
Notice of Allowance in Russian Patent Application No. 2017104496, dated Oct. 18, 2022, 18 pages (with English Translation).
Notice of Allowance in Russian Patent Application No. 2018134943, dated Oct. 19, 2022, 20 pages (with English Translation).
Notice of Allowance in U.S. Appl. No. 15/554,577, dated Jul. 28, 2022, 13 pages.
Notice of Allowance in U.S. Appl. No. 15/750,712, dated Jun. 23, 2022, 8 pages.
Notice of Allowance in U.S. Appl. No. 15/750,712, dated Oct. 6, 2022, 10 pages.
Notice of Allowance in U.S. Appl. No. 15/934,242, dated Nov. 9, 2022, 12 pages.
Notice of Allowance in U.S. Appl. No. 16/465,277, dated Aug. 1, 2022, 37 pages.
Office Action in Australian Patent Application No. 2017249459, dated Mar. 16, 2022, 3 pages.
Office Action in Brazilian Patent Application No. BR112013021941-6, dated Jun. 7, 2022, 9 pages.
Office Action in Brazilian Patent Application No. BR1120190141278, dated Jul. 26, 2022, 8 pages (with English Translation).
Office Action in Canadian Patent Application No. 2978226, dated Oct. 3, 2022, 3 pages.
Office Action in Canadian Patent Application No. 2994224, dated Sep. 12, 2022, 4 pages.
Office Action in Canadian Patent Application No. 2994925, dated Sep. 15, 2022, 3 pages.
Office Action in European Patent Application No. 19733190.3, dated Jul. 5, 2022, 4 pages.
Office Action in Indian Patent Application No. 201747028834, dated Nov. 9, 2022, 3 pages (with English Translation).
Office Action in Israeli Patent Application No. 250454, dated Apr. 6, 2022, 4 pages.
Office Action in Israeli Patent Application No. 253946, dated Jun. 19, 2022, 12 pages (with English Translation).
Office Action in Japanese Patent Application No. P2020-182679, dated Jun. 7, 2022, 2 pages (with English Translation).
Office Action in Korean Patent Application No. 10-2017-7027616, dated May 11, 2022, 27 pages (with English Translation).
Office Action in Korean Patent Application No. 10-2018-7028053, dated Sep. 20, 2022, 7 pages (with English Translation).
Office Action in Korean Patent Application No. 10-2021-7037538, dated Sep. 23, 2022, 4 pages.
Office Action in Mexican Patent Application No. MX/a/2017/001980, dated Mar. 28, 2022, 9 pages (with English Translation).
Office Action in Mexican Patent Application No. MX/a/2019/013014, dated Mar. 2, 2022, 12 pages (with English Translation).
Office Action in Singaporean Patent Application No. 11201709335X, dated Jul. 15, 2022, 5 pages.
Office Action in U.S. Appl. No. 13/923,858, dated May 20, 2022, 10 pages.
Office Action in U.S. Appl. No. 15/573,197, dated May 3, 2022, 43 pages.
Office Action in U.S. Appl. No. 17/511,773, dated Sep. 6, 2022, 160 pages.
Official Notification in Brazilian Patent Application No. PI0418200-6, dated May 31, 2022, 15 pages (with English Translation).
Official Notification in Egyptian Patent Application No. PCT 283/2012, dated Apr. 11, 2022, 2 pages (with English Translation).
Search Report in European Patent Application No. 22180987.4, dated Sep. 26, 2022, 9 pages.
Submission Document in Brazilian Patent Application No. BR112013021941-6, dated Aug. 29, 2022, 22 pages (with English Translation).
Submission Document in Brazilian Patent Application No. BR1120190141278, dated Oct. 19, 2022, 4 pages (with English Translation).
Submission Document in Canadian Patent Application No. 2976325, dated Jul. 21, 2022, 13 pages.
Submission Document in European Patent Application No. 16755489.8, dated Aug. 18, 2022, 6 pages.
Submission Document in European Patent Application No. 16837150.8, dated Aug. 19, 2022, 68 pages.
Submission Document in Indian Patent Application No. 201947022655, dated Aug. 17, 2022, 45 pages.
Submission Document in Indian Patent Application No. 202148057534, dated Oct. 28, 2022, 5 pages.
Submission Document in Israeli Patent Application No. 250454, dated Jul. 31, 2022, 79 pages (with English Translation).
Submission Document in Israeli Patent Application No. 253946, dated Apr. 24, 2022, 16 pages (with English Translation).
Submission Document in Israeli Patent Application No. 253946, dated Oct. 11, 2022, 5 pages.
Submission Document in Korean Patent Application No. 10-2018-7028053, dated May 11, 2022, 86 pages (with English Translation).
Submission Document in Russian Patent Application No. 2017104496, dated Sep. 6, 2022, 13 pages.
Submission Document in Russian Patent Application No. 2018134943, dated Aug. 22, 2022, 23 pages (with English Translation).
Submission Document in Singaporean Patent Application No. 10202010137Y, dated Aug. 2, 2022, 20 pages.
Submission Document in U.S. Appl. No. 13/923,858, dated Jul. 20, 2022, 14 pages.
Submission Document in U.S. Appl. No. 15/750,712, dated Jun. 14, 2022, 5 pages.
Submission Document in U.S. Appl. No. 15/750,712, dated Sep. 22, 2022, 5 pages.
Submission Document in U.S. Appl. No. 15/934,242, dated Oct. 6, 2022, 13 pages.
Submission Document in U.S. Appl. No. 16/092,245, dated Jul. 25, 2022, 6 pages.
Submission Document in U.S. Appl. No. 16/465,277, dated Apr. 11, 2022, 16 pages.
Submission Document in U.S. Appl. No. 16/465,277, dated Oct. 28, 2022, 14 pages.
Submission Document in U.S. Appl. No. 17/228,025, dated Sep. 23, 2022, 6 pages.
Submission Document in U.S. Appl. No. 17/692,698, dated Oct. 21, 2022, 11 pages.

(56) References Cited

OTHER PUBLICATIONS

[No Author], "Report on the Deliberation Results—Brand Name: Lenvima Capsules 4mg, Lenvima Capsules 10 mg," Evaluation and Licensing Division, Pharmaceutical and Food Safety Bureau, Ministry of Health, Labour and Welfare, Jan. 26, 2015, 100 pages.
[No Author], "Study NCT02014636—A Phase I/II Study to Assess the Safety and Efficacy of Pazopanib and MK 3475 in Subjects With Advanced Renal Cell Carcinoma," v12, Sponsored by GlaxoSmithKline, Nov. 13, 2014, 11 pages.
[No Author], "Study NCT02133742—A Phase 1B, Open Label, Dose Finding Study to Evaluate Safety, Pharmacokinetics and Pharmacodynamics of Axitinib (Ag-013736) in Combination with MK-3475 in Patients with Advanced Renal Cell Cancer," v11, Sponsored by Pfizer, Feb. 10, 2015, 8 pages.
Eisai.mediaroom.com [online], "Positive Topline Results of Large Phase 3 Trial Show Eisai's Lenvatinib Meets Primary Endpoint in Unresectable Hepatocellular Carcinoma," Jan. 25, 2017, retrieved from: URL<https://eisai.mediaroom.com/2017-01-25-Positive-Topline-Results-of-Large-Phase-3-Trial-Show-Eisais-Lenvatinib-Meets-Primary-Endpoint-in-Unresectable-Hepatocellular-Carcinoma>, 4 pages.
Gaspar et al., "Lenvatinib with etoposide plus ifosfamide in patients with refractory or relapsed osteosarcoma (ITCC-050): a multicentre, open-label, multicohort, phase 1/2 study," The Lancet Oncology, 2021, 22(9):1312-1321.
Notice of Allowance in Australian Patent Application No. 2015384801, dated Dec. 16, 2021, 3 pages.
Notice of Allowance in Australian Patent Application No. 2016273230, dated Jan. 14, 2022, 3 pages.
Notice of Allowance in Chinese Patent Application No. 201880005026.1, dated Feb. 25, 2022, 8 pages (with English Translation).
Notice of Allowance in Egyptian Patent Application No. PCT 283/2012, dated Feb. 1, 2022, 2 pages (with English Translation).
Notice of Allowance in European Patent Application No. 17782552.8, dated Jan. 5, 2022, 1 page.
Notice of Allowance in European Patent Application No. 19151846.3, dated Feb. 25, 2022, 41 pages.
Notice of Allowance in Israeli Patent Application No. 267159, dated Mar. 2, 2022, 6 pages (with English Translation).
Notice of Allowance in Japanese Patent Application No. P2017-546075, dated Aug. 31, 2021, 6 pages (with English Translation).
Notice of Allowance in Korean Patent Application No. 10-2017-7003226, dated Aug. 18, 2021, 4 pages (with English Translation).
Notice of Allowance in Singaporean Patent Application No. 11201904020S, dated Sep. 30, 2021, 4 pages.
Notice of Allowance in Thai Patent Application No. 0401005163, dated Feb. 9, 2022, 2 pages (with English Translation).
Notice of Allowance in U.S. Appl. No. 15/554,577, dated Jan. 31, 2022, 19 pages.
Notice of Allowance in U.S. Appl. No. 15/750,712, dated Aug. 26, 2021, 11 pages.
Notice of Allowance in U.S. Appl. No. 15/750,712, dated Dec. 8, 2021, 11 pages.
Notice of Allowance in U.S. Appl. No. 15/750,712, dated Mar. 15, 2022, 5 pages.
Notice of Allowance in U.S. Appl. No. 16/465,277, dated Sep. 16, 2021, 43 pages.
Notice of Allowance in U.S. Appl. No. 16/465,277, dated Jan. 12, 2022, 11 pages.
Notice of Allowance in U.S. Appl. No. 17/022,675, dated Sep. 22, 2021, 17 pages.
Notice of Allowance in U.S. Appl. No. 17/022,675, dated Nov. 4, 2021, 5 pages.
Notification of Information Provision in Canadian Patent Application No. 2978226, dated Sep. 28, 2021, 15 pages.
Notification of Information Provision in European Patent Application No. 16755489.8, dated Oct. 25, 2021, 77 pages.
Notification of Information Provision in Japanese Patent Application No. P2020-182679, dated Oct. 12, 2021, 2 pages (with English Translation).
Office Action in Australian Patent Application No. 2016273230, dated Dec. 21, 2021, 19 pages.
Office Action in Brazilian Patent Application No. BR112012032462-4, dated Aug. 31, 2021, 9 pages (with English Translation).
Office Action in Brazilian Patent Application No. BR112015009004-4, dated Sep. 21, 2021, 11 pages (with English Translation).
Office Action in Brazilian Patent Application No. BR1120170028271, dated Sep. 21, 2021, 5 pages (with English Translation).
Office Action in Brazilian Patent Application No. BR1120170174286, dated Sep. 21, 2021, 9 pages (with English Translation).
Office Action in Brazilian Patent Application No. BR1120170241960, dated Sep. 21, 2021, 9 pages (with English Translation).
Office Action in Brazilian Patent Application No. BR1120180027324, dated Sep. 21, 2021, 12 pages (with English Translation).
Office Action in Canadian Patent Application No. 2976325, dated Apr. 1, 2022, 5 pages.
Office Action in Canadian Patent Application No. 2978226, dated Nov. 1, 2021, 5 pages.
Office Action in Canadian Patent Application No. 2985596, dated Mar. 7, 2022, 5 pages.
Office Action in Chinese Patent Application No. 201880005026.1, dated Dec. 9, 2021, 17 pages (with English Translation).
Office Action in Chinese Patent Application No. 201880005026.1, dated Dec. 21, 2021, 6 pages (with English Translation).
Office Action in Egyptian Patent Application No. PCT 283/2012, dated Aug. 8, 2021, 9 pages (with English Translation).
Office Action in European Patent Application No. 17782552.8, dated Oct. 15, 2021, 2 pages.
Office Action in European Patent Application No. 17782552.8, dated Dec. 21, 2021, 65 pages.
Office Action in Indian Patent Application No. 201747040368, dated Sep. 29, 2021, 16 pages.
Office Action in Indian Patent Application No. 201947022655, dated Oct. 25, 2021, 2 pages (with English Translation).
Office Action in Indian Patent Application No. 202148057534, dated Feb. 4, 2022, 5 pages (with English Translation).
Office Action in Israeli Patent Application No. 253946, dated Dec. 27, 2021, 11 pages (with English Translation).
Office Action in Israeli Patent Application No. 267159, dated Oct. 6, 2021, 8 pages (with English Translation).
Office Action in Japanese Patent Application No. P2020-182679, dated Oct. 12, 2021, 10 pages (with English Translation).
Office Action in Korean Patent Application No. 10-2018-7028053, dated Nov. 12, 2021, 11 pages (with English Translation).
Office Action in Mexican Patent Application No. MX/a/2017/001980, dated Oct. 5, 2021, 6 pages (with English Translation).
Office Action in Mexican Patent Application No. MX/a/2018/012193, dated Aug. 18, 2021, 13 pages (with English Translation).
Office Action in Mexican Patent Application No. MX/a/2018/012193, dated Jan. 12, 2022, 13 pages (with English Translation).
Office Action in Mexican Patent Application No. MX/a/2019/013014, dated Nov. 8, 2021, 4 pages (with English Translation).
Office Action in Mexican Patent Application No. MX/a/2019/013014, dated Nov. 18, 2021, 15 pages (with English Translation).
Office Action in Pakistani Patent Application No. 548/2015, dated Nov. 5, 2021, 14 pages.
Office Action in Russian Patent Application No. 2017104496, dated Nov. 3, 2021, 11 pages (with English Translation).
Office Action in Russian Patent Application No. 2017104496, dated Mar. 11, 2022, 17 pages (with English Translation).
Office Action in Russian Patent Application No. 2018134943, dated Dec. 23, 2021, 85 pages (with English Translation).
Office Action in Russian Patent Application No. 2018134943, dated Feb. 22, 2022, 17 pages (with English Translation).
Office Action in Russian Patent Application No. 2019134940, dated Aug. 20, 2021, 30 pages (with English Translation).
Office Action in Singaporean Patent Application No. 10202010137Y, dated Mar. 2, 2022, 7 pages.
Office Action in U.S. Appl. No. 13/923,858, dated Jan. 24, 2022, 2 pages.
Office Action in U.S. Appl. No. 15/934,242, dated Apr. 6, 2022, 21 pages.

(56) References Cited

OTHER PUBLICATIONS

Office Action in U.S. Appl. No. 16/092,245, dated Dec. 22, 2021, 13 pages.
Office Action in U.S. Appl. No. 16/092,245, dated Jan. 24, 2022, 29 pages.
Office Action in U.S. Appl. No. 16/809,301, dated Sep. 13, 2021, 26 pages.
Office Action in U.S. Appl. No. 17/022,675, dated Aug. 20, 2021, 149 pages.
Office Action in U.S. Appl. No. 17/228,025, dated Mar. 25, 2022, 12 pages.
Office Action in U.S. Appl. No. 17/228,025, dated Nov. 19, 2021, 8 pages.
Official Notification in European Patent Application No. 19151846.3, dated Dec. 17, 2021, 2 pages.
Pfizer.com [Online], "Press Release—Pfizer and Merck to Collaborate on Innovative Anti-Cancer Combination Studies," Feb. 5, 2014, [Retrieved on Dec. 1, 2021], retrieved from: URL<https://www.pfizer.com/news/press-release/press-release-detail/pfizer_and_merck_to_collaborate_on_innovative_anti_cancer_combination_studies>, 5 pages.
Submission Document in Australian Patent Application No. 2015384801, dated Nov. 8, 2021, 17 pages.
Submission Document in Brazilian Patent Application No. BR1120170174286, dated Dec. 14, 2021, 26 pages (with English Translation).
Submission Document in Brazilian Patent Application No. BR1120170241960, dated Dec. 20, 2021, 28 pages (with English Translation).
Submission Document in Brazilian Patent Application No. BR1120180027324, dated Dec. 16, 2021, 20 pages (with English Translation).
Submission Document in Canadian Patent Application No. 3019682, dated Apr. 14, 2022, 22 pages.
Submission Document in Chinese Patent Application No. 201880005026.1, dated Feb. 14, 2022, 17 pages (with English Translation).
Submission Document in European Patent Application No. 19151846.3, dated Dec. 29, 2021, 98 pages.
Submission Document in European Patent Application No. 19151846.3, dated Jan. 10, 2022, 95 pages.
Submission Document in European Patent Application No. 20207489.4, dated Oct. 29, 2021, 45 pages.
Submission Document in European Patent Application No. 20207489.4, dated Nov. 8, 2021, 12 pages.
Submission Document in Gulf Cooperation Council Patent Application No. GC2015-40053, dated Sep. 16, 2021, 104 pages (with English Translation).
Submission Document in Indian Patent Application No. 201947022655, dated Dec. 10, 2021, 5 pages.
Submission Document in Indian Patent Application No. 201947044328, dated Oct. 22, 2021, 4 pages.
Submission Document in Indian Patent Application No. 201947044328, dated Jan. 3, 2022, 3 pages.
Submission Document in Indian Patent Application No. 202148057534, dated Dec. 10, 2021, 129 pages.
Submission Document in Israeli Patent Application No. 250454, dated Mar. 27, 2022, 3 pages (with English Translation).
Submission Document in Mexican Patent Application No. MX/a/2018/012193, dated Dec. 17, 2021, 24 pages (with English Translation).
Submission Document in Mexican Patent Application No. MX/a/2019/013014, dated Jan. 21, 2022, 34 pages (with English Translation).
Submission Document in Russian Patent Application No. 2017104496, dated Jan. 12, 2022, 20 pages (with English Translation).
Submission Document in Singaporean Patent Application No. 11201709335X, dated Sep. 23, 2021, 10 pages.
Submission Document in U.S. Appl. No. 13/923,858, dated Jan. 14, 2022, 20 pages.
Submission Document in U.S. Appl. No. 13/923,858, dated Feb. 1, 2022, 5 pages.
Submission Document in U.S. Appl. No. 15/573,197, dated Nov. 12, 2021, 21 pages.
Submission Document in U.S. Appl. No. 15/750,712, dated Nov. 22, 2021, 5 pages.
Submission Document in U.S. Appl. No. 15/750,712, dated Mar. 4, 2022. 5 pages.
Submission Document in U.S. Appl. No. 15/934,242, dated Feb. 18, 2022, 16 pages.
Submission Document in U.S. Appl. No. 16/465,277, dated Dec. 10, 2021, 20 pages.
Submission Document in U.S. Appl. No. 17/022,675, dated Sep. 3, 2021, 53 pages.
Submission Document in U.S. Appl. No. 17/022,675, dated Oct. 25, 2021, 7 pages.
Submission Document in U.S. Appl. No. 17/228,025, dated Oct. 5, 2021, 4 pages.
Submission Document in U.S. Appl. No. 17/228,025, dated Feb. 18, 2022, 7 pages.
Thornton, "Nivolumab, a Novel Anti-PD-1 Monoclonal Antibody for the Treatment of Solid and Hematologic Malignancies," Personalized Medicine in Oncology, Part 2, 2014, 13 pages.
Walsh et al., "Playing hide and seek with poorly tasting paediatric medicines: Do not forget the excipients," Advanced Drug Delivery Reviews, 2014, 73:14-33.
[No Author], "Assessment Report: Lenvima—Procedure No. EMEA/H/C/003727/0000," European Medicines Agency, Science Medicines Health, Committee for Medicinal Products for Human Use (CHMP), 2015, 169 pages.
[No Author], "Bone sarcomas: ESMO Clinical Practice Guidelines for diagnosis, treatment and follow-up," Annals of Oncology, ESMO (European Sarcoma Network Working Group), 2014, 25(Supplement 3):iii113-iii123, 11 pages.
[No Author], "Eisai Launches Anticancer Agent Lenvimatm in the United States," Eisai News Release, Mar. 2, 2015, 2 pages.
[No Author], "Excerpt NDA 2.3.S.2 Manufacture," Eisai, 3 pages.
[No Author], "Guidance for Industry—Genotoxic and Carcinogenic Impurities in Drug Substances and Products: Recommended Approaches," U.S. Department of Health and Human Services, Food and Drug Administration, Center for Drug Evaluation and Research (CDER), Pharmacology and Toxicology, Dec. 2008, 16 pages.
[No Author], "ICH guideline S9 on nonclinical evaluation for anticancer pharmaceuticals—Step 5," European Medicines Agency, May 2010, 10 pages.
[No Author], "ICH Topic Q 3 B (R2)—Impurities in New Drug Products," European Medicines Agency, Jun. 2006, 14 pages.
[No Author], "ICH Topic Q 6 A—Specifications: Test Procedures and Acceptance Criteria for New Drug Substances and New Drug Products: Chemical Substances," European Medicines Agency, May 2000, 32 pages.
[No Author], "Impurities: Guideline for Residual Solvents Q3c(R5)," ICH Harmonised Tripartite Guideline, Feb. 4, 2011, 29 pages.
[No Author], "International Conference on Harmonisation; Draft Guidance on Specifications: Test Procedures and Acceptance Criteria for New Drug Substances and New Drug Products: Chemical Substances," Food and Drug Administration HHS, Federal Register, 1997, 62(227):62890-62910.
[No Author], "Material Safety Data Sheet for 4-Chloroquinoline," Supplier: Santa Cruz Biotechnology, Inc., Oct. 29, 2009, 10 pages.
Adachi et al., "E7386, a selective inhibitor of the interaction between β-catenin and CREB-binding protein (CBP), enhances antitumor activity in combination with lenvatinib (LEN), and LEN + anti-PD-1 antibody in a preclinical tumor model," Poster 1837, Presented at AACR 2023, Jun. 2-6, 2023, 1 page.
Anderson's Practical Process Research & Development—A guide for Organic Chemists, 2nd ed., Cover Page with Table of Content, Academic Press, 7 pages.
Benigni et al., "Structural alerts of mutagens and carcinogens," Current Computer-Aided Drug Design, 2006, 2:169-176.

(56) References Cited

OTHER PUBLICATIONS

Blacker et al., "Pharmaceutical Process Development: Current Chemical and Engineering Challenges," RSC Publishing, 2011, Chapter 13, pp. 283-316.

Botter et al., "Recent advances in osteosarcoma," Current Opinion in Pharmacology, 2014, 16:15-23.

Bruheim et al., "Antitumor activity of oral E7080, a novel inhibitor of multiple tyrosine kinases, in human sarcoma xenografts," International Journal of Cancer, 2011, 129:742-750.

ClinicalTrials.gov [online], "History of Changes for Study: NCT02432274—Study of Lenvatinib in Children and Adolescents with Refractory or Relapsed Solid Malignancies," Version: Jun. 1, 2015, (Latest Version Submitted Sep. 2, 2021), [Retrieved on Feb. 21, 2022], retrieved from: URL<https://clinicaltrials.gov/ct2/history/NCT02432274?A=2&B=2&C=merged#StudyPageTop>, 8 pages.

Fleuren et al., "Targeting receptor tyrosine kinases in osteosarcoma and Ewing sarcoma: Current hurdles and future perspectives," Biochimica et Biophysica Acta, 2014, 1845:266-276.

Gaspar et al., "A Multicenter, Open-label, Randomized, Phase 2 Study to Compare the Efficacy and Safety of Lenvatinib in Combination With Ifosfamide and Etoposide Versus Ifosfamide and Etoposide in Children, Adolescents, and Young Adults With Relapsed or Refractory Osteosarcoma (OLIE)," Poster presented at: the Connective Tissue Oncology Society Annual Meeting; Nov. 16-19, 2022, 1 page.

Gaspar et al., "Lenvatinib with etoposide plus ifosfamide in patients with refractory or relapsed osteosarcoma (ITCC-050):a multicentre, open-label, multicohort, phase 1/2 study "Supplementary appendix"," Lancet Oncol, Aug. 17, 2021, 179 pages.

Ikeda et al., "A Phase 1b Study of E7386, a CREB-Binding Protein/β-Catenin Interaction Inhibitor, in Combination with Lenvatinib in Patients With Advanced Hepatocellular Carcinoma," Abstract #4075, Presented at the American Society for Clinical Oncology Symposium, Jun. 2-6, 2023, 1 page.

Kamiya et al., "Antimutagenic Structure Modification of Quinoline: Fluorine-Substitution at Position-3," Antimutagenesis and Anticarcinogenesis Mechanisms II, 1990, pp. 441-446.

Kawano et al., "E7386, a selective inhibitor of the interaction between β-catenin and CREB-binding protein (CBP), in combination with lenvatinib (LEN), exerts antitumor activity in preclinical tumor models with prior immune checkpoint inhibitor (ICI)-based combination treatment," Poster_1830, Presented at AACR 2023, Jun. 2-6, 2023, 1 page.

Kondo et al., "A Phase 1 Study of E7386, a CREB-Binding Protein/B-Catenin Interaction Inhibitor, in Patients with Advanced Solid Tumors Including Colorectal Cancer: Updated Dose-Escalation Part," Poster Presentation, Presented at the American Society of Clinical Oncology Gastrointestinal Cancers Symposium, San Francisco, CA, USA, Jan. 19-21, 2023, 1 page.

Kondo et al., "A Phase 1b Study of E7386, a CREB-Binding Protein (CBP)/β-Catenin Interaction Inhibitor, in Combination with Lenvatinib in Patients With Advanced Solid Tumors," Poster Presentation, Presented at ESMO Asia Congress, Singapore, Dec. 2-4, 2022, 1 page.

Lund's the Pharmaceutical Codex—Principles and Practice of Pharmaceutics, 12th Ed., The Pharmaceutical Press, 1994, pp. 342-349.

Mutschler et al., "Mutschler Drug Effects," Textbook of Pharmacology and Toxicology, 2001, Chapter 10, pp. 120-122 (with English Translation).

Mutschler et al.'s Mutschler Drug Reactions, Pharmacological and Toxicological Textbook, 8th Ed., Wissenschaftliche Verlagsgesellschaft mbH, 2001, pp. 123-124 (with Partial Translation).

Mutschler et al.'s Mutschler Drug Reactions, Pharmacological and Toxicological Textbook, 8th Ed., Wissenschaftliche Verlagsgesellschaft mbH, 2001, pp. 882-891 (with Partial Translation).

Nakamura, "Except Study Report HOPE(HE130)," Experimental Period: Feb. 12, 2013-Feb. 21, 2013, dated Jul. 11, 2013, 3 pages.

Notice of Allowance in Brazilian Patent Application No. BR1120170028271, dated Mar. 7, 2023, 7 pages (with English Translation).

Notice of Allowance in Canadian Patent Application No. 2976325, dated Apr. 18, 2023, 6 pages.

Notice of Allowance in Canadian Patent Application No. 2976325, dated Feb. 16, 2023, 4 pages (with English Translation).

Notice of Allowance in Canadian Patent Application No. 2994925, dated Apr. 24, 2023, 1 page.

Notice of Allowance in European Patent Application No. 16755489.8, dated May 24, 2023, 51 pages.

Notice of Allowance in European Patent Application No. 18751614.1, dated Jun. 26, 2023, 66 pages.

Notice of Allowance in Gulf Cooperation Council Patent Application No. GC2011-17812, dated Nov. 13, 2022, 2 pages (with English Translation).

Notice of Allowance in Gulf Cooperation Council Patent Application No. GC2015-29939, dated Nov. 13, 2022, 2 pages (with English Translation).

Notice of Allowance in Gulf Cooperation Council Patent Application No. GC2015-40053, dated Nov. 13, 2022, 2 pages (with English Translation).

Notice of Allowance in Israeli Patent Application No. 250454, dated Feb. 27, 2023, 5 pages (with English Translation).

Notice of Allowance in Japanese Patent Application No. P2020-560740, dated Nov. 14, 2023, 5 pages (with English Translation).

Notice of Allowance in Korean Patent Application No. 10-2018-7003723, dated Sep. 7, 2023, 7 pages (with English Translation).

Notice of Allowance in Korean Patent Application No. 10-2019-7016853, dated Mar. 24, 2023, 7 pages (with English Translation).

Notice of Allowance in Korean Patent Application No. 10-2021-7037538, dated Jan. 31, 2023, 7 pages (with English Translation).

Notice of Allowance in Thai Patent Application No. 1201000221, dated Jul. 25, 2023, 2 pages (with English Translation).

Notice of Allowance in U.S. Appl. No. 15/750,712, dated Aug. 17, 2023, 14 pages.

Notice of Allowance in U.S. Appl. No. 15/750,712, dated Jan. 25, 2023, 11 pages.

Notice of Allowance in U.S. Appl. No. 15/750,712, dated May 9, 2023, 11 pages.

Notice of Allowance in U.S. Appl. No. 16/465,277, dated Apr. 4, 2023, 6 pages.

Notice of Allowance in U.S. Appl. No. 16/465,277, dated Dec. 6, 2023, 6 pages.

Notice of Allowance in U.S. Appl. No. 16/465,277, dated Dec. 7, 2022, 13 pages.

Notice of Allowance in U.S. Appl. No. 16/465,277, dated Jul. 20, 2023, 15 pages.

Notice of Allowance in U.S. Appl. No. 16/465,277, dated Mar. 9, 2023, 13 pages.

Notice of Allowance in U.S. Appl. No. 16/465,277, dated Nov. 2, 2023, 12 pages.

Notice of Allowance in U.S. Appl. No. 16/465,277, dated Nov. 21, 2022, 11 pages.

Notice of Allowance in U.S. Appl. No. 16/465,277, dated Sep. 18, 2023, 6 pages.

Notice of Allowance in U.S. Appl. No. 17/511,773, dated Jul. 20, 2023, 14 pages.

Notice of Allowance in U.S. Appl. No. 17/511,773, dated Mar. 15, 2023, 14 pages.

Notice of Opposition in European Patent Application No. 19151846.3, Opponent: Accord Healthcare, Ltd, dated May 10, 2023, 19 pages.

Notice of Opposition in European Patent Application No. 19151846.3, Opponent: Aechter, Mr Bernd, dated May 10, 2023, 15 pages.

Notice of Opposition in European Patent Application No. 19151846.3, Opponent: Elkington and Fife LLP, dated May 4, 2023, 28 pages.

Notice of Opposition in European Patent Application No. 19151846.3, Opponent: Generics (UK) Limited, dated May 10, 2023, 23 pages.

Notice of Opposition in European Patent Application No. 19151846.3, Opponent: Hansen Norbert, dated May 9, 2023, 354 pages.

(56) References Cited

OTHER PUBLICATIONS

Notice of Opposition in European Patent Application No. 19151846.3, Opponent: Maiwald GmbH, dated May 10, 2023, 23 pages.
Notice of Opposition in European Patent Application No. 19151846.3, Opponent: Stada Arzneimittel AG, dated May 10, 2023, 22 pages.
Notice of Opposition in European Patent Application No. 19151846.3, Opponent: Teva Pharmaceutical Industries Ltd., dated May 9, 2023, 24 pages.
Notice of Opposition in European Patent Application No. 19151846.3, Opponent: Welding GmbH & Co. KG, dated May 10, 2023, 22 pages.
Office Action in Australian Patent Application No. 2017249459, dated Feb. 24, 2023, 3 pages.
Office Action in Australian Patent Application No. 2018219637, dated Jun. 30, 2023, 3 pages.
Office Action in Australian Patent Application No. 2018219637, dated Mar. 14, 2023, 9 pages.
Office Action in Brazilian Patent Application No. BR1120170028271, dated Nov. 16, 2022, 12 pages (with English Translation).
Office Action in Brazilian Patent Application No. BR112017017428-6, dated Dec. 6, 2022, 7 pages (with English Translation).
Office Action in Brazilian Patent Application No. BR112018002732-4, dated Feb. 28, 2023, 12 pages (with English Translation).
Office Action in Brazilian Patent Application No. BR112018002732-4, dated Nov. 21, 2023, 13 pages (with English Translation).
Office Action in Brazilian Patent Application No. BR122023002744-2, dated May 30, 2023, 10 pages (with English Translation).
Office Action in Brazilian Patent Application No. BR122023002748-5, dated May 30, 2023, 10 pages (with English Translation).
Office Action in Canadian Patent Application No. 3019682, dated May 31, 2023, 3 pages.
Office Action in European Patent Application No. 16755489.8, dated Dec. 23, 2022, 2 pages.
Office Action in European Patent Application No. 16837150.8, dated Jan. 19, 2023, 11 pages.
Office Action in European Patent Application No. 16837150.8, dated Jan. 30, 2023, 5 pages.
Office Action in European Patent Application No. 16837150.8, dated Jul. 12, 2023, 20 pages.
Office Action in European Patent Application No. 17782552.8, dated Nov. 28, 2022, 4 pages.
Office Action in Indian Patent Application No. 201747004829, dated Oct. 9, 2023, 2 pages.
Office Action in Indian Patent Application No. 201747040368, dated Jul. 6, 2023, 2 pages.
Office Action in Indian Patent Application No. 201847003846, dated Jan. 19, 2023, 3 pages (with English Translation).
Office Action in Indian Patent Application No. 202148057534, dated Mar. 14, 2023, 2 pages (with English Translation).
Office Action in Indian Patent Application No. 202148057534, dated May 1, 2023, 2 pages.
Office Action in Israeli Patent Application No. 253946, dated Jul. 17, 2023, 13 pages (with English Translation).
Office Action in Israeli Patent Application No. 302218, dated Apr. 19, 2023, 5 pages (with English Translation).
Office Action in Israeli Patent Application No. 302218, dated Oct. 18, 2023, 6 pages.
Office Action in Japanese Patent Application No. P2020-560740, dated May 16, 2023, 4 pages (with English Translation).
Office Action in Japanese Patent Application No. P2022-161848, dated Oct. 31, 2023, 12 pages (with English Translation).
Office Action in Korean Patent Application No. 10-2017-7022544, dated Apr. 14, 2023, 12 pages (with English Translation).
Office Action in Korean Patent Application No. 10-2017-7022544, dated Oct. 10, 2023, 5 pages (with English Translation).
Office Action in Korean Patent Application No. 10-2018-7003723, dated May 8, 2023, 5 pages (with English Translation).
Office Action in Korean Patent Application No. 10-2019-7016853, dated Jan. 8, 2023, 7 pages (with English Translation).
Office Action in Korean Patent Application No. 10-2023-7009398, dated Jul. 31, 2023, 4 pages (with English Translation).
Office Action in Singaporean Patent Application No. 10202010137Y, dated Jul. 28, 2023, 8 pages.
Office Action in U.S. Appl. No. 13/923,858, dated Dec. 21, 2022, 7 pages.
Office Action in U.S. Appl. No. 13/923,858, dated Mar. 1, 2023, 13 pages.
Office Action in U.S. Appl. No. 16/092,245, dated Jun. 8, 2023, 17 pages.
Office Action in U.S. Appl. No. 17/052,133, dated Sep. 13, 2023, 6 pages.
Office Action in U.S. Appl. No. 17/228,025, dated May 23, 2023, 18 pages.
Office Action in U.S. Appl. No. 17/228,025, dated Sep. 11, 2023, 19 pages.
Official Notification in European Patent Application No. 16837150.8, dated Jul. 21, 2023, 3 pages.
Official Notification in European Patent Application No. 16837150.8, dated Sep. 29, 2023, 43 pages.
Official Notification in Indian Patent Application No. 201747028834, dated Jan. 2, 2023, 2 pages.
Official Notification in Jordan Patent Application No. 225/2020, dated Sep. 4, 2023, 2 pages (with English Translation).
Official Notification in U.S. Appl. No. 13/923,858, dated Jan. 19, 2023, 2 pages.
Official Notification in U.S. Appl. No. 13/923,858, dated Jun. 13, 2023, 19 pages.
Official Notification in U.S. Appl. No. 13/923,858, dated May 23, 2023, 2 pages.
Opposition, [No Author Listed], "Assessment Report—Lenvima (lenvatinib)," European Medicines Agency, Mar. 26, 2015, Exhibit HW5 in European Patent Application No. 19151846.3, Opponent: Welding GmbH & Co. KG, dated May 10, 2023, 170 pages.
Opposition, [No Author Listed], "Datasheet for Decision; Lenvatinib mesylate polymorphs—Crystal of salt of 4-(3-chloro-4-(cyclopropylaminocarbonyl)amino-phenoxy)-7-methoxy-6-quinolinecarboxamide or of solvate thereof and processes for producing these," Board of Appeal of the European Patent Office, Jun. 18, 2014, Exhibit D10 in European Patent Application No. 19151846.3, Opponent: Generics (UK) Limited, dated May 10, 2023, 16 pages.
Opposition, [No Author Listed], "Drugs@FDA: FDA-Approved Drugs Lenvima," NDA: 206947, Company: Eisai Inc, Fda Drug Database, Exhibit D12 in European Patent Application No. 19151846.3, Opponent: Maiwald GmbH, dated May 10, 2023, 4 pages.
Opposition, [No Author Listed], "Experimental Data," Exhibit D11 in European Patent Application No. 19151846.3, Opponent: Maiwald GmbH, dated May 10, 2023, 3 pages.
Opposition, [No Author Listed], "Experimental Report—Purge of Compound (I) from Lenvatinib," Exhibit E17 in European Patent Application No. 19151846.3, Opponent: Hansen Norbert, dated May 9, 2023, 5 pages.
Opposition, [No Author Listed], "Guideline on the limits of genotoxic impurities," Committee for Medicinal Products for Human Use, European Medicines Agency, Jun. 28, 2006, Exhibit HW3 in European Patent Application No. 19151846.3, Opponent: Welding GmbH & Co. KG, dated May 10, 2023, 8 pages.
Opposition, [No Author Listed], "ICH guideline M7 on assessment and control of DNA reactive (mutagenic) impurities in pharmaceuticals to limit potential carcinogenic risk," European Medicines Agency, May 2013, Exhibit E10 in European Patent Application No. 19151846.3, Opponent: Hansen Norbert, dated May 9, 2023, 27 pages.
Opposition, [No Author Listed], "Translation of JP 2014-174062 (first priority)," Aug. 28, 2014, Exhibit E1 in European Patent Application No. 19151846.3, Opponent: Hansen Norbert, dated May 9, 2023, 43 pages.
Opposition, [No Author Listed], "Translation of JP 2015-034729 (second priority)," Feb. 25, 2015, Exhibit E2 in European Patent Application No. 19151846.3, Opponent: Hansen Norbert, dated May 9, 2023, 51 pages.

(56) References Cited

OTHER PUBLICATIONS

Opposition, [No Author Listed], "Transmittal of Annual Reports for Drugs and Biologics for Human Use—Summary of Manufacturing Changes," Department of Health and Human Services, Food and Drug Administration, Feb. 13, 2018, Exhibit E13 in European Patent Application No. 19151846.3, Opponent: Hansen Norbert, dated May 9, 2023, 9 pages.
Opposition, Ahuja et al.'s, Handbook of Pharmaceutical Analysis by HPLC, 1st ed., Elsevier, 2005, Exhibit D9 in European Patent Application No. 19151846.3, Opponent: Teva Pharmaceutical Industries Ltd., dated May 9, 2023, pp. 19-22, 43, 44, 123-127, 133, 134, 200-203, 212, 262, 274, 275, 370-377.
Opposition, anzeninfo.mhlw.go.jp [Online], "Newly notified chemical substances (36 substances) confirmed to have mutagenicity," Dec. 11, 2012, [Retrieved on or before May 9, 2023], retrieved from: URL<https://anzeninfo.mhlw.go.jp/user/anzen/kag/20121211_heni.html>, Exhibits E11 & E11a in European Patent Application No. 19151846.3, Opponent: Hansen Norbert, dated May 9, 2023, 7 pages (with English Translation).
Opposition, Eisai.com [Online], "U.S. FDA Approves Anticancer Agent Lenvima (Lenvatinib Mesylate) as Treatment for Radioactive Iodine-Refractory Differentiated Thyroid Cancer, " Feb. 16, 2015, [Retrieved on or before May 4, 2023], retrieved from: URL<https://www.eisai.com/news/news201510.html>, Exhibit D10 in European Patent Application No. 19151846.3, Opponent: Elkington and Fife LLP, dated May 4, 2023, 2 pages.
Opposition, Honma, "AMES/QSAR International Collaborative Study," with Class A list, Division of Genetics and Mutagenesis, National Institute of Health Sciences, Jun. 2019, [Retrieved on or before May 9, 2023], retrieved from: URL<http://www.nihs.go.jp/dgm/amesqsar.html>, Exhibits E12 & E12a in European Patent Application No. 19151846.3, Opponent: Hansen Norbert, dated May 9, 2023, 20 pages.
Opposition, Jeffery et al.'s, Vogel's Textbook of Quantitative Chemical Analysis, 5th ed., Longman Scientific & Technical, 1989, Exhibit D10 in European Patent Application No. 19151846.3, Opponent: Teva Pharmaceutical Industries Ltd., dated May 9, 2023, pp. 216, 220-229, 232-233.
Opposition, Müller et al., "A rationale for determining, testing, and controlling specific impurities in pharmaceuticals that possess potential for genotoxicity," Regulatory Toxicology and Pharmacology, 2006, Exhibit HW4 in European Patent Application No. 19151846.3, Opponent: Welding GmbH & Co. KG, dated May 10, 2023, 44:198-211.
Opposition, Patentee's Brief, dated Dec. 9, 2021, Exhibit D13 in European Patent Application No. 19151846.3, Opponent: Teva Pharmaceutical Industries Ltd., dated May 9, 2023, 11 pages.
Opposition, Shumaker et al., "Effect of Rifampicin on the Pharmacokinetics of Lenvatinib in Healthy Adults," Clin. Drug Investig., 2014, Exhibit D10 in European Patent Application No. 19151846.3, Opponent: Maiwald GmbH, dated May 10, 2023, 34:651-659.
Opposition, Snyder's Practical HPLC Method Development, 2nd ed., John Wiley & Sons Inc., 1998, Exhibit D9 in European Patent Application No. 19151846.3, Opponent: Elkington and Fife LLP, dated May 4, 2023, pp. 1-14, 292-317.
Opposition, Waters.com [Online], "X-Bridge HPLC Columns Brochure," Feb. 2015, [Retrieved on or before May 4, 2023], retrieved from: URL<https://www.waters.com/webassets/cms/library/docs/720001255en.pdf>, Exhibit D8 in European Patent Application No. 19151846.3, Opponent: Elkington and Fife LLP, dated May 4, 2023, 23 pages.
Reed et al., "β-catenin/CBP activation of mTORC1 signaling promotes partial epithelial-mesenchymal states in head and neck cancer," Translational Research, Jun. 21, 2023, 1-15.
Robinson, "Control of genotoxic impurities in active pharmaceutical ingredients: a review and perspective," Organic Process Research & Development, 2010, 14(4):946-959.
Sadineni et al., "Novel method for the synthesis of lenvatinib using 4-nitrophenyl cyclopropylcarbamate and their pharmaceutical salts," Chemical Papers, 2021, 75:1475-1483.
Search Report in European Patent Application No. 17782552.8, dated May 19, 2023, 6 pages.
Submission Document in Australian Patent Application No. 2017249459, dated Feb. 22, 2023, 89 pages.
Submission Document in Australian Patent Application No. 2018219637, dated Jun. 7, 2023, 17 pages.
Submission Document in Brazilian Patent Application No. BR1120170028271, dated Feb. 14, 2023, 54 pages (with English Translation).
Submission Document in Brazilian Patent Application No. BR112018002732-4, dated May 29, 2023, 64 pages (with English Translation).
Submission Document in Brazilian Patent Application No. BR122023002744-2, dated Aug. 24, 2023, 46 pages (with English Translation).
Submission Document in Brazilian Patent Application No. BR122023002748-5, dated Aug. 25, 2023, 33 pages (with English Translation).
Submission Document in Canadian Patent Application No. 2994925, dated Dec. 30, 2022, 8 pages.
Submission Document in Canadian Patent Application No. 3019682, dated Sep. 28, 2023, 22 pages.
Submission Document in European Patent Application No. 16755489.8, dated Feb. 17, 2023, 6 pages.
Submission Document in European Patent Application No. 16837150.8, dated Jul. 5, 2023, 10 pages.
Submission Document in European Patent Application No. 19151846.3, dated Dec. 4, 2023, 50 pages.
Submission Document in European Patent Application No. 19151846.3, dated May 17, 2023, 203 pages.
Submission Document in European Patent Application No. 19733190.3, dated Jan. 13, 2023, 10 pages.
Submission Document in European Patent Application No. 22180987.4, dated May 15, 2023, 116 pages.
Submission Document in Indian Patent Application No. 201747028834, dated Dec. 19, 2022, 15 pages.
Submission Document in Israeli Patent Application No. 253946, dated Nov. 6, 2023, 8 pages (with English Translation).
Submission Document in Korean Patent Application No. 10-2017-7022544, dated Jun. 9, 2023, 40 pages (with English Translation).
Submission Document in Korean Patent Application No. 10-2017-7022544, dated Nov. 30, 2023, 29 pages (with English Translation).
Submission Document in Korean Patent Application No. 10-2018-7003723, dated Jun. 29, 2023, 14 pages (English Translation).
Submission Document in Korean Patent Application No. 10-2019-7016853, dated Mar. 7, 2023, 25 pages (with English Translation).
Submission Document in Korean Patent Application No. 10-2021-7037538, dated Nov. 9, 2022, 31 pages (with English Translation).
Submission Document in U.S. Appl. No. 13/923,858, dated Jan. 10, 2023, 4 pages.
Submission Document in U.S. Appl. No. 15/750,712, dated Apr. 24, 2023, 5 pages.
Submission Document in U.S. Appl. No. 15/750,712, dated Aug. 8, 2023, 1 page.
Submission Document in U.S. Appl. No. 15/750,712, dated Jan. 6, 2023, 3 pages.
Submission Document in U.S. Appl. No. 15/750,712, dated Nov. 16, 2023, 14 pages.
Submission Document in U.S. Appl. No. 15/934,242, dated Nov. 18, 2022, 3 pages.
Submission Document in U.S. Appl. No. 16/092,245, dated Feb. 14, 2023, 21 pages.
Submission Document in U.S. Appl. No. 16/092,245, dated Nov. 30, 2023, 6 pages.
Submission Document in U.S. Appl. No. 16/465,277, dated Dec. 6, 2023, 2 pages.
Submission Document in U.S. Appl. No. 16/465,277, dated Feb. 17, 2023, 18 pages.
Submission Document in U.S. Appl. No. 16/465,277, dated Jun. 8, 2023, 14 pages.

(56) References Cited

OTHER PUBLICATIONS

Submission Document in U.S. Appl. No. 16/465,277, dated Oct. 19, 2023, 14 pages.
Submission Document in U.S. Appl. No. 17/052,133, dated Nov. 10, 2023, 2 pages.
Submission Document in U.S. Appl. No. 17/228,025, dated Apr. 20, 2023, 13 pages.
Submission Document in U.S. Appl. No. 17/228,025, dated Aug. 7, 2023, 37 pages.
Submission Document in U.S. Appl. No. 17/228,025, dated Nov. 14, 2023, 25 pages.
Submission Document in U.S. Appl. No. 17/228,025, dated Sep. 22, 2023, 1 page.
Submission Document in U.S. Appl. No. 17/511,773, dated Mar. 3, 2023, 17 pages.
Tung et al., "Crystallization of Organic Compounds, an Industrial Perspective," Wiley, 2009, Chapter 5, pp. 101-116.
Van Winkle et al., "Ifosfamide, Carboplatin, and Etoposide (ICE) Reinduction Chemotherapy in a Large Cohort of Children and Adolescents With Recurrent/Refractory Sarcoma: The Children's Cancer Group (CCG) Experience," Pediatr. Blood Cancer, 2005, 44:338-347.
Yamada et al., "E7386 Opportunity Overview—Inhibitor of Protein-Protein Interaction of CBP/β-catenin as a Wnt Signaling Modulator," Presentation Slides, Eisai, Dec. 2022, 29 pages.
Zheng et al., "The mechanism of solvent-mediated desolvation transformation of lenvatinib mesylate from dimethyl sulfoxide solvate to form D," Acta Crystallographica Section B: Structural Science, Crystal Engineering and Materials, 2020, B76:343-352.
[No Author], "Chromatographic Purification of Lenvatinib," Experimental Report, Aug. 2023, 2 pages.
[No Author], "Experimental Data," provided as Evidence 12 by the Cancellation Petitioner on Feb. 17, 2024, in Taiwanese Patent Application No. 104127982, 3 pages.
[No Author], "How to give medicines: tablets," Medicines for Children, Dec. 2011, 2 pages.
[No Author], "Information of compound (I)," on the NITE Chemical Risk Information Platform website, Dec. 11, 2012, 3 pages (with English Translation).
[No Author], "Original Specification of Opposed Application," Eisai R&D Management Co., Ltd, Jun. 7, 2019, 40 pages.
[No Author], "Purified Lenvatinib analysis report," Experimental Report, Mar. 2024, 1 page.
[No Author], "Report on the Regulatory Uses and Applications in OECD Member Countries of (Quantitative) Structure-Activity Relationship [(Q)SAR] Models in the Assessment of New and Existing Chemicals," ENV/JM/MONO(2006)25, OECD, 2007, Paris, France, available from URL: <http://oecd.org/>, 79 pages.
Aulton et al., "Pharmaceutics: The Science of Dosage Form Design," Churchill Livingstone, 2002, Chapters 1, 23, 27 and 29, 96 pages.
ClinicalTrials.gov [online], NCT database, "A Multicenter, Randomized, Double-Blind, Placebo-Controlled, Trial of Lenvatinib(E7080) in 131I-Refractory Differentiated Thyroid Cancer(DTC)(SELECT)," NCT01321554, Dec. 18, 2014, retrieved from: URL <https://clinicaltrials.gov/study/NCT01321554?cond=NCT01321554&rank=1&tab=histo ry&a=19>, 17 pages.
ClinicalTrials. gov [online], NCT database, "A Phase 1, Open-Label, Single-Dose, Pharmacokinetic and Safety Study of E7080(24mg) Administered to Subjects With Mild, Moderate, and Severe Renal Impairment and to Healthy Subjects," NCT02199379, Feb. 12, 2015, retrieved from: URL <https://clinicaltrials.gov/study/NCT02199379?intr-Lenvatinib&term=dose&rank=26&ta b=history &a-2>, 13 pages.
ClinicalTrials.gov [online], NCT database, "A Study of E7080 in Subjects With Solid Tumor," NCT01268293, Feb. 21, 2015, retrieved from: URL <https://clinicaltrails.gov/study/NCT01268293?intr-Lenvatinib&studyComp=2016-02-10&rank=2&tab=history&a-6>, 20 pages.
Felton, "Remington Essentials of Pharmaceutics," Pharmaceutical Press, 2013, Chapters 17 and 20, 71 pages.
Heretsch, "Experimental Report—Synthesis of Lenvatinib mesylate following prior art patent US 2007/0078159 A1—Prof. Heretsch with Annexes 1-3," Mar. 12, 2024, 23 pages.
Kudo et al., "Analysis of Tumor Biomarkers in Patients with Advanced Hepatocellular Carcinoma from a Phase 1b Study of E7386, a CREB-Binding Protein/ß-Catenin Interaction Inhibitor, in Combination with Lenvatinib—Abstract #535," Poster, ASCO Gastrointestinal Cancers Symposium, Jan. 18-20, 2024, San Francisco, CA, USA, 1 page.
Kudo et al., "Analysis of Tumor Biomarkers in Patients with Advanced Hepatocellular Carcinoma from a Phase 1b Study of E7386, a CREB-Binding Protein/β-Catenin Interaction Inhibitor, in Combination with Lenvatinib—Abstract #535," Slideshow, ASCO Gastrointestinal Cancers Symposium, Jan. 18-20, 2024, San Francisco, CA, USA, 6 pages.
Lynch et al., "The Sense of Taste," Nova Science Publishers, 2012, pp. 237-276.
Notice of Allowance in Israeli Patent Application No. 302218, dated Feb. 20, 2024, 3 pages.
Notice of Allowance in Japanese Patent Application No. P2022-161848, dated May 28, 2024, 8 pages (with English Translation).
Notice of Allowance in U.S. Appl. No. 15/750,712, dated Feb. 2, 2024, 11 pages.
Notice of Allowance in U.S. Appl. No. 15/750,712, dated May 15, 2024, 13 pages.
Notice of Allowance in U.S. Appl. No. 16/465,277, dated Jan. 30, 2024, 6 pages.
Notice of Allowance in U.S. Appl. No. 16/465,277, dated Jul. 9, 2024, 12 pages.
Notice of Allowance in U.S. Appl. No. 16/465,277, dated Mar. 26, 2024, 11 pages.
Notice of Allowance in U.S. Appl. No. 17/511,773, dated May 20, 2024, 4 pages.
Notice of Allowance in U.S. Appl. No. 17/511,773, dated May 6, 2024, 27 pages.
Office Action in Argentinian Patent Application No. P190102193, dated May 16, 2024, 11 pages (with English Translation).
Office Action in Brazilian Application No. BR122023002744-2, dated Jun. 4, 2024, 8 pages (with English Translation).
Office Action in Brazilian Application No. BR122023002748-5, dated Jun. 4, 2024, 8 pages (with English Translation).
Office Action in Brazilian Patent Application No. BR122023002744-2, dated Feb. 15, 2024, 20 pages (with English Translation).
Office Action in Brazilian Patent Application No. BR122023002748-5, dated Feb. 15, 2024, 19 pages (with English Translation).
Office Action in Canadian Patent Application No. 3019682, dated Apr. 4, 2024, 4 pages.
Office Action in Canadian Patent Application No. 3044658, dated Feb. 20, 2024, 4 pages.
Office Action in Chinese Patent Application No. 202110939882.8, dated Apr. 11, 2024, 17 pages (with English Translation).
Office Action in European Patent Application No. 16837150.8, dated Feb. 1, 2024, 25 pages.
Office Action in European Patent Application No. 17782552.8, dated Dec. 18, 2023, 7 pages.
Office Action in European Patent Application No. 19151846.3, dated Apr. 2, 2024, 21 pages.
Office Action in European Patent Application No. 20207489.4, dated Jun. 3, 2024, 5 pages.
Office Action in Indian Patent Application No. 201747004829, dated Jan. 1, 2024, 3 pages.
Office Action in Indian Patent Application No. 201947022655, dated Aug. 6, 2024, 2 pages.
Office Action in Indian Patent Application No. 201947022655, dated Feb. 13, 2024, 335 pages.
Office Action in Indian Patent Application No. 201947022655, dated Jul. 3, 2024, 2 pages.
Office Action in Indian Patent Application No. 201947022655, dated May 14, 2024, 2 pages.
Office Action in Indian Patent Application No. 6971/CHENP/2015, dated Feb. 22, 2024, 5 pages.
Office Action in Indian Patent Application No. 6971/CHENP/2015, dated Mar. 22, 2024, 10 pages.

(56) References Cited

OTHER PUBLICATIONS

Office Action in Israeli Patent Application No. 262076, dated Dec. 18, 2023, 4 pages.
Office Action in Korean Patent Application No. 10-2017-7022544, dated Jun. 18, 2024, 11 pages (with English Translation).
Office Action in Pakistani Patent Application No. 548/2015, dated Dec. 14, 2023, 2 pages.
Office Action in Pakistani Patent Application No. 807/2021, dated Dec. 14, 2023, 2 pages.
Office Action in Singaporean Patent Application No. 10202010137Y, dated Feb. 6, 2024, 9 pages.
Office Action in Singaporean Patent Application No. 10202100272R, dated Jul. 30, 2024, 10 pages.
Office Action in Taiwanese Patent Application No. 104127982, dated Feb. 17, 2024, 178 pages (with English Translation).
Office Action in U.S. Appl. No. 16/092,245, dated Dec. 22, 2023, 33 pages.
Office Action in U.S. Appl. No. 17/052,133, dated Jan. 8, 2024, 9 pages.
Official Notification in European Patent Application No. 16755489.8, dated Jul. 17, 2024, 26 pages.
Official Notification in European Patent Application No. 16755489.8, dated Jun. 26, 2024, 31 pages.
Official Notification in European Patent Application No. 17782552.8, dated Jun. 5, 2024, 3 pages.
Official Notification in European Patent Application No. 19151846.3, dated May 23, 2024, 37 pages.
Official Notification in U.S. Appl. No. 17/228,025, dated Mar. 6, 2024, 9 pages.
PubChem Substance Record for SID 135264024, "Lenvatinib Mesylate," National Library of Medicine, Mar. 21, 2012, 8 pages.
Rowe et al., "Handbook of Pharmaceutical Excipients," Pharmaceutical Press, 2009, Sixth ed., pp. 86-87.
Submission Document in Brazilian Patent Application No. B112018002732-4, dated Jan. 22, 2024, 32 pages (with English Translation).
Submission Document in Brazilian Patent Application No. BR122023002744-2, dated Aug. 2, 2024, 37 pages (with English Translation).
Submission Document in Brazilian Patent Application No. BR122023002744-2, dated May 15, 2024, 65 pages (with English Translation).
Submission Document in Brazilian Patent Application No. BR122023002748-5, dated Aug. 2, 2024, 36 pages (with English Translation).
Submission Document in Brazilian Patent Application No. BR122023002748-5, dated May 15, 2024, 54 pages (with English Translation).
Submission Document in Canadian Patent Application No. 3044658, dated Jun. 17, 2024, 12 pages.
Submission Document in European Patent Application No. 16837150.8, dated Dec. 1, 2023, 9 pages.
Submission Document in European Patent Application No. 16837150.8, dated May 29, 2024, 21 pages.
Submission Document in European Patent Application No. 17782552.8, dated May 17, 2024, 12 pages.
Submission Document in European Patent Application No. 19151846.3, dated Mar. 12, 2024, 10 pages.
Submission Document in European Patent Application No. 19151846.3, dated Mar. 13, 2024, 25 pages.
Submission Document in Indian Patent Application No. 201947022655, dated May 10, 2024, 19 pages.
Submission Document in Indian Patent Application No. 201947022655, dated May 28, 2024, 9 pages.
Submission Document in Israeli Patent Application No. 262076, dated Apr. 11, 2024, 29 pages (with English Translation).
Submission Document in Israeli Patent Application No. 302218, dated Feb. 15, 2024, 20 pages (with English Translation).
Submission Document in Japanese Patent Application No. P2022-161848, dated Mar. 27, 2024, 9 pages (with English Translation).
Submission Document in Korean Patent Application No. 10-2017-7022544, dated Jul. 23, 2024, 19 pages (with English Translation).
Submission Document in U.S. Appl. No. 15/750,712, dated May 1, 2024, 23 pages.
Submission Document in U.S. Appl. No. 16/465,277, dated Jan. 19, 2024, 7 pages.
Submission Document in U.S. Appl. No. 16/465,277, dated Jun. 26, 2024, 10 pages.
Submission Document in U.S. Appl. No. 16/465,277, dated Mar. 8, 2024, 5 pages.
Submission Document in U.S. Appl. No. 17/228,025, dated Apr. 18, 2024, 11 pages.
Swarbrick, "Encyclopedia of Pharmaceutical Technology," CRC Press, 2006, Third ed., vol. 1, 16 pages.
Waters.com [online], "Waters Chromatography cols. and Supplies," 2009, retrieved from: URL <https://www.waters.com/webassets/cms/library/docs/720002784en>, 9 pages.
White et al., "Handbook of Drug Administration via Enteral Feeding Tubes," Pharmaceutical Press, 2007, 22 pages.
"Wikipedia.org [online]," "Alkaloid," Extract of the Internet Archive website, Feb. 23, 2015, 19 pages.

* cited by examiner

TREATMENT OF HEPATOCELLULAR CARCINOMA

TECHNICAL FIELD

The present application relates generally to methods of treating hepatocellular carcinoma.

BACKGROUND ART

Hepatocellular carcinoma (HCC) is the second leading cause of cancer death worldwide and is responsible for nearly 745,000 deaths each year. It usually occurs in a background of chronic liver disease, particularly in cirrhosis, which limits the feasibility of surgical resection. Sorafenib, an oral multikinase inhibitor, extends overall survival when used as a first-line treatment for HCC, demonstrating a median improvement of 2.8 months compared with placebo (10.7 months vs. 7.9 months; hazard ratio [HR]:0.69; P<0.001) despite a low response rate of 2% (Llovet, N Engl. J Med., 359:378-390, 2008).

Drug development in HCC ire the past 10 years is marked by four failed phase 3 trials (of sunitinib, brivanib, linifanib, and erlotinib plus sorafenib) that did not demonstrate non-inferiority (Cheng, J. Clin. Oncol., 31:4067-4075, 2013; Johnson, J. Clin. Oncol., 31:36517-3524, 2013; Cainap, J. Clin. Oncol., 33:172479, 2015) or superiority (Zhu, J. Clin. Oncol., 33(6):559-66, 2015) to sorafenib in overall survival. Therefore, unresectable HCC represents a highly unmet medical need.

SUMMARY OF INVENTION

This disclosure relates, in part, to methods of treating a subject with a HCC (e.g., advanced HCC, unresectable HCC (uHCC), or advanced uHCC) with lenvatinib or a pharmaceutically acceptable salt thereof. In some embodiments, lenvatinib or a pharmaceutically acceptable salt thereof is administered as a first-line single agent to patients with unresectable HCC. In some embodiments, the dosage of lenvatinib or a pharmaceutically acceptable salt thereof is modified upon the occurrence of one or more adverse events in the treated subject.

In a first aspect, the disclosure features a method of treating unresectable hepatocellular carcinoma. The method comprises administering to a human subject that has an unresectable hepatocellular carcinoma a dosage regimen of lenvatinib or a pharmaceutically acceptable salt thereof that is: (i) 12 mg/day if the body weight of the human subject is equal to or more than 60 kg or (ii) 8 mg/day if the body weight of the human subject is less than 60 kg. In certain embodiments, lenvatinib or a pharmaceutically acceptable salt thereof is administered orally. In certain embodiments, lenvatinib or a pharmaceutically acceptable salt thereof is administered once daily. In certain embodiments, lenvatinib or a pharmaceutically acceptable salt thereof is administered orally, once daily.

In a second aspect, the disclosure features a method of treating unresectable hepatocellular carcinoma. The method comprises administering to a human subject that has an unresectable hepatocellular carcinoma and moderate hepatic impairment classified in Child-Pugh class B under Child-Pugh Classification a dosage regimen of lenvatinib or a pharmaceutically acceptable salt thereof that is 8 mg/day. In certain embodiments, lenvatinib or a pharmaceutically acceptable salt thereof is administered orally. In certain embodiments, lenvatinib or a pharmaceutically acceptable salt thereof is administered once daily. In certain embodiments, lenvatinib or a pharmaceutically acceptable salt thereof is administered orally once daily.

As used throughout this disclosure, a dosage regimen comprising lenvatinib or a pharmaceutically acceptable salt thereof at a specified dose means that lenvatinib or a pharmaceutically acceptable salt thereof is present in the dosage regimen at the specified dose. Although such a dosage regimen can contain additional components, lenvatinib or a pharmaceutically acceptable salt thereof is present only at the specific dose listed. The dose of lenvatinib or a pharmaceutically acceptable salt thereof (e.g., 12 mg, 8 mg, or 4 mg) as used throughout refers to the dose of the free form of lenvatinib.

In a third aspect, the disclosure provides a method of treating unresectable hepatocellular carcinoma that comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. In carrying out this method, the human subject develops an occurrence of a first Grade 3 nonhematologic toxicity during treatment with the first dosage regimen. Thereupon, the method further comprises terminating administration of the first dosage regimen after the occurrence of the first Grade 3 nonhematologic toxicity until the first Grade 3 nonhematologic toxicity is resolved to Grade 0-1 or baseline, and administering to the human subject a second dosage regimen comprising lenvatinib or a pharmaceutically acceptable salt thereof at a dose of (i) 9 mg/day if the body weight of the human subject is equal to or more than 60 kg or (ii) 4 mg/day if the body weight of the human subject is less than 60 kg. In certain embodiments, the human subject develops an occurrence of a second Grade 3 nonhematologic toxicity during treatment with the second dosage regimen. In such embodiments, the method further comprises terminating administration of the second dosage regimen after the occurrence of the second Grade 3 nonhematologic toxicity until the second Grade 3 nonhematologic toxicity is resolved to Grade 0-1 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg. In certain embodiments, the human subject develops an occurrence of a third Grade 3 nonhematologic toxicity during treatment with the third dosage regimen. In such embodiments, the method further comprises terminating administration of the third dosage regimen after the occurrence of the third Grade 3 nonhematologic toxicity until the third Grade 3 nonhematologic toxicity is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day.

In a fourth aspect, the disclosure provides a method of treating unresectable hepatocellular carcinoma that comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 mg/day. In carrying out this method, the human subject develops an occurrence of a first Grade 3 nonhematologic toxicity during treatment with the first dosage regimen. Thereupon, the method further comprises terminating administration of the first dosage regimen after the occurrence of the first Grade 3 nonhematologic toxicity until the first Grade 3 nonhematologic toxicity is resolved to Grade 0-1 or baseline, and administering to the human subject a second dosage regimen comprising lenvatinib or a pharmaceutically acceptable salt thereof at a dose of 4 mg/day. In certain embodiments, the human subject develops an occurrence of a second Grade 3 nonhematologic toxicity during treatment with the second dosage regimen. In such embodiments, the method further comprises terminating administration of the second dosage regimen after the occurrence of the second Grade 3 nonhematologic toxicity until the second Grade 3 nonhematologic toxicity is resolved to Grade 0-1 or baseline, and administering to the human subject a third dosage regimen comprising lenvatinib or a pharmaceutically acceptable salt thereof at a dose of 4 mg every other day. In certain embodiments, the human subject develops an occurrence of a third Grade 3 nonhematologic toxicity during treatment with the third dosage regimen. In such embodiments, the method further comprises terminating administration of the third dosage regimen after the occurrence of the third Grade 3 nonhematologic toxicity.

In a fifth aspect, the disclosure provides a method of treating unresectable hepatocellular carcinoma that comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. In carrying out this method, the human subject develops an occurrence of a first persistent and intolerable Grade 2 or Grade 3 nonhematologic toxicity during treatment with the first dosage regimen. Thereupon, the method further comprises terminating administration of the first dosage regimen after the occurrence of the first persistent and intolerable Grade 2 or Grade 3 nonhematologic toxicity until the first persistent and intolerable Grade 2 or Grade 3 nonhematologic toxicity is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. In certain embodiments, the human subject develops an occurrence of a second persistent and intolerable Grade 2 or Grade 3 nonhematologic toxicity during treatment with the second dosage regimen. In such embodiments, the method further comprises terminating administration of the second dosage regimen after the occurrence of the second persistent and intolerable Grade 2 or Grade 3 nonhematologic toxicity until the second persistent and intolerable Grade 2 or Grade 3 nonhematologic toxicity is resolved to Grade 0-1 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg. In certain embodiments, the human subject develops an occurrence of a third persistent and intolerable Grade 2 or Grade 3 nonhematologic toxicity during treatment with the third dosage regimen. In such embodiments, the method further comprises terminating administration of the third dosage regimen after the occurrence of the third persistent and intolerable Grade 2 or Grade 3 nonhematologic toxicity until the third persistent and intolerable Grade 2 or Grade 3 nonhematologic toxicity is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day.

In a sixth aspect, the disclosure provides a method of treating unresectable hepatocellular carcinoma that comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 mg/day. In carrying out this method, the human subject develops an occurrence of a first persistent and intolerable Grade 2 or Grade 3 nonhematologic toxicity during treatment with the first dosage regimen. Thereupon, the method further comprises terminating administration of the first dosage regimen after the occurrence of the first persistent and intolerable Grade 2 or Grade 3 nonhematologic toxicity until the first persistent and intolerable Grade 2 or Grade 3 nonhematologic toxicity is resolved to Grade 0-1 or baseline, and administering to the human subject a second dosage regimen comprising lenvatinib or a pharmaceutically acceptable salt thereof at a dose 4 mg/day. In certain embodiments, the human subject develops an occurrence of a second persistent and intolerable Grade 2 or Grade 3 nonhematologic toxicity during treatment with the second dosage regimen. In such embodiments, the method further comprises terminating administration of the second dosage regimen after the occurrence of the second persistent and intolerable Grade 2 or Grade 3 nonhematologic toxicity until the second persistent and intolerable Grade 2 or Grade 3 nonhematologic toxicity is resolved to Grade 0-1 or baseline, and administering to the human subject a third dosage regimen comprising lenvatinib or a pharmaceutically acceptable salt thereof at a dose of 4 mg every other day. In certain embodiments, the human subject develops an occurrence of a third persistent and intolerable Grade 2 or Grade 3 nonhematologic toxicity during treatment with the third dosage regimen. In such embodiments, the method further comprises terminating administration of the third dosage regimen after the occurrence of the third persistent and intolerable Grade 2 or Grade 3 nonhematologic toxicity.

In a seventh aspect, the disclosure provides a method of treating unresectable hepatocellular carcinoma that comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. In carrying out this method, the human subject develops an occurrence of a first persistent and intolerable Grade 2 or Grade 3 nonhematologic toxicity or non-life threatening Grade 4 laboratory abnormality during treatment with the first dosage regimen. Thereupon, the method further comprises terminating administration of the first dosage regimen after the occurrence of the first persistent and intolerable Grade 2 or Grade 3 nonhematologic toxicity or non-life threatening Grade 4 laboratory abnormality until the first persistent and intolerable Grade 2 or Grade 3 nonhematologic toxicity or non-life threatening Grade 4 laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. In certain embodiments, the human subject develops an occurrence of a second persistent and intolerable Grade 2 or Grade 3 nonhematologic toxicity or non-life threatening Grade 4 laboratory abnormality during treatment with the second dosage regimen. In such embodiments, the method further comprises terminating administration of the second dosage regimen after the occurrence of the second persistent and intolerable Grade 2 or Grade 3 nonhematologic toxicity or non-life threatening Grade 4 laboratory abnormality until the second persistent and intolerable Grade 2 or Grade 3 nonhematologic toxicity or non-life threatening Grade 4 laboratory abnormality is resolved to Grade 0-1 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg. In certain embodiments, the human subject develops an occurrence of a third persistent and intolerable Grade 2 or Grade 3 nonhematologic toxicity or non-life threatening Grade 4 laboratory abnormality during treatment with the third dosage regimen. In such embodiments, the method further comprises terminating administration of the third dosage regimen after the occurrence of the third persistent and intolerable Grade 2 or Grade 3 nonhematologic toxicity or non-life threatening Grade 4 laboratory abnormality until the third persistent and intolerable Grade 2 or Grade 3 nonhematologic toxicity or non-life threatening Grade 4 laboratory abnormality is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day.

In an eighth aspect, the disclosure provides a method of treating unresectable hepatocellular carcinoma that comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 mg/day. In carrying out this method, the human subject develops an occurrence of a first persistent and intolerable Grade 2 or Grade 3 nonhematologic toxicity or non-life threatening Grade 4 laboratory abnormality during treatment with the first dosage regimen. Thereupon, the method further comprises terminating administration of the first dosage regimen after the occurrence of the first persistent and intolerable Grade 2 or Grade 3 nonhematologic toxicity or non-life threatening Grade 4 laboratory abnormality until the first persistent and intolerable Grade 2 or Grade 3 nonhematologic toxicity or non-life threatening Grade 4 laboratory abnormality is resolved to Grade 0-1 or baseline, and administering to the human subject a second dosage regimen comprising lenvatinib or a pharmaceutically acceptable salt thereof at a dose of 4 mg/day. In certain embodiments, the human subject develops an occurrence of a second persistent and intolerable Grade 2 or Grade 3 nonhematologic toxicity or non-life threatening Grade 4 laboratory abnormality during treatment with the second dosage regimen. In such embodiments, the method further comprises terminating administration of the second dosage regimen after the occurrence of the second persistent and intolerable Grade 2 or Grade 3 nonhematologic toxicity or non-life threatening Grade 4 laboratory abnormality until the second persistent and intolerable Grade 2 or Grade 3 nonhematologic toxicity or non-life threatening Grade 4 laboratory abnormality is resolved to Grade 0-1 or baseline, and administering to the human subject a third dosage regimen comprising lenvatinib or a pharmaceutically acceptable salt thereof at a dose of 4 mg every other day. In certain embodiments, the human subject develops an occurrence of a third persistent and intolerable Grade 2 or Grade 3 nonhematologic toxicity or non-life threatening Grade 4 laboratory abnormality during treatment with the third dosage regimen. In such embodiments, the method further comprises terminating administration of the third dosage regimen after the occurrence of the third persistent and intolerable Grade 2 or Grade 3 nonhematologic toxicity or non-life threatening Grade 4 laboratory abnormality.

In some embodiments of the third to eighth aspects, following or during treatment with the second dosage regimen, the human subject does not develop an occurrence of a second persistent and intolerable Grade 2 or Grade 3 nonhematologic toxicity or non-life threatening Grade 4 laboratory abnormality. In such embodiments, the method further comprises continuing administration of the second dosage regimen to the human subject (i.e., not lowering the dose being given in the second dosage regimen).

In some embodiments of the third to eighth aspects, following or during treatment with the third dosage regimen, the human subject does not develop an occurrence of a third persistent and intolerable Grade 2 or Grade 3 nonhematologic toxicity or non-life threatening Grade 4 laboratory abnormality. In such embodiments, the method further comprises continuing administration of the third dosage regimen to the human subject (i.e., not lowering the dose being given in the third dosage regimen).

In certain embodiments, the human subject develops an occurrence of a Grade 4 nonhematologic toxicity excluding a non-life-threatening Grade 4 laboratory abnormality during treatment with the above dosage regimens. In such embodiments, the method further comprises terminating administration of the dosage regimen after the occurrence of the Grade 4 nonhematologic toxicity excluding non-life-threatening Grade 4 laboratory abnormality.

In a ninth aspect, the disclosure provides a method of treating unresectable hepatocellular carcinoma that comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. In carrying out this method, the human subject develops an occurrence of a first Grade 3 hematologic toxicity or proteinuria during treatment with the first dosage regimen. Thereupon, the method further comprises terminating administration of the first dosage regimen after the occurrence of the first Grade 3 hematologic toxicity or proteinuria until the first Grade 3 hematologic toxicity or proteinuria is resolved to Grade 0-2 or baseline, and administering to the human subject a second dosage regimen comprising lenvatinib or a pharmaceutically acceptable salt thereof at a close of (i) 12 mg/day if the body weight of the human subject is equal to or more than 60 kg or (ii) 8 mg/day if the body weight of the human subject is less than 60 kg. In certain embodiments, the human subject develops an occurrence of a second Grade 3 hematologic toxicity or proteinuria during treatment with the second dosage regimen. In such embodiments, the method further comprises terminating administration of the second dosage regimen after the occurrence of the second Grade 3 hematologic toxicity or proteinuria until the second Grade 3 hematologic toxicity or proteinuria is resolved to Grade 0-2 or baseline, and administering to the human subject a third dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. In certain embodiments, the human subject develops an occurrence of a third Grade 3 hematologic toxicity or proteinuria during treatment with the third dosage regimen. In such embodiments, the method further comprises terminating administration of the third dosage regimen after the occurrence of the third Grade 3 hematologic toxicity or proteinuria until the third Grade 3 hematologic toxicity or proteinuria is resolved to Grade 0-2 or baseline, and administering to the human subject a fourth dosage regimen comprising lenvatinib or a pharmaceutically acceptable salt thereof at a close of (i) 4 mg/day if the body weight of the human subject is equal to or more than 60 kg or (ii) 4 mg every other day if the body weight of the human subject is less than 60 kg. In certain embodiments, the human subject develops an occurrence of a fourth Grade 3 hematologic toxicity or proteinuria during treatment with the fourth dosage regimen. In such embodiments, the method further comprises terminating administration of the fourth dosage regimen after the occurrence of the fourth Grade 3 hematologic toxicity or proteinuria until the fourth Grade 3 hematologic toxicity or proteinuria is resolved to Grade 0-2 or baseline, and, if the body weight of the human subject is equal to or more than 60 kg, administering to the human subject a fifth dosage regimen comprising lenvatinib or a pharmaceutically acceptable salt thereof at a dose of 4 mg every other day.

In a tenth aspect, the disclosure provides a method of treating unresectable hepatocellular carcinoma that comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 mg/day. In carrying out this method, the human subject develops an occurrence of a first Grade 3 hematologic toxicity or proteinuria during treatment with the first dosage regimen. Thereupon, the method further comprises terminating administration of the first dosage regimen after the occurrence of the first Grade 3 hematologic toxicity or proteinuria until the first Grade 3 hematologic toxicity or proteinuria is resolved to Grade 0-2 or baseline, and administering to the human subject a second dosage regimen comprising lenvatinib or a pharmaceutically acceptable salt thereof at a dose of 8 mg/day. In certain embodiments, the human subject develops an occurrence of a second Grade 3 hematologic toxicity or proteinuria during treatment with the second dosage regimen. In such embodiments, the method further comprises terminating administration of the second dosage regimen after the occurrence of the second Grade 3 hematologic toxicity or proteinuria until the second Grade 3 hematologic toxicity or proteinuria is resolved to Grade 0-2 or baseline, and administering to the human subject a third dosage regimen comprising lenvatinib or a pharmaceutically acceptable salt thereof at a dose of 4 mg/day. In certain embodiments, the human subject develops an occurrence of a third Grade 3 hematologic toxicity or proteinuria during treatment with the third dosage regimen. In such embodiments, the method further comprises terminating administration of the third dosage regimen after the occurrence of the third Grade 3 hematologic toxicity or proteinuria until the third Grade 3 hematologic toxicity or proteinuria is resolved to Grade 0-2 or baseline, and administering to the human subject a fourth dosage regimen comprising lenvatinib or a pharmaceutically acceptable salt thereof at a dose of 4 mg every other day. In certain embodiments, the human subject develops an occurrence of a fourth Grade 3 hematologic toxicity or proteinuria during treatment with the fourth dosage regimen. In such embodiments, the method further comprises terminating administration of the fourth dosage regimen after the occurrence of the fourth Grade 3 hematologic toxicity or proteinuria.

In some embodiments of the ninth or tenth aspects, following or during treatment with the second dosage regimen, the human subject does not develop an occurrence of a second Grade 3 hematologic toxicity or proteinuria. In such embodiments, the method further comprises continuing administration of the second dosage regimen to the human subject (i.e., not lowering the dose being given in the second dosage regimen).

In some embodiments of the ninth or tenth aspects, following or during treatment with the third dosage regimen, the human subject does not develop an occurrence of a third Grade 3 hematologic toxicity or proteinuria. In such embodiments, the method further comprises continuing administration of the third dosage regimen to the human subject (i.e., not lowering the dose being given in the third dosage regimen).

In some embodiments of the ninth or tenth aspects, following or during treatment with the fourth dosage regimen, the human subject does not develop an occurrence of a fourth Grade 3 hematologic toxicity or proteinuria. In such embodiments, the method further comprises continuing administration of the fourth dosage regimen to the human subject (i.e., not lowering the dose being given in the fourth dosage regimen).

In an eleventh aspect, the disclosure provides a method of treating unresectable hepatocellular carcinoma, the method comprising administering to a human subject that has an unresectable hepatocellular carcinoma a first dosage regimen comprises lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. In carrying out this method, the human subject develops an occurrence of a first Grade 4 hematologic toxicity during treatment with the first dosage regimen. Thereupon, the method further comprises terminating administration of the first dosage regimen after the occurrence of the first Grade 4 hematologic toxicity until the first Grade 4 hematologic toxicity is resolved to Grade 0-2 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. In certain embodiments, the human subject develops an occurrence of a second Grade 4 hematologic toxicity during treatment with the second dosage regimen. In such embodiments, the method further comprises terminating administration of the second dosage regimen after the occurrence of the second Grade 4 hematologic toxicity until the second Grade 4 hematologic toxicity is resolved to Grade 0-2 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg. In certain embodiments, the human subject develops an occurrence of a third Grade 4 hematologic toxicity during treatment with the third dosage regimen. In such embodiments, the method further comprises terminating administration of the third dosage regimen after the occurrence of the third Grade 4 hematologic toxicity until the third Grade 4 hematologic toxicity is resolved to Grade 0-2 or baseline, and, if the body weight of the human subject is equal to or more than 60 kg, administering to the human subject a fourth dosage regimen comprising lenvatinib or a pharmaceutically acceptable salt thereof at a dose of 4 mg every other day.

In a twelfth aspect, the disclosure provides a method of treating unresectable hepatocellular carcinoma, the method comprising administering to a human subject that has an unresectable hepatocellular carcinoma and moderate hepatic impairment classified in Child-Pugh class B under Child-Pugh Classification a first dosage regimen comprises lenvatinib or a pharmaceutically acceptable salt thereof at a dose of 8 mg/day. In carrying out this method, the human subject develops an occurrence of a first Grade 4 hematologic toxicity during treatment with the first dosage regimen. Thereupon, the method further comprises terminating administration of the first dosage regimen after the occurrence of the first Grade 4 hematologic toxicity until the first Grade 4 hematologic toxicity is resolved to Grade 0-2 or baseline, and administering to the human subject a second dosage regimen comprising lenvatinib or a pharmaceutically acceptable salt thereof at a dose of 4 mg/day. In certain embodiments, the human subject develops an occurrence of a second Grade 4 hematologic toxicity during treatment with the second dosage regimen. In such embodiments, the method further comprises terminating administration of the second dosage regimen after the occurrence of the second Grade 4 hematologic toxicity until the second Grade 4 hematologic toxicity is resolved to Grade 0-2 or baseline, and administering to the human subject a third dosage regimen comprising lenvatinib or a pharmaceutically acceptable salt thereof at a dose of 4 mg every other day, in certain embodiments, the human subject develops an occurrence of a third Grade 4 hematologic toxicity during treatment with the third dosage regimen. In such embodiments, the method further comprises terminating administration of the third dosage regimen after the occurrence of the third Grade 4 hematologic toxicity.

In a thirteenth aspect, the disclosure features a method of treating unresectable hepatocellular carcinoma. The method comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. If the human subject develops an occurrence of a first Grade 3 hematologic toxicity or proteinuria excluding non-clinically relevant laboratory abnormality during treatment with the first dosage regimen, then the method further comprises terminating administration of the first dosage regimen after the occurrence of the first Grade 3 hematologic toxicity or proteinuria excluding non-clinically relevant laboratory abnormality until the first Grade 3 hematologic toxicity or proteinuria excluding non-clinically relevant laboratory abnormality is resolved to Grade 0-2 or baseline, and administering to the human subject a second dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. If the human subject develops an occurrence of a first Grade 4 hematologic toxicity during treatment with the first dosage regimen, then the method further comprises terminating administration of the first dosage regimen after the occurrence of the first Grade 4 hematologic toxicity until the first Grade 4 hematologic toxicity is resolved to Grade 0-2 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. If the human subject develops an occurrence of a first persistent and intolerable Grade 2 nonhematologic toxicity during treatment with the first dosage regimen, then the method further comprises terminating administration of the first dosage regimen after the occurrence of the first persistent and intolerable Grade 2 nonhematologic toxicity, and with or without interruption of the first dosage regimen until the first persistent and intolerable Grade 2 nonhematologic toxicity is resolved to Grade 0-1 or baseline, administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. If the human subject develops an occurrence of a first Grade 3 nonhematologic toxicity excluding non-clinically relevant laboratory abnormality during treatment with the first dosage regimen, then the method further comprises terminating administration of the first dosage regimen after the occurrence of the first Grade 3 nonhematologic toxicity excluding non-clinically relevant laboratory abnormality until the first Grade 3 nonhematologic toxicity excluding non-clinically relevant laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. If the human subject develops an occurrence of a Grade 4 nonhematologic toxicity excluding nonlife-threatening laboratory abnormality during treatment with the first dosage regimen, then the method further comprises terminating administration of the dosage regimen after the occurrence of the Grade 4 nonhematologic toxicity excluding nonlife-threatening laboratory abnormality.

In a fourteenth aspect, the disclosure features a method of treating unresectable hepatocellular carcinoma. The method comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 mg/day. If the human subject develops an occurrence of a first Grade 3 hematologic toxicity or proteinuria excluding non-clinically relevant laboratory abnormality during treatment with the first dosage regimen, then the method further comprises terminating administration of the first dosage regimen after the occurrence of the first Grade 3 hematologic toxicity or proteinuria excluding non-clinically relevant laboratory abnormality until the first Grade 3 hematologic toxicity or proteinuria excluding non-clinically relevant laboratory abnormality is resolved to Grade 0-2 or baseline, and administering to the human subject a second dosage regimen comprising lenvatinib or a pharmaceutically acceptable salt thereof at a dose of 8 mg/day. If the human subject develops an occurrence of a first Grade 4 hematologic toxicity during treatment with the first dosage regimen, then the method further comprises terminating administration of the first dosage regimen after the occurrence of the first Grade 4 hematologic toxicity until the first Grade 4 hematologic toxicity is resolved to Grade 0-2 or baseline, and administering to the human subject a second dosage regimen comprising lenvatinib or a pharmaceutically acceptable salt thereof at a dose of 4 mg/day. If the human subject develops an occurrence of a first persistent and intolerable Grade 2 nonhematologic toxicity during treatment with the first dosage regimen, then the method further comprises terminating administration of the first dosage regimen after the occurrence of the first persistent and intolerable Grade 2 nonhematologic toxicity and with or without interruption of the first dosage regimen until the first persistent and intolerable Grade 2 nonhematologic toxicity is resolved to Grade 0-1 or baseline, administering to the human subject a second dosage regimen comprising lenvatinib or a pharmaceutically acceptable salt thereof at a dose of 4 mg/day. If the human subject develops an occurrence of a first Grade 3 nonhematologic toxicity excluding non-clinically relevant laboratory abnormality during treatment with the first dosage regimen, then the method further comprises terminating administration of the first dosage regimen after the occurrence of the first Grade 3 nonhematologic toxicity excluding non-clinically relevant laboratory abnormality until the first Grade 3 nonhematologic toxicity excluding non-clinically relevant laboratory abnormality is resolved to Grade 0-1 or baseline, and administering to the human subject a second dosage regimen comprising lenvatinib or a pharmaceutically acceptable salt thereof at a dose of 4 mg/day. If the human subject develops an occurrence of a Grade 4 nonhematologic toxicity excluding nonlife-threatening laboratory abnormality during treatment with the first dosage regimen, then the method further comprises terminating administration of the dosage regimen after the occurrence of the Grade 4 nonhematologic toxicity excluding nonlife-threatening laboratory abnormality.

In some embodiments of the eleventh to fourteenth aspects, following or during treatment with the second dosage regimen, the human subject does not develop an occurrence of a second Grade 4 hematologic toxicity. In such embodiments, the method further comprises continuing administration of the second dosage regimen to the human subject (i.e., not lowering the dose being given in the second dosage regimen).

In some embodiments of the eleventh to fourteenth aspects, following or during treatment with the third dosage regimen, the human subject does not develop an occurrence of a third Grade 4 hematologic toxicity. In such embodiments, the method further comprises continuing administration of the third dosage regimen to the human subject (i.e., not lowering the dose being given in the third dosage regimen).

In a fifteenth aspect, the disclosure features a method of treating unresectable hepatocellular carcinoma. In some instances, the method comprises administering to a human subject that has an unresectable hepatocellular carcinoma a dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject was previously treated with a prior dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, and wherein the human subject developed an occurrence of a Grade 3 nonhematologic toxicity during treatment with the prior dosage regimen. In other instances, the method comprises administering to a human subject that has an unresectable hepatocellular carcinoma a dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject was previously treated with a prior dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, and wherein the human subject developed an occurrence of a Grade 3 nonhematologic toxicity during treatment with the prior dosage regimen. In yet other instances, the method comprises administering to a human subject that has an unresectable hepatocellular carcinoma a dosage regimen comprising lenvatinib or a pharmaceutically acceptable salt thereof at a dose of 4 mg every other day, wherein the body weight of the human subject is equal to or more than 60 kg, wherein the human subject was previously treated with a prior dosage regimen comprising lenvatinib or a pharmaceutically acceptable salt thereof at a dose of 4 mg/day, and wherein the human subject developed an occurrence of a Grade 3 nonhematologic toxicity during treatment with the prior dosage regimen.

In a sixteenth aspect, the disclosure features a method of treating unresectable hepatocellular carcinoma. In some instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg/day, wherein the human subject was previously treated with a prior dosage regimen comprising lenvatinib or a pharmaceutically acceptable salt thereof at a dose of 8 mg/day and wherein the human subject developed an occurrence of a Grade 3 nonhematologic toxicity during treatment with the prior dosage regimen. In other instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg every other day, wherein the human subject was previously treated with a prior dosage regimen comprising lenvatinib or a pharmaceutically acceptable salt thereof at a dose of 4 mg/day, and wherein the human subject developed an occurrence of a Grade 3 nonhematologic toxicity during treatment with the prior dosage regimen.

In a seventeenth aspect, the disclosure features a method of treating unresectable hepatocellular carcinoma. In some instances, the method comprises administering to a human subject that has an unresectable hepatocellular carcinoma a dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject was previously treated with a prior dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, and wherein the human subject developed an occurrence of a persistent and intolerable Grade 2 or Grade 3 nonhematologic toxicity during treatment with the prior dosage regimen. In other instances, the method comprises administering to a human subject that has unresectable hepatocellular carcinoma a dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject was previously treated with a prior dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, and wherein the human subject developed an occurrence of a persistent and intolerable Grade 2 or Grade 3 nonhematologic toxicity during treatment with the prior dosage regimen. In yet other instances, the method comprises administering to a human subject that has an unresectable hepatocellular carcinoma a dosage regimen comprising lenvatinib or a pharmaceutically acceptable salt thereof at a dose of 4 mg every other day, wherein the body weight of the human subject is equal to or more than 60 kg, wherein the human subject was previously treated with a prior dosage regimen comprising lenvatinib or a pharmaceutically acceptable salt thereof at a dose of 4 mg/day and wherein the human subject developed an occurrence of a persistent and intolerable Grade 2 or Grade 3 nonhematologic toxicity during treatment with the prior dosage regimen.

In an eighteenth aspect, the disclosure features a method of treating unresectable hepatocellular carcinoma. In some instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg/day, wherein the human subject was previously treated with a prior dosage regimen comprising lenvatinib or a pharmaceutically acceptable salt thereof at a dose of 8 mg/day, and wherein the human subject developed an occurrence of a persistent and intolerable Grade 2 or Grade 3 nonhematologic toxicity during treatment with the prior dosage regimen. In other instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg every other day, wherein the human subject was previously treated with a prior dosage regimen comprising lenvatinib or a pharmaceutically acceptable salt thereof at a dose of 4 mg/day, and wherein the human subject developed an occurrence of a persistent and intolerable Grade 2 or Grade 3 nonhematologic toxicity during treatment with the prior dosage regimen.

In a nineteenth aspect, the disclosure features a method of treating unresectable hepatocellular carcinoma. In some instances, the method comprises administering to a human subject that has an unresectable hepatocellular carcinoma a dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject was previously treated with a prior dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, and wherein the human subject developed an occurrence of a persistent and intolerable Grade 2 or Grade 3 nonhematologic toxicity or non-life-threatening Grade 4 laboratory abnormality during treatment with the prior dosage regimen. In other instances, the method comprises administering to a human subject that has an unresectable hepatocellular carcinoma a dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject was previously treated with a prior dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, and wherein the human subject developed an occurrence of a persistent and intolerable Grade 2 or Grade 3 nonhematologic toxicity or non-life-threatening Grade 4 laboratory abnormality during treatment with the prior dosage regimen, in certain instances, the method comprises administering to a human subject that has an unresectable hepatocellular carcinoma a dosage regimen comprising lenvatinib or a pharmaceutically acceptable salt thereof at a dose of 4 mg every other day, wherein the body weight of the human subject is equal to or more than 60 kg, wherein the human subject was previously treated with a prior dosage regimen comprising lenvatinib or a pharmaceutically acceptable salt thereof at a dose of 4 mg/day, and wherein the human subject developed an occurrence of a persistent and intolerable Grade 2 or Grade 3 nonhematologic toxicity or non-life-threatening Grade 4 laboratory abnormality during treatment with the prior dosage regimen.

In a twentieth aspect, the disclosure features a method of treating unresectable hepatocellular carcinoma. In some instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg/day, wherein the human subject was previously treated with a prior dosage regimen comprising lenvatinib or a pharmaceutically acceptable salt thereof at a dose of 8 mg/day and wherein the human subject developed an occurrence of a persistent and intolerable Grade 2 or Grade 3 nonhematologic toxicity or non-life-threatening Grade 4 laboratory abnormality during treatment with the prior dosage regimen. In other instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg every other day, wherein the human subject was previously treated with a prior dosage regimen comprising lenvatinib or a pharmaceutically acceptable salt thereof at a dose of 4 mg/day, and wherein the human subject developed an occurrence of a persistent and intolerable Grade 2 or Grade 3 nonhematologic toxicity or non-lifethreatening Grade 4 laboratory abnormality during treatment with the prior dosage regimen.

In a twenty first aspect, the disclosure features a method of treating unresectable hepatocellular carcinoma. In some instances, the method comprises administering to a human subject that has an unresectable hepatocellular carcinoma a dosage regimen comprising lenvatinib or a pharmaceutically acceptable salt thereof at a dose of (i) 12 mg/day if the body weight of the human subject is equal to or more than 60 kg or GO 8 mg/day if the body weight of the human subject is less than 60 kg, wherein the human subject was previously treated with a prior dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, and wherein the human subject developed an occurrence of a Grade 3 hematologic toxicity or proteinuria during treatment with the prior dosage regimen. In some instances, the method comprises administering to a human subject that has an unresectable hepatocellular carcinoma a dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject was previously treated with a prior dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, and wherein the human subject developed an occurrence of a Grade 3 hematologic toxicity or proteinuria during treatment with the prior dosage regimen. In certain instances, the method comprises administering to a human subject that has an unresectable hepatocellular carcinoma a dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject was previously treated with a prior dosage regimen comprising lenvatinib or a pharmaceutically acceptable salt thereof at a dose of (i) 8 mg/clay if the body weight of the human subject is equal to or more than 60 kg or (ii) 4 mg/day if the body weight of the human subject is less than 60 kg, and wherein the human subject developed an occurrence of a Grade 3 hematologic toxicity or proteinuria during treatment with the prior dosage regimen. In other instances, the method comprises administering to a human subject that has an unresectable hepatocellular carcinoma a dosage regimen comprising lenvatinib or a pharmaceutically acceptable salt thereof at a dose of 4 mg every other day wherein the body weight of the human subject is equal to or more than 60 kg, wherein the human subject was previously treated with a prior dosage regimen comprising lenvatinib or a pharmaceutically acceptable salt thereof at a dose of 4 mg/day, and wherein the human subject developed an occurrence of a Grade 3 hematologic toxicity or proteinuria during treatment with the prior dosage regimen.

In a twenty second aspect, the disclosure features a method of treating unresectable hepatocellular carcinoma. In some instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 8 mg/day wherein the human subject was previously treated with a prior dosage regimen comprising lenvatinib or a pharmaceutically acceptable salt thereof at a dose of 8 mg/day and wherein the human subject developed an occurrence of a Grade 3 hematologic toxicity or proteinuria during treatment with the prior dosage regimen. In other instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg/day, wherein the human subject was previously treated with a prior dosage regimen comprising lenvatinib or a pharmaceutically acceptable salt thereof at a dose of 8 mg/day, and wherein the human subject developed an occurrence of a Grade 3 hematologic toxicity or proteinuria during treatment with the prior dosage regimen. In yet other instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg every other day, wherein the human subject was previously treated with a prior dosage regimen comprising lenvatinib or a pharmaceutically acceptable salt thereof at a dose of 4 mg/day, and wherein the human subject developed an occurrence of a Grade 3 hematologic toxicity or proteinuria during treatment with the prior dosage regimen.

In a twenty third aspect, the disclosure features a method of treating unresectable hepatocellular carcinoma. In some instances, the method comprises administering to a human subject that has an unresectable hepatocellular carcinoma a dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject was previously treated with a prior dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, and wherein the human subject developed an occurrence of a Grade 4 hematologic toxicity during treatment with the prior dosage regimen. In other instances, the method comprises administering to a human subject that has an unresectable hepatocellular carcinoma a dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject was previously treated with a prior dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, and wherein the human subject developed an occurrence of a Grade 4 hematologic toxicity during treatment with the prior dosage regimen. In yet other instances, the method comprises administering to a human subject that has an unresectable hepatocellular carcinoma a dosage regimen comprising lenvatinib or a pharmaceutically acceptable salt thereof at a dose of 4 mg every other day, wherein the body weight of the human subject is equal to or more than 60 kg, wherein the human subject was previously treated with a prior dosage regimen comprising lenvatinib or a pharmaceutically acceptable salt thereof at a dose of 4 mg/day; and wherein the human subject developed an occurrence of a Grade 4 hematologic toxicity during treatment with the prior dosage regimen.

In a twenty fourth aspect, the disclosure features a method of treating unresectable hepatocellular carcinoma. In some instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg/day, wherein the human subject was previously treated with a prior dosage regimen comprising lenvatinib or a pharmaceutically acceptable salt thereof at a dose of 8 mg/day, and wherein the human subject developed an occurrence of a Grade 4 hematologic toxicity during treatment with the prior dosage regimen. In some instances, the method comprises administering to a human subject that has an unresectable hepatocellular carcinoma and moderate hepatic impairment classified in Child-Pugh class B under Child-Pugh Classification a dosage regimen comprising lenvatinib or a pharmaceutically acceptable salt thereof at a dose of 4 mg every other day; wherein the human subject was previously treated with a prior dosage regimen comprising lenvatinib or a pharmaceutically acceptable salt thereof at a dose of 4 mg/day, and wherein the human subject developed an occurrence of a Grade 4 hematologic toxicity during treatment with the prior dosage regimen.

In a twenty fifth aspect, the disclosure features a method of treating unresectable hepatocellular carcinoma. The method comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. The human subject develops an occurrence of a first persistent and intolerable Grade 2 or Grade 3 adverse reaction or Grade 4 laboratory abnormality during treatment with the first dosage regimen. In some instances, the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a close of (i) 8 mg/day if the body weight of the human subject is equal to or more than 60 kg or (ii) 4 mg/day if the body weight of the human subject is less than 60 kg wherein the human subject develops an occurrence of a second persistent and intolerable Grade 2 or Grade 3 adverse reaction or Grade 4 laboratory abnormality during treatment with the second dosage regimen. The method further comprises terminating administration of the second dosage regimen after the occurrence of the second persistent and intolerable Grade 2 or Grade 3 adverse reaction or Grade 4 laboratory abnormality until the second persistent and intolerable Grade 2 or Grade 3 adverse reaction or Grade 4 laboratory abnormality is resolved to Grade 0-1 or baseline, and administering to the human subject a third dosage regimen comprising lenvatinib or a pharmaceutically acceptable salt thereof at a close of (i) 4 mg/day if the body weight of the human subject is equal to or more than 60 kg or (ii) 4 mg every other day if the body weight of the human subject is less than 60 kg, wherein the human subject develops an occurrence of a third persistent and intolerable Grade 2 or Grade 3 adverse reaction or Grade 4 laboratory abnormality during treatment with the third dosage regimen. The method further comprises terminating administration of the third dosage regimen after the occurrence of the third persistent and intolerable Grade 2 or Grade 3 adverse reaction or Grade 4 laboratory abnormality until the third persistent and intolerable Grade 2 or Grade 3 adverse reaction or Grade 4 laboratory abnormality is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day. In instances wherein the human subject develops an occurrence of a Grade 4 adverse reaction excluding Grade 4 laboratory abnormality during treatment with the first, second, third, or fourth dosage regimen, the method further comprises terminating administration of the dosage regimen after the occurrence of the Grade 4 adverse reaction excluding Grade 4 laboratory abnormality. In the above aspects, Grade 3 hypertension, Grade 4 hypertension, Grade 3 cardiac dysfunction, Grade 4 cardiac dysfunction, any grade arterial thromboembolic event, Grade 3 hepatotoxicity, Grade 4 hepatotoxicity, 2 g or greater proteinuria in 24 hours, Grade 3 renal failure or impairment, Grade 4 renal failure or impairment, any Grade gastrointestinal perforation, Grade 3 fistula, Grade 4 fistula, a greater than 500 ms QT/QTc interval prolongation, a greater than 60 ins increase from baseline QT/QTc interval prolongation, and any Grade reversible posterior leukoencephalopathy syndrome are excluded from the persistent and intolerable Grade 2, Grade 3 or Grade 4 adverse reaction or Grade 4 laboratory abnormality.

In a twenty sixth aspect, the disclosure features a method of treating unresectable hepatocellular carcinoma. The method comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 mg/day. The human subject develops an occurrence of a first persistent and intolerable Grade 2 or Grade 3 adverse reaction or Grade 4 laboratory abnormality during treatment with the first dosage regimen. In some instances, the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of 4 mg/day, wherein the human subject develops an occurrence of a second persistent and intolerable Grade 2 or Grade 3 adverse reaction or Grade 4 laboratory abnormality during treatment with the second dosage regimen. The method further comprises terminating administration of the second dosage regimen after the occurrence of the second persistent and intolerable Grade 2 or Grade 3 adverse reaction or Grade 4 laboratory abnormality until the second persistent and intolerable Grade 2 or Grade 3 adverse reaction or Grade 4 laboratory abnormality is resolved to Grade 0-1 or baseline, and administering to the human subject a third dosage regimen comprising lenvatinib or a pharmaceutically acceptable salt thereof at a dose of 4 mg every other day wherein the human subject develops an occurrence of a third persistent and intolerable Grade 2 or Grade 3 adverse reaction or Grade 4 laboratory abnormality during treatment with the third dosage regimen. The method further comprises terminating administration of the third dosage regimen after the occurrence of the third persistent and intolerable Grade 2 or Grade 3 adverse reaction or Grade 4 laboratory abnormality. In instances wherein the human subject develops an occurrence of a Grade 4 adverse reaction excluding Grade 4 laboratory abnormality during treatment with the first, second, third, or fourth dosage regimen, the method further comprises terminating administration of the dosage regimen after the occurrence of the Grade 4 adverse reaction excluding Grade 4 laboratory abnormality. In the above aspects, Grade 3 hypertension, Grade 4 hypertension, Grade 3 cardiac dysfunction, Grade 4 cardiac dysfunction, any grade arterial thromboembolic event, Grade 3 hepatotoxicity, Grade 4 hepatotoxicity, 2 g or greater proteinuria in 24 hours, Grade 3 renal failure or impairment, Grade 4 renal failure or impairment, any Grade gastrointestinal perforation, Grade 3 fistula, Grade 4 fistula, a greater than 500 ms QT/QTc interval prolongation, a greater than 60 ms increase from baseline QT/QTc interval prolongation, and any Grade reversible posterior leukoencephalopathy syndrome are excluded from the persistent and intolerable Grade 2, Grade 3 or Grade 4 adverse reaction or Grade 4 laboratory abnormality.

In a twenty seventh aspect, the disclosure features a method of treating unresectable hepatocellular carcinoma. The method comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. In instances where the human subject develops an occurrence of a first persistent and intolerable Grade 2 or Grade 3 adverse reaction or Grade 4 laboratory abnormality during treatment with the first dosage regimen, the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. In instances where the human subject develops an occurrence of a Grade 4 adverse reaction excluding Grade 4 laboratory abnormality during treatment with the first dosage regimen, then the method further comprises terminating administration of the dosage regimen after the occurrence of the Grade 4 adverse reaction excluding Grade 4 laboratory abnormality. In the above aspects, Grade 3 hypertension, Grade 4 hypertension, Grade 3 cardiac dysfunction, Grade 4 cardiac dysfunction, any grade arterial thromboembolic event, Grade 3 hepatotoxicity, Grade 4 hepatotoxicity, 2 g or greater proteinuria in 24 hours, Grade 3 renal failure or impairment, Grade 4 renal failure or impairment, any Grade gastrointestinal perforation, Grade 3 fistula, Grade 4 fistula, a greater than 500 ms QT/QTc interval prolongation, a greater than 60 ms increase from baseline QT/QTc interval prolongation, and any Grade reversible posterior leukoencephalopathy syndrome are excluded from the persistent and intolerable Grade 2, Grade 3 or Grade 4 adverse reaction or Grade 4 laboratory abnormality.

In a twenty eighth aspect, the disclosure features a method of treating unresectable hepatocellular carcinoma. The method comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a close of 8 mg/day. In instances where the human subject develops an occurrence of a first persistent and intolerable Grade 2 or Grade 3 adverse reaction or Grade 4 laboratory abnormality during treatment with the first dosage regimen, the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of 4 mg/day. In instances where the human subject develops an occurrence of a Grade 4 adverse reaction excluding Grade 4 laboratory abnormality during treatment with the first dosage regimen, then the method further comprises terminating administration of the dosage regimen after the occurrence of the Grade 4 adverse reaction excluding Grade 4 laboratory abnormality. In the above aspects, Grade 3 hypertension, Grade 4 hypertension, Grade 3 cardiac dysfunction, Grade 4 cardiac dysfunction, any grade arterial thromboembolic event, Grade 3 hepatotoxicity, Grade 4 hepatotoxicity, 2 g or greater proteinuria in 24 hours, Grade 3 renal failure or impairment. Grade 4 renal failure or impairment, any Grade gastrointestinal perforation, Grade 3 fistula, Grade 4 fistula, a greater than 500 ms QT/QTc interval prolongation, a greater than 60 ms increase from baseline QT/QTc interval prolongation, and any Grade reversible posterior leukoencephalopathy syndrome are excluded from the persistent and intolerable Grade 2, Grade 3 or Grade 4 adverse reaction or Grade 4 laboratory abnormality.

In a twenty ninth aspect, the disclosure features a method of treating unresectable hepatocellular carcinoma. The method comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. The human subject develops an occurrence of a first persistent and intolerable Grade 2 or Grade 3 adverse reaction or Grade 4 laboratory abnormality during treatment with the first dosage regimen. In some instances, the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject develops an occurrence of a second persistent and intolerable Grade 2 or Grade 3 adverse reaction or Grade 4 laboratory abnormality during treatment with the second dosage regimen. The method further comprises terminating administration of the second dosage regimen after the occurrence of the second persistent and intolerable Grade 2 or Grade 3 adverse reaction or Grade 4 laboratory abnormality until the second persistent and intolerable Grade 2 or Grade 3 adverse reaction or Grade 4 laboratory abnormality is resolved to Grade 0-1 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject develops an occurrence of a third persistent and intolerable Grade 2 or Grade 3 adverse reaction or Grade 4 laboratory abnormality during treatment with the third dosage regimen. The method further comprises terminating administration of the third dosage regimen after the occurrence of the third persistent and intolerable Grade 2 or Grade 3 adverse reaction or Grade 4 laboratory abnormality until the third persistent and intolerable Grade 2 or Grade 3 adverse reaction or Grade 4 laboratory abnormality is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day. In instances wherein the human subject develops an occurrence of a Grade 4 adverse reaction excluding Grade 4 laboratory abnormality during treatment with the first, second, third, or fourth dosage regimen, the method further comprises terminating administration of the dosage regimen after the occurrence of the Grade 4 adverse reaction excluding Grade 4 laboratory abnormality. In the above aspects, hypertension, cardiac dysfunction, arterial thromboembolic event, hepatotoxicity, proteinuria, renal failure or impairment, gastrointestinal perforation, fistula, QT/QTc interval prolongation, and reversible posterior leukoencephalopathy syndrome are excluded from the persistent and intolerable Grade 2, Grade 3, or Grade 4 adverse reaction or Grade 4 laboratory abnormality.

In a thirtieth aspect, the disclosure features a method of treating unresectable hepatocellular carcinoma. The method comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 mg/day. The human subject develops an occurrence of a first persistent and intolerable Grade 2 or Grade 3 adverse reaction or Grade 4 laboratory abnormality during treatment with the first dosage regimen. In some instances, the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of 4 mg/day, wherein the human subject develops an occurrence of a second persistent and intolerable Grade 2 or Grade 3 adverse reaction or Grade 4 laboratory abnormality during treatment with the second dosage regimen. The method further comprises terminating administration of the second dosage regimen after the occurrence of the second persistent and intolerable Grade 2 or Grade 3 adverse reaction or Grade 4 laboratory abnormality until the second persistent and intolerable Grade 2 or Grade 3 adverse reaction or Grade 4 laboratory abnormality is resolved to Grade 0-1 or baseline, and administering to the human subject a third dosage regimen comprising lenvatinib or a pharmaceutically acceptable salt thereof at a dose of 4 mg every other day, wherein the human subject develops an occurrence of a third persistent and intolerable Grade 2 or Grade 3 adverse reaction or Grade 4 laboratory abnormality during treatment with the third dosage regimen. The method further comprises terminating administration of the third dosage regimen after the occurrence of the third persistent and intolerable Grade 2 or Grade 3 adverse reaction or Grade 4 laboratory abnormality. In instances wherein the human subject develops an occurrence of a Grade 4 adverse reaction excluding Grade 4 laboratory abnormality during treatment with the first, second, third, or fourth dosage regimen, the method further comprises terminating administration of the dosage regimen after the occurrence of the Grade 4 adverse reaction excluding Grade 4 laboratory abnormality. In the above aspects, hypertension, cardiac dysfunction, arterial thromboembolic event, hepatotoxicity, proteinuria, renal failure or impairment, gastrointestinal perforation, fistula, QT/QTc interval prolongation, and reversible posterior leukoencephalopathy syndrome are excluded from the persistent and intolerable Grade 2, Grade 3, or Grade 4 adverse reaction or Grade 4 laboratory abnormality.

In a thirty first aspect, the disclosure features a method of treating unresectable hepatocellular carcinoma. The method comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. In instances where the human subject develops an occurrence of a first persistent and intolerable Grade 2 or Grade 3 adverse reaction or Grade 4 laboratory abnormality during treatment with the first dosage regimen, the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. In instances where the human subject develops an occurrence of a Grade 4 adverse reaction excluding Grade 4 laboratory abnormality during treatment with the first dosage regimen, then the method further comprises terminating administration of the dosage regimen after the occurrence of the Grade 4 adverse reaction excluding Grade 4 laboratory abnormality. In the above aspects, hypertension, cardiac dysfunction, arterial thromboembolic event, hepatotoxicity, proteinuria, renal failure or impairmerit, gastrointestinal perforation, fistula, QT/QTc interval prolongation, and reversible posterior leukoencephalopathy syndrome are excluded from the persistent and intolerable Grade 2, Grade 3, or Grade 4 adverse reaction or Grade 4 laboratory abnormality.

In a thirty second aspect, the disclosure features a method of treating unresectable hepatocellular carcinoma. The method comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 mg/day. In instances where the human subject develops an occurrence of a first persistent and intolerable Grade 2 or Grade 3 adverse reaction or Grade 4 laboratory abnormality during treatment with the first dosage regimen, the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of 4 mg/day. In instances where the human subject develops an occurrence of a Grade 4 adverse reaction excluding Grade 4 laboratory abnormality during treatment with the first dosage regimen, then the method further comprises terminating administration of the dosage regimen after the occurrence of the Grade 4 adverse reaction excluding Grade 4 laboratory abnormality. In the above aspects, hypertension, cardiac dysfunction, arterial thromboembolic event, hepatotoxicity, proteinuria, renal failure or impairment, gastrointestinal perforation, fistula, QT/QTc interval prolongation, and reversible posterior leukoencephalopathy syndrome are excluded from the persistent and intolerable Grade 2, Grade 3, or Grade 4 adverse reaction or Grade 4 laboratory abnormality.

In a thirty third aspect, the disclosure features a method of treating unresectable hepatocellular carcinoma. The method comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. If the human subject develops an occurrence of a Grade 3 hypertension during treatment with the first dosage regimen, then the method further comprises terminating administration of the first dosage regimen after the occurrence of the Grade 3 hypertension until the Grade 3 hypertension is controlled at less than or equal to Grade 2, and administering to the human subject the second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg.

In a thirty fourth aspect, the disclosure features a method of treating unresectable hepatocellular carcinoma. The method comprises administering to a human subject that has an unresectable hepatocellular carcinoma and moderate hepatic impairment classified. In Child-Pugh class B under Child-Pugh Classification a first dosage regimen comprising lenvatinib or a pharmaceutically acceptable salt thereof at a dose of 8 mg/day. If the human subject develops an occurrence of a Grade 3 hypertension during treatment with the first dosage regimen, then the method further comprises terminating administration of the first dosage regimen after the occurrence of the Grade 3 hypertension until the Grade 3 hypertension is controlled at less than or equal to Grade 2, and administering to the human subject the second dosage regimen comprising lenvatinib or a pharmaceutically acceptable salt thereof at a dose of 4 mg/day.

In a thirty fifth aspect, the disclosure features a method of treating unresectable hepatocellular carcinoma. The method comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. If the human subject develops an occurrence of a 2 g or greater proteinuria in 24 hours during treatment with the first dosage regimen, then the method further comprises terminating administration of the dosage regimen after the occurrence of the 2 g or greater proteinuria in 24 hours until the proteinuria is less than or equal to 2 g of proteinuria in 24 hours and, administering to the human subject the second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg. In the above aspect, the human subject develops an occurrence of a nephrotic syndrome during treatment with the first dosage regimen, and the method further comprises terminating administration of the dosage regimen after the occurrence of the nephrotic syndrome.

In a thirty sixth aspect, the disclosure features a method of treating unresectable hepatocellular carcinoma. The method comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 tug/day. If the human subject develops an occurrence of a 2 g or greater proteinuria in 24 hours during treatment with the first dosage regimen, then the method further comprises terminating administration of the dosage regimen after the occurrence of the 2 g or greater proteinuria in 24 hours until the proteinuria is less than or equal to 2 g of proteinuria in 24 hours and, administering to the human subject the second dosage regimen comprising lenvatinib or a pharmaceutically acceptable salt thereof at a dose of 4 mg/day. In the above aspect, the human subject develops an occurrence of a nephrotic syndrome during treatment with the first dosage regimen, and the method further comprises terminating administration of the dosage regimen after the occurrence of the nephrotic syndrome.

In a thirty seventh aspect, the disclosure features a method of treating unresectable: hepatocellular carcinoma. The method comprises administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg. If the human subject develops an occurrence of a greater than 500 ms QT/QTc interval prolongation or a greater than 60 ms increase from baseline QT/QTc interval prolongation during treatment with the first dosage regimen, then the method further comprises terminating administration of the dosage regimen after the occurrence of the greater than 500 ms QT/QTc interval prolongation or a greater than 60 ins increase from baseline QT/QTc interval prolongation until the QT/QTc interval prolongation improves to less than or equal to 480 ms or baseline and, administering to the human subject the second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg.

In a thirty eighth aspect, the disclosure features a method of treating unresectable hepatocellular carcinoma. The method comprises administering to a human subject that has an unresectable hepatocellular carcinoma and moderate hepatic impairment classified in Child-Pugh class B under Child-Pugh Classification a first dosage regimen comprising lenvatinib or a pharmaceutically acceptable salt thereof at a dose of 8 mg/day. If the human subject develops an occurrence of a greater than 500 ms QT/QTc interval prolongation or a greater than 60 ms increase from baseline QT/QTc interval prolongation during treatment with the first dosage regimen, then the method further comprises terminating administration of the dosage regimen after the occurrence of the greater than 500 ms QT/QTc interval prolongation or a greater than 60 ms increase from baseline QT/QTc interval prolongation until the QT/QTc interval prolongation improves to less than or equal to 480 ms or baseline and, administering to the human subject the second dosage regimen comprising lenvatinib or a pharmaceutically acceptable salt thereof at a dose of 4 mg/day if the body weight of the human subject is less than 60 kg.

In some embodiments of the above aspects, median overall survival is 13.6 months.

In some embodiments of the above aspects, median overall survival with 95% confidence interval is between 12.1 and 14.9 months.

In some embodiments of the above aspects, hazard ratio of overall survival compared with sorafenib at a dosage of 400 mg twice daily is 0.92.

In some embodiments of the above aspects, hazard ratio of overall survival compared with sorafenib at a dosage of 400 mg twice daily with 95% confidence interval is between 0.79 and 1.06.

In some embodiments of the above aspects, overall survival is shown in FIG. 1 (Kaplan-Meier Plot of Overall Survival).

In some embodiments of the above aspects, median progression-free survival is 7.4 months.

In some embodiments of the above aspects, wherein median progression-free survival with 95% confidence interval is between 6.9 to 8.8 months.

In some embodiments of the above aspects, hazard ratio of progression-free survival compared with sorafenib at a dosage of 400 mg twice daily is 0.66.

In some embodiments of the above aspects, hazard ratio of progression-free survival compared with sorafenib at a dosage of 400 mg twice daily with 95% confidence interval is between 0.57 and 0.77.

In some embodiments of the above aspects, progression-free survival is shown in FIG. 2 (Kaplan-Meier Plot of Progression-Free Survival).

In some embodiments of the above aspects, median time to progression is 8.9 months.

In some embodiments of the above aspects, median time to progression with 95% confidence interval is between 7.4 to 9.2 months.

In some embodiments of the above aspects, hazard ratio of time to progression compared with sorafenib at a dosage of 400 mg twice daily is 0.63.

In some embodiments of the above aspects, hazard ratio of time to progression compared with sorafenib at a dosage of 400 mg twice daily with 95% confidence interval is between 0.53 and 0.73.

In some embodiments of the above aspects, time to progression is shown in FIG. 6 (Kaplan-Meier Plot of Time to Progression), In some embodiments of the above aspects, the objective response rate is 24.1%.

In some embodiments of the above aspects, the odds ratio of objective response rate compared with sorafenib at a dosage of 400 mg twice daily is 3.13.

In some embodiments of the above aspects, the odds ratio of objective response rate compared with sorafenib at a dosage of 400 mg twice daily with 95% confidence interval is between 2.15 to 4.56.

In some embodiments of the above aspects, the method comprises achieving the results shown in Table 2 or Table 10 (Efficacy Results in HCC).

In some embodiments of the above aspects, the method comprises achieving the results shown in FIG. 15 (Quality of Life).

In some embodiments of the above aspects, the human subject consists essentially of the subject with mild hepatic impairment classified in Child-Pugh class A under Child-Pugh Classification.

In some embodiments of the above aspects, the human subject is categorized to stage B or stage C based on Barcelona Clinic Liver Cancer (BCLC) staging system.

In some embodiments of the above aspects, medical management of each of the first, second, and third persistent and intolerable Grade 2 or Grade 3 nonhematologic toxicities or non-life-threatening Grade 4 laboratory abnormality is initiated prior to terminating administration of the dosage regimen administered at the time of onset of the Grade 2 or Grade 3 nonhematologic toxicity or non-life-threatening Grade 4 laboratory abnormality.

In some embodiments of the above aspects, medical management of each of the first, second, third, and fourth Grade 3 hematologic toxicities or proteinuria is initiated prior to terminating administration of the dosage regimen administered at the time of onset of the Grade 3 hematologic toxicities or proteinuria.

In some embodiments of the above aspects, medical management of each of the first, second, and third Grade 4 hematologic toxicities is initiated prior to terminating administration of the dosage regimen administered at the time of onset of the Grade 4 hematologic toxicities.

In some embodiments of the above aspects, the first persistent and intolerable Grade 2 or Grade 3 nonhematologic toxicity or non-life-threatening Grade 4 laboratory abnormality is the same as the second and/or third persistent and intolerable Grade 2 or Grade 3 nonhematologic toxicity or non-life-threatening Grade 4 laboratory abnormality.

In some embodiments of the above aspects, the first Grade 3 hematologic toxicity or proteinuria is the same as the second and/or third Grade 3 hematologic toxicity or proteinuria.

In some embodiments of the above aspects, the first Grade 4 hematologic toxicity is the same as the second and/or third Grade 4 hematologic toxicity.

In some embodiments of any of the above aspects, the Grade 3 nonhematologic toxicity is selected from the group consisting of Grade 3 hypertension, Grade 3 diarrhea, Grade 3 decreased appetite, Grade 3 fatigue, Grade 3 arthralgia, Grade 3 myalgia, Grade 3 decreased weight, Grade 3 dysphonia, Grade 3 nausea, Grade 3 abdominal pain, Grade 3 QT/QTc interval prolongation, Grade 3 hypothyroidism, Grade 3 vomiting, Grade 3 constipation, Grade 3 rash, and Grade 3 palmar-plantar erythrodysesthesia.

In some embodiments of any of the above aspects, the Grade 2 or Grade 3 nonhematologic toxicity is selected from the group consisting of Grade 3 hypertension, Grade 2 hypertension, Grade 3 diarrhea, Grade 2 diarrhea, Grade 3 decreased appetite, Grade 2 decreased appetite, Grade 3 fatigue, Grade 2 fatigue, Grade 3 arthralgia, Grade 2 arthralgia, Grade 3 myalgia, Grade 2 myalgia, Grade 3 decreased weight, Grade 2 decreased weight, Grade 2 alopecia, Grade 3 dysphonia, Grade 2 dysphonia, Grade 3 nausea, Grade 2 nausea, Grade 3 abdominal pain, Grade 2 abdominal pain, Grade 3 QT/QTc interval prolongation, Grade 2 QT/QTc interval prolongation, Grade 3 hypothyroidism, Grade 2 hypothyroidism, Grade 3 vomiting, Grade 2 vomiting, Grade 3 constipation, Grade 2 constipation, Grade 3 rash, Grade 2 rash, Grade 3 palmar-plantar erythrodysesthesia, and Grade 2 palmar-plantar erythrodysesthesia.

In some embodiments of any of the above aspects, the Grade 4 laboratory abnormality is selected from the group consisting of Grade 4 increase in aspartate aminotransferase, Grade 4 increase in alanine aminotransferase, Grade 4 increase in alkaline phosphatase, Grade 4 hypokalemia, Grade 4 hyponatremia, Grade 4 hypoglycemia, Grade 4 increase in blood bilirubin, and Grade 4 increase in gamma glutamyl transferase.

In some embodiments of any of the above aspects, the Grade 3 hematologic toxicity or proteinuria is selected from the group consisting of Grade 3 proteinuria, Grade 3 thrombopenia (thrombocytopenia), Grade 3 anemia, Grade 3 decrease in white blood cell count, Grade 3 neutropenia, and Grade 3 lymphocytopenia.

In some embodiments of any of the above aspects, the Grade 4 hematologic toxicity is selected from the group consisting of Grade 4 thrombopenia (thrombocytopenia), Grade 4 anemia, Grade 4 decrease in white blood cell count, Grade 4 neutropenia, and Grade 4 lymphocytopenia.

In some embodiments of the above aspects, lenvatinib or the pharmaceutically acceptable salt thereof is formulated as a capsule.

In some embodiments of the above aspects, lenvatinib or the pharmaceutically acceptable salt thereof is administered to the human subject orally.

In some embodiments of the above aspects, lenvatinib or a pharmaceutically acceptable salt thereof is lenvatinib mesylate.

Also encompassed by the disclosure is a dosage regimen described herein of lenvatinib or a pharmaceutically acceptable salt thereof for use in treating hepatocellular carcinoma (e.g., unresectable hepatocellular carcinoma) according to any of the methods described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

DESCRIPTION OF EMBODIMENTS

Figure 1:
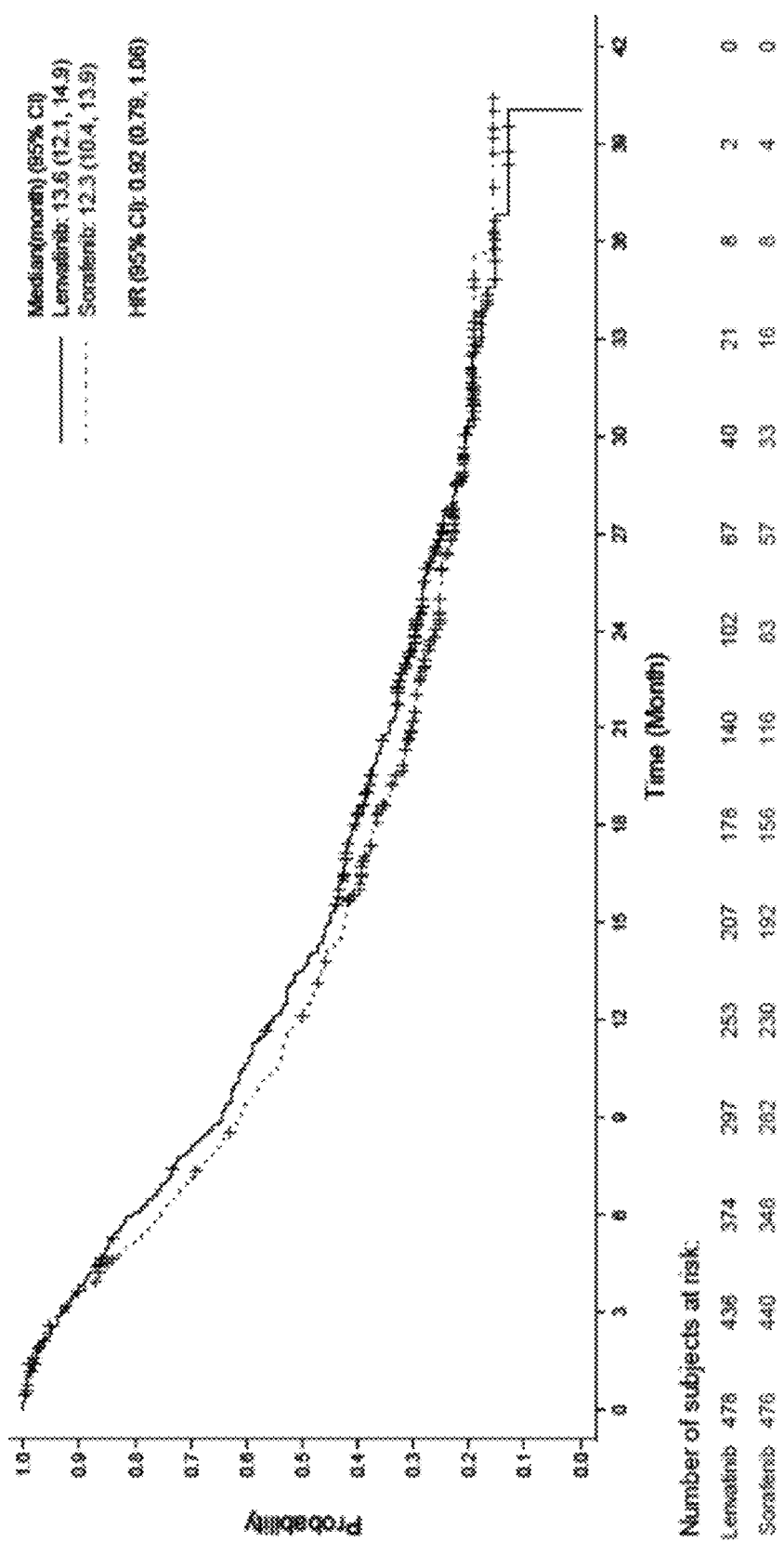
FIG. 1 depicts Kaplan-Meier estimates of overall survival by treatment group. CI denotes confidence interval, and HR hazard ratio.

This disclosure provides methods of treating a human subject that has a hepatocellular carcinoma (e.g., advanced HCC, unresectable HCC, or unresectable advanced HCC). The method comprises administering to the subject a starting dose of lenvatinib or a pharmaceutically acceptable salt thereof. The starting dose is determined based on the body weight of the subject: 12 mg/day if the body weight of the human subject is equal to or more than 60 kg, and 8 mg/day if the body weight of the human subject is less than 60 kg. However, if the human subject has moderate hepatic impairment classified in Child-Pugh class B under the Child-Pugh Classification, then the starting dose can be 8 mg/day regardless of the body weight of the subject. If the subject develops one or more adverse events as a result of the treatment with lenvatinib or a pharmaceutically acceptable salt thereof, the disclosure provides modifications of the treatment regimen as well as adjusted dosing regimens (reduced doses of lenvatinib or a pharmaceutically acceptable salt thereof). These dose modifications enable the subject to continue treatment with lenvatinib or a pharmaceutically acceptable salt thereof. If the subject does not develop an adverse reaction as a result of administration of a particular dose of lenvatinib or a pharmaceutically acceptable salt thereof, the subject can be maintained on the same dosage regimen.

Hepatocellular Carcinoma

Primary liver cancer is the sixth most common cancer worldwide with approximately 782,000 new cases worldwide in 2012. A total of 83% of the world's cases occur in less-developed regions and more than 50% occur in China alone; however, the incidence of liver cancer has been rising in a number of low-rate areas such as Australia, the United Kingdom, and the United States. In all populations, males have higher rates of liver cancer than do females. Liver cancer is the third most common cause of cancer death worldwide, accounting for an estimated 746,000 cancer deaths annually.

Hepatocellular carcinoma (HCC) accounts for 85% to 90% of primary cancer of the liver and occurs predominantly in patients with underlying chronic liver disease, in particular cirrhosis. Major causes of cirrhosis include hepatitis B virus (HBV), hepatitis C virus (HCV), and alcoholic liver disease. Hepatitis B is the most frequent underlying cause of HCC, with an estimated 300 million people with chronic infection worldwide. Chronic HBV carriers have a 5- to 15-fold increased risk of developing HCC compared with the general population. Chronic HCV infection is also a major risk factor for HCC. The risk of HCC was 17-fold higher in HCV-infected patients compared with HCV-negative controls.

To reduce mortality rates, it is important not only to prevent onset and promote early detection of HCC in patients in whom the hepatitis virus cannot be eradicated, but also to develop effective therapeutic interventions for patients who have already developed HCC.

For HCC, at least eight different staging systems are available. These include the Barcelona Clinic Liver Cancer (BCLC) system, the Okuda stage system, the TNM staging system, the JIS score, the CLIP score, the CUPI score, the French classification, and the ER system (Pons et al., HPB, 7(1):35-41, 2005). The BCLC system categorizes HCC based on characteristics of the tumor, liver function, performance status, and cancer-related symptoms. BCLC stage groupings include:

Very early stage. The tumor is smaller than 2 cm. There is no increased pressure in the portal vein. Bilirubin levels are normal. Surgery is usually recommended.
Early stage. The tumor is smaller than 5 cm. Liver function varies. There may be no increased pressure in the portal vein, increased portal vein pressure and normal bilirubin levels, or increased portal vein pressure and increased bilirubin levels. People with early-stage disease may be candidates for a liver transplant, surgery, or radiofrequency ablation (RFA).
Intermediate stage. The tumor may be large or there may be multiple tumors. Doctors usually recommend regional therapies, such as transarterial chemoembolization.
Advanced stage. The tumor has invaded the portal vein or spread to other parts of the body, such as the lungs and bones: Targeted therapy is generally recommended.

Evidence-based guidelines for the diagnosis and treatment of HCC have been established and adopted (El-Serag, et al., Ann. Intern. Med., 139(10):817-23, 2003; Llovet, et at, Lancet, 362(9399):1907-17, 2003). Recent technological advances for patients with early-stage HCC include surgical resection, localized treatments such as radiofrequency ablation (RFA), percutaneous ethanol injection (PEI), cryotherapy and transarterial chemoembolization (TACE). Treatment options for HCC are determined by stage of the disease. For very early stage HCC, surgical resection is the treatment of choice in patients without cirrhosis. Among patients who have underlying cirrhosis, orthotopic liver transplantation is the treatment option associated with the lowest risk of tumor recurrence. For patients with early-stage HCC who are not eligible for surgical resection or transplantation, RFA is likely the best alternative treatment, although PEI and cryoablation are also routinely performed. Other locoregional treatment options for HCC include transarterial TACE, which has been shown to improve survival among patients with preserved liver function and unresectable HCC whose disease is either too large or too multifocal for percutaneous ablation techniques, as well as radioembolization, which has been used as palliative treatment in intermediate-stage HCC. However, recurrence due to residual tumor cells is a clinical characteristic of HCC and ultimately leads to an advanced stage where surgery, RFA, and TACE are no longer appropriate.

This disclosure provides methods of treating unresectable HCC using lenvatinib or a pharmaceutically acceptable salt thereof.

Lenvatinib

A number of kinase inhibitors have been developed as antitumor agents. For example, a group of compounds having inhibitory activity against receptor tyrosine kinases, such as vascular endothelial growth factor receptor (VEGFR), are known to inhibit angiogenesis and are regarded as a new class of antitumor agents. Lenvatinib is a multi-target receptor tyrosine kinase inhibitor that inhibits the kinase activities of VEGFR1 (FLT1), VEGFR2 (KDR), and VEGFR3 (FLT4). Lenvatinib inhibits other receptor tyrosine kinases that have been implicated in pathogenic angiogenesis, tumor growth, and cancer progression in addition to their normal cellular functions, including fibroblast growth factor (FGF) receptors FGFR1, FGFR2, FGFR3, and FGFR4; rearranged during transfection receptor (RET), KIT, and platelet-derived growth factor receptor alpha (PDGFRα). Lenvatinib also exhibits antiproliferative activity in hepatocellular carcinoma cell lines dependent on activated FGFR signaling with a concurrent inhibition of FGF-receptor substrate 2α (FRS2α) phosphorylation.

The term "lenvatinib" refers to 4-(3-chloro-4(cyclopropylaminocarbonyl)aminophenoxy)-7-methoxy-6-quinolinecarboxamide. This compound is disclosed in Example 368 (see, column 270) of U.S. Pat. No. 7,253,286. U.S. Pat. No. 7,253,286 is incorporated by reference in its entirety herein. The term "pharmaceutically acceptable salt" is not particularly restricted as to the type of salt. Examples of such salts include, but are not limited to, inorganic acid addition salt such as hydrochloric acid salt, sulfuric acid salt, carbonic acid salt, bicarbonate salt, hydrobromic acid salt, and hydriodic acid salt; organic carboxylic acid addition salt such as acetic acid salt, maleic acid salt, lactic acid salt, tartaric acid salt, and trifluoroacetic acid salt; organic sulfonic acid addition salt such as methanesulfonic acid salt, hydroxymethanesulfonic acid salt, hydroxyethanesulfonic acid salt, benzenesulfonic acid salt, toluenesulfonic acid salt, and taurine salt; amine addition salt such as trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, and phenethylbenzylamine salt; and amino acid addition salt such as arginine salt, lysine salt, serine salt, glycine salt, aspartic acid salt, and glutamic acid salt. In one embodiment, the pharmaceutically acceptable salt is a methanesulfonic acid salt ("mesylate"). The methanesulfonic acid salt form (i.e., the mesylate) of lenvatinib is disclosed in U.S. Pat. No. 7,612,208, which is incorporated by reference herein in its entirety. The chemical name of lenvatinib mesylate is 4-[3-chloro-4-(N'-cyclopropylureido) phenoxy]-7-methoxyquinoline-6-carboxamide methanesulfonate and it chemical structure is provided below:

[Chem. 1]

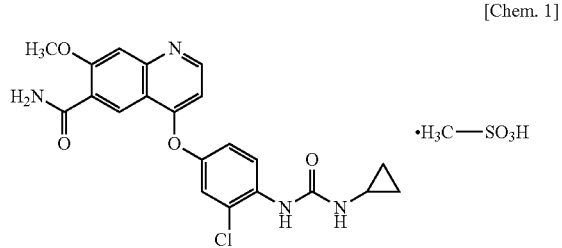

Lenvatinib mesylate is also referred to as LENVIMA<sup>(registered trademark)</sup>.

Lenvatinib mesylate is a white to pale reddish yellow powder. It is slightly soluble in water and practically insoluble in ethanol (dehydrated). The dissociation constant (pKa value) of lenvatinib mesylate is 5.05 at 25° C. The partition coefficient (log P value) is 3.30.

Administration

As shown in the Examples, which describe, inter alia, the results of an open-label phase 3 human clinical trial in subjects with unresectable HCC, lenvatinib was shown to be noninferior to sorafenib in overall survival (median 13.6 months with lenvatinib vs. 12.3 months with sorafenib; hazard ratio [HR]:0.92; 95% confidence interval [CI], 0.79 to 1.06). Lenvatinib prolonged progression-free survival (median 7.3 vs. 3.6 months; HR: 0.64; 95% CI, 0.55 to 0.75; P<0.001) versus sorafenib. Objective response rate was 41% with lenvatinib versus 12% with sorafenib (P<0.001). In sum, lenvatinib improved progression-free survival, time to progression, and objective response rate versus sorafenib. Thus, lenvatinib can be used for the treatment of HCC.

Lenvatinib or a pharmaceutically acceptable salt thereof may be administered orally to a human subject in need thereof (e.g., a human subject having advanced HCC, uHCC, or advanced uHCC) by any means that the health care provider deems useful.

For oral administration, the lenvatinib compound can be in the form of, e.g., a tablet, capsule, suspension, or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient(s) may also be administered by injection as a composition wherein, for example, saline, dextrose or water may be used as a suitable pharmaceutically acceptable carrier.

In one embodiment, lenvatinib or a pharmaceutically acceptable salt thereof (e.g., lenvatinib mesylate) is administered to the human subject as a capsule. The capsule can contain, lenvatinib or a pharmaceutically acceptable salt thereof (e.g., lenvatinib mesylate) equivalent to 1 mg, 2 mg, 3 mg, 4 mg, 5 mg, 6 mg, 7 mg, 8 mg, 9 mg, 10 mg, 11 mg, or 12 mg of lenvatinib. In certain instances, the capsule contains lenvatinib mesylate equivalent to 4 mg lenvatinib. In certain instances, the capsule contains lenvatinib mesylate equivalent to 8 mg lenvatinib. In certain instances, the capsule contains lenvatinib mesylate equivalent to 12 mg lenvatinib. In some embodiments, these capsules also contain one or more of the following inactive ingredients: calcium carbonate, mannitol, microcrystalline cellulose, hydroxypropylcellulose, hydroxypropyl cellulose (type H), and talc. In some embodiments, the shell of these capsules is a hypromellose shell and can contain one or more of: titanium dioxide, ferric oxide yellow, and ferric oxide red. The printing ink used on the capsule may contain one or more of: shellac, black iron oxide, potassium hydroxide, and propylene glycol.

In certain embodiments, lenvatinib or a pharmaceutically acceptable salt thereof (e.g., lenvatinib mesylate) is administered to the human subject at a dose of 12 mg once daily. This dose can be administered, e.g., as three 4 mg capsules orally once daily. In other embodiments, lenvatinib or a pharmaceutically acceptable salt thereof (e.g., lenvatinib mesylate) is administered to the human subject at a dose of 8 mg once daily. This dose can be administered, e.g., as two 4 mg capsules orally once daily. In some embodiments, lenvatinib or a pharmaceutically acceptable salt thereof (e.g., lenvatinib mesylate) is administered to the human subject at a dose of 4 mg once daily. This dose can be administered, e.g., as one 4 mg capsule orally once daily. In some embodiments, lenvatinib or a pharmaceutically acceptable salt thereof (e.g., lenvatinib mesylate) is administered to the human subject at a dose of 4 mg every other day. This dose can be administered, e.g., as one 4 mg capsule orally once every other day.

It is recommended that the subject take lenvatinib or a pharmaceutically acceptable salt thereof one time each day at about the same time, with or without food.

If the patient is unable to swallow the lenvatinib capsules whole, the patient may use a cup to measure about one tablespoon of water or apple juice into a glass and place the drug capsules into the liquid without breaking or crushing them. The capsules should be left in the liquid for at least 10 minutes and the contents then stirred for at least 3 minutes. The patient can then drink this mixture. After drinking, the patient should rinse the glass with a small amount of additional water or apple juice and swallow the liquid.

In certain embodiments, lenvatinib or the pharmaceutically acceptable salt thereof is administered to a subject that has a HCC (e.g., advanced HCC or unresectable HCC) once daily for at least 7 weeks, at least 14 weeks, at least 2.8 weeks, at least 56 weeks, at least 84 weeks, at least 112 weeks, at least 140 weeks, at least 168 weeks, or at least 196 weeks.

Methods of Treatment to Control, Reduce, or Prevent Adverse Events

A major problem in treating a subject with a new therapy is the development of a treatment-emergent adverse event(s) (TEAE). A treatment-emergent adverse event is as any adverse event not present in the subject prior to the initiation of the treatment, or any adverse event already present that worsens in either intensity or frequency following exposure to the treatment. In certain embodiments, the adverse event is a persistent and intolerable adverse event.

The National Cancer Institute Common Terminology Criteria for Adverse Events v4.0 (CTCAE, published: May 28, 2009; v4.03: Jun. 14, 2010) (incorporated by reference herein in its entirety) is a descriptive terminology that can be utilized for adverse event reporting. The CTCAE provides a grading (severity) scale for each adverse event term. An Adverse Event (AE) is any unfavorable and unintended sign (including an abnormal laboratory finding), symptom, or disease temporally associated with the use of a medical treatment or procedure that may or may not be considered related to the medical treatment or procedure. An AE is a term that is a unique representation of a specific event used for medical documentation and scientific analyses. An AE can be graded. The CTCAE grade refers to the severity of the AE. The CTCAE displays Grades 1 through 5 with unique clinical descriptions of severity for each AL based on this guideline:
  Grade 1: Mild; asymptomatic or mild symptoms; clinical or diagnostic observations only; intervention not indicated.
  Grade 2: Moderate; minimal, local or noninvasive intervention indicated; limiting age-appropriate instrumental Activities of Daily Living (ADL). ["Instrumental ADL" refer to preparing meals, shopping for groceries or clothes, using the telephone, managing money, etc.]
  Grade 3: Severe or medically significant but not immediately life-threatening; hospitalization or prolongation of hospitalization indicated; disabling; limiting self-care ADL. ["Self-care ADL" refers to bathing, dressing and undressing, feeding self, using the toilet, taking medications, and not bedridden.]
  Grade 4: Life-threatening consequences; urgent intervention indicated.
  Grade 5: Death related to AE.

Not all Grades are appropriate for all AEs. Therefore, some AEs are listed in the CTC AE with fewer than five options for Grade selection.

Therapy with lenvatinib or a pharmaceutically acceptable salt thereof (e.g., lenvatinib mesylate) can lead to treatment-emergent adverse events (see Examples). In certain embodiments, the adverse event associated with therapy with lenvatinib or a pharmaceutically acceptable salt thereof is a persistent and intolerable AE. In certain instances, the persistent and intolerable AE is a Grade 2 AL. In other instances, the persistent and intolerable AE is a Grade 3 AE. In certain embodiments, the adverse event associated with the therapy using lenvatinib or a pharmaceutically acceptable salt thereof is a Grade 4 AE. In yet other instances, the persistent and intolerable AE is a Grade 4 laboratory abnormality. In certain cases, the Grade 2 or Grade 3 AE is a nonhematological toxicity. In other cases, the Grade 3 or Grade 4 AE is a hematological toxicity. In yet other cases, the Grade 3 AE is proteinuria. The most common adverse reactions observed in lenvatinib-treated HCC subjects were, in order of decreasing frequency, hypertension, fatigue, diarrhea, decreased appetite, arthralgia/myalgia, and decreased weight.

Hypertension is a disorder characterized by a pathological increase in blood pressure; a repeatedly elevation in the blood pressure exceeding 140 over 90 mm Hg, and is graded as follows:
  Grade 1: Prehypertension (systolic BP 120-139 mm Hg or diastolic BP 80-89 mm Hg)
  Grade 2: Stage 1 hypertension (systolic BP 140-159 mm Hg or diastolic BP 90-99 mm Hg); medical intervention indicated; recurrent or persistent (>=24 hrs); symptomatic increase by >20 mm Hg (diastolic) or to >140/90 mm Hg if previously WNL; monotherapy indicated Pediatric: recurrent or persistent (>=2.4 hrs) BP>ULN; monotherapy indicated
  Grade 3: Stage 2 hypertension (systolic BP>=160 mm Hg or diastolic BP>=100 mm Hg); medical intervention indicated; more than one drug or more intensive therapy than previously used indicated Pediatric: Same as adult
  Grade 4: Life-threatening consequences (e.g., malignant hypertension, transient or permanent neurologic deficit, hypertensive crisis); urgent intervention indicated Pediatric: Same as adult
  Grade 5: Death Fatigue is a disorder characterized by a state of generalized weakness with a pronounced inability to summon sufficient energy to accomplish daily activities and is graded as follows:
  Grade 1: Fatigue relieved by rest.
  Grade 2: Fatigue not relieved by rest or limiting instrumental activities of daily living (ADL). Instrumental ADL refer to preparing meals, shopping for groceries or clothes, using the telephone, managing money, etc.
  Grade 3: Fatigue not relieved by rest, limiting self-care ADL. Self-care ADL refer to bathing, dressing and undressing, feeding self, using the toilet, taking medications, and not bedridden.
  Grade 4: Grade is not available.
  Grade 5: Grade is not available.

Diarrhea is a disorder characterized by frequent and watery bowel movements and is graded as follows:
  Grade 1: Increase of <4 stools per day over baseline; mild increase in ostomy output compared to baseline
  Grade 2: Increase of 4-6 stools per day over baseline; moderate increase in ostomy output compared to baseline
  Grade 3: Increase of >=7 stools per day over baseline; incontinence; hospitalization indicated; severe increase in ostomy output compared to baseline; limiting self-care ADL
  Grade 4: Life-threatening consequences; urgent intervention indicated
  Grade 5: death Decreased appetite (anorexia) is a disorder characterized by a loss of appetite, and is graded as follows:
  Grade 1: Loss of appetite without alteration in eating habits
  Grade 2: Oral intake altered without significant weight loss or malnutrition; oral nutritional supplements indicated.
  Grade 3: Associated with significant weight loss or malnutrition (e.g., inadequate oral caloric and/or fluid intake); tube feeding or TPN indicated
  Grade 4: Life-threatening consequences; urgent intervention indicated Grade 5: Death Arthralgia is a disorder characterized by a sensation of marked discomfort in a joint, and is graded as follows:
  Grade 1: Mild pain
  Grade 2: Moderate pain; limiting instrumental ADL
  Grade 3: Severe pain; limiting self care ADL
  Grade 4: Not available
  Grade 5: Not available Myalgia is a disorder characterized by marked discomfort sensation originating from a muscle or group of muscles, and is graded as follows:
  Grade 1: Mild pain
  Grade 2: Moderate pain; limiting instrumental ADL
  Grade 3: Severe pain; limiting self care ADL
  Grade 4: Not available
  Grade 5: Not available Decreased weight (weight loss) is a finding characterized by a decrease in overall body weight; for pediatrics, less than the baseline growth curve, and is graded as follows:
  Grade 1: Weight loss 5 to <1.0% from baseline; intervention not indicated
  Grade 2: 10-<20% from baseline; nutritional support indicated
  Grade 3: >=20% from baseline; tube feeding or TPN indicated
  Grade 4: Not available
  Grade 5: Not available The most common serious adverse reactions (≥2%) in LENVIMA-treated patients were hepatic encephalopathy (4%), hepatic failure (3%), ascites (3%), and decreased appetite (2%).

Hepatic encephalopathy comprises hepatobiliary disorders, and is graded as follows:
  Grade 1: Asymptomatic or mild symptoms; clinical or diagnostic observations only; intervention not indicated
  Grade 2: Moderate; minimal, local or noninvasive intervention indicated; limiting age appropriate instrumental ADL
  Grade 3: Severe or medically significant but not immediately life-threatening; hospitalization or prolongation of existing hospitalization indicated; disabling; limiting self care ADL
  Grade 4: Life-threatening consequences; urgent intervention indicated.
  Grade 5: Death Hepatic failure is a disorder characterized by the inability of the liver to metabolize chemicals in the body. Laboratory test results reveal abnormal plasma levels of ammonia, bilirubin, lactic dehydrogenase, and alkaline phosphatase. Hepatic failure is graded as follows:
  Grade 1: Not available
  Grade 2: Not available
  Grade 3: Asterixis or mild encephalopathy or limiting self-care ADL
  Grade 4: Moderate to severe encephalopathy or coma or life-threatening consequences
  Grade 5: Death Ascites is disorder characterized by accumulation of serous or hemorrhagic fluid in the peritoneal cavity and is graded as follows:
  Grade 1: Asymptomatic or clinical or diagnostic observations only or intervention not indicated
  Grade 2: Symptomatic or medical intervention indicated
  Grade 3: Severe symptoms or invasive intervention indicated
  Grade 4: Life-threatening consequences or urgent operative intervention indicated
  Grade 5: Death Adverse reactions led to dose reduction or interruption in about 62% of patients receiving LENVIMA. The most common adverse reactions (>5%) resulting in dose reduction or interruption of LENVIMA were fatigue (9%), decreased appetite (8%), diarrhea (8%), proteinuria (7%), hypertension (6%), and palmar-plantar erythrodysesthesia syndrome (5%).

Proteinuria is disorder characterized by laboratory test results that indicate the presence of excessive protein in the urine. It is predominantly albumin, but also globulin, and is graded as follows:
  Grade 1: 1+ proteinuria; urinary protein<1.0 g/24 hrs
  Grade 2: Adults: 2+ proteinuria; urinary protein 1.0-3.4 g/24 hrs; Pediatric: urine P/C (Protein/Creatinine) ratio 0.5-1.9
  Grade 3: Adults: urinary protein>=3.5 g/24 hrs; Pediatric: urine P/C>1.9
  Grade 4: Not Available
  Grade 5: Not Available Palmar-plantar erythrodysesthesia syndrome is a disorder characterized by redness, marked discomfort, swelling, and tingling in the palms of the hands or the soles of the feet, and is graded as follows:
  Grade 1: Minimal skin changes or dermatitis (e.g., erythema, edema, or hyperkeratosis) without pain
  Grade 2: Skin changes (e.g., peeling, blisters, bleeding, edema, or hyperkeratosis) with pain; limiting instrumental ADL
  Grade 3: Severe skin changes (e.g., peeling, blisters, bleeding, edema, or hyperkeratosis) with pain; limiting self-care ADL
  Grade 4: Not Available
  Grade 5: Not Available Treatment discontinuation due to adverse reactions occurred in 20% of patients in the LENVIMA-treated group. The most common adverse reactions (≥1%) resulting in discontinuation of LENVIMA were fatigue (1%), hepatic encephalopathy (1%), hyperbilirubinemia (1%), and hepatic failure (1%).

Hyperbilirubinemia ("Blood bilirubin increased") is a finding based on laboratory test results that indicate an abnormally high level of bilirubin in the blood. Excess bilirubin is associated with jaundice,
  Grade 1: >1.0 ULN–1.5×ULN (upper limit of the normal range (ULN)).
  Grade 2: >1.5 ULN–3.0×ULN
  Grade 3: >3.0 ULN–10.0×ULN
  Grade 4: >10.0×ULN
  Grade 5: Not Available This disclosure provides dose modifications for therapy comprising lenvatinib or a pharmaceutically acceptable salt thereof upon the occurrence of a treatment-emergent adverse event(s) during the course of treatment. In certain embodiments, a subject who has a baseline body weight of 60 kg or greater and who has a HCC is administered a first dosage regimen comprising lenvatinib or a pharmaceutically acceptable salt thereof at a dose of 12 mg/day. In other embodiments, a subject who has a baseline body weight of less than 60 kg and who has a HCC is administered a first dosage regimen comprising lenvatinib or a pharmaceutically acceptable salt thereof at a dose of 8 mg/day. In some embodiments, if a subject who has HCC and has moderate hepatic impairment classified in Child-Pugh class B under the Child-Pugh Classification, then the subject is administered a first dosage regimen comprising lenvatinib or a pharmaceutically acceptable salt thereof at a dose 8 mg/day regardless of the body weight of the subject.

Exemplary recommendations for dose interruption, reduction, and discontinuation of LENVIMA for some adverse reactions are listed in Table I below.

TABLE 1

Table I. Dose Modifications for Exemplary Adverse Reactions

| Adverse Reaction | Severity[a] | Dose Modifications for LENVIMA |
|---|---|---|
| Hypertension | Grade 3 | Withhold for Grade 3 that persists despite optimal antihypertensive therapy. Resume at reduced dose when hypertension is controlled at less than or equal to Grade 2. |
|  | Grade 4 | Permanently discontinue for life-threatening hypertension. |
| Cardiac Dysfunction | Grade 3 | Withhold until improves to Grade 0 or 1 or baseline. Resume at a reduced dose or discontinue depending on the severity and persistence of adverse reaction. |
|  | Grade 4 | Permanently discontinue. |
| Arterial Thromboembolic Event | Any Grade | Permanently discontinue. |
| Hepatotoxicity | Grade 3 or 4 | Withhold until improves to Grade 0 to 1 or baseline. Either resume at a reduced dose or discontinue depending on severity and persistence of hepatotoxicity. Permanently discontinue for hepatic failure. |
| Renal Failure or Impairment | Grade 3 or 4 | Withhold until improves to Grade 0 to 1 or baseline. Resume at a reduced dose or discontinue depending on severity and persistence of renal impairment. |

TABLE 2

Table I. (cont.) Dose Modifications for Exemplary Adverse Reactions

| Adverse Reaction | Severity[a] | Dose Modifications for LENVIMA |
|---|---|---|
| Proteinuria | 2 g or greater proteinuria in 24 hours | Withhold until less than or equal to 2 grams of proteinuria per 24 hours. Resume at a reduced dose. Discontinue for nephrotic syndrome. |
| Gastrointestinal Perforation | Any Grade | Permanently discontinue. |
| Fistula Formation | Grade 3 or 4 | Permanently discontinue. |
| QT Prolongation | Greater than 500 ms or greater than 60 ms increase from baseline | Withhold until improves to less than or equal to 480 ms or baseline. Resume at a reduced dose. |
| Reversible Posterior Leukoencephalopathy Syndrome | Any Grade | Withhold until fully resolved. Resume at a reduced dose or discontinue depending on severity and persistence of neurologic symptoms. |
| Other Adverse | Persistent or intolerable Grade 2 or 3 adverse reaction Grade 4 laboratory abnormality | Withhold until improves to Grade 0 or 1 or baseline Resume at reduced dose. |
|  | Grade 4 adverse reaction | Permanently discontinue. |

[a]National Cancer Institute Common Terminology Criteria for Adverse Events, version 4.0.

Non-Hematologic Toxicity

In some cases, the subject may develop a Grade 1 or tolerable Grade 2 adverse reaction (e.g., nonhematological toxicity) after being administered the first dosage regimen. In such instances, treatment of the subject can continue without any changes to the first dosage regimen. Following or during treatment period with the first dosage regimen comprising lenvatinib or a pharmaceutically acceptable salt thereof at a dose of 12 mg/day or 8 mg/day, if the human subject does not develop an intolerable Grade 2 or Grade 3 adverse reaction or non-life-threatening Grade 4 laboratory abnormality (e.g., nonhematological toxicity), the dosage regimen can be maintained without any changes to the first dosage regimen.

In some embodiments, the subject develops an intolerable Grade 2 or Grade 3 adverse reaction or non-life-threatening Grade 4 laboratory abnormality (e.g., non-hematologic toxicity) during the period of treatment with the first dosage regimen that is related to lenvatinib toxicity. In certain instances, the subject develops a Grade 2 or Grade 3 non-hematologic toxicity or non-life-threatening Grade 4 laboratory abnormality within 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks after the administration of the first dosage regimen. In one embodiment, the subject develops an intolerable Grade 2 or Grade 3 nonhematologic toxicity or non-life-threatening Grade 4 laboratory abnormality within 12 weeks after the administration of the first dosage regimen. In another embodiment, the subject develops an intolerable Grade 2 or Grade 3 nonhematologic toxicity or non-life-threatening Grade 4 laboratory abnormality within 16 weeks after the administration of the first dosage regimen. In certain instances, the intolerable Grade 2 or Grade 3 non-hematologic toxicity is Grade 3 hypertension, Grade 2 hypertension, Grade 3 fatigue, Grade 2 fatigue, Grade 3 palmar-plantar erythrodysesthesia, Grade 2 palmar-plantar erythrodysesthesia, Grade 3 diarrhea, Grade 2 diarrhea, Grade 3 decreased appetite, Grade 2 decreased appetite, Grade 3 fatigue, Grade 2 fatigue, Grade 3 arthralgia, Grade 2 arthralgia, Grade 3 myalgia, Grade 2 myalgia, Grade 3 decreased weight, Grade 2 decreased weight, Grade 2 alopecia, Grade 3 dysphonia, Grade 2 dysphonia, Grade 3 nausea, Grade 2 nausea, Grade 3 abdominal pain, Grade 2 abdominal pain, Grade 3 QT/QTc interval prolongation (Electrocardiogram QT corrected interval prolonged), Grade 2 QT/QTc interval prolongation, Grade 3 hypothyroidism, Grade 2 hypothyroidism, Grade 3 vomiting, Grade 2 vomiting, Grade 3 constipation, Grade 2 constipation, Grade 3 rash, and Grade 2 rash. In specific cases, the persistent and intolerable Grade 2 or Grade 3 non-hematologic toxicity is Grade 3 hypertension, Grade 2 hypertension, Grade 3 fatigue, Grade 2 fatigue, Grade 3 diarrhea, Grade 2 diarrhea, Grade 3 decreased appetite, Grade 2 decreased appetite, Grade 3 arthralgia, Grade 2 arthralgia, Grade 3 myalgia, Grade 2 myalgia, Grade 3 decreased weight, or Grade 2 decreased weight. In certain instances, Grade 2 toxicities can be determined to be tolerable or intolerable by both the subject and healthcare provider. In certain instances, the Grade 4 laboratory abnormality is Grade 4 increase in aspartate aminotransferase, Grade 4 increase in alanine aminotransferase, Grade 4 increase in alkaline phosphatase, Grade 4 hypokalemia, Grade 4 hyponatremia, Grade 4 hypoglycemia, Grade 4 increase in blood bilirubin, or Grade 4 increase in gamma glutamyl transferase. In the above embodiments, the healthcare provider can determine whether the Grade 4 laboratory abnormality is life-threatening or not.

If the subject develops an intolerable Grade 2 or Grade 3 nonhematologic toxicity or non-life-threatening Grade 4 laboratory abnormality, after being administered the first dosage regimen (i.e., lenvatinib or a pharmaceutically acceptable salt thereof at a dose of 12 mg/day (if the patient has a baseline body weight of greater than or equal to 60 kg) or 8 mg/day (if the patient has a baseline body weight of less than 60 kg)), the healthcare provider can terminate the first dosage regimen and administer to the subject a second dosage regimen comprising lenvatinib or a pharmaceutically acceptable salt thereof at a dose of 8 mg/day (if the patient has a baseline body weight of greater than or equal to 60 kg) or 4 mg/day (if the patient has a baseline body weight of less than 60 kg). In certain instances, the second dosage regimen is administered after interruption of the first dosage regimen and after the nonhematologic toxicity observed after the first dosage regimen is resolved to Grade 0-1 or baseline. In some instances, the first dosage regimen is terminated only after commencement of medical management of the intolerable Grade 2 or Grade 3 nonhematologic toxicity or non-life-threatening Grade 4 laboratory abnormality. In specific embodiments, the intolerable Grade 2 or Grade 3 adverse reaction is hypertension, fatigue, diarrhea, arthralgia/myalgia, decreased appetite, or decreased weight. If the Grade 3 nonhematologic toxicity is hypertension, in one embodiment, the subject is provided antihypertensive therapy and treatment with lenvatinib or a pharmaceutically acceptable salt thereof is resumed at a lower dose (e.g., 8 or 4 mg/day) when hypertension is controlled at less than or equal to Grade 1; however, therapy with lenvatinib or a pharmaceutically acceptable salt thereof is discontinued for life-threatening hypertension.

In some cases, even after administration of the second dosage regimen, a subject may develop an adverse reaction (e.g., nonhematologic toxicity). In certain instances, the subject develops an intolerable Grade 2 or Grade 3 nonhematologic toxicity or non-life-threatening Grade 4 laboratory abnormality within 1 week, 2 weeks, 3 weeks, 4 weeks, 5 weeks, 6 weeks, 7 weeks, 8 weeks, 9 weeks, 10 weeks, 11 weeks, or 12 weeks after the administration of the second dosage regimen. The nonhematologic toxicity after the second dosage regimen may be the same as, or different from, the nonhematologic toxicity after the first dosage regimen. The nonhematologic toxicity after the second dosage regimen may be an intolerable Grade 2 or Grade 3 nonhematologic toxicity or non-life-threatening Grade 4 laboratory abnormality. In some instances, the nonhematologic toxicity is hypertension. In some instances, the nonhematologic toxicity is fatigue. In some instances, the nonhematologic toxicity is arthralgia. In some instances, the nonhematologic toxicity is myalgia. In some instances, the nonhematologic toxicity is diarrhea. In some instances, the nonhematologic toxicity is decreased appetite. In some instances, the nonhematologic toxicity is decreased weight.

If the subject develops an intolerable Grade 2 or Grade 3 nonhematologic toxicity or non-life-threatening Grade 4 laboratory abnormality, after being administered the second dosage regimen (i.e., lenvatinib or a pharmaceutically acceptable salt thereof at a dose of 8 mg/day (if the patient has a baseline body weight of greater than or equal to 60 kg) or 4 mg/day (if the patient has a baseline body weight of less than 60 kg)), the healthcare provider can terminate the second dosage regimen and administer to the subject a third dosage regimen comprising lenvatinib or a pharmaceutically acceptable salt thereof at a dose of 4 mg/day (if the patient has a baseline body weight of greater than or equal to 60 kg) or 4 mg every other day (if the patient has a baseline body weight of less than 60 kg). In certain instances, the third dosage regimen is administered after interruption of the second dosage regimen and after the nonhematologic toxicity observed after the second dosage regimen is resolved to Grade 0-1 or baseline. In some instances, the second dosage regimen is terminated only after commencement of medical management of the intolerable Grade 2 or Grade 3 nonhematologic toxicity or non-life-threatening Grade 4 laboratory abnormality. In specific embodiments, the intolerable Grade 2 or Grade 3 nonhematologic toxicity is hypertension, fatigue, diarrhea, decreased appetite, arthralgia/myalgia, or decreased weight. If the Grade 3 nonhematologic toxicity is hypertension, in one embodiment, the subject is provided antihypertensive therapy and treatment with lenvatinib or a pharmaceutically acceptable salt thereof is resumed at a lower dose (e.g., 4 mg every other day) when hypertension is controlled at less than or equal to Grade 1; however, therapy with lenvatinib or a pharmaceutically acceptable salt thereof is discontinued for life-threatening hypertension.

In some cases, even after administration of the third dosage regimen, a subject may develop an adverse reaction (e.g., nonhematologic toxicity). In certain instances, the subject develops an intolerable Grade 2 or Grade 3 nonhematologic toxicity or non-life-threatening Grade 4 laboratory abnormality within 1 week, 2 weeks, 3 weeks, 4 weeks, 5 weeks, 6 weeks, 7 weeks, 8 weeks, 9 weeks, 10 weeks, 11 weeks, or 12 weeks after the administration of the third dosage regimen. The nonhematologic toxicity after the third dosage regimen may be the same as, or different from, the nonhematologic toxicity after the second dosage regimen. The nonhematologic toxicity after the third dosage regimen may be an intolerable Grade 2 or Grade 3 nonhematologic toxicity or non-life-threatening Grade 4 laboratory abnormality. In some instances, the nonhematologic toxicity is hypertension. In some instances, the nonhematologic toxicity is fatigue. In some instances, the nonhematologic toxicity is arthralgia. In some instances, the nonhematologic toxicity is myalgia. In some instances, the nonhematologic toxicity is diarrhea. In some instances, the nonhematologic toxicity is decreased appetite. In some instances, the nonhematologic toxicity is decreased weight.

If the subject develops an intolerable Grade 2 or Grade 3 nonhematologic toxicity or non-life-threatening Grade 4 laboratory abnormality, after being administered the third dosage regimen (i.e., lenvatinib or a pharmaceutically acceptable salt thereof at a dose of 4 mg/day (if the patient has a baseline body weight of greater than or equal to 60 kg) or 4 mg every other day (if the patient has a baseline body weight of less than 60 kg)), the healthcare provider can terminate the third dosage regimen and administer to the subject a fourth dosage regimen comprising lenvatinib or a pharmaceutically acceptable salt thereof at a dose of 4 mg every other day (if the patient has a baseline body weight of greater than or equal to 60 kg). If the patient has a baseline body weight of less than 60 kg, in certain instances, lenvatinib therapy may be discontinued. In certain instances, the fourth dosage regimen is administered after interruption of the third dosage regimen and after the nonhematologic toxicity observed after the third dosage regimen is resolved to Grade 0-1 or baseline. In some instances, the third dosage regimen is terminated only after commencement of medical management of the intolerable Grade 2 or Grade 3 nonhematologic toxicity or non-life-threatening Grade 4 laboratory abnormality. In specific embodiments, the persistent and intolerable Grade 2 or Grade 3 nonhematologic toxicity is hypertension, fatigue, diarrhea, decreased appetite, arthralgia/myalgia, or decreased weight. If the Grade 3 nonhematologic toxicity is hypertension, in one embodiment, the subject is provided antihypertensive therapy and treatment with lenvatinib or a pharmaceutically acceptable salt thereof is resumed at a lower dose when hypertension is controlled at less than or equal to Grade 1; however, therapy with lenvatinib or a pharmaceutically acceptable salt thereof is discontinued for life-threatening hypertension.

In some embodiments, if the subject develops a Grade 4 nonhematologic toxicity excluding non-life-threatening Grade 4 laboratory abnormality after being administered the first, second, third, or fourth dosage regimen, the healthcare provider can terminate administration of the dosage regimen after the occurrence of the Grade 4 nonhematologic toxicity excluding non-life-threatening Grade 4 laboratory abnormality.

In some embodiments, a Grade 3 laboratory abnormality that is not clinically relevant based on a judgment of healthcare provider is excluded from a Grade 3 nonhematologic toxicity.

In the above embodiments, a Grade 3 proteinuria is excluded from a Grade 3 nonhematologic toxicity to those dosage regimens.

Grades 1 to 3 Hematologic Toxicity and/or Grades 1 to 3 Proteinuria

In some embodiments, the subject may develop a Grade 1 or Grade 2 hematologic toxicity or Grade 1 or Grade 2 proteinuria during the period of treatment with the first dosage regimen (i.e., lenvatinib or a pharmaceutically acceptable salt thereof at a dose of 12 mg/day (if the patient has a baseline body weight of greater than or equal to 60 kg) or 8 mg/day (if the patient has a baseline body weight of less than 60 kg)) that is related to lenvatinib toxicity. In such instances, the subject can continue with treatment with the first dosage regimen. However, in some cases, the subject may develop a Grade 3 adverse reaction (e.g., hematologic toxicity or proteinuria) during the period of treatment with the first dosage regimen that is related to lenvatinib toxicity. In certain instances, the subject develops a Grade 3 hematologic toxicity or Grade 3 proteinuria within 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks after the administration of the first dosage regimen. In one embodiment, the subject develops a Grade 3 hematologic toxicity or Grade 3 proteinuria within 12 weeks after the administration of the first dosage regimen. In another embodiment, the subject develops a Grade 3 hematologic toxicity or Grade 3 proteinuria within 16 weeks after the administration of the first dosage regimen. In certain instances, the Grade 3 hematologic toxicity is Grade 3 thrombopenia (thrombocytopenia; platelet count decreased), Grade 3 anemia (hemoglobin decreased), Grade 3 decrease in white blood cell count (leukocyte count decreased; white blood cell decreased), Grade 3 neutropenia (neutrophil count decreased), or Grade 3 lymphocytopenia (lymphocyte count decreased).

If the subject develops a Grade 3 hematologic toxicity or Grade 3 proteinuria, after being administered the first dosage regimen lenvatinib or a pharmaceutically acceptable salt thereof at a dose of 12 mg/day (if the patient has a baseline body weight of greater than or equal to 60 kg) or 8 mg/day (if the patient has a baseline body weight of less than 60 kg)), the healthcare provider can terminate the first dosage regimen and administer to the subject a second dosage regimen comprising lenvatinib or a pharmaceutically acceptable salt thereof at a dose of 12 mg/day (if the patient has a baseline body weight of greater than or equal to 60 kg) or 8 mg/day (if the patient has a baseline body weight of less than 60 kg). In certain instances, the second dosage regimen is administered after interruption of the first dosage regimen and after the nonhematologic toxicity observed after the first dosage regimen is resolved to Grade 0-2 or baseline. In some instances, the first dosage regimen is terminated only after commencement of medical management of the Grade 3 hematologic toxicity. In specific embodiments, the Grade 3 hematologic toxicity is Grade 3 thrombopenia (thrombocytopenia), Grade 3 anemia, Grade 3 decrease in white blood cell count, Grade 3 neutropenia, or Grade 3 lymphocytopenia.

In some cases, even after administration of the second dosage regimen, a subject may develop a Grade 3 hematologic toxicity or Grade 3 proteinuria. In certain instances, the subject develops a Grade 3 hematologic toxicity or Grade 3 proteinuria within 1 week, 2 weeks, 3 weeks, 4 weeks, 5 weeks, 6 weeks, 7 weeks, 8 weeks, 9 weeks, 10 weeks, 11 weeks, or 12 weeks after the administration of the second dosage regimen. The Grade 3 hematologic toxicity or Grade 3 proteinuria after the second dosage regimen may be the same as, or different from, the Grade 3 hematologic toxicity or Grade 3 proteinuria after the first dosage regimen. The hematologic toxicity or proteinuria after the second dosage regimen may be a Grade 3 hematologic toxicity or Grade 3 proteinuria.

If the subject develops a Grade 3 hematologic toxicity or Grade 3 proteinuria, after being administered the second dosage regimen (i.e., lenvatinib or a pharmaceutically acceptable salt thereof at a dose of 12 mg/day (if the patient has a baseline body weight of greater than or equal to 60 kg) or 8 mg/day (if the patient has a baseline body weight of less than 60 kg)), the healthcare provider can terminate the second dosage regimen and administer to the subject a third dosage regimen comprising lenvatinib or a pharmaceutically acceptable salt thereof at a dose of 8 mg/day (if the patient has a baseline body weight of greater than or equal to 60 kg) or 4 mg/day (if the patient has a baseline body weight of less than 60 kg). In certain instances, the third dosage regimen is administered after interruption of the second dosage regimen and after the Grade 3 hematologic toxicity or Grade 3 proteinuria observed after the second dosage regimen is resolved to Grade 0-2 or baseline. In some instances, the second dosage regimen is terminated only after commencement of medical management of the Grade 3 hematologic toxicity or Grade 3 proteinuria.

In some cases, even after administration of the third dosage regimen, a subject may develop a Grade 3 hematologic toxicity or Grade 3 proteinuria. In certain instances, the subject develops a Grade 3 hematologic toxicity or Grade 3 proteinuria within 1 week, 2 weeks, 3 weeks, 4 weeks, 8 weeks, 6 weeks, 7 weeks, 8 weeks, 9 weeks, 10 weeks, 11 weeks, or 12 weeks after the administration of the third dosage regimen. The Grade 3 hematologic toxicity or Grade 3 proteinuria after the third dosage regimen may be the same as, or different from, the Grade 3 hematologic toxicity or Grade 3 proteinuria after the second dosage regimen. The Grade 3 hematologic toxicity or Grade 3 proteinuria after the third dosage regimen may be a Grade 3 hematologic toxicity or Grade 3 proteinuria.

If the subject develops a Grade 3 hematologic toxicity or Grade 3 proteinuria, after being administered the third dosage regimen (i.e., lenvatinib or a pharmaceutically acceptable salt thereof at a dose of 8 mg/day (if the patient has a baseline body weight of greater than or equal to 60 kg) or 4 mg/day (if the patient has a baseline body weight of less than 60 kg)), the healthcare provider can terminate the third dosage regimen and administer to the subject a fourth dosage regimen comprising lenvatinib or a pharmaceutically acceptable salt thereof at a dose of 4 mg/day (if the patient has a baseline body weight of greater than or equal to 60 kg) or 4 mg every other day (if the patient has a baseline body weight of less than 60 kg). In certain instances, the fourth dosage regimen is administered after interruption of the third dosage regimen and after the Grade 3 hematologic toxicity or Grade 3 proteinuria observed after the third dosage regimen is resolved to Grade 0-2 or baseline. In some instances, the third dosage regimen is terminated only after commencement of medical management of the Grade 3 hematologic toxicity or Grade 3 proteinuria.

In some cases, even after administration of the fourth dosage regimen, a subject may develop a Grade 3 hematologic toxicity or Grade 3 proteinuria. In certain instances, the subject develops a Grade 3 hematologic toxicity or Grade 3 proteinuria within 1 week, 2 weeks, 3 weeks, 4 weeks, 5 weeks, 6 weeks, 7 weeks, 8 weeks, 9 weeks, 10 weeks, 11 weeks, or 12 weeks after the administration of the third dosage regimen. The Grade 3 hematologic toxicity or Grade 3 proteinuria after the third dosage regimen may be the same as, or different from, the Grade 3 hematologic toxicity or Grade 3 proteinuria after the second dosage regimen. The Grade 3 hematologic toxicity or Grade 3 proteinuria after the third dosage regimen may be a Grade 3 hematologic toxicity or Grade 3 proteinuria.

If the subject develops a Grade 3 hematologic toxicity or Grade 3 proteinuria, after being administered the fourth dosage regimen (i.e., lenvatinib or a pharmaceutically acceptable salt thereof at a dose of 4 mg/day (if the patient has a baseline body weight of greater than or equal to 60 kg) or 4 mg every other day (if the patient has a baseline body weight of less than 60 kg)), the healthcare provider can terminate the fourth dosage regimen and administer to the subject a fifth dosage regimen comprising lenvatinib or a pharmaceutically acceptable salt thereof at a dose of 4 mg every other day (if the patient has a baseline body weight of greater than or equal to 60 kg). In some cases, if the patient has a baseline body weight of less than 60 kg, lenvatinib treatment may be discontinued. In certain instances, the fifth dosage regimen is administered after interruption of the fourth dosage regimen and after the Grade 3 hematologic toxicity or Grade 3 proteinuria observed after the third dosage regimen is resolved to Grade 0-2 or baseline. In some instances, the fourth dosage regimen is terminated only after commencement of medical management of the Grade 3 hematologic toxicity or Grade 3 proteinuria.

In some embodiments, a Grade 3 laboratory abnormality that is not clinically relevant based on a judgment of healthcare provider is excluded from a Grade 3 hematologic toxicity.

Grade 4 Hematologic Toxicity

In some embodiments, the subject may develop a Grade 4 hematologic toxicity during the period of treatment with the first dosage regimen (i.e., lenvatinib or a pharmaceutically acceptable salt thereof at a dose of 12 mg/day (if the patient has a baseline body weight of greater than or equal to 60 kg) or 8 mg/day (if the patient has a baseline body weight of less than 60 kg)) that is related to lenvatinib toxicity. In certain instances, the subject develops the Grade 4 hematologic toxicity within 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks after the administration of the first dosage regimen. In one embodiment, the subject develops Grade 4 hematologic toxicity within 12 weeks after the administration of the first dosage regimen. In another embodiment, the subject develops the Grade 4 hematologic toxicity within 16 weeks after the administration of the first dosage regimen. In certain instances, the Grade 4 hematologic toxicity is Grade 4 thrombopenia (thrombocytopenia; platelet count decreased), Grade 4 anemia, Grade 4 decrease in white blood cell count, Grade 4 neutropenia, or Grade 4 lymphocytopenia.

If the subject develops the Grade 4 hematologic toxicity after being administered the first dosage regimen (i.e., lenvatinib or a pharmaceutically acceptable salt thereof at a dose of 12 mg/day (if the patient has a baseline body weight of greater than or equal to 60 kg) or 8 mg/day (if the patient has a baseline body weight of less than 60 kg)), the healthcare provider can terminate the first dosage regimen and administer to the subject a second dosage regimen comprising lenvatinib or a pharmaceutically acceptable salt thereof at a dose of 8 mg/day (if the patient has a baseline body weight of greater than or equal to 60 kg) or 4 mg/day (if the patient has a baseline body weight of less than 60 kg). In certain instances, the second dosage regimen is administered after interruption of the first dosage regimen and after the Grade 4 hematologic toxicity observed after the first dosage regimen is resolved to Grade 0-2 or baseline. In some instances, the first dosage regimen is terminated only after commencement of medical management of the Grade 4 hematologic toxicity. In specific embodiments, the Grade 4 hematologic toxicity is Grade 4 thrombopenia (thrombocytopenia), Grade 4 anemia, Grade 4 decrease in white blood cell count, Grade 4 neutropenia, or Grade 4 lymphocytopenia.

In some cases, even after administration of the second dosage regimen, a subject may develop a Grade 4 hematologic toxicity. In certain instances, the subject develops a Grade 4 hematologic toxicity within 1 week, 2 weeks, 3 weeks, 4 weeks, 5 weeks, 6 weeks, 7 weeks, 8 weeks, 9 weeks, 10 weeks, 11 weeks, or 12 weeks after the administration of the second dosage regimen. The Grade 4 hematologic toxicity after the second dosage regimen may be the same as, or different from, the Grade 4 hematologic toxicity after the first dosage regimen. The hematologic toxicity after the second dosage regimen may be a persistent and intolerable Grade 4 hematologic toxicity.

If the subject develops a Grade 4 hematologic toxicity after being administered the second dosage regimen (i.e., lenvatinib or a pharmaceutically acceptable salt thereof at a dose of 8 mg/day (if the patient has a baseline body weight of greater than or equal to 60 kg) or 4 mg/day (if the patient has a baseline body weight of less than 60 kg)), the healthcare provider can terminate the second dosage regimen and administer to the subject a third dosage regimen comprising lenvatinib or a pharmaceutically acceptable salt thereof at a dose of 4 mg/day (if the patient has a baseline body weight of greater than or equal to 60 kg) or 4 mg every other day (if the patient has a baseline body weight of less than 60 kg). In certain instances, the third dosage regimen is administered after interruption of the second dosage regimen and after the Grade 4 hematologic toxicity observed after the second dosage regimen is resolved to Grade 0-2 or baseline. In some instances, the second dosage regimen is terminated only after commencement of medical management of the Grade 4 hematologic toxicity.

In some cases, even after administration of the third dosage regimen, a subject may develop a Grade 4 hematologic toxicity. In certain instances, the subject develops a Grade 4 hematologic toxicity within 1 week, 2 weeks, 3 weeks, 4 weeks, 5 weeks, 6 weeks, 7 weeks, 8 weeks, 9 weeks, 10 weeks, 11 weeks, or 12 weeks after the administration of the third dosage regimen. The Grade 4 hematologic toxicity after the third dosage regimen may be the same as, or different from, the Grade 4 hematologic toxicity after the second dosage regimen. The Grade 4 hematologic toxicity after the third dosage regimen may be a persistent and intolerable Grade 4 hematologic toxicity.

If the subject develops a Grade 4 hematologic toxicity after being administered the third dosage regimen (i.e., lenvatinib or a pharmaceutically acceptable salt thereof at a dose of 4 mg/day (if the patient has a baseline body weight of greater than or equal to 60 kg) or 4 mg every other day (if the patient has a baseline body weight of less than 60 kg)), the healthcare provider can terminate the third dosage regimen and administer to the subject a fourth dosage regimen comprising lenvatinib or a pharmaceutically acceptable salt thereof at a dose of 4 mg every other day (if the patient has a baseline body weight of greater than or equal to 60 kg). If the patient has a baseline body weight of less than 60 kg, lenvatinib therapy can, in some embodiments, be discontinued. In certain instances, the fourth dosage regimen is administered after interruption of the third dosage regimen and after the Grade 4 hematologic toxicity observed after the third dosage regimen is resolved to Grade 0-2 or baseline. In some instances, the third dosage regimen is terminated only after commencement of medical management of the Grade 4 hematologic toxicity.

The dose modifications discussed above can be helpful in permitting a subject who develops an adverse reaction to the lenvatinib therapy (e.g., a nonhematologic toxicity, a hematologic toxicity, proteinuria, or a laboratory abnormality) to continue with and benefit from the lenvatinib therapy.

Table II below lists exemplary dose reductions for LENVIMA due to adverse reactions after administration of a first dosage regimen discussed above.

TABLE 3

Table II. Exemplary Dose Modifications for LENVIMA

| Indication | First Dosage Reduction To | Second Dosage Reduction To | Third Dosage Reduction To |
|---|---|---|---|
| HCC (e.g., unresectable HCC) | | | |
| Actual weight 60 kg or greater | 8 mg once daily | 4 mg once daily | 4 mg every other day |
| Actual weight less than 60 kg | 4 mg once daily | 4 mg every other day | Discontinue |

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

EXAMPLES

Example 1: Lenvatinib for Unresectable Hepatocellular Carcinoma

This Example describes the open-label phase 3 noninferiority study using lenvatinib in unresectable HCC. In this study 478 patients were randomized to lenvatinib (body weight≥60 kg: 12 mg/day; <60 kg: 8 mg/day) and 476 to sorafenib 400 mg twice daily. The primary endpoint was overall survival. Secondary endpoints included progression-free survival, time to progression, objective response rate, safety, and quality of life.

Materials & Methods

Study Eligibility

Patients who were eligible for enrollment had unresectable HCC with diagnosis confirmed histologically or cytologically or with diagnosis confirmed clinically in accordance with the American Association for the Study of Liver Diseases criteria. Included patients also had ≥1 measureable target lesion, based on modified Response Evaluation Criteria in Solid Tumors (Lencioni 2010); Barcelona Clinic Liver Cancer stage B or C categorization (Bruix Hepatology 2011); Child-Pugh class A; and Eastern Cooperative Oncology Group performance status ≤1. All eligible patients had controlled blood pressure (≤150/90 mm Hg), and adequate organ function. Patients with ≥50% liver occupation, clear bile duct invasion, or portal vein invasion at the main portal vein were excluded. Patients also were excluded if that had received prior systemic therapy for HCC.

Study Oversight

The study was approved by all relevant institutional review boards and was conducted in accordance with the Declaration of Helsinki and local laws. The trial was registered before the start of patient enrollment. All patients provided written informed consent before undergoing any study-specific procedures. The study was overseen by an independent data monitoring committee.

Study Design

This multicenter phase 3 randomized open-label noninferiority study was conducted throughout the Asia-Pacific, European, and North American regions. Patients were recruited from Mar. 1, 2013 through Jul. 30, 2016. Randomization was stratified according to region (Asia-Pacific or Western regions), macroscopic portal vein invasion and/or extrahepatic spread (yes or no), Eastern Cooperative Oncology Group performance status (0 or 1), and body weight (<60 kg or ≥60 kg). Within stratification factors, patients were randomly assigned (1:1) to receive oral lenvatinib at a dosage of 12 mg per day (for body weight≥60 kg) or 8 mg per day (for body weight<60 kg) or sorafenib at a dosage of 400 mg twice daily in 28-day cycles. Dosage interruptions and reductions for lenvatinib-related toxicities (to 8 and 4 mg per day or 4 mg every other day) were permitted. Modifications to sorafenib dosage were implemented according to prescribing information in each region.

Endpoints and Assessments

The primary endpoint was overall survival. Secondary endpoints included progression-free survival, time to progression, objective response rate, and quality of life as measurements including use of EORTC QLQ-C30 (Cocks, J, Clin. Oncol., 29:89-96, 2011, Giesinger, J., Clin. Epidemiol., 69:79-88, 2016) and HCC-specific EORTC QLQ-HCC18 (Chie, Hepatology, 55(4):1122-9, 2012) health questionnaires.

Tumors were evaluated in accordance with mRECIST (Lencioni R., Semin Liver Dis., 30(1):52-60, 2010); RECIST 1.1 was applied for nonhepatic lesions (Eisenhauer, Eur J Cancer, 45(2):228-47, 2009). The liver was examined with computed tomography or magnetic resonance imaging was performed using a triphasic scanning technique. Assessments were performed every 8 weeks until disease progression. Quality of life questionnaires were administered at baseline, on day 1 of each subsequent treatment cycle, and at the off-treatment visit.

Safety assessments included recording of vital signs, hematologic and biochemical laboratory testing, urinalysisand electrocardiography. Adverse events were graded , according to the National Cancer Institute Common Terminology Criteria for Adverse Events version 4.0 (CTCAE v4.0, NCI 2013).

Statistical Analysis

The primary endpoint of overall survival was first tested for noninferiority then for superiority. The required number of events for the primary analysis was 700 deaths, based on the fill analysis set. The HR and its 95% confidence interval (CI) were estimated from a Cox proportional hazard model with treatment group as a factor and with the analysis stratified according to the same factors applied for randomization. The noninferiority margin was set at 1.08 based on previous phase 3 trials of sorafenib (Llovet NEJM 2008, Cheng Lancet Oncol 2009).

A fixed-sequence procedure was followed to control the overall type I error rate of analyses for both the primary and secondary efficacy endpoints at α=0.05 (2-sided). After noninferiority was declared, secondary efficacy endpoints were tested. Differences in progression-free survival and time to progression were evaluated using a stratified log-rank test with randomization stratification factors, with the associated HR and its 95% CI. A difference in the objective response rate was evaluated using the Cochran-Mantel-Haenszel chi-square test with randomized stratification factors as strata, with associated odds ratio and its 95% CI. To assess futility, 2 interim analyses (at 30% and 70% of the target number of events) were performed using Bayesian predictive probability in a noninferiority design by the independent data monitoring committee.

Patients

Figure 5:
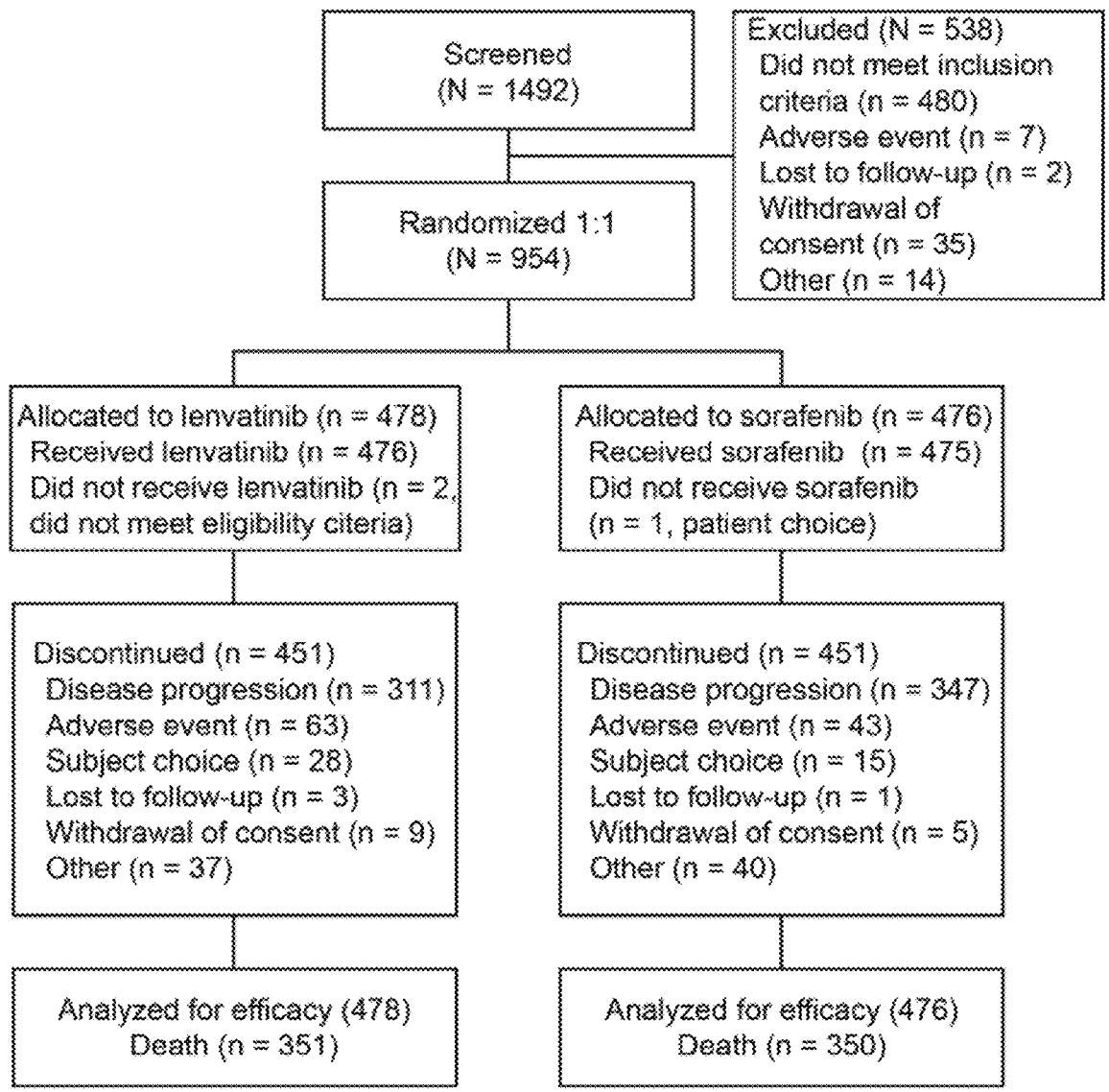
FIG. 5 provides a schematic representation of the enrollment, randomization, and treatment of the 954 patients in the phase 3 trial.

A total of 954 patients from 20 countries were randomly assigned to receive lenvatinib (478 patients) or sorafenib (476 patients) (FIG. 5). The efficacy analysis followed the intent to treat principle. Only patients who received treatment (lenvatinib, 476 patients; sorafenib, 475 patients) were included in the safety analysis. Patient characteristics at baseline were well balanced between treatment groups, with the exception of baseline hepatitis C and alpha-fetoprotein level (Table 1).

TABLE 4

Table 1. Demographic and Disease Characteristics at Baseline.

|  | Lenvatinib (N = 478) | Sorafenib (N = 476) | Total (N = 954) |
|---|---|---|---|
| Age - yr | | | |
| Mean | 61.3 | 61.2 | 61.3 |
| Standard Deviation | 11.7 | 12.0 | 11.8 |
| Age group (yr) - no. (%) | | | |
| <65 | 270 (56.5) | 283 (59.5) | 553 (58.0) |
| ≥65 to <75 | 150 (31.4) | 126 (26.5) | 276 (28.9) |
| ≥75 | 58 (12.1) | 67 (14.1) | 125 (13.1) |
| Sex - no. (%) | | | |
| Male | 405 (84.7) | 401 (84.2) | 806 (84.5) |
| Female | 73 (15.3) | 75 (15.8) | 148 (15.5) |
| Region - no. (%) | | | |
| Western | 157 (32.8) | 157 (33.0) | 314 (32.9) |
| Asia-Pacific | 321 (67.2) | 319 (67.0) | 640 (67.1) |
| Race - no. (%) | | | |
| White | 135 (28.2) | 141 (29.6) | 276 (28.9) |
| Asian | 334 (69.9) | 326 (68.5) | 660 (69.2) |
| Body weight (kg) - no. (%) | | | |
| <60 | 153 (32.0) | 146 (30.7) | 299 (31.3) |
| ≥60 | 325 (68.0) | 330 (69.3) | 655 (68.7) |
| ECOG performance status - no. (%) | | | |
| 0 | 304 (63.6) | 301 (63.2) | 605 (63.4) |
| 1 | 174 (36.4) | 175 (36.8) | 349 (36.6) |
| Child-Pugh class - no. (%) | | | |
| CP-A | 475 (99.4) | 471 (98.9) | 946 (99.2) |
| CP-B | 3 (0.6) | 5 (1.1) | 8 (0.8) |
| Macroscopic portal vein invasion - no. (%) | | | |
| Yes | 109 (22.8) | 90 (18.9) | 199 (20.9) |
| No | 369 (77.2) | 386 (81.1) | 755 (79.1) |
| Extrahepatic spread - no. (%) | | | |
| Yes | 291 (60.9) | 295 (62.0) | 586 (61.4) |
| No | 187 (39.1) | 181 (38.0) | 368 (38.6) |
| Macroscopic portal vein invasion, extrahepatic spread, or both - no. (%) | | | |
| Yes | 329 (68.8) | 336 (70.6) | 665 (69.7) |
| No | 149 (31.2) | 140 (29.4) | 289 (30.3) |
| Underlying cirrhosis based on medical history - no. (%) | | | |
| Yes | 243 (50.8) | 231 (48.5) | 474 (49.7) |
| No | 235 (49.2) | 245 (51.5) | 480 (50.3) |

TABLE 5

Table 1. (cont.) Demographic and Disease Characteristics at Baseline.

|  | Lenvatinib (N = 478) | Sorafenib (N = 476) | Total (N = 954) |
|---|---|---|---|
| Barcelona Clinic Liver Cancer stage - no. (%) | | | |
| B (intermediate stage) | 104 (21.8) | 92 (19.3) | 196 (20.5) |
| C (advanced stage) | 374 (78.2) | 384 (80.7) | 758 (79.5) |
| Involved disease sites - no. (%) | | | |
| Liver | 441 (92.3) | 430 (90.3) | 871 (91.3) |
| Lung | 163 (34.1) | 144 (30.3) | 307 (32.2) |
| Involved disease sites per patient - no. (%) | | | |
| 1 | 207 (43.3) | 207 (43.5) | 414 (43.4) |
| 2 | 167 (34.9) | 183 (38.4) | 350 (36.7) |
| ≥3 | 103 (21.5) | 86 (18.1) | 189 (19.8) |

TABLE 5-continued

Table 1. (cont.) Demographic and Disease Characteristics at Baseline.

|  | Lenvatinib (N = 478) | Sorafenib (N = 476) | Total (N = 954) |
|---|---|---|---|
| Etiology of chronic liver disease - no. (%) | | | |
| Hepatitis B | 251 (52.5) | 228 (47.9) | 479 (50.2) |
| Hepatitis C | 91 (19.0) | 126 (26.5) | 217 (22.7) |
| Alcohol | 36 (7.5) | 21 (4.4) | 57 (6.0) |
| Other | 38 (7.9) | 32 (6.7) | 70 (7.3) |
| Unknown | 62 (13.0) | 69 (14.5) | 131 (13.7) |
| Baseline alpha-fetoprotein level - ng/ml | | | |
| No. of patients | 471 | 463 | 934 |
| Mean | 17507.7 | 16678.5 | 17096.5 |
| Standard deviation | 105137.4 | 94789.5 | 100088.8 |
| Median | 133.1 | 71.2 | 89.0 |
| Range | 0-1567470 | 0-1446396 | 0-1567470 |
| Baseline alpha-fetoprotein level group (ng/mL) - no. (%) | | | |
| <200 | 255 (53.3) | 286 (60.1) | 541 (56.7) |
| ≥200 | 222 (46.4) | 187 (39.3) | 409 (42.9) |
| Missing | 1 (0.2) | 3 (0.6) | 4 (0.4) |
| Concomitant systemic antiviral therapy for Hepatitis B or C - no. (%) | 163 (34.1) | 149 (31.3) | 312 (32.7) |
| Prior therapy - no. (%) | | | |
| Prior anticancer procedures | 327 (68.4) | 344 (72.3) | 671 (70.3) |
| Radiotherapy | 49 (10.3) | 60 (12.6) | 109 (11.4) |

ECOG, Eastern Cooperative Oncology Group.
At the time of data cutoff (Nov. 13, 2016) the median duration of follow-up was 27.7 months in the lenvatinib group and 27.2 months in the sorafenib group.

Efficacy

Figure 3:
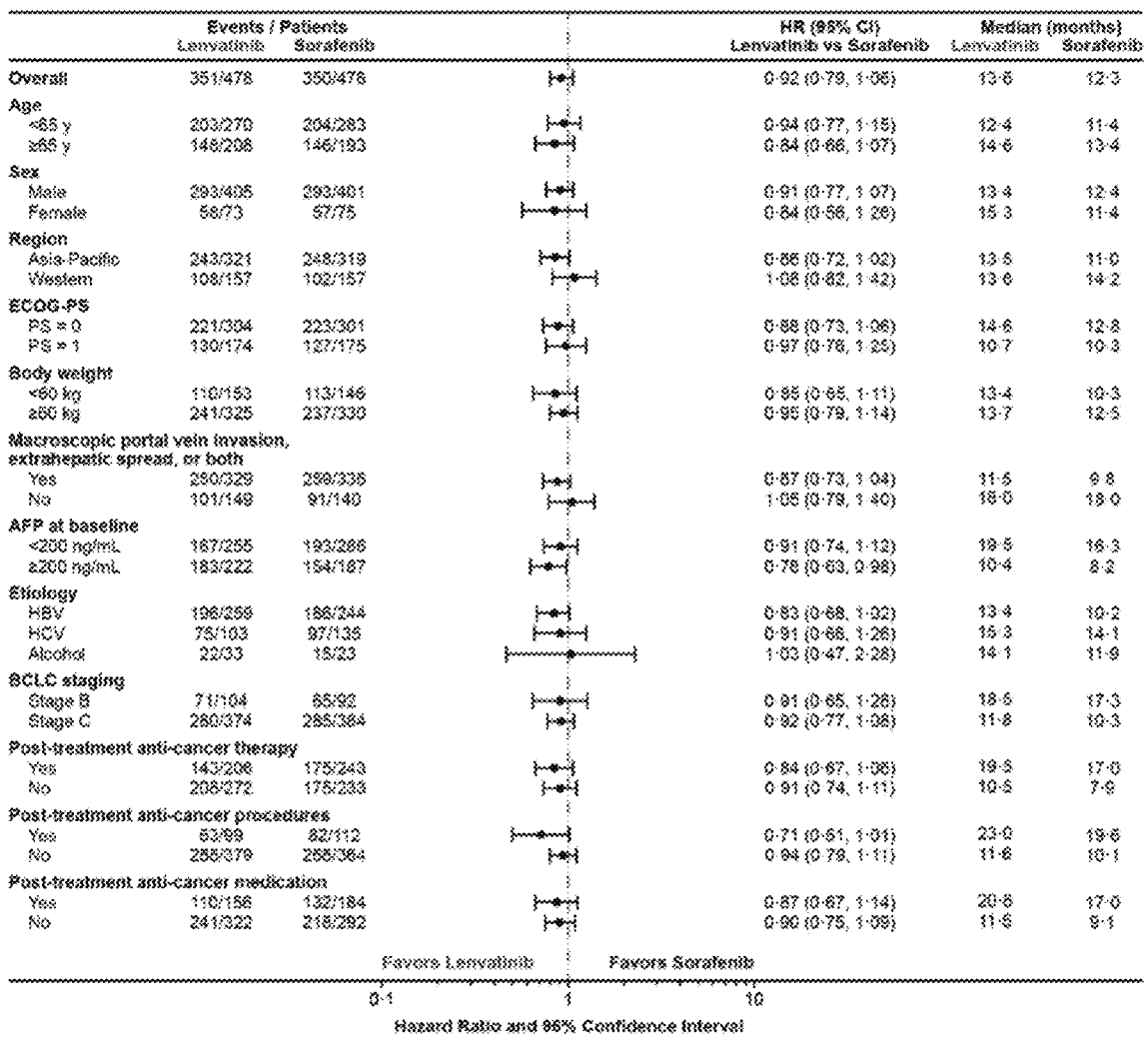
FIG. 3 provides a subgroup analyses of overall survival indicating associated hazard ratio and 95% confidence interval. AFP denotes alpha-fetoprotein, BCLC Barcelona Clinic Liver Cancer, CI confidence interval, and HR hazard ratio.

Lenvatinib demonstrated noninferiority in overall survival compared with sorafenib. The median overall survival was 13.6 months (95% CI, 12.1 to 14.9) with lenvatinib compared with 12.3 months (95% CI, 10.4 to 13.9) with sorafenib (HR: 0.92; 95% CI, 0.79 to 1.06) (FIG. 1). Median overall survival for the lenvatinib treatment arm was numerically longer in all the prespecified strata, with the exception of the patients from Western regions subgroup; and was the same in patients who had neither macroscopic portal vein invasion nor extrahepatic spread (FIG. 3). Patients with baseline alpha-fetoprotein <200 ng/mL had longer overall survival than those with alpha-fetoprotein ≥200 ng/mL (FIG. 3). The FIR was <1 favoring lenvatinib in both alpha-fetoprotein subgroups, but there were more patients with baseline alpha-fetoprotein level <200 ng/mL in the sorafenib arm (60.1%) compared with the lenvatinib arm (53.3%, Table 1).

Figure 2:
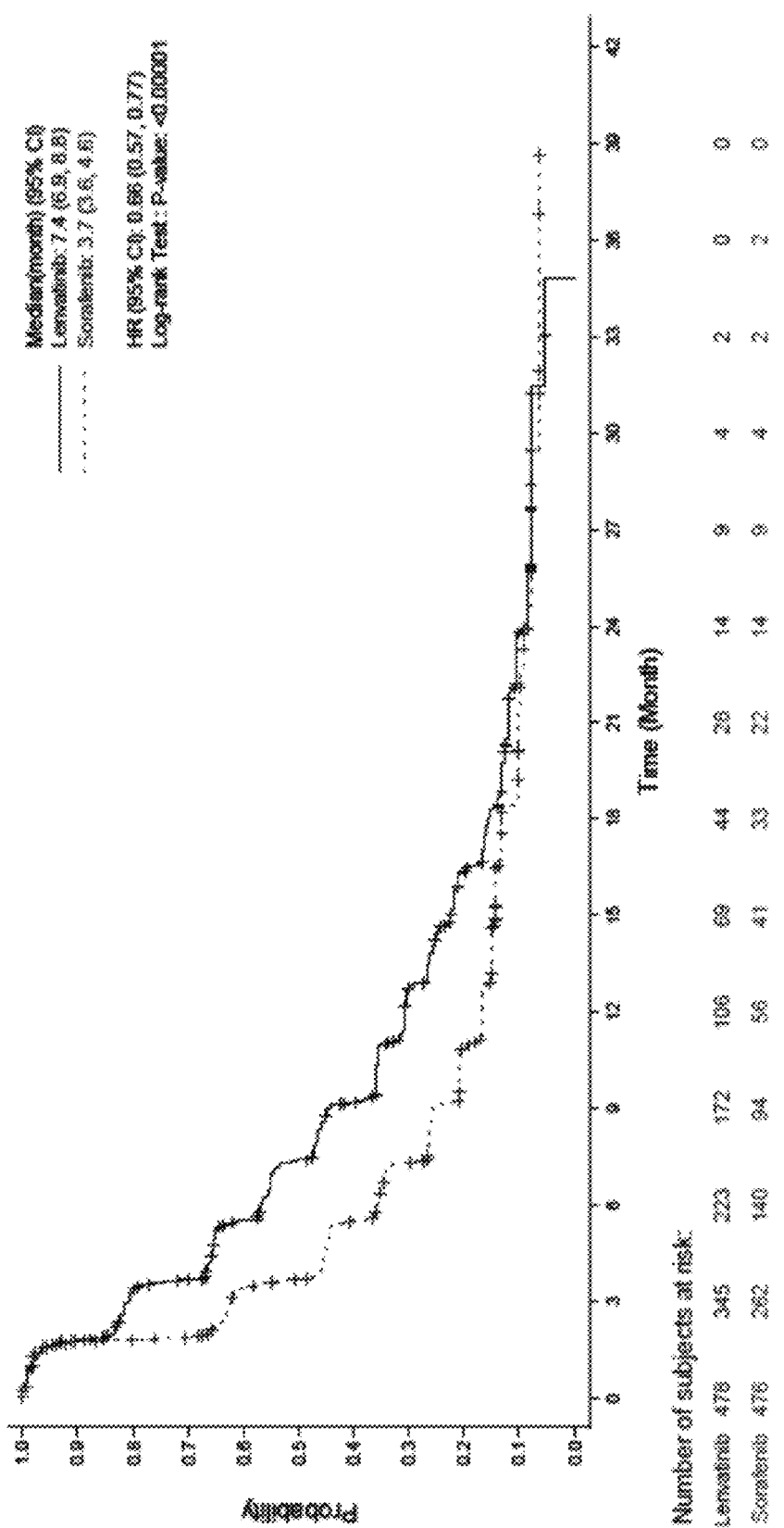
FIG. 2 shows progression-free survival by modified Response Evaluation Criteria in Solid Tumors (mRECIST). CI denotes confidence interval, and HR hazard ratio.
Figure 4:
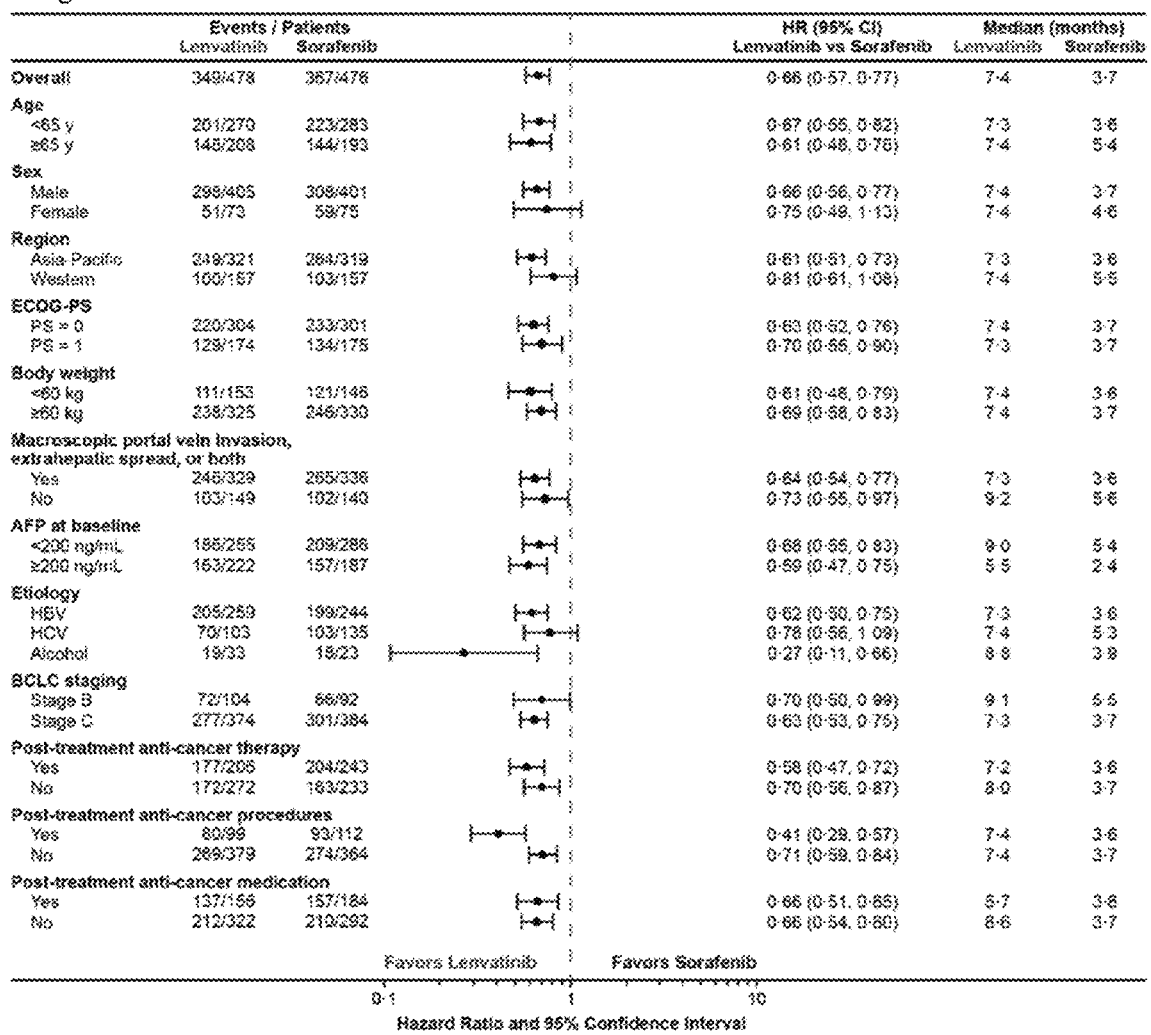
FIG. 4 provides subgroup analyses of progression-free survival indicating the associated hazard ratio and 95% confidence interval. AFP denotes alpha-fetoprotein, BCLC Barcelona Clinic Liver Cancer, CI confidence interval, and HR hazard ratio.
Figure 6:
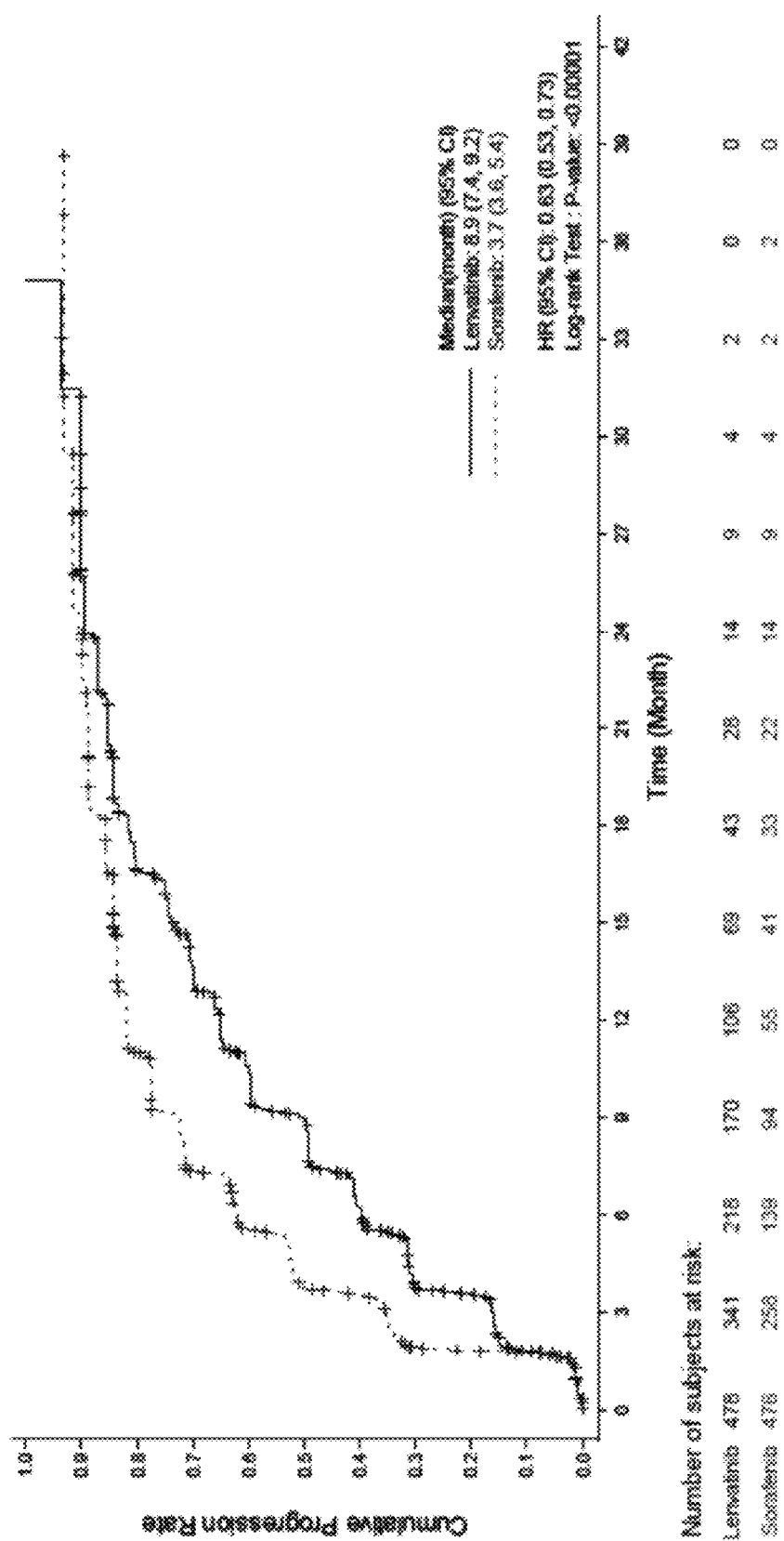
FIG. 6 is a graph providing a Kaplan-Meier Estimate of time to progression. CI denotes confidence interval, and hazard ratio.
Figure 7:
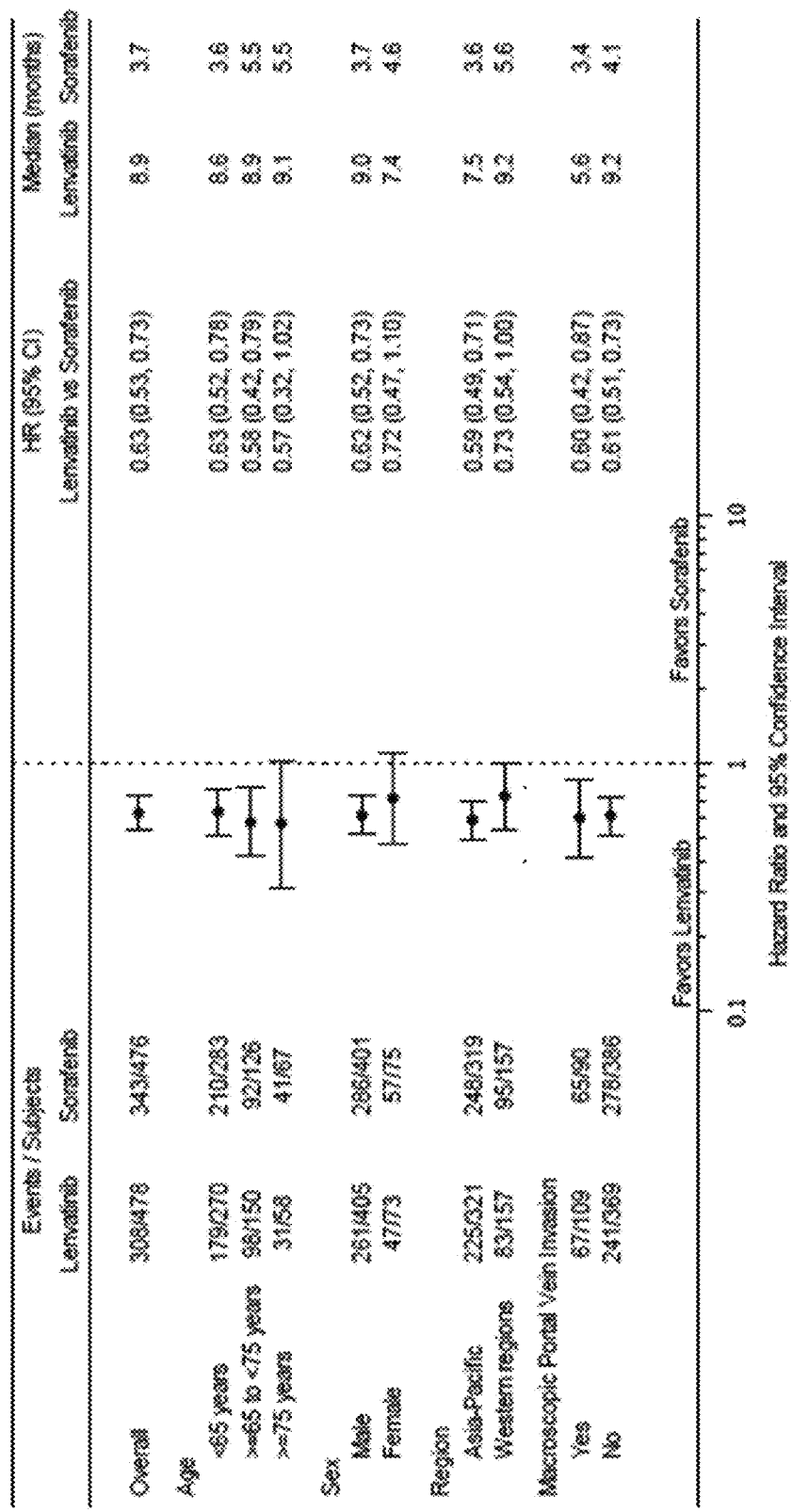
FIG. 7 provides Forest plots indicating hazard ratios for time to progression in the subgroup analyses. AFP, alpha-fetoprotein; BCLC, Barcelona Clinic Liver Cancer; CI, confidence interval; HR, hazard ratio.
Figure 8:
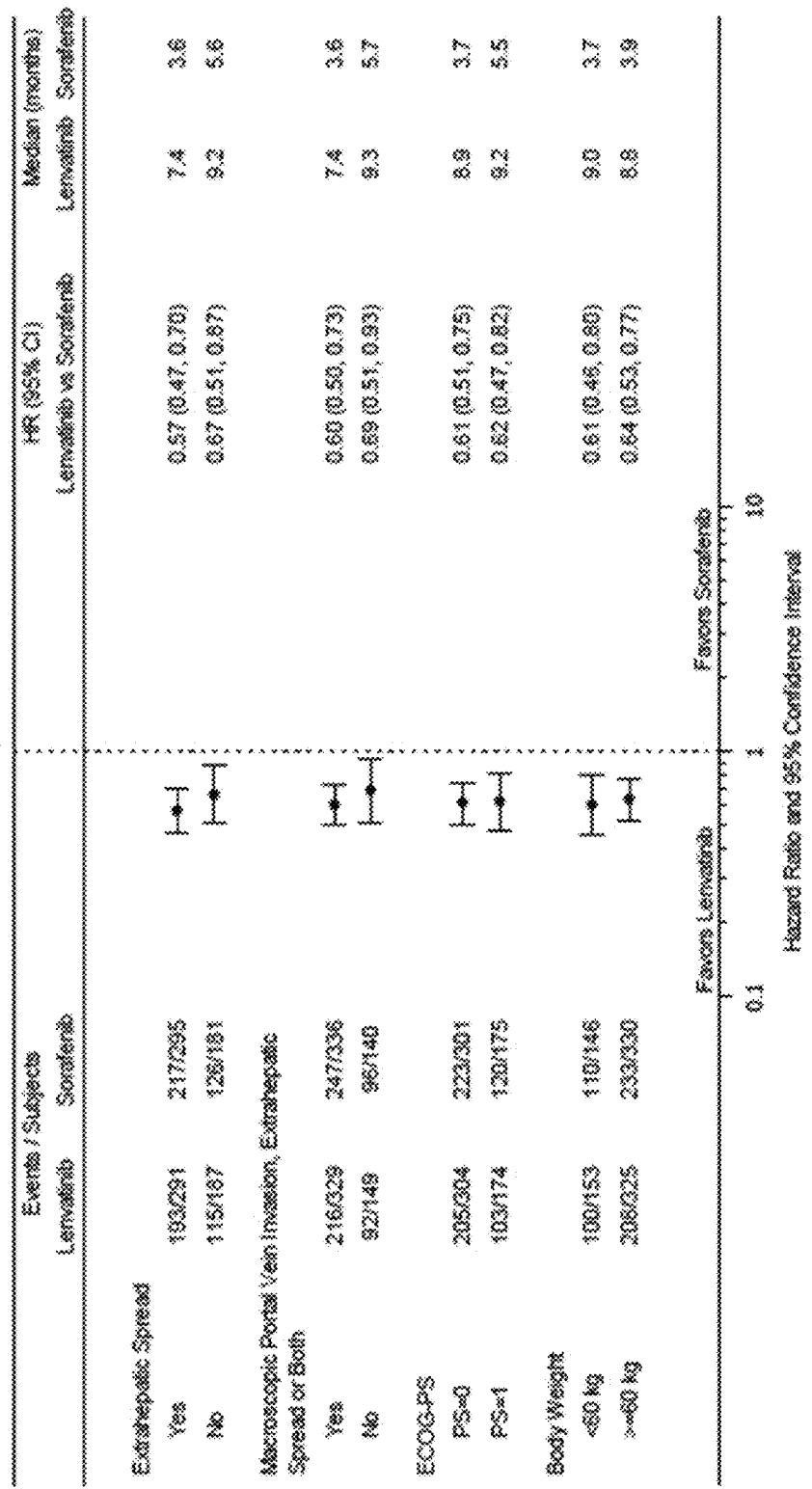
FIG. 8 provides Forest plots indicating hazard ratios for time to progression in the subgroup analyses. AFP, alpha-fetoprotein; BCLC, Barcelona Clinic Liver Cancer; CI, confidence interval; HR, hazard ratio.
Figure 9:
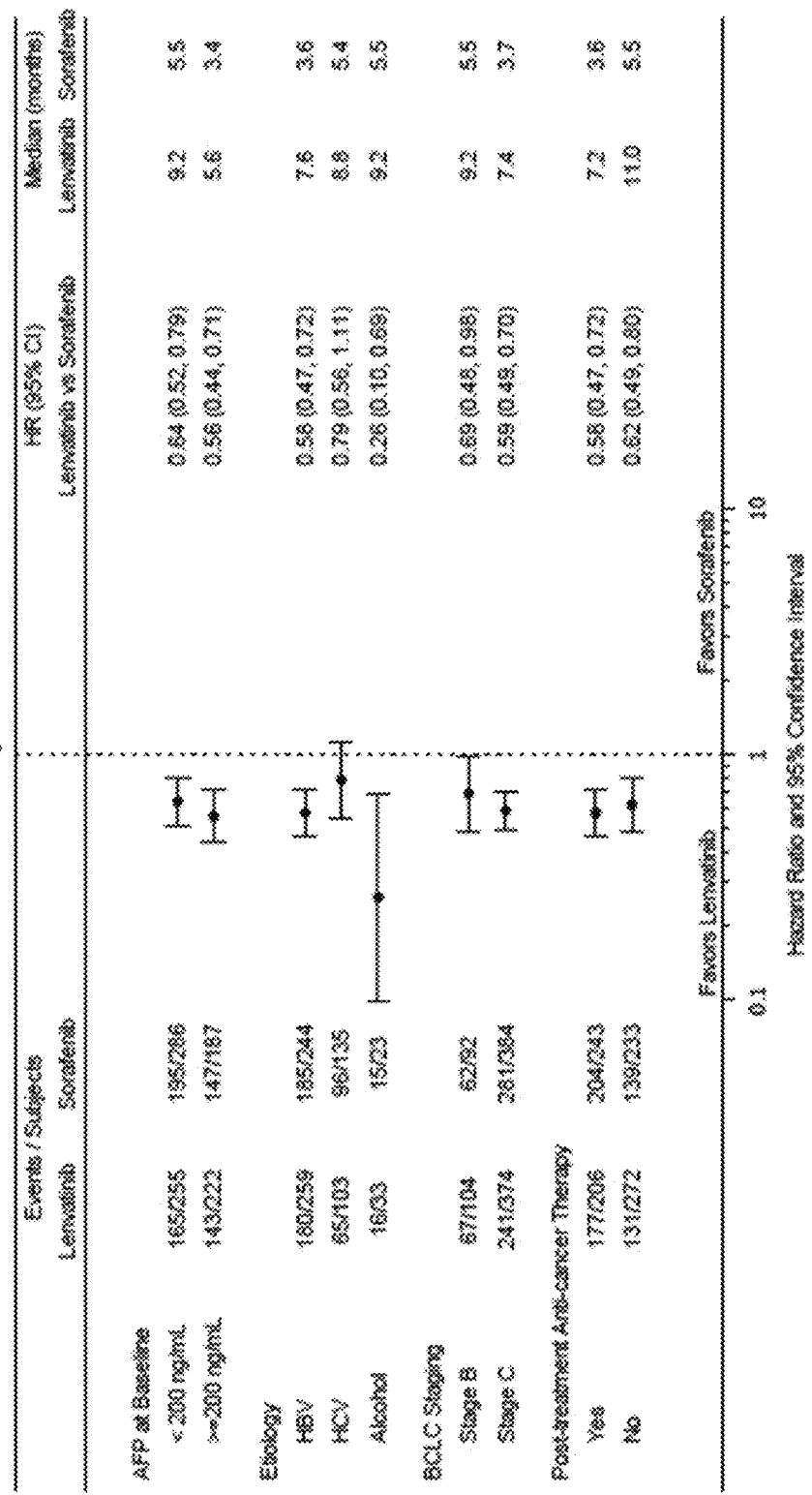
FIG. 9 provides Forest plots indicating hazard ratios for time to progression in the subgroup analyses. AFP, alpha-fetoprotein; BCLC, Barcelona Clinic Liver Cancer; CI, confidence interval; HR, hazard ratio.
Figure 10:
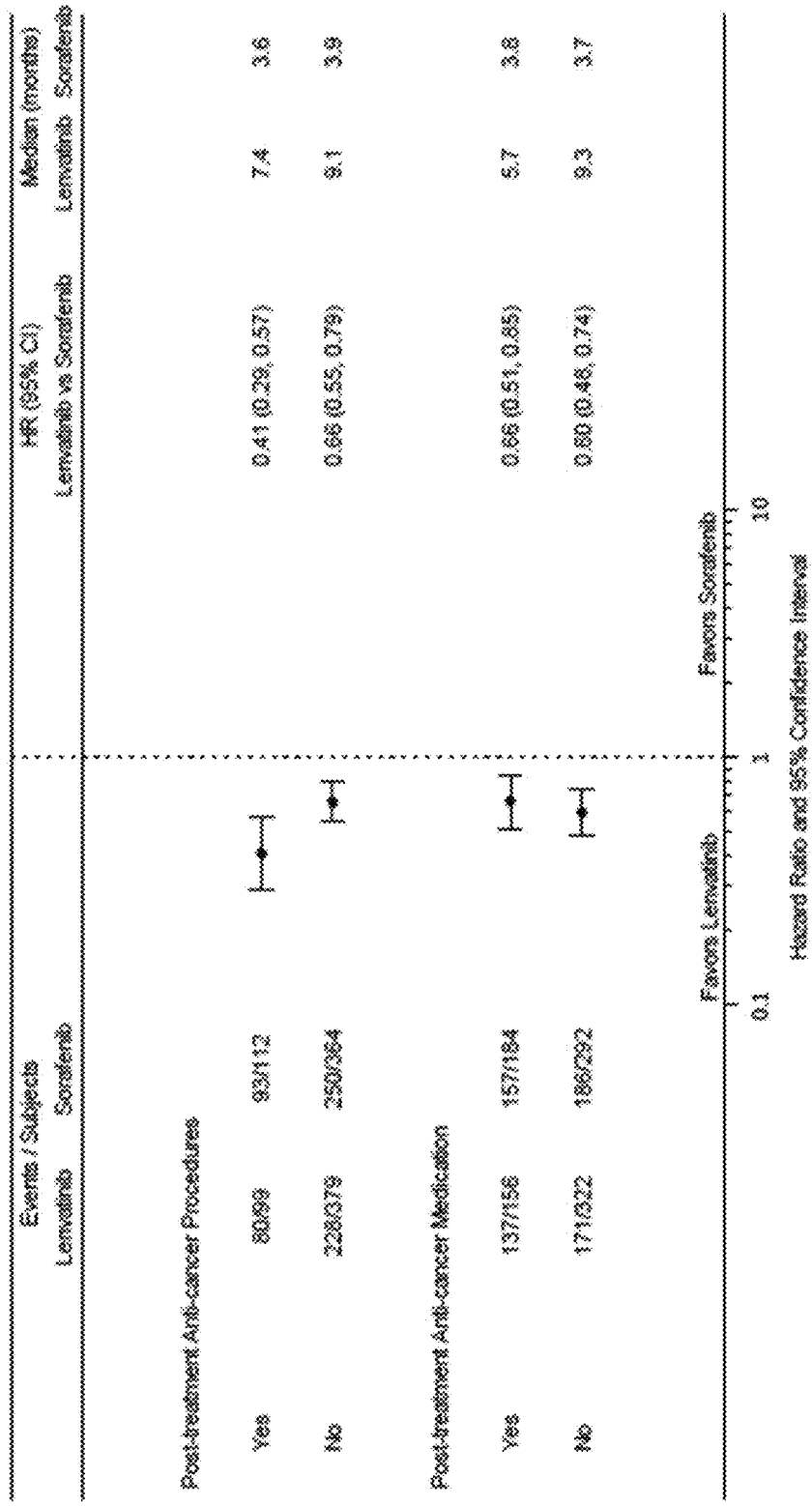
FIG. 10 provides Forest plots indicating hazard ratios for time to progression in the subgroup analyses. AFP, alpha-fetoprotein; BCLC, Barcelona Clinic Liver Cancer; CI, confidence interval; HR, hazard ratio.

Lenvatinib demonstrated a statistically significant improvement compared to sorafenib in all secondary efficacy endpoints as determined by tumor assessment based on mRECIST. Median progression-free survival for lenvatinib was 7.4 months (95% CI, 6.9 to 8.8 months) compared with 3.7 months (95% CI, 3.6 to 4.6 months) with sorafenib (HR: 0.66; 95% CI, 0.57 to 0.77; P<0.001) (FIG. 2). In addition, progression-free survival in each of the prespecified subgroups was longer with lenvatinib compared with sorafenib (FIG. 4). The median time to progression was 8.9 months (95% CI, 7.4 to 9.2 months) for patients in the lenvatinib group compared with 3.7 months (95% CI, 3.6 to 5.4 months) for patients in the sorafenib group (HR: 0.63; 95% CI, 0.53 to 0.73; P<0.001) (Table 2 and FIG. 6).

TABLE 6

Table 2. Efficacy Measures.

| Outcome | Lenvatinib (N = 478) | Sorafenib (N = 476) | Hazard Ratio (95% CI) |
|---|---|---|---|
| Median (95% CI) overall survival - mo | 13.6 | 12.3 | 0.92 |
|  | (12.1-14.9) | (10.4-13.9) | (0.79-1.06) |
| Median (95% CI) progress-ion-free survival - mo | 7.4 | 3.7 | 0.66 |
|  | (6.9-8.8) | (3.6-4.6) | (0.57-0.77) |
|  |  |  | P < 0.001 |
| Median (95% CI) time to progression - mo | 8.9 | 3.7 | 0.63 |
|  | (7.4-9.2) | (3.6-5.4) | (0.53-0.73) |
|  |  |  | P < 0.001 |
| Objective response rate* - no. (%) | 115 (24.1) | 44 (9.2) | 3.13† |
| 95% CI | 20.2-27.9 | 6.6-11.8 | (2.15-4.56) |
| Complete response | 6 (1.3) | 2 (0.4) | P < 0.001 |
| Partial response | 109 (22.8) | 42 (8.8) |  |

TABLE 6-continued

Table 2. Efficacy Measures.

| Outcome | Lenvatinib (N = 478) | Sorafenib (N = 476) | Hazard Ratio (95% CI) |
|---|---|---|---|
| Stable disease | 246 (51.5) | 244 (51.3) | |
| Durable stable disease lasting ≥23 wk | 167 (34.9) | 139 (29.2) | |
| Progressive disease | 71 (14.9) | 147 (30.9) | |
| Unknown/not evaluable | 46 (9.6) | 41 (8.6) | |
| Disease control rate‡ - no. (%) | | | |
| 95% CI | 361 (75.5]) 71.7-79.4 | 288 (60.5) 56.1-64.9 | |

*The objective response rate was determined according to mRECIST (modified Response Evaluation Criteria in Solid Tumors).
†Odds ratio.
‡The disease control rate is computed as follows: complete response + partial response + stable disease.
CI, confidence interval.

Figure 11:
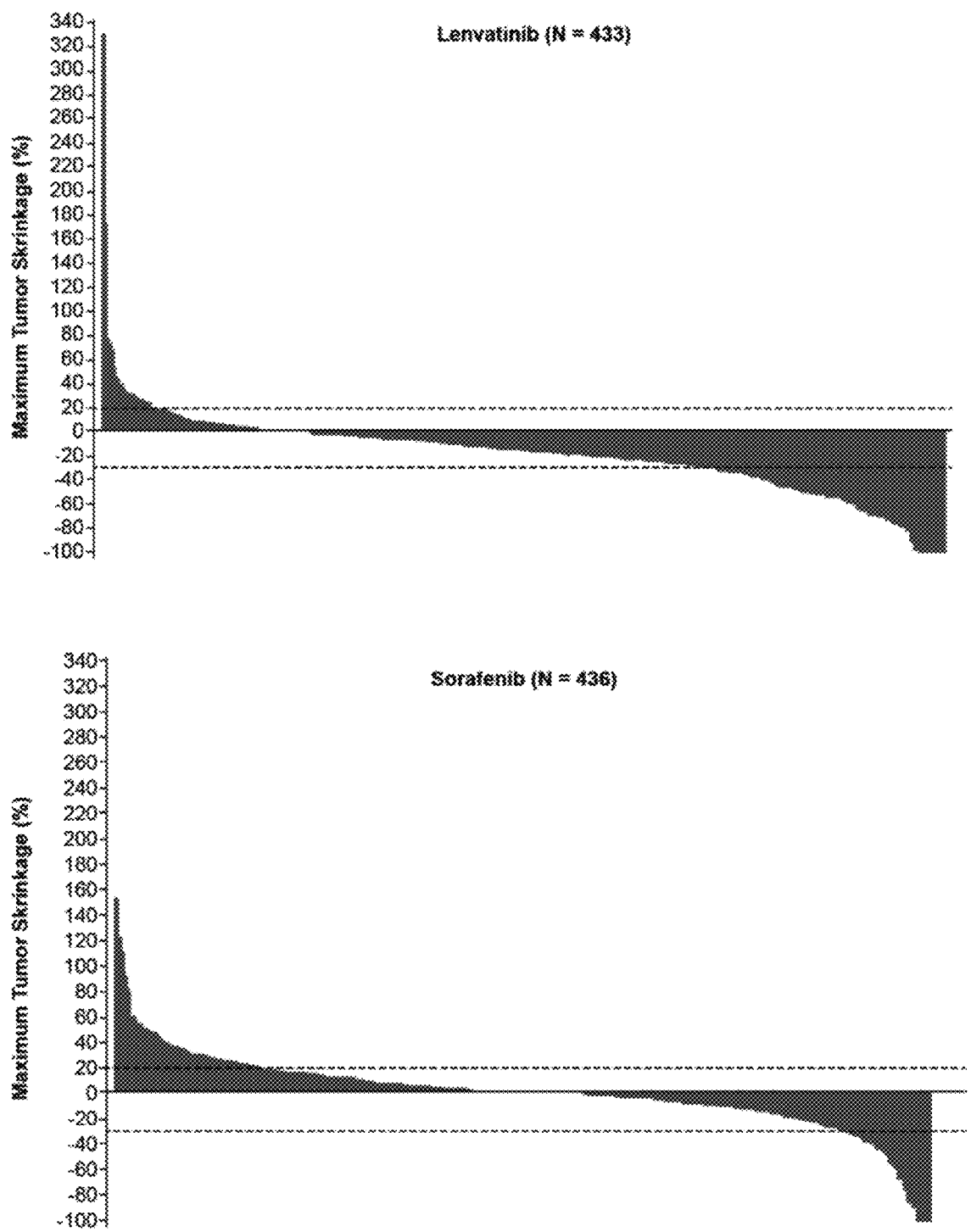
FIG. 11 depicts waterfall graphs of percentage change in summed diameter of target lesions. The percentage change in lesion size is shown from baseline to nadir.
Figure 12:
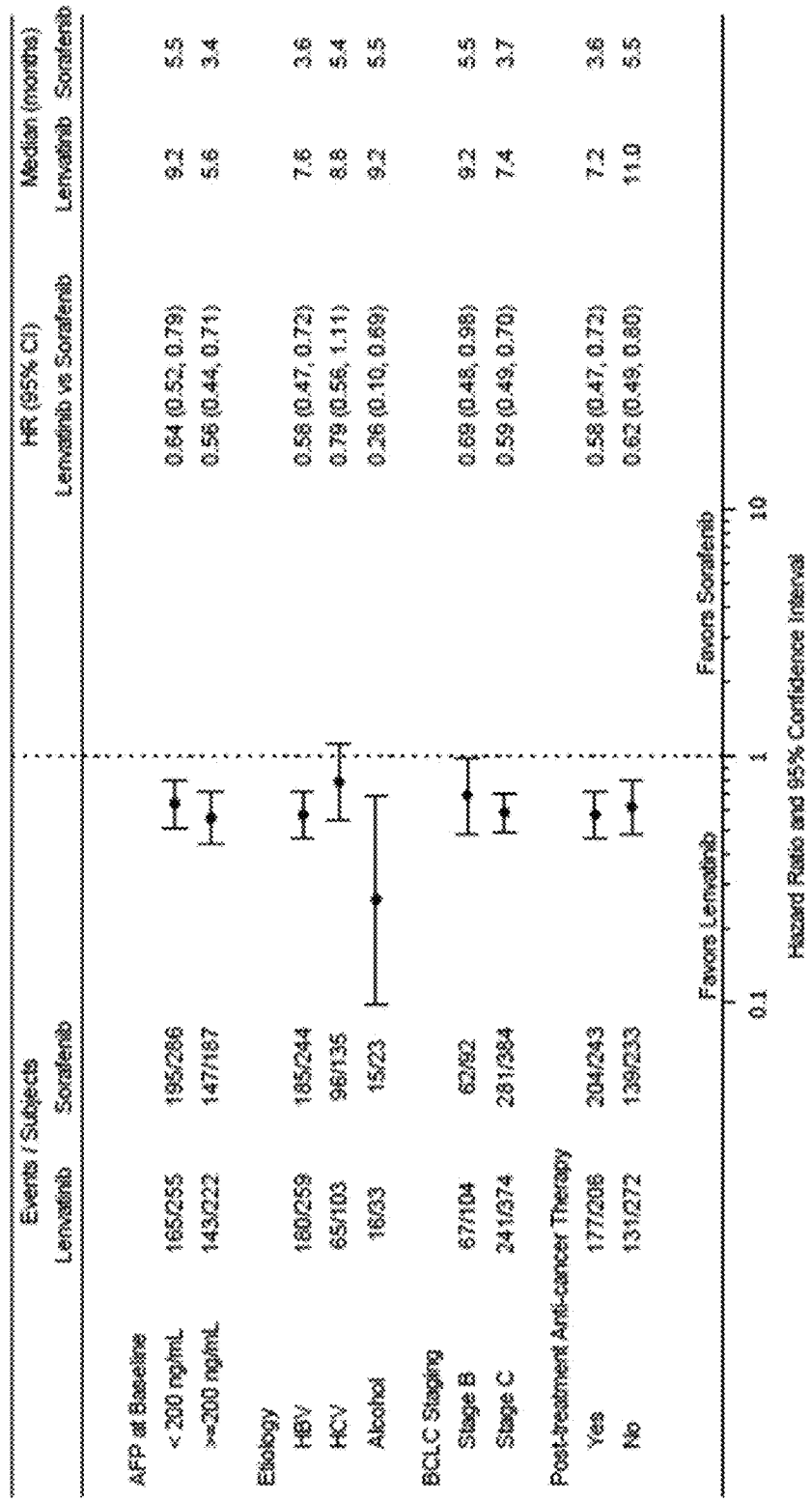
FIG. 12 provides Forest plots indicating hazard ratios for time to progression in the subgroup analyses. AFP, alpha-fetoprotein; BCLC, Barcelona Clinic Liver Cancer; CI, confidence interval; HR, hazard ratio.
Figure 13:
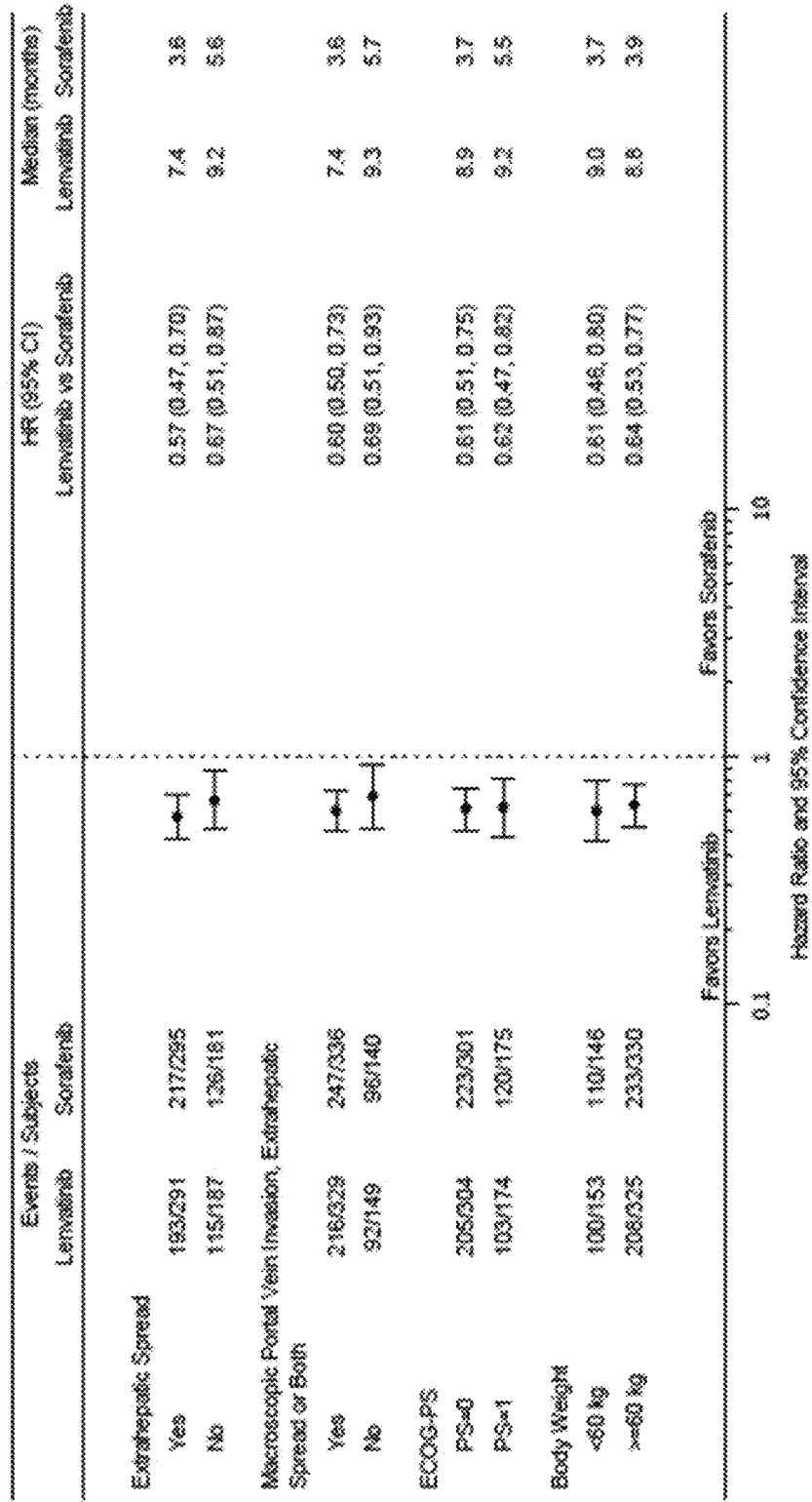
FIG. 13 provides Forest plots indicating hazard ratios for time to progression in the subgroup analyses. AFP, alpha-fetoprotein; BCLC, Barcelona Clinic Liver Cancer; CI, confidence interval; HR, hazard ratio.
Figure 14:
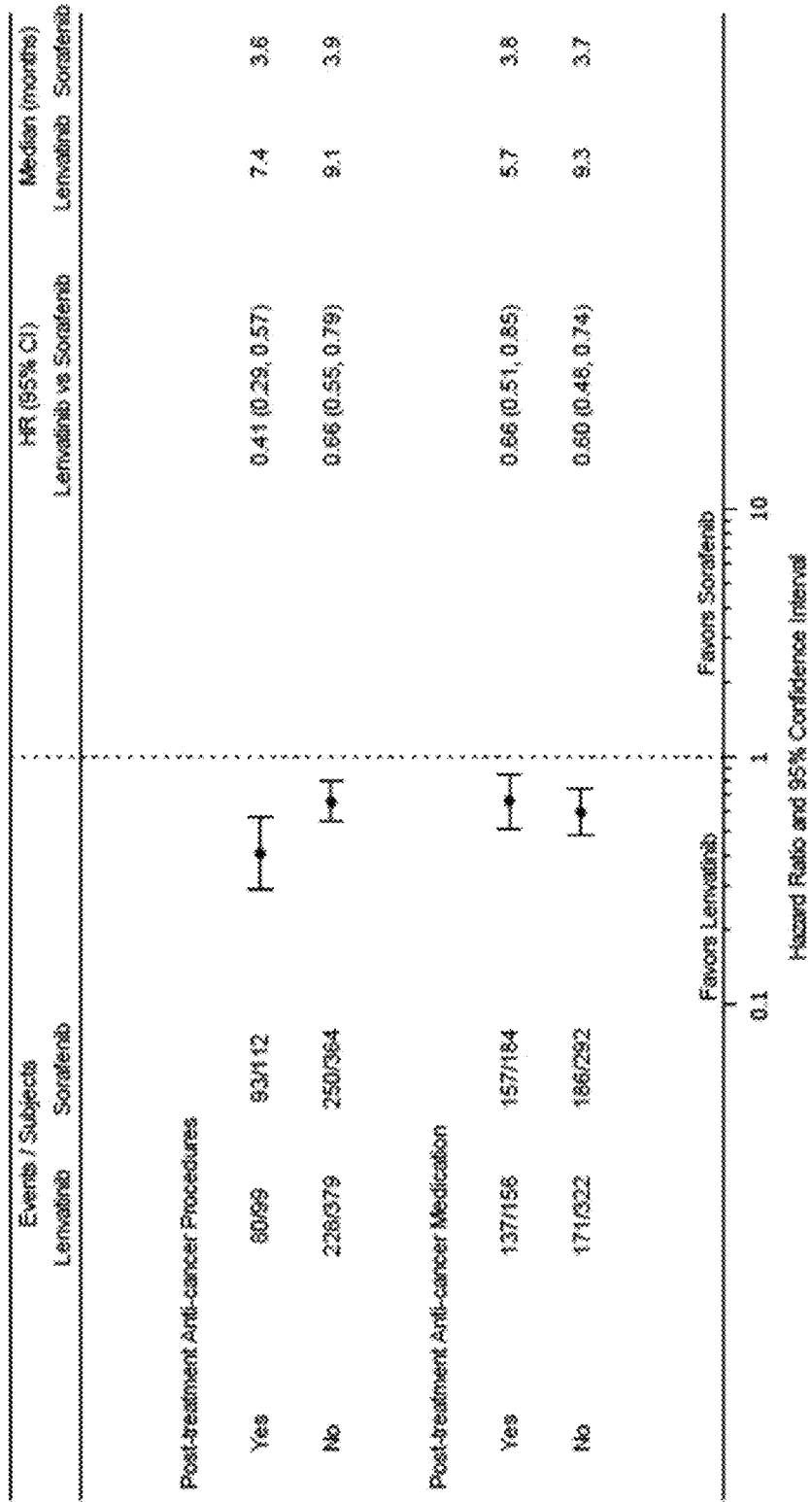
FIG. 14 provides Forest plots indicating hazard ratios for time to progression in the subgroup analyses. AFP, alpha-fetoprotein; BCLC, Barcelona Clinic Liver Cancer; CI, confidence interval; HR, hazard ratio.

Median time to progression with lenvatinib treatment was also numerically longer in each of the prespecified strata compared with sorafenib (FIGS. 7-10). Lenvatinib showed an objective response rate of 24.1% versus 9.2% for sorafenib (odds ratio, 3.13; 95% CI, 2.15 to 4.56; P<0.000 (Table 2 and FIG. 11). The odds ratio favored lenvatinib in all prespecified subgroups, with the exception of the alcohol etiology subgroup (FIGS. 12-14). Analysis for overall survival with stratification factors and other subgroups supports the robustness of the noninferiority result (Table 3).

TABLE 7

Table 3. Overall Survival with Stratification Factors Adjusted by Baseline Characteristics.

| Baseline Characteristics | Hazard Ratio for (Lenvatinib/Sorafenib) (95% CI) |
|---|---|
| Overall | 0.916 (0.789-1.064) |
| Age (<65, ≥65 to <75, ≥75 yr) | 0.919 (0.791-1.067) |
| Sex (male, female) | 0.916 (0.789-1.064) |
| Region (Asia-Pacific, Western) | 0.915 (0.789-1.062) |
| Macroscopic portal vein invasion (yes, no) | 0.910 (0.784-1.057) |
| Extrahepatic spread (yes, no) | 0.915 (0.788-1.062) |
| Macroscopic portal vein invasion, extrahepatic spread or both (yes, no) | 0.908 (0.783-1.054) |
| ECOG-PS (0, ≥1) | 0.923 (0.795-1.071) |
| Body weight (<60 kg, ≥60 kg) | 0.923 (0.796-1.071) |

TABLE 7-continued

Table 3. Overall Survival with Stratification Factors Adjusted by Baseline Characteristics.

| Baseline Characteristics | Hazard Ratio for (Lenvatinib/Sorafenib) (95% CI) |
|---|---|
| AFP at baseline (<200 ng/mL, ≥200 ng/mL) | 0.856 (0.736-0.995) |
| Antiviral therapy for HCB or HCV (yes, no) | 0.912 (0.785-1.059) |
| No. of disease sites at baseline (1, 2, ≥3) | 0.878 (0.755-1.020) |
| Etiology (HBV, HCV, alcohol) | 0.855 (0.721-1.013) |
| Underlying cirrhosis (yes, no) | 0.916 (0.789-1.063) |
| BCLC staging (stage B, stage C) | 0.918 (0.791-1.067) |
| Prior procedure (yes, no) | 0.902 (0.777-1.048) |

AFP, alpha-fetoprotein; BCLC, Barcelona Clinic Liver Cancer;
ECOG-PS, Eastern Cooperative Oncology Group performance status;
HBV, hepatitis B virus;
HCV, hepatitis C virus.

Of note, 32.6% patients in the lenvatinib arm and 38.7% in the sorafenib arm received a post-study anticancer medication (including investigational therapy). Of these, 25.3% of patients in the lenvatinib arm and 11.8 in the sorafenib arm, respectively, received sorafenib during survival follow-up. In the Western region, 26.1% of patients in the lenvatinib arm received any anticancer medication during survival follow-up versus 38.9% in the sorafenib arm (Table 4).

TABLE 8

Table 4. Post-study Anticancer Therapy During Survival Follow-up.

| | Lenvatinib | | | Sorafenib | | |
|---|---|---|---|---|---|---|
| | Asia-Pacific Subgroup (N = 321) | Western Subgroup (N = 157) | Total (N = 478) | Pacific Asia-Subgroup (N = 319) | Western Subgroup (N = 157) | Total (N = 478) |
| Received any anticancer medication (not given for any procedure) during survival follow-up - no. (%) | 115 (35.8) | 41 (26.1) | 156 (32.6) | 123 (38.6) | 61 (38.9) | 184 (38.7) |
| Underwent any anticancer procedure during survival follow-up - no. (%) | 111 (34.6) | 11 (7.0) | 122 (25.5) | 112 (35.1) | 18 (11.5) | 130 (27.3) |

In the lenvatinib arm, 7.0% of patients in the Western region had any anticancer procedure during follow-up compared with 11.0% of patients in the sorafenib arm in this region.

Safety and Side-Effect Profile

Median duration of study treatment for patients in the lenvatinib group was longer than for patients in the sorafenib group (5.7 vs. 3.7 months). Treatment-emergent adverse events occurred in 98.7% of patients who received lenvatinib and 99.4% of patients who received sorafenib. Adjusted by patient-years, the adverse event rate was 18.9 in the lenvatinib group and 19.7 in the sorafenib group. Treatment-emergent adverse events of grade 3 or higher occurred in 75.0% of patients who received lenvatinib and 66.5% of patients who received sorafenib (adverse event rate: 3.2 vs. 3.3). The most common treatment-emergent adverse events among patients who received lenvatinib (at a dosage of 8 mg or 12 mg per day) were hypertension (8 mg per day, 43.0%; 12 mg per day, 41.8%), diarrhea (35.1%; 40.3%), decreased appetite (33.1%; 34.5%), and decreased weight (28.5%; 32.0%). In the sorafenib arm, the most common treatment-emergent adverse events were palmar-plantar erythrodysesthesia (52.4%), diarrhea (46.3%), hypertension (30.3%), and decreased appetite (26.7%) (Table 5).

Fatal adverse events occurred throughout treatment and appeared to occur at similar rates in both arms. Fatal adverse events determined by the investigator to be related to lenvatinib treatment occurred in 11 patients (2.3%) and included hepatic failure (3 patients), cerebral hemorrhage (3 patients), and respiratory failure (2 patients). In the sorafenib group, treatment-related fatal adverse events occurred in 4 patients (0.8%) and included tumor hemorrhage, ischemic stroke, respiratory failure, and sudden death (1 event per patient).

Lenvatinib dose reduction, drug interruption, and discontinuation due to adverse events occurred in 184 (38.7%), 248 (52.1%), and 94 (19.7%) patients, respectively. In the sorafenib arm, dose reduction, drug interruption, and discontinuation due to adverse events occurred in 185 (38.9%), 193 (40.6%), and 69 (14.5%) patients, respectively. The mean lenvatinib dose intensity was 7.0 mg (87.7%) in the 8 mg/day group and 10.5 mg (87.5%) in the 12 mg/day group. The mean sorafenib dose intensity was 663.8 mg (83.0%).

Quality of Life

Figure 15:
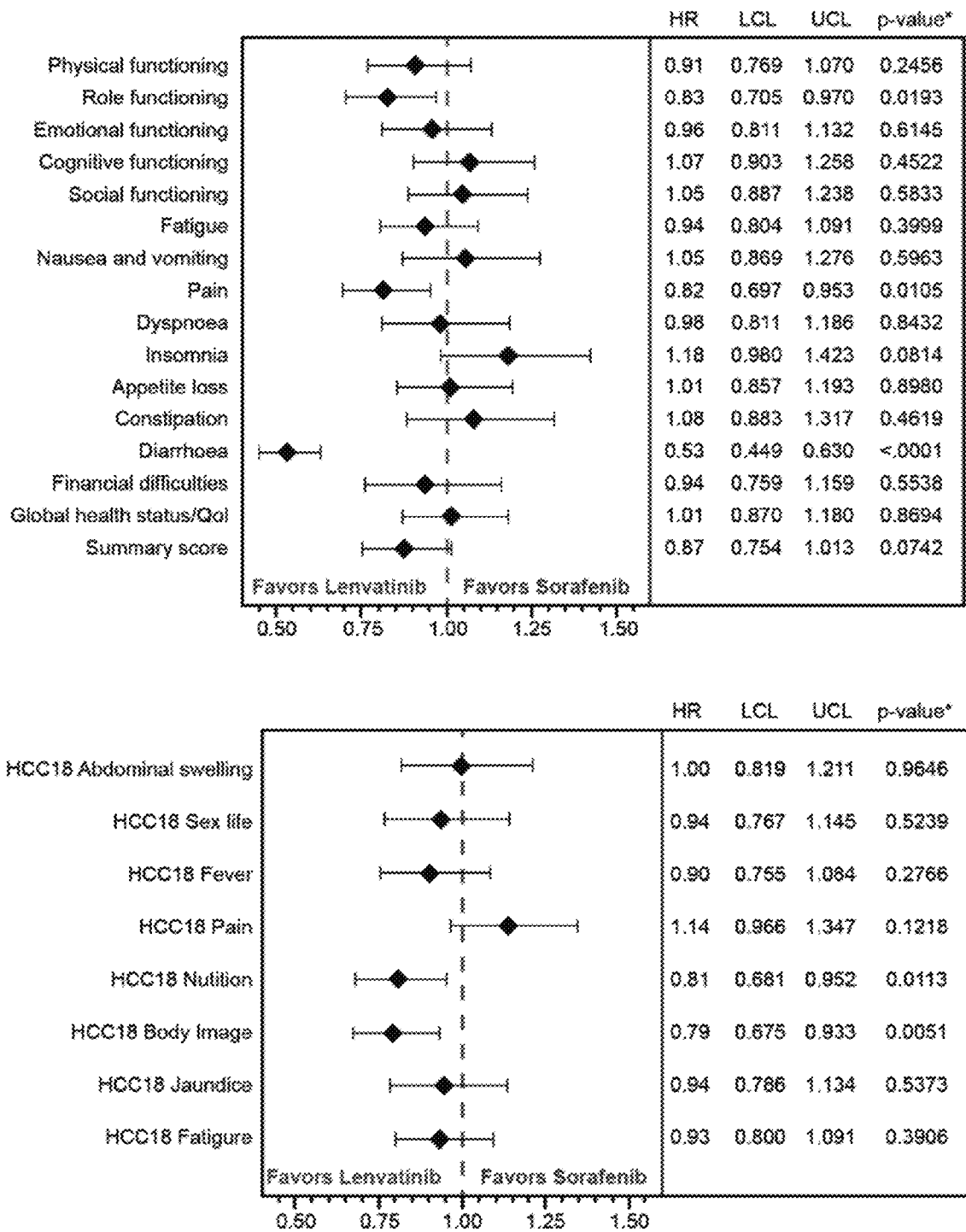
FIG. 15 provides Forest plots of hazard ratio of time to clinically meaningful worsening of QLQC30 questionnaire scores (top) and HCC18 questionnaire scores (bottom) comparing lenvatinib to sorafenib. * Nominal p-value; HR, hazard ratio; LCL, lower control limit; UCL, upper control limit.

Baseline scores on the EORTC QLQ-C30 and EORTC QLQ-HCC18 health questionnaires were similar in the lenvatinib and sorafenib treatment groups (FIG. 15). Following treatment, scores declined in both groups. The analysis of time to clinically meaningful deterioration showed that the role functioning, pain, and diarrhea from QLQ-C30 and nutrition and body image from QLQ-HCC18 deterioration was observed earlier in patients treated with sorafenib than with lenvatinib (nominal P<0.05).

Patients who received lenvatinib experienced fewer instances of palmar-plantar erythrodysesthesia, diarrhea, and alopecia and more instances of hypertension, proteinuria, dysphonia, and hypothyroidism than did patients who received sorafenib. Although quality of life scores declined in both groups after treatment, a clinically meaningful delay in deterioration for multiple domains was observed with lenvatinib compared with sorafenib.

The median duration of lenvatinib treatment was 1.5 times longer than that of sorafenib, which may have contributed to the higher incidence of adverse events. When

TABLE 9

Table 5. Adverse Events.

| | Lenvatinib (N = 476) | | Sorafenib (N = 475) | |
|---|---|---|---|---|
| Total treatment-related treatment-emergent adverse events - no. (%) | 447 (93.9) | | 452 (95.42) | |
| Treatment-related treatment-emergent adverse events of grade ≥3 - no. (%) | 270 (56.7) | | 231 (48.6) | |
| Serious treatment-emergent adverse events - no. (%) | 205 (43.1) | | 144 (30.3) | |
| Treatment emergent adverse events occurring in ≥15% of patients in either treatment group Number of patients (percent) | Any grade | Grade ≥3 | Any grade | Grade ≥3 |
| Palmar-plantar erythrodysesthesia | 128 (26.9) | 14 (2.9) | 249 (52.4) | 54 (11.4) |
| Diarrhea | 184 (38.7) | 20 (4.2) | 220 (46.3) | 20 (4.2) |
| Hypertension | 201 (42.2) | 111 (23.3) | 144 (30.3) | 68 (14.3) |
| Decreased appetite | 162 (34.0) | 22 (4.6) | 127 (26.7) | 6 (1.3) |
| Decreased weight | 147 (30.9) | 36 (7.6) | 106 (22.3) | 14 (2.9) |
| Fatigue | 141 (29.6) | 18 (3.8) | 119 (25.1) | 17 (3.6) |
| Alopecia | 14 (2.9) | 0 (0) | 119 (25.1) | 0 (0) |
| Proteinuria | 117 (24.6) | 27 (5.7) | 54 (11.4) | 8 (1.7) |
| Dysphonia | 113 (23.7) | 1 (0.2) | 57 (12.0) | 0 (0) |
| Nausea | 93 (19.5) | 4 (0.8) | 68 (14.3) | 4 (0.8) |
| Abdominal pain | 81 (17.0) | 8 (1.7) | 87 (18.3) | 13 (2.7) |
| Decreased platelet count | 87 (18.3) | 26 (5.5) | 58 (12.2) | 16 (3.4) |
| Elevated aspartate aminotransferase | 65 (13.7) | 24 (5.0) | 80 (16.8) | 38 (8.0) |
| Hypothyroidism | 78 (16.4) | 0 (0) | 8 (1.7) | 0 (0) |
| Vomiting | 77 (16.2) | 6 (1.3) | 36 (7.6) | 5 (1.1) |
| Constipation | 76 (16.0) | 3 (0.6) | 52 (10.9) | 0 (0) |
| Rash | 46 (9.7) | 0 (0) | 76 (16.0) | 2 (0.4) | adjusted for treatment duration, almost all episodes were comparable for the lenvatinib and sorafenib arms. The dosages of lenvatinib for HCC (8 or 12 mg per day based on body weight) are lower than the lenvatinib dosage for radioiodine-refractory differentiated thyroid cancer (24 mg per day). In the phase 1 study of lenvatinib in HCC, patients with HCC who received 12 mg of lenvatinib per day and patients with solid tumors who received 25 mg of lenvatinib per days had similar lenvatinib plasma concentration at 24 hours, possibly because lenvatinib is metabolized in the liver. In the current phase 3 study, similar clinical activities and safety profiles were observed for both the 8 mg and 12 mg per day lenvatinib starting dosages.

In conclusion, the results of this study demonstrated noninferiority of lenvatinib in overall survival to sorafenib and statistically significant and clinically meaningful improvement in progression-free survival, time to progression, and objective response rate. The safety profiles of lenvatinib and sorafenib in this study appear consistent with the known safety profiles of these agents in HCC and no new safety signals were identified. Based on these results, lenvatinib may be a potential treatment option in advanced HCC.

Example 2: Dose Interruption and Dose Reduction for Lenvatinib Toxicity

Lenvatinib capsules were taken orally once daily (QD) in continuous 28-day cycles. The dose of lenvatinib was based on the subject's baseline body weight (BW) as shown below.

TABLE 10

| Drug Name | Baseline BW | Strength | Oral Dose Form | Number Dispensed and Frequency |
|---|---|---|---|---|
| Lenvatinib | ≥60 kg | 12 mg | capsule | 3 × 4-mg capsules, once daily at the same time each day |
|  | <60 kg | 8 mg | capsule | 2 × 4-mg capsules, once daily at the same time each day |

Lenvatinib toxicity was managed by treatment interruption, dose reduction, and/or treatment discontinuation. Dose adjustment for management of lenvatinib toxicity (with the exception of hypertension) was done in accordance with Table 6.

TABLE 11

Table 6: Lenvatinib Dose Reductions and Interruption Instructions

|  | Management | Dose Adjustment |
|---|---|---|
| Nonhematologic Toxicities | | |
| Treatment-Related Toxicity[a,b] | | |
| Grade 1 or Tolerable Grade 2 | Continue treatment[c] | No change |
| Intolerable Grade 2[e] or Grade 3[d,e] | | |
| First occurrence | Interrupted until resolved to Grade 0-1 or baseline | One-level reduction |
| Second occurrence (same toxicity or new toxicity) | Interrupted until resolved to Grade 0-1 or baseline | One-level reduction |
| Third occurrence[f] (same toxicity or new toxicity) | Interrupted until resolved to Grade 0-1 or baseline | One-level reduction |
| Fourth occurrence (same toxicity or new toxicity) | Interrupted until resolved to Grade 0-1 or baseline | Discuss with sponsor |
| Grade 4:[g] Discontinue Lenvatinib Hematologic Toxicities and Proteinuria | | |
| Treatment-Related Toxicity[a] | | |
| Grade 1 or Grade 2[e] | Continue treatment | No change |
| Grade 3[e] | | |
| First occurrence | Interrupted until resolved to Grade 0-2 or Baseline | No change |
| Second occurrence (same toxicity or new toxicity) | Interrupted until resolved to Grade 0-2 or Baseline | One-level reduction |
| Third occurrence (same toxicity or new toxicity) | Interrupted until resolved to Grade 0-2 or Baseline | One-level reduction |
| Fourth occurrence[f] (same toxicity or new toxicity) | Interrupted until resolved to Grade 0-2 or Baseline | One-level reduction |
| Fifth occurrence (same toxicity or new toxicity) | Interrupted until resolved to Grade 0-2 or Baseline | Discuss with sponsor |

Dose reductions occurred in succession based on the previous dose level (12, 8, and 4 mg/day, and 4 mg every other day [QOD]).
Any dose reduction below 4 mg QOD was discussed with the sponsor. Once the dose was reduced, it was not increased at a later date.

TABLE 12

Table 6 (cont.): Lenvatinib Dose Reductions and Interruption Instructions Grade 4

| First occurrence | Interrupted until resolved to Grade 0-2 or Baseline | One-level reduction |
|---|---|---|
| Second occurrence (same toxicity or new toxicity) | Interrupted until resolved to Grade 0-2 or Baseline | One-level reduction |
| Third occurrence[f] (same toxicity or new toxicity) | Interrupted until resolved to Grade 0-2 or Baseline | One-level reduction |

TABLE 12-continued

Table 6 (cont.): Lenvatinib Dose Reductions and Interruption Instructions Grade 4

| | | |
|---|---|---|
| Fourth occurrence (same toxicity or new toxicity) | Interrupted until resolved to Grade 0-2 or Baseline | Discuss with sponsor |

Note:
Grading according to CTCAE v4.0.
ALP = alkaline phosphatase;
ALT = alanine aminotransferase;
AST = aspartate aminotransferase;
CTCAE v4.0 = Common Terminology Criteria for Adverse Events Version 4.0;
ULN = upper limit of normal;
γ-GTP = international normalized ratio.

[a] An interruption of lenvatinib for more than 28 days (due to treatment-related toxicities) required sponsor's approval before treatment was resumed. During treatment interruption, AE assessment was repeated at least every 7 days (until administration was restarted).
[b] Initiated optimal medical management for nausea, vomiting, diarrhea, and/or hypothyroidism prior to any lenvatinib treatment, interruption, or dose reduction.
[c] Grade 2 toxicities were determined to be tolerable or intolerable by both the subject and investigator. If the Grade 2 toxicity was determined to be intolerable, the dose of study drug was reduced with or without dose interruption. Interruption for Grade 3 toxicity was mandatory.
[d] Obese subjects with weight loss did not need to return to baseline or Grade 1 weight loss to restart lenvatinib. If there was no weight loss for at least 1 week, subjects were restarted at the lower dose, and normal body mass index was used for further dose reductions.
[e] Not applicable to abnormal clinical laboratory values that were not clinically relevant based on the judgment of the investigator (e.g., ALT, AST, γ-GTP values <10 × ULN, and sodium).
[f] Not applicable for subjects who started at 8 mg QD.
[g] Excluding laboratory abnormalities judged to be non-life-threatening, which were managed as Grade 3.

Management of Hypertension

Hypertension is a recognized side effect of treatment with drugs inhibiting vascular endothelial growth factor (VEGF) signaling. Subjects enrolled in the trial had BP≤150/90 mm Hg at the time of study entry and, if they were known to be hypertensive, had been on a stable dose of antihypertensive therapy for at least 1 week before Cycle 1/Day 1. Early detection and effective management of hypertension were important to minimize the need for lenvatinib dose interruptions and reductions.

Antihypertensive agents were started as soon as elevated BP (systolic BP≥140 mm Hg or diastolic BP≥90 mm Hg) was confirmed on 2 assessments a minimum of 1-hour apart. One BP assessment was defined as the mean value of 3 measurements at least 5 minutes apart. The choice of antihypertensive treatment was individualized to the subject's clinical circumstances and followed standard medical practice. For previously normotensive subjects, appropriate antihypertensive therapy was started when systolic BP≥140 mm Hg or diastolic BP≥90 mm Hg was first observed on 2 assessments a minimum of 1-hour apart. For those subjects who were already on antihypertensive medication, treatment modification may have been necessary if hypertension persisted. For subjects with hypertension and proteinuria, appropriate therapy, e.g., angiotensin-converting enzyme inhibitor or angiotensin-II receptor antagonist was preferred.

Lenvatinib was withheld in any instance where a subject was at imminent risk to develop a hypertensive crisis or had significant risk factors for severe complications of uncontrolled hypertension (e.g., BP≥160/100 mm Hg, significant risk factors for cardiac disease, intracerebral hemorrhage, or other significant co-morbidities). Once the subject was on the same antihypertensive medications for at least 48 hours and the BP was controlled, lenvatinib was resumed as described below.

During the Treatment Period, both in the Randomization Phase and in the Extension Phase, subjects with systolic BP≥160 mm Hg or diastolic BP≥100 mm Hg had their BP monitored every 2 weeks (on Day 15 or more frequently as clinical indicated) until systolic BP was ≤150 mm Hg and diastolic BP was ≤95 mm Hg for 3 consecutive months. If a repeat event of systolic BP≥160 mm Hg or diastolic BP≥100 mm Hg occurred, the subject resumed the Day 15 evaluation until systolic BP was ≤150 mm Hg and diastolic BP was ≤95 mm Hg for 3 consecutive months.

The following guidelines were followed for the management of systolic BP≥160 mm Hg or diastolic BP≥100 mm Hg confirmed on repeat measurements after 1 hour:

Lenvatinib was continued and antihypertensive therapy was instituted for subjects not already receiving antihypertensive medication For those subjects already on antihypertensive medication, dose or medication choice was modified as per the investigator.

If systolic BP≥160 mm Hg or diastolic BP≥100 mm Hg persisted despite maximal antihypertensive therapy, then lenvatinib administration was interrupted and restarted at a dose of 8 mg QD (one dose level reduction as specified in Table 6) only when systolic BP≤150 mm Hg and diastolic BP≤95 mm Hg and the subject was on a stable dose of antihypertensive medication for at least 48 hours.

If systolic BP≥160 mm Hg or diastolic BP≥100 mm Hg recurred on the 8-mg QD dose despite optimal management of hypertension with antihypertensive medications (either by dose increase or the addition of a different class of antihypertensive), then lenvatinib administration was interrupted and restarted at a dose of 4-mg QD (1 more dose level reduction as specified in Table 6) only when systolic BP≤150 mm Hg and diastolic BP≤95 mm Hg and the subject was on a stable dose of antihypertensive medication for at least 48 hours.

If systolic BP≥160 mm Hg or diastolic BP≥100 mm Hg recurred on the 4-mg QD dose despite optimal management of hypertension with antihypertensive medications (either by dose increase or the addition of a different class of antihypertensive), then lenvatinib administration was interrupted and restarted at a dose of 4-mg QOD (1 more dose level reduction as specified in Table 6) only when systolic BP≤150 mm Hg and diastolic BP≤195 mm Hg and the subject was on a stable dose of antihypertensive medication for at least 48 hours.

If systolic BP≥160 mm Hg or diastolic BP≥100 mm Hg recurred on the 4-mg QOD dose despite optimal management of hypertension with antihypertensive medications (either by dose increase or the addition of a different class of antihypertensive), then lenvatinib administration was interrupted and restart of study medication was discussed with the sponsor.

The following guidelines were followed for the management of Grade 4 hypertension (life-threatening consequences):

Appropriate medical management was instituted.
Study drug was discontinued.

Management of Proteinuria

Regular assessment for proteinuria was conducted. Guidelines for assessment and management of proteinuria were as follows:

Initial episode of proteinuria: If proteinuria≥2+ was detected on urine dipstick testing, study drug was continued and a 24-hour urine collection for total protein was obtained as soon as possible within 72 hours to verify the grade of proteinuria. Grading according to CTCAE v4.0 was based on the 24-hour urine collection for total protein result. Additionally, a spot protein-creatinine ratio test was performed on the 24-hour urine sample as soon as possible within 72 hours. Management of lenvatinib administration was based on the grade of proteinuria according to 7.

During the Treatment Period, both in the Randomization Phase and the Extension Phase, urine dipstick testing for subjects with proteinuria ≥2+ was performed every 2 weeks (on Day 15 or more frequently as clinically indicated) until the results were 1+ or negative for 3 consecutive months. Any subsequent increases in the level of proteinuria≥2+ on urine dipstick testing were confirmed with a 24-hour urine collection and graded according to the dose reduction and interruption instructions provided in 7. A spot protein-creatinine ratio test was performed on the 24 hour urine sample as soon as possible. If a new event of proteinuria≥2+ occurred, the subject resumed the Day 15 urine dipstick testing for evaluation of proteinuria until results were 1+ or negative for 3 consecutive months.

A 24-hour urine collection for protein quantitation was required in the following situations:

The first (initial) occurrence of 2+, 3+, or 4+ proteinuria on urine dipstick while on study drug A subsequent apparent increase in severity of urine dipstick proteinuria (from the prior measurement which was ≥2+) occurring on the same lenvatinib dose level When there was a lenvatinib dose reduction and on follow-up, the urine protein dipstick result is 2+, 3+, or 4+ (at the new dose level)

The 24-hour urine collection was not required. In the following situations:
  Persistence of the same severity of proteinuria by urine dipstick at the same study dose level when a 24-hour urine collection has already been collected at that dose level)
  Subsequent occurrences of 2+, 3+, or 4+ proteinuria by urine dipstick when the subject was off study drug Management of Hepatotoxicity Regular monitoring of liver function tests (e.g., alanine transaminase [ALT], aspartate transaminase [AST], bilirubin levels) was conducted as clinically indicated. If signs occurred indicating a decrease in liver function by 1 grade or more from Baseline, the instructions in Table 6 were followed. Appropriate supportive care was provided together with close monitoring. If hepatic failure occurred the study drug was discontinued.

Management of Thromboembolic Events

Subjects were advised to pay attention to the symptoms suggestive of venous thromboembolic events, which included acute onset of dyspnea, chest pain, cough, hemoptysis, tachypnea, tachycardia, cyanosis, and deep vein thrombosis signs including lower extremity swelling, redness, and warmth to touch or tenderness. If any of these signs or symptoms appeared, subjects were instructed to report such signs and symptoms promptly to the treating physician. If a thromboembolic event was confirmed, instructions contained in Table 6 were followed. If a subject experienced life-threatening (Grade 4) thromboembolic reactions, including pulmonary embolism, the study drug was discontinued.

Management of Posterior Reversible Encephalopathy Syndrome

In clinical studies with lenvatinib, events of posterior reversible encephalopathy syndrome (PRES), a neurological disorder that can present with headache, seizure, lethargy, confusion, altered mental function, blindness, and other visual or neurological disturbances, were reported in less than 1% of lenvatinib-treated subjects. Mild to severe hypertension also could be present. A magnetic resonance imaging (MRI) was necessary to confirm the diagnosis of PRES. In subjects with signs or symptoms of PRES, appropriate measures were to be taken to control blood pressure, and instructions in Table 6 were followed.

Example 3: Adverse Events that Required Dose Reduction or Interruption of Study Drug A summary of TEAEs occurring in ≥10% of subjects in the lenvatinib or sorafenib treatment arm, in decreasing order of frequency in the total lenvatinib arm, is presented in Table 7.

TABLE 13

Table 7: Treatment-emergent Adverse Events Occurring in at Least 10% of Subjects in Either Treatment Arm, by Preferred Term

| Preferred Term | Lenvatinib 8 mg$^a$ (N = 151) n (%) | Lenvatinib 12 mg$^a$ (N = 325) n (%) | Lenvatinib Total (N = 476) n (%) | Sorafenib (N = 475) n (%) |
|---|---|---|---|---|
| Subjects with Any TEAEs | 151 (100.0) | 319 (98.2) | 470 (98.7) | 472 (99.4) |
| Hypertension | 65 (43.0) | 136 (41.8) | 201 (42.2) | 144 (30.3) |
| Diarrhea | 53 (35.1) | 131 (40.3) | 184 (38.7) | 220 (46.3) |
| Decreased appetite | 50 (33.1) | 112 (34.5) | 162 (34.0) | 127 (26.7) |
| Weight decreased | 43 (28.5) | 104 (32.0) | 147 (30.9) | 106 (22.3) |
| Fatigue | 42 (27.8) | 99 (30.5) | 141 (29.6) | 119 (25.1) |
| Palmar-plantar erythrodysesthesia syndrome | 35 (23.2) | 93 (28.6) | 128 (26.9) | 249 (52.4) |
| Proteinuria | 37 (24.5) | 80 (24.6) | 117 (24.6) | 54 (11.4) |
| Dysphonia | 28 (18.5) | 85 (26.2) | 113 (23.7) | 57 (12.0) |
| Nausea | 24 (15.9) | 69 (21.2) | 93 (19.5) | 68 (14.3) |
| Platelet count decreased | 26 (17.2) | 61 (18.8) | 87 (18.3) | 58 (12.2) |
| Abdominal pain | 19 (12.6) | 62 (19.1) | 81 (17.0) | 87 (18.3) |
| Hypothyroidism | 25 (16.6) | 53 (16.3) | 78 (16.4) | 8 (1.7) |
| Vomiting | 22 (14.6) | 55 (16.9) | 77 (16.2) | 36 (7.6) |
| Constipation | 19 (12.6) | 57 (17.5) | 76 (16.0) | 52 (10.9) |
| Blood bilirubin increased | 23 (15.2) | 48 (14.8) | 71 (14.9) | 63 (13.3) |
| Pyrexia | 24 (15.9) | 45 (13.8) | 69 (14.5) | 63 (13.3) |
| Ascites | 21 (13.9) | 47 (14.5) | 68 (14.3) | 44 (9.3) |
| Edema peripheral | 23 (15.2) | 43 (13.2) | 66 (13.9) | 33 (6.9) |
| Aspartate aminotransferase increased | 21 (13.9) | 44 (13.5) | 65 (13.7) | 80 (16.8) |
| Abdominal pain upper | 21 (13.9) | 37 (11.4) | 58 (12.2) | 40 (8.4) |
| Asthenia | 14 (9.3) | 40 (12.3) | 54 (11.3) | 48 (10.1) |

TABLE 13-continued

Table 7: Treatment-emergent Adverse Events Occurring in at Least 10% of Subjects in Either Treatment Arm, by Preferred Term

| | Lenvatinib | | | Sorafenib |
|---|---|---|---|---|
| Preferred Term | 8 mg$^a$ (N = 151) n (%) | 12 mg$^a$ (N = 325) n (%) | Total (N = 476) n (%) | (N = 475) n (%) |
| Alanine aminotransferase increased | 17 (11.3) | 36 (11.1) | 53 (11.1) | 52 (10.9) |
| Back pain | 11 (7.3) | 39 (12.0) | 50 (10.5) | 31 (6.5) |
| Rash | 18 (11.9) | 28 (8.6) | 46 (9.7) | 76 (16.0) |
| Stomatitis | 11 (7.3) | 34 (10.5) | 45 (9.5) | 56 (11.8) |
| Alopecia | 5 (3.3) | 9 (2.8) | 14 (2.9) | 119 (25.1) |

TABLE 14

[Data cutoff date: Nov. 13, 2016; Percentages are based on the total number of subjects within the relevant treatment group in the Safety Analysis Set.
Display is in decreasing order of frequency of TEAEs in the lenvatinib total group.
Subjects with 2 or more TEAEs in the same preferred term were counted only once.
Adverse Event terms were coded using MedDRA version 19.1.
MedDRA = Medical Dictionary for Regulatory Activities;
TEAE = treatment-emergent adverse event.
$^a$8 mg and 12 mg were the lenvatinib starting doses based on the subjects' body weight (<60 kg, >60 kg) at Baseline.]

A TEAE occurred in all but 6 and 3 subjects in the lenvatinib and sorafenib arms, respectively. The most frequently reported TEAEs (>30% of subjects) were hypertension, diarrhea, decreased appetite, and weight decreased for lenvatinib and palmar-plantar erythrodysaesthesia (PPE) syndrome, diarrhea, and hypertension for sorafenib. Adverse events that occurred in ≥10% more subjects in the lenvatinib arm than in the sorafenib arm were: hypertension (42.2% vs 30.3%), proteinuria (24.6% vs 11.4%), dysphonia (23.7% vs 12.0%), and hypothyroidism (16.4% vs 1.7%). These AEs are consistent with the known safety profile of lenvatinib in other cancer indications. Other AEs with a subject incidence of <10% but that were reported in a higher proportion of lenvatinib-treated subjects compared with sorafenib (≥10 episodes in 1 treatment arm and a difference between treatments of ≥0.1 episodes per SY) when adjusted by treatment duration included: proteinuria (0.5 vs 0.31 episodes per SY), dysphonia (0.4 vs 0.28), hypothyroidism (0.24 vs 0.03), WBC count deceased (0.25 vs 0.15), neutrophil count decreased (0.21 vs 0.06), and hepatic encephalopathy (0.17 vs 0.04).

An algorithm of dose interruption followed by dose reduction was used for the management of lenvatinib toxicity (see, Table 6). Unadjusted for treatment duration, adverse events (AEs) leading to dose reduction or interruption were reported in 61.8% of subjects in the lenvatinib arm and 55.6% of subjects in the sorafenib arm (Table 8).

TABLE 15

Table 8: Treatment-emergent Adverse Events Leading to Dose Reduction/Interruption of Study Drug in at Least 1% of Subjects in Either Treatment Arm, by System Organ Class and Preferred Term - Safety Analysis Set

| | Lenvatinib | | | Sorafenib |
|---|---|---|---|---|
| System Organ Class Preferred Term | 8 mg$^a$ (N = 151) n (%) | 12 mg$^a$ (N = 325) n (%) | Total (N = 476) n (%) | (N = 475) n (%) |
| Subjects with any TEAEs leading to Dose Reduction or Interruption | 81 (53.6) | 213 (65.5) | 294 (61.8) | 264 (55.6) |
| Blood and lymphatic system disorders | 5 (3.3) | 11 (3.4) | 16 (3.4) | 13 (2.7) |
| Neutropenia | 0 (0.0) | 6 (1.8) | 6 (1.3) | 0 (0.0) |
| Thrombocytopenia | 2 (1.3) | 4 (1.2) | 6 (1.3) | 4 (0.8) |
| Anemia | 2 (1.3) | 1 (0.3) | 3 (0.6) | 8 (1.7) |
| Gastrointestinal disorders | 22 (14.6) | 65 (20.0) | 87 (18.3) | 72 (15.2) |
| Diarrhea | 8 (5.3) | 28 (8.6) | 36 (7.6) | 35 (7.4) |
| Nausea | 2 (1.3) | 14 (4.3) | 16 (3.4) | 9 (1.9) |
| Vomiting | 1 (0.7) | 11 (3.4) | 12 (2.5) | 6 (1.3) |
| Ascites | 3 (2.0) | 7 (2.2) | 10 (2.1) | 5 (1.1) |
| Abdominal pain | 2 (1.3) | 4 (1.2) | 6 (1.3) | 8 (1.7) |
| Stomatitis | 2 (1.3) | 4 (1.2) | 6 (1.3) | 2 (0.4) |
| Abdominal pain upper | 2 (1.3) | 3 (0.9) | 5 (1.1) | 2 (0.4) |
| Esophageal varices hemorrhage | 0 (0.0) | 5 (1.5) | 5 (1.1) | 1 (0.2) |
| General disorders and administration site conditions | 17 (11.3) | 50 (15.4) | 67 (14.1) | 35 (7.4) |
| Fatigue | 5 (3.3) | 22 (6.8) | 27 (5.7) | 17 (3.6) |
| Asthenia | 3 (2.0) | 13 (4.0) | 16 (3.4) | 9 (1.9) |
| Pyrexia | 4 (2.6) | 8 (2.5) | 12 (2.5) | 5 (1.1) |
| Edema peripheral | 2 (1.3) | 4 (1.2) | 6 (1.3) | 3 (0.6) |
| Malaise | 2 (1.3) | 3 (0.9) | 5 (1.1) | 0 (0.0) |
| Hepatobiliary disorders | 2 (1.3) | 25 (7.7) | 27 (5.7) | 19 (4.0) |
| Hepatic function abnormal | 0 (0.0) | 2 (0.6) | 2 (0.4) | 9 (1.9) |

TABLE 16

Table 8 (cont.): Treatment-emergent Adverse Events Leading to Dose Reduction/Interruption of Study Drug in at Least 1% of Subjects in Either Treatment Arm, by System Organ Class and Preferred Term - Safety Analysis Set

| System Organ Class Preferred Term | Lenvatinib 8 mg$^a$ (N = 151) n (%) | Lenvatinib 12 mg$^a$ (N = 325) n (%) | Lenvatinib Total (N = 476) n (%) | Sorafenib (N = 475) n (%) |
|---|---|---|---|---|
| Investigations | 24 (15.9) | 57 (17.5) | 81 (17.0) | 52 (10.9) |
| Platelet count decreased | 9 (6.0) | 13 (4.0) | 22 (4.6) | 12 (2.5) |
| Blood bilirubin increased | 8 (5.3) | 12 (3.7) | 20 (4.2) | 14 (2.9) |
| Weight decreased | 3 (2.0) | 17 (5.2) | 20 (4.2) | 4 (0.8) |
| Neutrophil count decreased | 4 (2.6) | 7 (2.2) | 11 (2.3) | 5 (1.1) |
| Aspartate aminotransferase increased | 4 (2.6) | 5 (1.5) | 9 (1.9) | 18 (3.8) |
| Gamma-glutamyltransferase increased | 1 (0.7) | 6 (1.8) | 7 (1.5) | 4 (0.8) |
| Alanine aminotransferase increased | 2 (1.3) | 4 (1.2) | 6 (1.3) | 9 (1.9) |
| White blood cell count decreased | 3 (2.0) | 3 (0.9) | 6 (1.3) | 4 (0.8) |
| Metabolism and nutrition disorders | 21 (13.9) | 31 (9.5) | 52 (10.9) | 19 (4.0) |
| Decreased appetite | 15 (9.9) | 21 (6.5) | 36 (7.6) | 15 (3.2) |
| Dehydration | 3 (2.0) | 3 (0.9) | 6 (1.3) | 0 (0.0) |
| Hyponatremia | 2 (1.3) | 3 (0.9) | 5 (1.1) | 0 (0.0) |
| Musculoskeletal and connective tissue disorders | 4 (2.6) | 14 (4.3) | 18 (3.8) | 9 (1.9) |
| Myalgia | 1 (0.7) | 4 (1.2) | 5 (1.1) | 0 (0.0) |
| Nervous system disorders | 7 (4.6) | 28 (8.6) | 35 (7.4) | 14 (2.9) |
| Hepatic encephalopathy | 4 (2.6) | 16 (4.9) | 20 (4.2) | 3 (0.6) |
| Renal and urinary disorders | 5 (3.3) | 35 (10.8) | 40 (8.4) | 9 (1.9) |
| Proteinuria | 4 (2.6) | 29 (8.9) | 33 (6.9) | 7 (1.5) |
| Respiratory, thoracic and mediastinal disorders | 4 (2.6) | 12 (3.7) | 16 (3.4) | 12 (2.5) |
| Dyspnea | 2 (1.3) | 6 (1.8) | 8 (1.7) | 4 (0.8) |
| Skin and subcutaneous tissue disorders | 5 (3.3) | 23 (7.1) | 28 (5.9) | 111 (23.4) |
| Palmar-plantar erythrodysesthesia syndrome | 4 (2.6) | 21 (6.5) | 25 (5.3) | 88 (18.5) |
| Rash | 0 (0.0) | 2 (0.6) | 2 (0.4) | 10 (2.1) |
| Rash maculo-papular | 0 (0.0) | 0 (0.0) | 0 (0.0) | 5 (1.1) |

TABLE 17

Table 8 (cont.): Treatment-emergent Adverse Events Leading to Dose Reduction/Interruption of Study Drug in at Least 1% of Subjects in Either Treatment Arm, by System Organ Class and Preferred Term - Safety Analysis Set

| System Organ Class Preferred Term | Lenvatinib 8 mg$^a$ (N = 151) n (%) | Lenvatinib 12 mg$^a$ (N = 325) n (%) | Lenvatinib Total (N = 476) n (%) | Sorafenib (N = 475) n (%) |
|---|---|---|---|---|
| Vascular disorders | 3 (2.0) | 30 (9.2) | 33 (6.9) | 19 (4.0) |
| Hypertension | 3 (2.0) | 26 (8.0) | 29 (6.1) | 18 (3.8) |

[The data cutoff date for this table was Nov. 13, 2016.
Percentages are based on the total number of subjects within the relevant treatment group in the Safety Analysis Set.
Subjects with 2 or more TEAEs reported in the same system organ class or preferred term were only counted once.
Adverse Events terms were coded using MedDRA version 19.1.
MedDRA = Medical Dictionary for Regulatory Activities;
TEAR treatment-emergent adverse event.
$^a$8 mg and 12 mg were the lenvatinib starting doses based on the subjects' body weight (<60 kg, ≥60 kg) at baseline.]

Adverse events leading to dose reduction or interruption of lenvatinib were most frequently (≥10% of subjects) coded to the SOCs of Gastrointestinal disorders (18.3%), Investigations (17.0%), General disorders and Administration Site Conditions (14.1%), and Metabolism and Nutrition disorders (10.9%).

Adverse events that led to dose reduction or interruption in 5% or more of subjects in the lenvatinib or sorafenib arm, respectively, were decreased appetite (7.6% vs 3.2%), diarrhea (7.6% vs 7.4%), proteinuria (6.9% vs 1.5%), hypertension (6.1% vs 3.8%), fatigue (5.7% vs 3.6%), and PPE syndrome (5.3% vs 18.5%). Except for PPE syndrome, which occurred more frequently with sorafenib, these treatment-emergent adverse events (TEAEs) led to dose modification either at similar rates in the 2 treatment arms, or at a higher frequency in the lenvatinib arm.

Other TEAEs that led to dose modification in a higher percentage of subjects in the lenvatinib arm (total incidence >2% to <5% but [approximately]>2 times the rate) than in the sorafenib arm were hepatic encephalopathy (4.2% vs 0.6%), weight decreased (4.2% vs 0.8%), pyrexia (2.5% vs 1.1%), vomiting (2.5% vs 1.3%), neutrophil count decreased (2.3% vs 1.1%), and ascites (2.1% vs 1.1%). The only TEAE that led to dose modification in a higher percentage of subjects in the sorafenib arm (total incidence >2% to <5% but at least double the rate) than in the lenvatinib arm was AST increased (3.8% vs 1.9%)

As of the data cutoff date for the primary analysis, the majority of subjects had ended treatment; treatment was ongoing for 27 (5.6%) lenvatinib and 25 (5.3%) sorafenib subjects. The most frequent reason for discontinuation of treatment was disease progression. Fewer subjects ended treatment due to disease progression in the lenvatinib arm (311; 65.1%) than in the sorafenib arm (347; 72.9%). Adverse events were cited by the investigators as the reason for ending treatment in 13.2% (n=63) of lenvatinib and 9.0% (n=43) of sorafenib subjects (see, Table 9).

TABLE 18

Table 9: Subject Disposition and Reasons for Discontinuation of Treatment during Randomization Phase

|  | Lenvatinib (N = 478) n (%) | Sorafenib (N = 476) n (%) | Total (N = 954) n (%) |
|---|---|---|---|
| Randomized | 478 (100.0) | 476 (100.0) | 954 (100.0) |
| Not treated | 2 (0.4) | 1 (0.2) | 3 (0.3) |
| Treated | 476 (99.6) | 475 (99.8) | 951 (99.7) |
| Treatment ongoing at data cutoff date | 27 (5.6) | 25 (5.3) | 52 (5.5) |
| Discontinued Treatment[b] | 451 (94.4) | 451 (94.7) | 902 (94.5) |
| Primary Reason for Discontinuation of Treatment |  |  |  |
| Disease Progression | 311 (65.1) | 347 (72.9) | 658 (69.0) |
| Adverse event | 63 (13.2) | 43 (9.0) | 106 (11.1) |
| Subject choice | 28 (5.9) | 15 (3.2) | 43 (4.5) |
| Lost to follow-up | 3 (0.6) | 1 (0.2) | 4 (0.4) |
| Withdrawal of consent | 9 (1.9) | 5 (1.1) | 14 (1.5) |

TABLE 18-continued

Table 9: Subject Disposition and Reasons for Discontinuation of Treatment during Randomization Phase

|  | Lenvatinib (N = 478) n (%) | Sorafenib (N = 476) n (%) | Total (N = 954) n (%) |
|---|---|---|---|
| Other[a] | 37 (7.7) | 40 (8.4) | 77 (8.1) |
| Discontinued Treatment but in Survival Follow-up | 82 (17.2) | 82 (17.2) | 164 (17.2) |

Data cutoff date: Nov. 13, 2016.
Percentages are based on the total number of subjects within the relevant treatment group in the Full Analysis Set.
[a]These reasons were collected as investigator comments under the "Other" category in the case report form.
[b]Includes the 3 subjects who were not treated after randomization.

The percentage of the subjects who discontinued lenvatinib treatment due to adverse events was 13.2% (n=62). This low percentage of discontinuation could not have been achieved without the use of dose modifications (see Table 6).

Example 4: Efficacy Results in Hepatocellular Carcinoma Clinical Study

The efficacy of LENVIMA was evaluated in a randomized, open-label, multicenter, international study (REFLECT; NCT0761266) conducted in patients with previously untreated unresectable hepatocellular carcinoma (HCC). The study enrolled adults with Child-Pugh A and Barcelona Clinic Liver Cancer (BCLC) Stage C or B HCC who were ineligible for local liver-directed therapy; had an ECOG PS of 0 or 1; had received no prior systemic therapy for HCC; and had at least one measurable target lesion according to modified RECIST for HCC. Efficacy results are summarized in Table 10.

TABLE 19

Table 10: Efficacy Results in Hepatocellular Carcinoma in REFLECT

|  | LENVIMA N = 478 | Sorafenib N = 476 |
|---|---|---|
| Overall Survival |  |  |
| Number of deaths (%) | 351 (73) | 350 (74) |
| Median OS in months (95% CI) | 13.6 (12.1, 14.9) | 12.3 (10.4, 13.9) |
| Hazard Ratio (95% CI)a | 0.92 (0.79, 1.06) |  |
| Progression-Free Survival[b] (mRECIST) |  |  |
| Number of Events (%) | 311 (65) | 323 (68) |
| Median PFS in months (95% CI) | 7.3 (5.6, 7.5) | 3.6 (3.6, 3.7) |
| Hazard Ratio (95% CI)[a] | 0.64 (0.55, 0.75) |  |
| P-value | <0.001 |  |
| Objective Response Rate[b] (mRECIST) |  |  |
| Objective response rate | 41% | 12% |
| Complete responses, n (%) | 10 (2.1) | 4 (0.8) |
| Partial responses, n (%) | 184 (38.5) | 55 (11.6) |
| 95% CI | (36%, 45%) | (9%, 15%) |
| Odds Ratio (95% CI) | 5.01 (3.59, 7.01) |  |
| P-value | <0.001 |  |
| Progression-Free Survival[b] (RECIST 1.1) |  |  |
| Number of Events (%) | 307 (64) | 320 (67) |
| Median PFS in months (95% CI) | 7.3 (5.6, 7.5) | 3.6 (3.6, 3.9) |
| Hazard Ratio (95% CI)[a] | 0.65 (0.56, 0.77) |  |
| Objective Response Rate[b] (RECIST 1.1) |  |  |
| Objective response rate | 19% | 7% |
| Complete responses, n (%) | 2 (0.4) | 1 (0.2) |
| Partial responses, n (%) | 88 (18.4) | 30 (6.3) |

TABLE 19-continued

Table 10: Efficacy Results in Hepatocellular Carcinoma in REFLECT

| | LENVIMA<br>N = 478 | Sorafenib<br>N = 476 |
|---|---|---|
| 95% CI | (15%, 22%) | (4%, 9%) |
| Odds Ratio (95% CI) | | 3.3 (2.2, 5.1) |

CI = confidence interval;
ECOG PS = Eastern Cooperative Oncology Group Performance Status;
HR = hazard ratio;
OS overall survival.
Non-inferiority margin for hazard ratio (lenvatinib vs sorafenib) is 1.08.
Per independent review.

Example 5: Drug Interaction Studies: Effect of Lenvatinib can Other Drugs

Clinical Studies with Substrates of CYP3A4 or CYP2C8: There is no projected significant drug-drug interaction risk between lenvatinib and midazolam (a CYP3A4 substrate) or repaglinide (a CYP2C8 substrate).

In Vitro Studies with Substrates of CYP or UDP-glucuronosyltransferase (UGT): Lenvatinib inhibits CYP2C8, CYP1A2, CYP2B6, CYP2C9, CYP2C19, CYP2D6, and CYP3A. Lenvatinib does not inhibit CYP2A6 and CYP2E1. Lenvatinib induces CYP3A, but it does not induce CYP1A1, CYP1A2, CYP2B6, and CYP2C9.

Lenvatinib inhibits UGT1A1, UGT1A4, and UGT1A9 in vitro, but likely only inhibits UGT1A1 in vivo in the gastrointestinal tract based on the expression of the enzyme in tissues. Lenvatinib does not inhibit UGT1A6, UGT2B7 or aldehyde oxidase. Lenvatinib does not induce UGT1A1, UGT1A4, UGT1A6, UGT1A9, or UGT2B7.

In Vitro Studies with Substrates of Transporters: Lenvatinib does not have the potential to inhibit MATE1, MATE2-K, OCT1, OCT2, OAT1, OAT3, BSEP, OATP1B1, or OATP1B3 in vivo.

CROSS-REFERENCE TO RELATED APPLICATIONS

This application claims the benefit of priority of U.S. Provisional Appl. No. 62/506,900, filed May 16, 2017, the contents of which are incorporated by reference herein in their entirety.

Other Embodiments

While the invention has been described in conjunction with the detailed description thereof the foregoing description is intended to illustrate and not limit the scope of the invention, which is defined by the scope of the appended claims. Other aspects, advantages, and modifications are within the scope of the following claims.

The invention claimed is:

1. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, wherein the human subject develops an occurrence of a
first Grade 3 nonhematologic toxicity during treatment with the first dosage regimen, and the method further comprises:

(a) terminating administration of the first dosage regimen after the occurrence of the first Grade 3 nonhematologic toxicity until the first Grade 3 nonhematologic toxicity is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject develops an occurrence of a second Grade 3 nonhematologic toxicity during treatment with the second dosage regimen;

(b) terminating administration of the second dosage regimen after the occurrence of the second Grade 3 nonhematologic toxicity until the second Grade 3 nonhematologic toxicity is resolved to Grade 0-1 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject develops an occurrence of a third Grade 3 nonhematologic toxicity during treatment with the third dosage regimen; and (c) terminating administration of the third dosage regimen after the occurrence of the third Grade 3 nonhematologic toxicity until the third Grade 3 nonhematologic toxicity is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day.

2. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, wherein the human subject develops an occurrence of a
first persistent and intolerable Grade 2 or Grade 3 nonhematologic toxicity during treatment with the first dosage regimen, and the method further comprises:

(a) terminating administration of the first dosage regimen after the occurrence of the first persistent and intolerable Grade 2 or Grade 3 nonhematologic toxicity until the first persistent and intolerable Grade 2 or Grade 3 nonhematologic toxicity is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject develops an occurrence of a second persistent and intolerable Grade 2 or Grade 3 nonhematologic toxicity during treatment with the second dosage regimen;

(b) terminating administration of the second dosage regimen after the occurrence of the second persistent and intolerable Grade 2 or Grade 3 nonhematologic toxicity until the second persistent and intolerable Grade 2 or Grade 3 nonhematologic toxicity is resolved to Grade 0-1 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject develops an occurrence of a third persistent and intolerable Grade 2 or Grade 3 nonhematologic toxicity during treatment with the third dosage regimen; and (c) terminating administration of the third dosage regimen after the occurrence of the third persistent and intolerable Grade 2 or Grade 3 nonhematologic toxicity until the third persistent and intolerable Grade 2 or Grade 3 nonhematologic toxicity is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day.

3. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, wherein the human subject develops an occurrence of a first persistent and intolerable Grade 2 or Grade 3 nonhematologic toxicity or non-life-threatening Grade 4 laboratory abnormality during treatment with the first dosage regimen, and the method further comprises:

(a) terminating administration of the first dosage regimen after the occurrence of the first persistent and intolerable Grade 2 or Grade 3 nonhematologic toxicity or non-life-threatening Grade 4 laboratory abnormality until the first persistent and intolerable Grade 2 or Grade 3 nonhematologic toxicity or non-life-threatening Grade 4 laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject develops an occurrence of a second persistent and intolerable Grade 2 or Grade 3 nonhematologic toxicity or non-life-threatening Grade 4 laboratory abnormality during treatment with the second dosage regimen;

(b) terminating administration of the second dosage regimen after the occurrence of the second persistent and intolerable Grade 2 or Grade 3 nonhematologic toxicity or non-life-threatening Grade 4 laboratory abnormality until the second persistent and intolerable Grade 2 or Grade 3 nonhematologic toxicity or non-life-threatening Grade 4 laboratory abnormality is resolved to Grade 0-1 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject develops an occurrence of a third persistent and intolerable Grade 2 or Grade 3 nonhematologic toxicity or non-life-threatening Grade 4 laboratory abnormality during treatment with the third dosage regimen; and (c) terminating administration of the third dosage regimen after the occurrence of the third persistent and intolerable Grade 2 or Grade 3 nonhematologic toxicity or non-life-threatening Grade 4 laboratory abnormality until the third persistent and intolerable Grade 2 or Grade 3 nonhematologic toxicity or non-life-threatening Grade 4 laboratory abnormality is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day.

4. The method of claim 1, wherein the human subject develops an occurrence of a Grade 4 nonhematologic toxicity excluding non-life-threatening Grade 4 laboratory abnormality during treatment with the first, second, third or fourth dosage regimen, and the method further comprises terminating administration of the dosage regimen after the occurrence of the Grade 4 nonhematologic toxicity excluding the non-life-threatening Grade 4 laboratory abnormality.

5. The method of claim 1, wherein medical management of each of the first, second, and third persistent and intolerable Grade 2 or Grade 3 nonhematologic toxicities or non-life-threatening Grade 4 laboratory abnormality is initiated prior to terminating administration of the dosage regimen administered at the time of onset of the Grade 2 or Grade 3 nonhematologic toxicity or non-life-threatening Grade 4 laboratory abnormality.

6. The method of claim 1, wherein the first persistent and intolerable Grade 2 or Grade 3 nonhematologic toxicity or non-life-threatening Grade 4 laboratory abnormality is the same as the second and/or third persistent and intolerable Grade 2 or Grade 3 nonhematologic toxicity or non-life-threatening Grade 4 laboratory abnormality.

7. The method of claim 1, wherein the Grade 3 nonhematologic toxicity is selected from the group consisting of Grade 3 hypertension, Grade 3 diarrhea, Grade 3 arthralgia, Grade 3 myalgia, Grade 3 decreased appetite, Grade 3 fatigue, Grade 3 decreased weight, Grade 3 dysphonia, Grade 3 nausea, Grade 3 abdominal pain, Grade 3 QT/QTc interval prolongation, Grade 3 hypothyroidism, Grade 3 vomiting, Grade 3 constipation, Grade 3 rash, and Grade 3 palmar-plantar erythrodysesthesia.

8. The method of claim 2, wherein the Grade 2 or Grade 3 nonhematologic toxicity is selected from the group consisting of Grade 3 hypertension, Grade 2 hypertension, Grade 3 diarrhea, Grade 2 diarrhea, Grade 3 decreased appetite, Grade 2 decreased appetite, Grade 3 arthralgia, Grade 2 arthralgia, Grade 3 myalgia, Grade 2 myalgia, Grade 3 fatigue, Grade 2 fatigue, Grade 3 decreased weight, Grade 2 decreased weight, Grade 2 alopecia, Grade 3 dysphonia, Grade 2 dysphonia, Grade 3 nausea, Grade 2 nausea, Grade 3 abdominal pain, Grade 2 abdominal pain, Grade 3 QT/QTc interval prolongation, Grade 2 QT/QTc interval prolongation, Grade 3 hypothyroidism, Grade 2 hypothyroidism, Grade 3 vomiting, Grade 2 vomiting, Grade 3 constipation, Grade 2 constipation, Grade 3 rash, Grade 2 rash, Grade 3 palmar-plantar erythrodysesthesia, and Grade 2 palmar-plantar erythrodysesthesia.

9. The method of claim 3, wherein the Grade 4 laboratory abnormality is selected from the group consisting of Grade 4 increase in aspartate aminotransferase, Grade 4 increase in alanine aminotransferase, Grade 4 increase in alkaline phosphatase, Grade 4 hypokalemia, Grade 4 hyponatremia, Grade 4 hypoglycemia, Grade 4 increase in blood bilirubin, and Grade 4 increase in gamma glutamyl transferase.

10. A method of treating unresectable hepatocellular carcinoma, the method comprising administering to a human subject that has an unresectable hepatocellular carcinoma:
   a dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject was previously treated with a prior dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, and wherein the human subject developed an occurrence of a Grade 3 nonhematologic toxicity during treatment with the prior dosage regimen;
   a dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject was previously treated with a prior dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, and wherein the human subject developed an occurrence of a Grade 3 nonhematologic toxicity during treatment with the prior dosage regimen; or
   a dosage regimen comprising lenvatinib or a pharmaceutically acceptable salt thereof at a dose of 4 mg every other day, wherein the body weight of the human subject is equal to or more than 60 kg, wherein the human subject was previously treated with a prior dosage regimen comprising lenvatinib or a pharmaceutically acceptable salt thereof at a dose of 4 mg/day, and wherein the human subject developed an occurrence of a Grade 3 nonhematologic toxicity during treatment with the prior dosage regimen.

11. A method of treating unresectable hepatocellular carcinoma, the method comprising administering to a human subject that has an unresectable hepatocellular carcinoma:
   a dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject was previously treated with a prior dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, and wherein the human subject developed an occurrence of a persistent and intolerable Grade 2 or Grade 3 nonhematologic toxicity during treatment with the prior dosage regimen;
   a dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject was previously treated with a prior dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, and wherein the human subject developed an occurrence of a persistent and intolerable Grade 2 or Grade 3 nonhematologic toxicity during treatment with the prior dosage regimen; or
   a dosage regimen comprising lenvatinib or a pharmaceutically acceptable salt thereof at a dose of 4 mg every other day, wherein the body weight of the human subject is equal to or more than 60 kg, wherein the human subject was previously treated with a prior dosage regimen comprising lenvatinib or a pharmaceutically acceptable salt thereof at a dose of 4 mg/day, and wherein the human subject developed an occurrence of a persistent and intolerable Grade 2 or Grade 3 nonhematologic toxicity during treatment with the prior dosage regimen.

12. A method of treating unresectable hepatocellular carcinoma, the method comprising administering to a human subject that has an unresectable hepatocellular carcinoma:
   a dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject was previously treated with a prior dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, and wherein the human subject developed an occurrence of a persistent and intolerable Grade 2 or Grade 3 nonhematologic toxicity or non-life-threatening Grade 4 laboratory abnormality during treatment with the prior dosage regimen;
   a dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject was previously treated with a prior dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, and wherein the human subject developed an occurrence of a persistent and intolerable Grade 2 or Grade 3 nonhematologic toxicity or non-life-threatening Grade 4 laboratory abnormality during treatment with the prior dosage regimen; or a dosage regimen comprising lenvatinib or a pharmaceutically acceptable salt thereof at a dose of 4 mg every other day, wherein the body weight of the human subject is equal to or more than 60 kg, wherein the human subject was previously treated with a prior dosage regimen comprising lenvatinib or a pharmaceutically acceptable salt thereof at a dose of 4 mg/day, and wherein the human subject developed an occurrence of a persistent and intolerable Grade 2 or Grade 3 nonhematologic toxicity or non-life-threatening Grade 4 laboratory abnormality during treatment with the prior dosage regimen.

13. The method of claim 10, wherein the Grade 3 nonhematologic toxicity is selected from the group consisting of Grade 3 hypertension, Grade 3 diarrhea, Grade 3 arthralgia, Grade 3 myalgia, Grade 3 decreased appetite, Grade 3 fatigue, Grade 3 decreased weight, Grade 3 dysphonia, Grade 3 nausea, Grade 3 abdominal pain, Grade 3 QT/QTc interval prolongation, Grade 3 hypothyroidism, Grade 3 vomiting, Grade 3 constipation, Grade 3 rash, and Grade 3 palmar-plantar erythrodysesthesia.

14. The method of claim 11, wherein the Grade 2 or Grade 3 nonhematologic toxicity is selected from the group consisting of Grade 3 hypertension, Grade 2 hypertension, Grade 3 diarrhea, Grade 2 diarrhea, Grade 3 decreased appetite, Grade 2 decreased appetite, Grade 3 arthralgia, Grade 2 arthralgia, Grade 3 myalgia, Grade 2 myalgia, Grade 3 fatigue, Grade 2 fatigue, Grade 3 decreased weight, Grade 2 decreased weight, Grade 2 alopecia, Grade 3 dysphonia, Grade 2 dysphonia, Grade 3 nausea, Grade 2 nausea, Grade 3 abdominal pain, Grade 2 abdominal pain, Grade 3 QT/QTc interval prolongation, Grade 2 QT/QTc interval prolongation, Grade 3 hypothyroidism, Grade 2 hypothyroidism, Grade 3 vomiting, Grade 2 vomiting, Grade 3 constipation, Grade 2 constipation, Grade 3 rash, Grade 2 rash, Grade 3 palmar-plantar erythrodysesthesia, and Grade 2 palmar-plantar erythrodysesthesia.

15. The method of claim 12, wherein the Grade 4 laboratory abnormality is selected from the group consisting of Grade 4 increase in aspartate aminotransferase, Grade 4 increase in alanine aminotransferase, Grade 4 increase in alkaline phosphatase, Grade 4 hypokalemia, Grade 4 hyponatremia, Grade 4 hypoglycemia, Grade 4 increase in blood bilirubin, and Grade 4 increase in gamma glutamyl transferase.

16. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, (I) wherein the human subject develops an occurrence of a first persistent and intolerable Grade 2 or Grade 3 adverse reaction or Grade 4 laboratory abnormality during treatment with the first dosage regimen, and the method further comprises:

(a) terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject develops an occurrence of a second persistent and intolerable Grade 2 or Grade 3 adverse reaction or Grade 4 laboratory abnormality during treatment with the second dosage regimen;

(b) terminating administration of the second dosage regimen after the occurrence of the second persistent and intolerable Grade 2 or Grade 3 adverse reaction or Grade 4 laboratory abnormality until the second persistent and intolerable Grade 2 or Grade 3 adverse reaction or Grade 4 laboratory abnormality is resolved to Grade 0-1 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject develops an occurrence of a third persistent and intolerable Grade 2 or Grade 3 adverse reaction or Grade 4 laboratory abnormality during treatment with the third dosage regimen; and (c) terminating administration of the third dosage regimen after the occurrence of the third persistent and intolerable Grade 2 or Grade 3 adverse reaction or Grade 4 laboratory abnormality until the third persistent and intolerable Grade 2 or Grade 3 adverse reaction or Grade 4 laboratory abnormality is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day; or (II) wherein the human subject develops an occurrence of a Grade 4 adverse reaction excluding Grade 4 laboratory abnormality during treatment with the first, second, third, or fourth dosage regimen, and the method further comprises terminating administration of the dosage regimen after the occurrence of the Grade 4 adverse reaction excluding Grade 4 laboratory abnormality;

provided that Grade 3 hypertension, Grade 4 hypertension, Grade 3 cardiac dysfunction, Grade 4 cardiac dysfunction, any grade arterial thromboembolic event, Grade 3 hepatotoxicity, Grade 4 hepatotoxicity, 2 g or greater proteinuria in 24 hours, Grade 3 renal failure or impairment, Grade 4 renal failure or impairment, any Grade gastrointestinal perforation, Grade 3 fistula, Grade 4 fistula, a greater than 500 ms QT/QTc interval prolongation, a greater than 60 ms increase from baseline QT/QTc interval prolongation, and any Grade reversible posterior leukoencephalopathy syndrome are excluded from the persistent and intolerable Grade 2, Grade 3, or Grade 4 adverse reaction or Grade 4 laboratory abnormality.

17. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, (I) wherein the human subject develops an occurrence of a first persistent and intolerable Grade 2 or Grade 3 adverse reaction or Grade 4 laboratory abnormality during treatment with the first dosage regimen, and the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg; or (II) wherein the human subject develops an occurrence of a Grade 4 adverse reaction excluding Grade 4 laboratory abnormality during treatment with the first dosage regimen, and the method further comprises terminating administration of the dosage regimen after the occurrence of the Grade 4 adverse reaction excluding Grade 4 laboratory abnormality;

provided that Grade 3 hypertension, Grade 4 hypertension, Grade 3 cardiac dysfunction, Grade 4 cardiac dysfunction, any grade arterial thromboembolic event, Grade 3 hepatotoxicity, Grade 4 hepatotoxicity, 2 g or greater proteinuria in 24 hours, Grade 3 renal failure or impairment, Grade 4 renal failure or impairment, any Grade gastrointestinal perforation, Grade 3 fistula, Grade 4 fistula, a greater than 500 ms QT/QTc interval prolongation, a greater than 60 ms increase from baseline QT/QTc interval prolongation, and any Grade reversible posterior leukoencephalopathy syndrome are excluded from the persistent and intolerable Grade 2, Grade 3 or Grade 4 adverse reaction or Grade 4 laboratory abnormality.

18. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, (I) wherein the human subject develops an occurrence of a first persistent and intolerable Grade 2 or Grade 3 adverse reaction or Grade 4 laboratory abnormality during treatment with the first dosage regimen, and the method further comprises:

(a) terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, wherein the human subject develops an occurrence of a second persistent and intolerable Grade 2 or Grade 3 adverse reaction or Grade 4 laboratory abnormality during treatment with the second dosage regimen;

(b) terminating administration of the second dosage regimen after the occurrence of the second persistent and intolerable Grade 2 or Grade 3 adverse reaction or Grade 4 laboratory abnormality until the second persistent and intolerable Grade 2 or Grade 3 adverse reaction or Grade 4 laboratory abnormality is resolved to Grade 0-1 or baseline, and administering to the human subject a third dosage regimen comprising lenvatinib or a pharmaceutically acceptable salt thereof at a dose of (i) 4 mg/day if the body weight of the human subject is equal to or more than 60 kg or (ii) 4 mg every other day if the body weight of the human subject is less than 60 kg, wherein the human subject develops an occurrence of a third persistent and intolerable Grade 2 or Grade 3 adverse reaction or Grade 4 laboratory abnormality during treatment with the third dosage regimen; and (c) terminating administration of the third dosage regimen after the occurrence of the third persistent and intolerable Grade 2 or Grade 3 adverse reaction or Grade 4 laboratory abnormality until the third persistent and intolerable Grade 2 or Grade 3 adverse reaction or Grade 4 laboratory abnormality is resolved to Grade 0-1 or baseline, and, if the body weight of the human subject is equal to or more than 60 kg, administering to the human subject a fourth dosage regimen comprising lenvatinib or a pharmaceutically acceptable salt thereof at a dose of 4 mg every other day; or (II) wherein the human subject develops an occurrence of a Grade 4 adverse reaction excluding Grade 4 laboratory abnormality during treatment with the first, second, third, or fourth dosage regimen, and the method further comprises terminating administration of the dosage regimen after the occurrence of the Grade 4 adverse reaction excluding Grade 4 laboratory abnormality;

provided that hypertension, cardiac dysfunction, arterial thromboembolic event, hepatotoxicity, proteinuria, renal failure or impairment, gastrointestinal perforation, fistula, QT/QTc interval prolongation, and reversible posterior leukoencephalopathy syndrome are excluded from the persistent and intolerable Grade 2, Grade 3, or Grade 4 adverse reaction or Grade 4 laboratory abnormality.

19. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, (I) wherein the human subject develops an occurrence of a first persistent and intolerable Grade 2 or Grade 3 adverse reaction or Grade 4 laboratory abnormality during treatment with the first dosage regimen, and the method further comprises terminating administration of the first dosage regimen after the occurrence of the first persistent and intolerable Grade 2 or Grade 3 adverse reaction or Grade 4 laboratory abnormality until the first persistent and intolerable Grade 2 or Grade 3 adverse reaction or Grade 4 laboratory abnormality is resolved to Grade 0-1 or baseline, and administering to the human subject a second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg; or (II) wherein the human subject develops an occurrence of a Grade 4 adverse reaction excluding Grade 4 laboratory abnormality during treatment with the first dosage regimen, and the method further comprises terminating administration of the dosage regimen after the occurrence of the Grade 4 adverse reaction excluding Grade 4 laboratory abnormality;

provided that hypertension, cardiac dysfunction, arterial thromboembolic event, hepatotoxicity, proteinuria, renal failure or impairment, gastrointestinal perforation, fistula, QT/QTc interval prolongation, and reversible posterior leukoencephalopathy syndrome are excluded from the persistent and intolerable Grade 2, Grade 3, or Grade 4 adverse reaction or Grade 4 laboratory abnormality.

20. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, wherein the human subject develops an occurrence of a Grade 3 hypertension during treatment with the first dosage regimen, and the method further comprises terminating administration of the first dosage regimen after the occurrence of the Grade 3 hypertension until the Grade 3 hypertension is controlled at less than or equal to Grade 2, and administering to the human subject the second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg.

21. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, wherein the human subject develops an occurrence of a 2 g or greater proteinuria in 24 hours during treatment with the first dosage regimen, and the method further comprises terminating administration of the dosage regimen after the occurrence of the 2 g or greater proteinuria in 24 hours until the proteinuria is less than or equal to 2 g of proteinuria in 24 hours and, administering to the human subject the second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg, provided that the human subject develops an occurrence of a nephrotic syndrome during treatment with the first dosage regimen, and the method further comprises terminating administration of the dosage regimen after the occurrence of the nephrotic syndrome.

22. A method of treating unresectable hepatocellular carcinoma, the method comprising administering to a human subject that has an unresectable hepatocellular carcinoma a first dosage regimen comprising lenvatinib or a pharmaceutically acceptable salt thereof at a dose of (i) 12 mg/day if the body weight of the human subject is equal to or more than 60 kg or (ii) 8 mg/day if the body weight of the human subject is less than 60 kg, wherein the human subject develops an occurrence of a greater than 500 ms QT/QTc interval prolongation or a greater than 60 ms increase from baseline QT/QTc interval prolongation during treatment with the first dosage regimen, and the method further comprises terminating administration of the dosage regimen after the occurrence of the greater than 500 ms QT/QTc interval prolongation or a greater than 60 ms increase from baseline QT/QTc interval prolongation until the QT/QTc interval prolongation improves to less than or equal to 480 ms or baseline and, administering to the human subject the second dosage regimen comprising lenvatinib or a pharmaceutically acceptable salt thereof at a dose of (i) 8 mg/day if the body weight of the human subject is equal to or more than 60 kg or (ii) 4 mg/day if the body weight of the human subject is less than 60 kg.

23. The method of claim 1, wherein lenvatinib or the pharmaceutically acceptable salt thereof is formulated as a capsule.

24. The method of claim 1, wherein lenvatinib or the pharmaceutically acceptable salt thereof is administered to the human subject orally.

25. The method of claim 1, wherein lenvatinib or a pharmaceutically acceptable salt thereof is lenvatinib mesylate.

* * * * *